United States Patent
Layton et al.

(10) Patent No.: US 9,108,937 B2
(45) Date of Patent: Aug. 18, 2015

(54) POSITIVE ALLOSTERIC MODULATORS OF MGLUR2

(75) Inventors: Mark E. Layton, Harleysville, PA (US); Michael J. Kelly, Wayne, PA (US); Timothy J. Hartingh, Blue Bell, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 227 days.

(21) Appl. No.: 13/581,819

(22) PCT Filed: Feb. 28, 2011

(86) PCT No.: PCT/US2011/026441
§ 371 (c)(1),
(2), (4) Date: Oct. 18, 2012

(87) PCT Pub. No.: WO2011/109277
PCT Pub. Date: Sep. 9, 2011

(65) Prior Publication Data
US 2013/0158002 A1    Jun. 20, 2013

Related U.S. Application Data

(60) Provisional application No. 61/310,414, filed on Mar. 4, 2010.

(51) Int. Cl.
| | |
|---|---|
| *C07D 285/14* | (2006.01) |
| *C07D 417/14* | (2006.01) |
| *C07D 491/107* | (2006.01) |
| *C07D 513/04* | (2006.01) |
| *C07D 471/10* | (2006.01) |
| *C07D 417/10* | (2006.01) |
| *C07D 491/113* | (2006.01) |
| *C07D 417/04* | (2006.01) |
| *C07D 417/12* | (2006.01) |
| *C07D 498/04* | (2006.01) |
| *C07D 519/00* | (2006.01) |

(52) U.S. Cl.
CPC ............ *C07D 285/14* (2013.01); *C07D 417/04* (2013.01); *C07D 417/10* (2013.01); *C07D 417/12* (2013.01); *C07D 417/14* (2013.01); *C07D 471/10* (2013.01); *C07D 491/107* (2013.01); *C07D 491/113* (2013.01); *C07D 498/04* (2013.01); *C07D 513/04* (2013.01); *C07D 519/00* (2013.01)

(58) Field of Classification Search
None
See application file for complete search history.

(56) References Cited

U.S. PATENT DOCUMENTS 7,601,722 B2 * 10/2009 McComas et al. ....... 514/254.03
2008/0293684 A1   11/2008 Pinkerton et al.

FOREIGN PATENT DOCUMENTS

| WO | 02/14275 A2 | 2/2002 |
| WO | 2004/087048 A2 | 10/2004 |
| WO | 2006/091496 A2 | 8/2006 |
| WO | 2011/109277 A1 | 9/2011 |

OTHER PUBLICATIONS

Shafer, S., Kolkhof, P. Failure is an option: learning from unsuccessful proof-of-concept trials. Drug Discovery Today. Nov. 13, 2008, 913-916.*
Horig, H., Pullman, W. From bench to clinic and back: Perspective on the 1st IQPC Translational Research conference. Journal of Translational Medicine. Dec. 2, 2004, 44.*
Conn et al., Promise of mGluR2/3 activator in psychiatry. Neuropsychopharmacology, 2009, 34, 248-249.*
Johnson, et al., "Discovery of Allosteric Potentiators for the Metabotropic Glutamate 2 Receptor: Synthesis and Subtype Selectivity . . ." J. Med. Chem., 2003, vol. 46, pp. 3189-3192.
Johnson, et al., "Allosteric modulators of metabotropic gluamate receptors: lessons learnt from MG1u1, , Glu2 and mGlu5 potentiators and antagonists," Biochenmical Society Transactions, 2004, vol. 32, Part 5, 881-887.
Galici, et al., "A Selective Potentiator of Metabotropic Glutamate (mGlu) 2 Receptors Has Effects to an Orthosteric . . ." The Journal of Pharmacology and Eperimental Therapeutics, vol. 315, No. 3, pp. 1181-1187, (2005).
Pinkerton, et al., "Phenyl-tetrazolyl Acetophenones: Discovery of Positive Allosteric Potentiators for the Metatabotropic Glutamate 2 Receptor," J. Med. Chem., 2004, vol. 47, pp. 4595-4599.
Woolley, et al., "The mGlu2 but not the mGlu3 receptor mediates the actions of the mGluR2/3 . . ." Phychopharmacology, 2008, vol. 196, pp. 431-440.
Jullian, et al., "Agonist Selectivity of mGluR1 and mGluR2 Metabotropic Receptors: A Different Environment but Similar Recognition . . . ," J. Med. Chem., 1999, vol. 42, pp. 1546-1555.
WO2011/109277, completed on May 13, 2011.

* cited by examiner

*Primary Examiner* — Michael Barker
*Assistant Examiner* — Po-Chih Chen
(74) *Attorney, Agent, or Firm* — Keith D. MacMillan; John C. Todaro

(57) ABSTRACT

The present invention is directed to 5-substituted 1,3-dihydro-2,1,3-benzothiadiazole 2,2-dioxide and 1,3-dihydro[1,2,5]thiadiazolo[3,4-b]pyridine 2,2,-dioxide derivatives which are potentiators of metabotropic glutamate receptors, particularly the mGluR2 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

26 Claims, No Drawings

POSITIVE ALLOSTERIC MODULATORS OF MGLUR2

BACKGROUND OF THE INVENTION

The excitatory amino acid L-glutamate (sometimes referred to herein simply as glutamate) through its many receptors mediates most of the excitatory neurotransmission within the mammalian central nervous system (CNS). The excitatory amino acids, including glutamate, are of great physiological importance, playing a role in a variety of physiological processes, such as long-term potentiation (learning and memory), the development of synaptic plasticity, motor control, respiration, cardiovascular regulation, and sensory perception.

Glutamate acts via at least two distinct classes of receptors. One class is composed of the ionotropic glutamate (iGlu) receptors that act as ligand-gated ionic channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGluR) receptor. Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The present invention relates to potentiators of mGlu receptors, in particular mGluR2 receptors. The mGluR receptors belong to the Type III G-protein coupled receptor (GPCR) superfamily. This superfamily of GPCR's including the calcium-sensing receptors, GABAB receptors and pheromone receptors, which are unique in that they are activated by binding of effectors to the amino-terminus portion of the receptor protein. The mGlu receptors are thought to mediate glutamate's demonstrated ability to modulate intracellular signal transduction pathways. Ozawa, Kamiya and Tsuzuski, Prog. Neurobio., 54, 581 (1998). They have been demonstrated to be localized both pre- and post-synaptically where they can regulate neurotransmitter release, either glutamate or other neurotransmitters, or modify the post-synaptic response of neurotransmitters, respectively.

At present, there are eight distinct mGlu receptors that have been positively identified, cloned, and their sequences reported. These are further subdivided based on their amino acid sequence homology, their ability to effect certain signal transduction mechanisms, and their known pharmacological properties. Ozawa, Kamiya and Tsuzuski, Prog. Neurobio., 54, 581 (1998). For instance, the Group I mGluR receptors, which include the mGlu1R and mGlu5R, are known to activate phospholipase C (PLC) via Gαq-proteins thereby resulting in the increased hydrolysis of phosphoinositides and intracellular calcium mobilization. There are several compounds that are reported to activate the Group I mGlu receptors including DHPG, (R/S)-3,5-dihydroxyphenylglycine. Schoepp, Goldworthy, Johnson, Salhoff and Baker, J. Neurochem., 63, 769 (1994); Ito, et al., keurorep., 3, 1013 (1992). The Group II mGlu receptors consist of the two distinct receptors, mGluR2 and mGluR3 receptors. Both have been found to be negatively coupled to adenylate cyclase via activation of Gαi-protein. These receptors can be activated by a selective compound such as 1S,2S,5R,6S-2 aminobicyclo [3.1.0]hexane-2,6-dicarboxylate. Monn, et al., J. Med. Chem., 40, 528 (1997); Schoepp, et al., Neuropharmacol., 36, 1 (1997). This activation leads to inhibition of glutamate release in the synapse (Cartmell et al, J Neurochem 75, 889 (2000)). Similarly, the Group III mGlu receptors, including mGluR4, mGluR6, mGluR7 and mGluR8, are negatively coupled to adenylate cyclase via Gαi and are potently activated by L-AP4 (L-(+)-2-amino-4-phosphonobutyric acid). Schoepp, Neurochem. Int., 24, 439 (1994).

Nonselective mGluR2/mGluR3 receptor agonists (Monn, et al., J. Med. Chem., 43, 4893, (2000)) have shown efficacy in numerous animal models of anxiety and psychosis as well as human clinical trials in schizophrenia patients; Patil et al, Nature Medicine, 13, 1102 (2007). Recent reports indicate that mGluR2 but not the mGluR3 receptor mediates the actions of the dual mGluR2/mGluR3 agonist LY379268 in mouse models predictive of antipsychotic activity. Woolley et al, Psycopharmacology, 196, 431 (2008). Additionally, recent animal studies demonstrate that selective potentiation of the mGluR2 receptor has similar effects to such non-selective agonists (Galici et al, Journal of Pharmacology and Experimental Therapeutics, 315, 1181 (2005)) suggesting an alternative strategy concerning the discovery of selective, positive allosteric modulators (PAMs or allosteric potentiators) of mGluR2 (Johnson et al, J. Med. Chem. 46, 3189, (2003); Pinkerton et al., J. Med. Chem., 47, 4595 (2004). These potentiators act by enabling the receptor to produce an enhanced response to endogenous glutamate. Such allosteric potentiators do not bind at the glutamate binding site also known as the "orthosteric site", and may benefit by binding to a site other than the highly conserved orthosteric site. A potential advantage to this approach includes the opportunity to have a distinct pharmacological profile by enhancing the activity of the endogenous ligand upon its binding to the orthosteric site. The pharmacological distinctions include the potential for pharmacological specificity between related receptor types that share the same endogenous ligand. In addition, positive allosteric modulators of mGluR2 have been shown to potentiate the response of mGluR2 agonists such as LY379268 (Johnson et. Al. Biochemical Soc. Trans. 32, 881 (2004) and this represents an alternative strategy for treatment using mGluR2 selective PAMs.

It has become increasingly clear that there is a link between modulation of excitatory amino acid receptors, including the glutamatergic system, through changes in glutamate release or alteration in postsynaptic receptor activation, and a variety of neurological and psychiatric disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction make the abatement of these neurological processes an important therapeutic goal.

SUMMARY OF THE INVENTION

The present invention is directed to 5-substituted 1,3-dihydro-2,1,3-benzothiadiazole 2,2-dioxide and 1,3-dihydro[1,2,5]thiadiazolo[3,4-b]pyridine 2,2,-dioxide derivatives which are potentiators of metabotropic glutamate receptors, particularly the mGluR2 receptor, and which are useful in the treatment or prevention of neurological and psychiatric disorders associated with glutamate dysfunction and diseases in which metabotropic glutamate receptors are involved. The invention is also directed to pharmaceutical compositions comprising these compounds and the use of these compounds and compositions in the prevention or treatment of such diseases in which metabotropic glutamate receptors are involved.

DETAILED DESCRIPTION OF THE INVENTION

The invention encompasses compounds according to Formula I

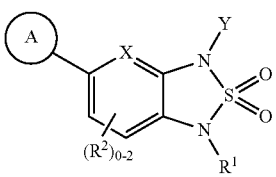

wherein:
X is selected from C and N;
Y is $C_{1-6}$alkyl;
$R^1$ is selected from the group consisting of:
(1) $C_{2-8}$alkyl,
(2) $C_{2-8}$alkenyl,
(3) $C_{2-8}$alkynyl,
(4) $C_{3-6}$cycloalkyl-$(CH_2)_p$—, wherein p is 1, 2, 3 or 4, and
(5) benzyl,
wherein groups (1) to (5) above are optionally substituted with 1 to 3 $R^2$ groups;
each $R^2$ is independently selected from the group consisting of: halo, OH, $C_{1-4}$alkyl, $C_{1-4}$alkoxy, $CF_3$, —$OCF_3$ and —CN;
ring A is selected from aryl and heteroaryl, wherein said aryl and heteroaryl are optionally substituted with one or more $R^3$ groups up to the maximum number of substitutable positions;
each $R^3$ is independently selected from the group consisting of:
(1) halo,
(2) $C_{1-8}$alkyl,
(3) $C_{2-6}$alkenyl,
(4) $C_{2-6}$alkynyl,
(5) $C_{3-6}$cycloalkyl,
(6) $C_{1-6}$alkoxy,
(7) $C_{3-6}$cycloalkoxy,
(8) —CN,
(9) —OH,
(10) —C(O)—O—$C_{1-4}$alkyl,
(11) —C(O)—$C_{1-4}$alkyl,
(12) —$N(R)_2$,
(13) —C(O)—$N(R)_2$,
(14) —$S(O)_k$—$C_{1-4}$alkyl, wherein k is 0, 1 or 2,
(15) -aryl,
(16) -heteroaryl,
(17) -heterocycle,
(18) —C(O)-aryl,
(19) —N(R)-aryl,
(20) benzyl,
(21) benzyloxy,
(22) aryl-O—,
(23) heteroaryl-O—,
(24) heterocycle-O—
(23) —$CO_2H$,
(24) —SH,
(25) —$SO_2N(R)R$,
(26) —N(R)C(O)N(R)R,
(27) —N(R)C(O)$C_{1-4}$alkyl,
(28) —N(R)$SO_2$N(R)R,
(29) —$B(OH)_2$,
(30) heteroaryl-$CH_2$—,
(31) heterocycle-$CH_2$—,
(32) aryl-C(O)—N(R)—$CH_2$—,
(33) heteroaryl-C(O)—N(R)—$CH_2$—,
(34) heterocycle-C(O)—N(R)—$CH_2$—,
(35) aryl-C(O)—N(R)—$CH_2$—,
(36) heteroaryl-$CH_2$—C(O)—N(R)—$CH_2$—,
(37) heterocycle-$CH_2$—C(O)—N(R)—$CH_2$—, and
(38) $C_{1-6}$alkyl-C(O)—N(R)—$CH_2$—,
wherein groups (2) to (7), (10), (11), (14) to (24), (27) and (30) to (38) above are optionally substituted from one up to the maximum number of substitutable positions with one or more substituents independently selected from the group consisting of: OH, CN, halo, —$N(R)_2$, —C(O)—$N(R)_2$, —$CH_2$—$N(R)_2$, —C(O)—$CH_2$—$N(R)_2$, carboxy, —C(O)—O—$C_{1-4}$alkyl, —C(O)—$C(R)_2$—C(O)—O—$C_{1-4}$alkyl, —$CH_2$—$C_{3-6}$cycloalkyl, $C_{1-4}$alkoxy, $C_{1-4}$alkylamino, acetyl, acetylamino, methylsulfonyl, methylsulfonylamino, phenyl, heterocycle, heteroaryl, heteroaryl-C(O)—, $C_{1-4}$alkyl and $C_{1-4}$alkyl-C(O)—, said $C_{1-4}$alkyl, $C_{1-4}$alkyl-C(O)—, heteroaryl and heteroaryl-C(O)-optionally substituted with 1 to 3 halogen atoms and hydroxy, and heteroaryl and heteroaryl-C(O)— additionally optionally substituted with methyl, and each R is independently selected from the group consisting of: H and $C_{1-4}$alkyl;
aryl at each occurrence is independently selected from the group consisting of: phenyl, naphthyl, anthryl and phenanthryl;
heteroaryl at each occurrence independently means a 5- or 6-membered monocyclic aromatic or 9- or 10-membered bicyclic aromatic, wherein at least one atom in the aromatic is selected from N(R), O and S, the sulfur optionally oxidized to sulfone or sulfoxide, and the remaining atoms are selected from C, N(R), O and S, the sulfur optionally oxidized to sulfone or sulfoxide; heterocycle at each occurrence independently means a 5- or 6-membered monocyclic non-aromatic ring or 9- or 10-membered bi- or spirocyclic non- or partially-aromatic ring, each optionally substituted with 1 to 2 oxo groups, wherein at least one atom is selected from N(R), O and S, the sulfur optionally oxidized to sulfone or sulfoxide, and the remaining atoms are selected from C, N(R), O and S, the sulfur optionally oxidized to sulfone or sulfoxide;
and pharmaceutically acceptable salts thereof.

The invention also encompasses a genus of compounds of Formula I

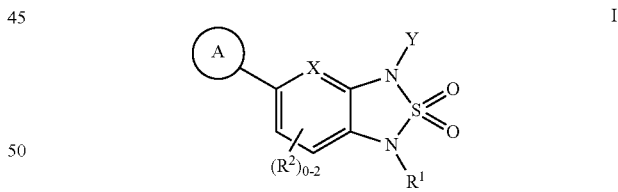

wherein:
X is selected from C and N;
Y is $C_{1-6}$alkyl;
$R^1$ is selected from the group consisting of:
(1) $C_{2-8}$alkyl,
(2) $C_{2-8}$alkenyl,
(3) $C_{2-8}$alkynyl,
(4) $C_{3-6}$cycloalkyl-$(CH_2)_p$—, wherein p is 1, 2, 3 or 4, and
(5) benzyl,
wherein groups (1) to (5) above are optionally substituted with 1 to 3 $R^2$ groups;
each $R^2$ is independently selected from the group consisting of: halo, OH, $C_{1-4}$alkyl, $C_{1-4}$alkoxy, $CF_3$, —$OCF_3$ and —CN;

ring A is selected from aryl and heteroaryl, wherein said aryl and heteroaryl are optionally substituted with one or more $R^3$ groups up to the maximum number of substitutable positions;

each $R^3$ is independently selected from the group consisting of:
(1) halo,
(2) $C_{1-8}$alkyl,
(3) $C_{2-6}$alkenyl,
(4) $C_{2-6}$alkynyl,
(5) $C_{3-6}$cycloalkyl,
(6) $C_{1-6}$alkoxy,
(7) $C_{3-6}$cycloalkoxy,
(8) —CN,
(9) —OH,
(10) —C(O)—O—$C_{1-4}$alkyl,
(11) —C(O)—$C_{1-4}$alkyl,
(12) —N(R)$_2$,
(13) —C(O)—N(R)$_2$,
(14) —S(O)$_k$—$C_{1-4}$alkyl, wherein k is 0, 1 or 2,
(15) -aryl,
(16) -heteroaryl,
(17) -heterocycle,
(18) —C(O)-aryl,
(19) —N(R)-aryl,
(20) benzyl,
(21) benzyloxy,
(22) aryl-O—,
(23) heteroaryl-O—,
(24) heterocycle-O—
(23) —CO$_2$H,
(24) —SH,
(25) —SO$_2$N(R)R,
(26) —N(R)C(O)N(R)R,
(27) —N(R)C(O)$C_{1-4}$alkyl,
(28) —N(R)SO$_2$N(R)R,
(29) —B(OH)$_2$,
(30) heteroaryl-CH$_2$—,
(31) heterocycle-CH$_2$—,
(32) aryl-C(O)—N(R)—CH$_2$—,
(33) heteroaryl-C(O)—N(R)—CH$_2$—,
(34) heterocycle-C(O)—N(R)—CH$_2$—, and
(35) aryl-C(O)—N(R)—CH$_2$—, wherein groups (2) to (7), (10), (11), (14) to (24), (27) and (30) to (35) above are optionally substituted from one up to the maximum number of substitutable positions with one or more substituents independently selected from the group consisting of: OH, CN, halo, —N(R)$_2$, —C(O)—N(R)$_2$, —CH$_2$—N(R)$_2$, carboxy, —C(O)—O—$C_{1-4}$alkyl, $C_{1-4}$alkoxy, $C_{1-4}$alkylamino, acetyl, acetylamino, methylsulfonyl, methylsulfonylamino, phenyl, heterocycle, heteroaryl, heteroaryl-C(O)—, $C_{1-4}$alkyl and $C_{1-4}$alkyl-C(O)—, said $C_{1-4}$alkyl, $C_{1-4}$alkyl-C(O)— and heteroaryl optionally substituted with 1 to 3 halogen atoms and hydroxy, and each R is independently selected from the group consisting of: H and $C_{1-4}$alkyl;

aryl at each occurrence is independently selected from the group consisting of: phenyl, naphthyl, anthryl and phenanthryl; heteroaryl at each occurrence independently means a 5- or 6-membered monocyclic aromatic or 9- or 10-membered bicyclic aromatic, wherein at least one atom in the aromatic is selected from N(R), O and S, the sulfur optionally oxidized to sulfone or sulfoxide, and the remaining atoms are selected from C, N(R), O and S, the sulfur optionally oxidized to sulfone or sulfoxide; heterocycle at each occurrence independently means a 5- or 6-membered monocyclic non-aromatic ring or 9- or 10-membered bi- or spiro-cyclic non- or partially-aromatic ring, each optionally substituted with 1 to 2 oxo groups, wherein at least one atom is selected from N(R), O and S, the sulfur optionally oxidized to sulfone or sulfoxide, and the remaining atoms are selected from C, N(R), O and S, the sulfur optionally oxidized to sulfone or sulfoxide;

and pharmaceutically acceptable salts thereof.

Within the genus, the invention encompasses a first sub-genus of compounds of Formula I wherein X is C.

Also within the genus, the invention encompasses a second sub-genus of compounds of Formula I wherein X is N.

Also within the genus, the invention encompasses a third sub-genus of compounds of Formula I wherein Y is methyl.

Also within the genus, the invention encompasses a fourth sub-genus of compounds of Formula I wherein $R^1$ is selected from the group consisting of: cyclopropylmethyl, 2,2-difluorocyclopropylmethyl, cyclobutylmethyl, 2,2-dimethylpropyl and benzyl, optionally substituted with methoxy or —OCF$_3$.

Also within the genus, the invention encompasses a fifth sub-genus of compounds of Formula Ia

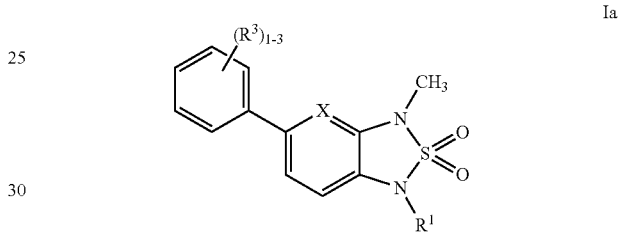

Ia and pharmaceutically acceptable salt thereofs.

Within the fifth sub-genus, the invention encompasses a first class of compounds of Formula Ia wherein $R^3$ is selected from the group consisting of: (1) —CN, (2) halo, (3) —CF$_3$, (4) 1,1-dioxidothiomorpholin-4-yl, (5) morpholin-4-ylmethyl, (6) —C(O)—O—$C_{1-4}$alkyl, (7) $C_{1-6}$alkoxy, (8) $C_{1-6}$alkyl, optionally substituted with hydroxy, (9) piperazinyl, optionally substituted with —C(O)—O—$C_{1-4}$alkyl or isoxazolylcarbonyl, and (10) piperidinyl, optionally substituted with —C(O)—O—$C_{1-4}$alkyl or isoxazolylcarbonyl.

Also within the genus, the invention encompasses a sixth sub-genus of compounds of Formula Ib

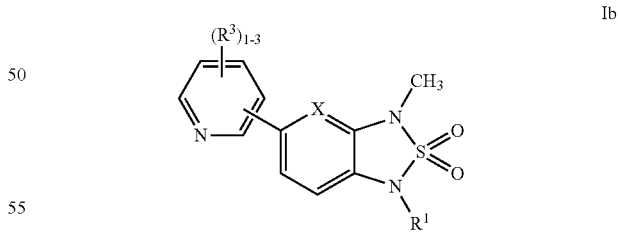

Ib and pharmaceutically acceptable salt thereofs.

Within the sixth sub-genus, the invention encompasses a second class of compounds of Formula Ib wherein $R^3$ is selected from the group consisting of: (1) —CN, (2) halo, (3) —CF$_3$, (4) 1,1-dioxidothiomorpholin-4-yl, (5) morpholin-4-ylmethyl, (6) —C(O)—O—$C_{1-4}$alkyl, (7) $C_{1-6}$alkoxy, (8) $C_{1-6}$alkyl, optionally substituted with hydroxy, (9) piperazinyl, optionally substituted with —C(O)—O—$C_{1-4}$alkyl or isoxazolylcarbonyl, and (10) piperidinyl, optionally substituted with —C(O)—O—$C_{1-4}$alkyl or isoxazolylcarbonyl.

Also within the genus, the invention encompasses a seventh sub-genus of compounds of Formula Ic

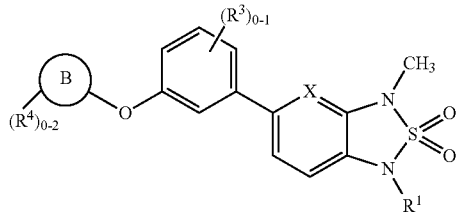

and pharmaceutically acceptable salts thereof, wherein
ring B is heteroaryl,
$R^3$ is CN, halo or $C_{1-4}$alkyl, optionally substituted with 1-5 halo atoms, and
each $R^4$ is independently selected from the group consisting of: —CN, halo, —N(R)$_2$, $C_{1-4}$alkoxy, —C(O)—O—$C_{1-4}$alkyl, and $C_{1-4}$alkyl, optionally substituted with hydroxy.

Also within the genus, the invention encompasses an eight sub-genus of compounds of Formula Id

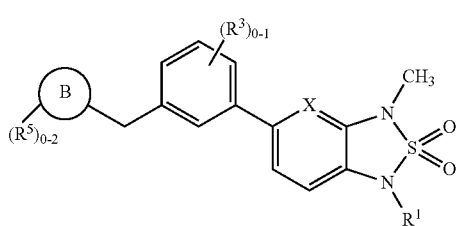

and pharmaceutically acceptable salts thereof, wherein
ring C is heterocycle,
$R^3$ is CN, halo or $C_{1-4}$alkyl, optionally substituted with 1-5 halo atoms, and
each $R^5$ is independently selected from the group consisting of: OH, acetyl, methylsulfonyl, acetylamino, —C(O)—O—$C_{1-4}$alkyl and $C_{1-4}$alkyl, optionally substituted with 1-3 halo atoms or hydroxy.

Also within the genus, the invention encompasses a ninth sub-genus of compounds of Formula Ie

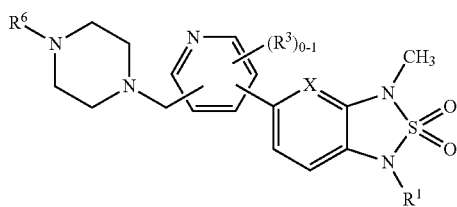

and pharmaceutically acceptable salts thereof, wherein
$R^3$ is CN, halo or $C_{1-4}$alkyl, optionally substituted with 1-5 halo atoms, and
$R^6$ is independently selected from the group consisting of: pyrimidinyl, pyridyl, methylsulfonyl, acetyl, 2-hydroxypropanoyl and 2-hydroxyethanoyl.

Also within the genus, the invention encompasses a tenth sub-genus of compounds of Formula If

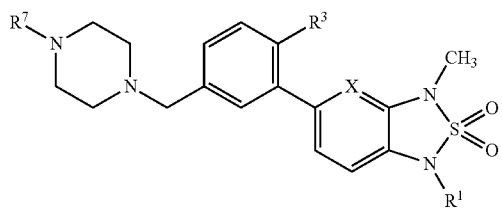

and pharmaceutically acceptable salts thereof, wherein
$R^3$ is CN, halo or $C_{1-4}$alkyl, optionally substituted with 1-5 halo atoms, and
$R^7$ is selected from the group consisting of: pyrimidinyl, pyridyl, methylsulfonyl, acetyl, 2-hydroxypropanoyl and 2-hydroxyethanoyl.

Also within the genus, the invention encompasses an eleventh sub-genus of compounds of Formula Ig

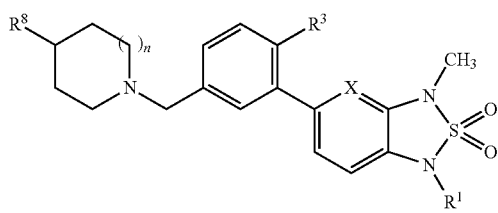

and pharmaceutically acceptable salts thereof, wherein
n is 0 or 1,
$R^3$ is CN, halo or $C_{1-4}$alkyl, optionally substituted with 1-5 halo atoms, and
$R^8$ is selected from the group consisting of: acetylamino, methylsulfonyl, methylsulfonylamino, pyrimidinyl, pyridyl, 2-oxo-1-pyrrolidinyl, —C(O)—N(R)$_2$ and $C_{1-4}$alkyl, said $C_{1-4}$alkyl optionally substituted with 1-3 halo atoms or hydroxy, and said pyridyl optionally substituted with fluoro.

Also within the genus, the invention encompasses a twelfth sub-genus of compounds of Formula Ih

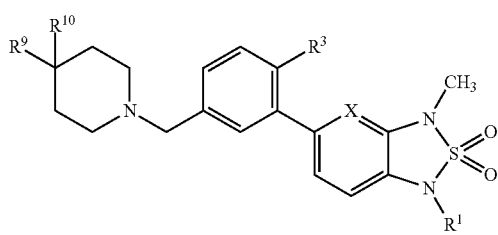

and pharmaceutically acceptable salts thereof, wherein
$R^3$ is CN, halo or $C_{1-4}$alkyl, optionally substituted with 1-5 halo atoms, and
$R^9$ is pyridyl and $R^{10}$ is hydroxy or $R^9$ and $R^{10}$ and joined together with the atom to which they are attached to form 5-oxo-imidazolidine, oxetane or azetidine, said azetidine optionally substituted with —C(O)—O—$C_{1-4}$alkyl.

Also within the genus, the invention encompasses a thirteenth sub-genus of compounds of Formula Ij

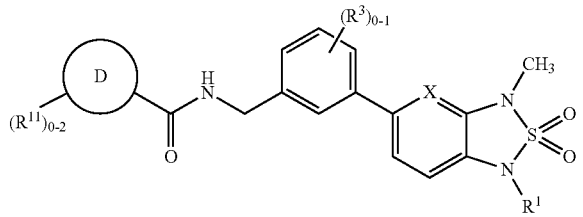

and pharmaceutically acceptable salts thereof, wherein
ring D is heteroaryl,
$R^3$ is CN, halo or $C_{1-4}$alkyl, optionally substituted with 1-5 halo atoms, and
each $R^{11}$ is independently selected from the group consisting of: —CN, halo, —N(R)$_2$, $C_{1-4}$alkoxy, —C(O)—O—$C_{1-4}$alkyl, and $C_{1-4}$alkyl, optionally substituted with hydroxy.

Also within the genus, the invention encompasses a fourteenth sub-genus of compounds of Formula Ik

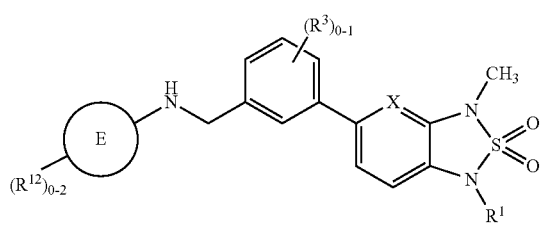

and pharmaceutically acceptable salt thereofs, wherein
ring E is heteroaryl,
$R^3$ is CN, halo or $C_{1-4}$alkyl, optionally substituted with 1-5 halo atoms, and
each $R^{12}$ is independently selected from the group consisting of: —CN, halo, —N(R)$_2$, $C_{1-4}$alkoxy, —C(O)—O—$C_{1-4}$alkyl, and $C_{1-4}$alkyl, optionally substituted with hydroxy.

Another embodiment of the invention encompasses compounds of Formula I wherein $R^1$ is 2,2-difluorocyclopropyl.

The invention also encompasses a compound of Formula II

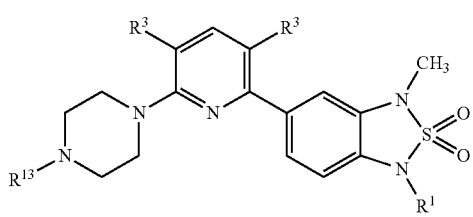

and pharmaceutically acceptable salts thereof, wherein:
one of the $R^3$ groups shown in Formula II is selected from H, CN or methyl; the other $R^3$ group is H; $R^{13}$ is selected from the group consisting of: —C(O)—CH$_2$—N(R)$_2$, —C(O)—O—$C_{1-4}$alkyl, —C(O)—C(R)$_2$—C(O)—O—$C_{1-4}$alkyl, —CH$_2$—$C_{3-6}$cycloalkyl, $C_{1-4}$alkoxy, methylsulfonyl, heteroaryl-C(O)—, $C_{1-4}$alkyl and $C_{1-4}$alkyl-C(O)—, said $C_{1-4}$alkyl, $C_{1-4}$alkyl-C(O)— and heteroaryl-C(O)— optionally substituted with 1 to 3 halogen atoms and hydroxy and heteroaryl-C(O)— additionally optionally substituted with methyl; each R is independently selected from the group consisting of: H and $C_{1-4}$alkyl; $R^1$ is selected from the group consisting of: (1) $C_{2-8}$alkyl, (2) $C_{2-8}$alkenyl, (3) $C_{2-8}$alkynyl, (4) $C_{3-6}$cycloalkyl-(CH$_2$)$_p$—, wherein p is 1, 2, 3 or 4, and (5) benzyl, wherein groups (1) to (5) above are optionally substituted with 1 to 3 $R^2$ groups; and each $R^2$ is independently selected from the group consisting of: halo, OH, $C_{1-4}$alkyl, $C_{1-4}$alkoxy, CF$_3$, —OCF$_3$ and —CN.

The invention also encompasses the examples that follow.

The invention also encompasses a pharmaceutical composition comprising a compound of Formula I in combination with a pharmaceutically acceptable carrier.

The invention also encompasses a method for treating a neurological or psychiatric disorder associated with glutamate dysfunction in a patient in need thereof comprising administering to the patient a therapeutically effective amount of a compound of Formula I. The invention also encompasses this method wherein the neurological or psychiatric disorder associated with glutamate dysfunction is schizophrenia.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono-, bi- or tri-cyclic structures, optionally combined with linear or branched structures, having the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

"Alkoxy" means alkoxy groups of a straight or branched having the indicated number of carbon atoms. $C_{1-6}$alkoxy, for example, includes methoxy, ethoxy, propoxy, isopropoxy, and the like.

"Cycloalkoxy" means cycloalkyl as defined above bonded to an oxygen atom, such as cyclopropyloxy.

Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Halogen" and "halo" includes fluorine, chlorine, bromine and iodine.

The point of attachment for Heterocycle may be through a carbon or nitrogen atom.

A heteroaryl group may be attached to the remainder of the molecule via a ring carbon or a ring nitrogen, provided that this is consistent with preservation of aromaticity.

The compounds of the present invention are potentiators of metabotropic glutamate (mGluR) receptor function, in particular they are potentiators of mGluR2 receptors. That is, the compounds of the present invention do not appear to bind at the glutamate recognition site on the mGluR receptor, but in the presence of glutamate or a glutamate agonist, the compounds of the present invention increase mGluR receptor response. The present potentiators are expected to have their effect at mGluR receptors by virtue of their ability to increase the response of such receptors to glutamate or glutamate agonists, enhancing the function of the receptors. It is recognized that the compounds of the present invention would be expected to increase the effectiveness of glutamate and glutamate agonists of the mGluR2 receptor. Thus, the potentiators of the present invention are expected to be useful in the treatment of various neurological and psychiatric disorders associated with glutamate dysfunction described to be treated herein and others that can be treated by such potentiators as are appreciated by those skilled in the art.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of generic formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. It will be understood that, as used herein, references to the compounds of Formula I are meant to also include a pharmaceutically acceptable salts.

Exemplifying the invention are the examples described below. The subject compounds are useful in a method of potentiating metabotropic glutamate receptor activity in a patient such as a mammal in need of such inhibition comprising the administration of an effective amount of the compound. The present invention is directed to the use of the subject compounds disclosed herein as potentiators of metabotropic glutamate receptor activity. In addition to primates, especially humans, a variety of other mammals can be treated according to the method of the present invention.

The present invention is further directed to a method for the manufacture of a medicament for potentiating metabotropic glutamate receptor activity in humans and animals comprising combining a compound of the present invention with a pharmaceutical carrier or diluent.

The subject treated in the present methods is generally a mammal, preferably a human being, male or female, in whom potentiation of metabotropic glutamate receptor activity is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of metabotropic glutamate receptor activity, in particular mGluR2 activity, may be demonstrated by methodology known in the art. Inhibition constants are determined as follows. The compounds of the present invention may be tested in a fluorescence laser imaging plate reader (FLIPR) based assay. This assay is a common functional assay to monitor $Ca^{2+}$ mobilization in whole cells expressing recombinant receptor coupled with a promiscuous G-protein. CHO dhfr– cells stably expressing recombinant human mGluR2 and Gα16 loaded with Fluo-4 AM (Invitrogen, Carlsbad Calif.) are treated with dose responses of compounds and the $Ca^{2+}$ response is monitored on a FLIPR384 (Molecular Devices, Sunnydale Calif.) for agonist activity. The potentiation response is monitored after a subsequent addition of an EC20 concentration of glutamate (900 nM). The maximum calcium response at each concentration of compound for agonist or potentiation are plotted as dose responses and the curves are fitted with a four parameters logistic equation giving EC50 and Hill coefficient using the iterative non linear curve fitting software program.

The compounds of the present invention may also be tested in a [$^{35}$S]-GTPγS assay. The stimulation of [$^{35}$S]-GTPγS binding is a common functional assay to monitor Gαi-coupled receptor in native and recombinant receptor membrane preparation. Membrane from cells stably expressing hmGlu2 CHO-K1 (50 µg) are incubated in a 96 well plate for 1 hour in the presence of GTPγS$^{35}$ (0.05 nM), GDP (5 µM) and compounds. The reaction is stopped by rapid filtration over Unifilter GF/B plate (Packard, Bioscience, Meriden Conn.) using a 96-well cell harvester (Brandel Gaithersburg, Md.). The filter plates are counted using Topcount counter (Packard, Bioscience, Meriden Conn., USA). When compounds are evaluated as potentiators they are tested in the presence of glutamate (1 µM). The activation (agonist) or the potentiation of glutamate (potentiator) curves are fitted with a four parameters logistic equation giving $EC_{50}$ and Hill coefficient using the iterative non linear curve fitting software GraphPad (San Diego Calif., USA).

In particular, compounds 1-5, 2-2 to 2-31, 3-1, 4-2 to 4-6, 5-2, 6-2, 7-2, 8-1, 9-2, 10-2, 11-1, 12-3 to 12-20, 13-3, 14-2, 15-3, 16-1, 17-2 to 17-4, 18-2, 19-2, 20-1 to 20-4, 21-1 to 21-3, 22-1 to 22-3, 23-4 to 23-8, 24-1, 24-2, 25-2 to 25-10, 26-7, 26-8, 27-1, 28-5, 28-6, 29-2 to 29-10, 30-2, 30-3, 31-4, 32-2, 33-1, 34-1, 35-1, 36-2 to 36-4, 37-2, 38-2 to 38-4, 39-2 to 39-37, 40-1, 40-2, 41-1, 41-2, 42-1 to 42-4, 43-3 to 43-5, 44-3, 44-4, 45-2, 45-3, 46-4 to 46-11 and 46-13 to 46-32, described below, were tested and demonstrated activity in potentiating the mGluR2 receptor in the FLIPR assay, generally with an $EC_{50}$ of less than about 1.5 µM. Certain compounds within the present invention were tested and had activity in potentiating the mGluR2 receptor in the FLIPR and GTPγS assays with an $EC_{50}$ of less than about 1.5 µM. Compounds 1-5, 2-2 to 2-31, 3-1, 4-2 to 4-6, 5-2, 6-2, 7-2, 8-1, 9-2, 10-2, 11-1, 12-3 to 12-20, 13-3, 14-2, 15-3, 16-1, 17-2 to 17-4, 18-2, 19-2, 20-1 to 20-4, 21-1 to 21-3, 22-1 to 22-3, 23-4 to 23-8, 24-1, 24-2, 25-2 to 25-10, 26-7, 26-8, 27-1, 28-5, 28-6, 29-2 to 29-10, 30-2, 30-3, 31-4, 32-2, 33-1, 34-1, 35-1, 36-2 to 36-4, 37-2, 38-2 to 38-4, 39-2 to 39-37, 40-1, 40-2, 41-1, 41-2, 42-1 to 42-4, 43-3 to 43-5, 44-3, 44-4, 45-2, 45-3, 46-4 to 46-11 and 46-13 to 46-32 resulted in a minimum 1.5-fold potentiation of glutamate response in the presence of an EC20 concentration of glutamate (900 nM). Such results are indicative of the intrinsic activity of the compounds in use as potentiators of mGluR2 receptor activity.

| Representative FLIPR $EC_{50}$ Values | | |
|---|---|---|
| Ex. | $IC_{50}$ (nM) | N |
| 1-5 | 5.0 | 2 |
| 8-1 | 110 | 2 |
| 12-4 | 0.5 | 3 |
| 17-2 | 22 | 2 |
| 24-1 | 130 | 2 |
| 20-1 | 0.8 | 2 |
| 3-1 | 490 | 1 |
| 25-2 | 24 | 2 |
| 30-2 | 9 | 2 |
| 32-2 | 140 | 2 |
| 36-2 | 3 | 3 |
| 38-3 | 25 | 2 |
| 42-3 | 9 | 2 |
| 39-2 | 11 | 5 |
| 43-3 | 8 | 7 |

Metabotropic glutamate receptors including the mGluR2 receptor have been implicated in a wide range of biological functions. This has suggested a potential role for these receptors in a variety of disease processes in humans or other species.

The compounds of the present invention have utility in treating, preventing, ameliorating, controlling or reducing the risk of a variety of neurological and psychiatric disorders associated with glutamate dysfunction, including one or more of the following conditions or diseases: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), autism, autism spectrum disorders, attention deficit/hyperactivity disorder, and conduct disorder.

In an embodiment the present invention provides a method for treating migraine, comprising: administering to a patient in need thereof an effective amount of a compound of formula I. In another embodiment the present invention provides a method for preventing or treating anxiety, comprising: administering to a patient in need thereof an effective amount of a compound of formula I. Particular anxiety disorders of the invention are generalized anxiety disorder, panic disorder, and obsessive compulsive disorder. In another embodiment the present invention provides a method for treating schizophrenia, comprising: administering to a patient in need thereof an effective amount of a compound of formula I. In yet another embodiment the present invention provides a method for treating epilepsy, comprising: administering to a patient in need thereof an effective amount of a compound of formula I.

In an embodiment, the present invention provides a method for the treatment of schizophrenia comprising: administering to a patient in need thereof an effective amount of a compound of formula I or a pharmaceutical composition thereof. In one of the available sources of diagnostic tools, The Merck Manual (2006-2007), schizophrenia is characterized by psychosis (loss of contact with reality), hallucinations (false perceptions), delusions (false beliefs), disorganized speech and behavior, flattened affect (restricted range of emotions), cognitive deficits (impaired reasoning and problem solving), and occupational and social dysfunction. The skilled artisan will recognize that there are alternative nomenclatures, nosologies, and classification systems for neurological and psychiatric disorders, including migraine, and that these systems evolve with medical scientific progress Thus, in an embodiment the present invention provides a method for treating migraine, comprising: administering to a patient in need thereof an effective amount of a compound of formula I or a pharmaceutical composition thereof. In one of the available sources of diagnostic tools, Dorland's Medical Dictionary (23'd Ed., 1982, W. B. Saunders Company, Philadelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another embodiment the present invention provides a method for treating anxiety, comprising: administering to a patient in need thereof an effective amount of a compound of Formula I or a pharmaceutical composition thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another embodiment the present invention provides a method for treating depression, comprising: administering to a patient in need thereof an effective amount of a compound of Formula I or a pharmaceutical composition thereof. At present, DSM-IV provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-IV.

In another embodiment the present invention provides a method for treating epilepsy, comprising: administering to a patient in need thereof an effective amount of a compound of Formula I or a pharmaceutical composition thereof. At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents, including an mGluR agonist.

The term "potentiated amount" refers to an amount of an mGluR agonist, that is, the dosage of agonist which is effective in treating the neurological and psychiatric disorders described herein when administered in combination with an effective amount of a compound of the present invention. A potentiated amount is expected to be less than the amount that is required to provided the same effect when the mGluR agonist is administered without an effective amount of a compound of the present invention.

A potentiated amount can be readily determined by the attending diagnostician, as one skilled in the art, by the use of conventional techniques and by observing results obtained under analogous circumstances. In determining a potentiated amount, the dose of an mGluR agonist to be administered in combination with a compound of formula I, a number of factors are considered by the attending diagnostician, including, but not limited to: the mGluR agonist selected to be administered, including its potency and selectivity; the compound of formula I to be coadministered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGluR agonist to be administered in combination with an effective amount of a compound of formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGlu agonist are able to be determined by one skilled in the art.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form may be utilized containing such other drugs and the compound of Formula I. However, the combination therapy may also includes therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention may be utilized. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require potentiation of metabotorpic glutamate receptor activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

When treating, preventing, controlling, ameliorating, or reducing the risk of neurological and psychiatric disorders associated with glutamate dysfunction or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein. The compounds of the present invention can be prepared in a variety of fashions.

All patents, publications and pending patent applications identified are hereby incorporated by reference.

Abbreviations used in the description of the chemistry and in the Examples that follow are: Ac2O (acetic anhydride); AcOH (acetic acid); AEBSF (p-aminoethylbenzenesulfonyl fluoride); Boc (di-tert-butyl carbamate); (Boc)$_2$O (di-tert-butyl dicarbonate); BSA (bovine serum albumin); BuLi (n-Butyl lithium); CDCl$_3$ (chloroform-d); CuI (copper iodide); CuSO4 (copper sulfate); DBU (1,8-DIAZABICYCLO [5.4.0]UNDEC-7-ENE); DCE (dichloroethane); DCM (dichloromethane); DEAD (diethyl azodicarboxylate); DIPEA (diisopropylethylamine); DMBA (1,3-dimethylbarbituric acid); DMF (N,N-dimethylformamide); DMP (Dess-Martin periodinane); DMSO (dimethyl sulfoxide); DPPA (diphenylphosphoryl azide); DTT (dithiothreitol); EDTA (ethylene-diamine-tetra-acetic acid); EGTA (ethylene-glycol-tetra-acetic acid); Et2O (diethylether); EtOAc (ethyl acetate); EtOH (ethanol); HOAc (acetic acid); HPLC (high-performance liquid chromatography); HRMS (high resolution mass spectrum); LAH (lithium aluminum hydride); LCMS (liquid chromatograph-mass spectrometer); LHMDS (lithium bis(trimethylsilyl)amide); LRMS (low resolution mass spectrum); mCPBA (3-chloroperoxybenzoic acid); MeOH (methanol); MOM-Cl (methoxymethyl chloride); MP-B(CN)H3 (Macroporous cyanoborohydride); NaHCO3 (sodium bicarbonate); Na2SO4 (sodium sulfate); Na(OAc) 3BH (sodium triacetoxyborohydride); NH4OAc (ammonium acetate); NBS (N-bromosuccinamide); NFSi (N-fluorobenzenesulfonimide); NMP (1-methyl-2-pyrrolidinone); NMR (nuclear magnetic resonance); PBS (phosphate buffered saline); PCR (polymerase chain reaction); Pd(dppf) ([1,1'-bis (diphenylphosphino)ferrocene]palladium); Pd(Ph3)4 (palladium(0)tetrakis-triphenylphosphine); POCl3 (phosphorous oxychloride); PS-DIEA (polystyrene diisopropylethylamine); PS—PPh3 (polystyrene-triphenyl phosphine); PTSA (para-toluene sulfonic acid); Pyr (pyridine); Selectfluor (1-chloromethyl-4-fluoro-1,4-diazoniabicyclo[2.2.2] octane bis(tetrafluoroborate); TBAF (tetrabutylammonium fluoride); T-BuOH (tert-butanol); THF (tetrahydrofuran); Tf (trifluoromethanesulfonyl); TFA (trifluoroacteic acid); and TMSCH2N2 (trimethylsilyldiazomethane).

The compounds of this invention may be prepared by employing reactions as shown in the following schemes and examples that follow, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes do not necessarily correlate to that used in the claims and often, for clarity, a single substituent is shown attached to the compound where multiple substituents are optionally allowed under the definitions of Formula I hereinabove. Examples provided are intended to assist in a further understanding of the invention. Particular materials employed, species and conditions are intended to be further illustrative of the invention and not limitative of the reasonable scope thereof. The reagents utilized in synthesizing the compounds depicted in the following tables are either commercially available or are readily prepared by one of ordinary skill in the art.

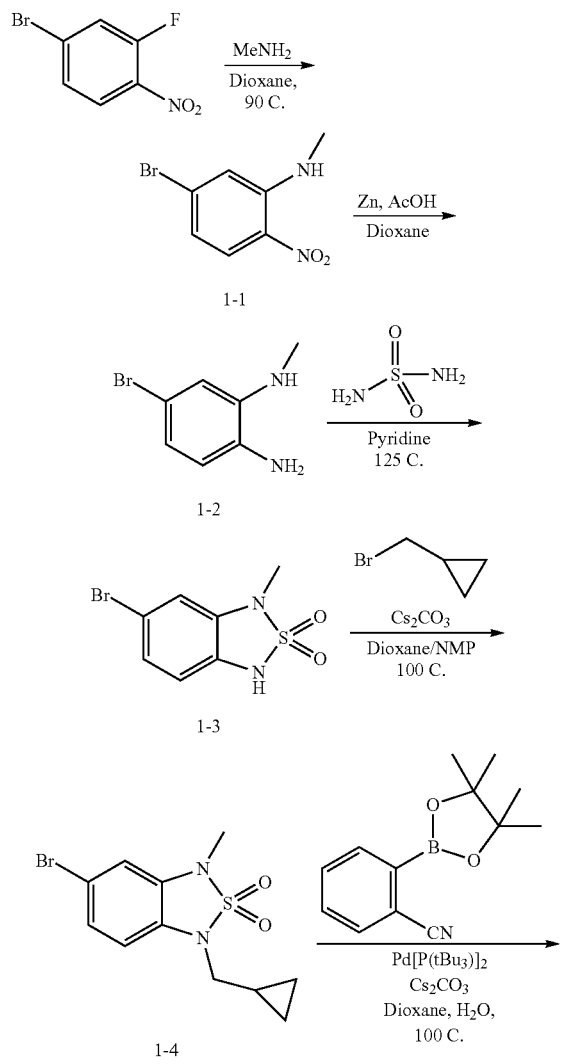

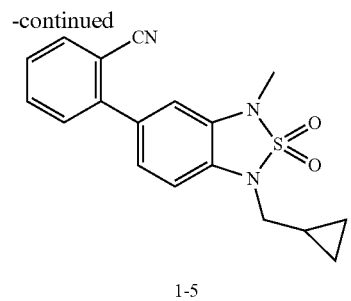

2-[1-(cyclopropylmethyl)-3-methyl-2,2-dioxido-1,3-dihydro-2,1,3-benzothiadiazol-5-yl]benzonitrile (1-5)

5-bromo-N-methyl-2-nitroaniline (1-1)

To a round bottom flask was added 4-bromo-2-fluoro-1-nitrobenzene (11.8 g, 53.7 mmol), anhydrous 1,4 Dioxane (100 mL), and a 2.0 M solution of methyl amine in methanol (56.4 mL, 113 mmol). The reaction mixture was then heated to 90° C. while stirring in a hot oil bath with a water cooled reflux condenser attached under an atmosphere of nitrogen for 3.5 hours. The crude reaction mixture was then allowed to cool to room temperature, and concentrated to give 5-bromo-N-methyl-2-nitroaniline (1-1). MS (M)$^+$: observed=230.9, calculated=231.05.

4-bromo-N$^2$-methylbenzene-1,2-diamine (1-2)

To a stirred solution of 5-bromo-N-methyl-2-nitroaniline (1-1) (12.4 g, 53.7 mmol) in 1,4 Dioxane (100 mL) at 0° C. was added powdered zinc (17.6 g, 269 mmol), followed by dropwise addition of glacial acetic acid (15.0 mL, 262 mmol). The reaction mixture was then permitted to warm to room temperature, sonicated for a few minutes, then permitted to stir at room temperature overnight, then heated to 90° C. in a hot oil bath for four hours. The crude reaction mixture was then cooled to room temperature, then suspended in ethyl acetate, cooled to 0° C. and neutralized with 6N NaOH while stirring until slightly basic. Crude mixture was then filtered. Filtrate organics were separated, then washed with a saturated solution of sodium bicarbonate, followed by water, then brine, dried over sodium sulfate, filtered, and concentrated to give 4-bromo-N$^2$-methylbenzene-1,2-diamine (1-2) as a black oil. MS (M)$^+$: observed=200.9, calculated=201.06.

6-bromo-1-methyl-1,3-dihydro-2,1,3-benzothiadiazole 2,2-dioxide (1-3)

To a round bottom flask was added 4-bromo-N$^2$-methylbenzene-1,2-diamine (1-2) (9.07 g, 45.1 mmol), sulfamide (8.84 g, 92 mmol), and finally anhydrous pyridine (75 mL). The reaction mixture was then heated to 125° C. while stirring in a hot oil bath with a water cooled reflux condenser attached under an atmosphere of nitrogen for 14 hours. The crude reaction mixture was then allowed to cool to room temperature, suspended in ethyl acetate and added 6N HCl until pH <3. Crude mixture was then filtered. Filtrate organics were separated, then washed with 6N HCl twice dried over sodium sulfate, filtered, and concentrated to give 6-bromo-1-methyl-1,3-dihydro-2,1,3-benzothiadiazole 2,2-dioxide (1-3). HRMS (M+H)$^+$: observed=262.9486, calculated=262.9484.

5-bromo-1-(cyclopropylmethyl)-3-methyl-1,3-dihydro-2,1,3-benzothiadiazole 2,2-dioxide (1-4)

To a round bottom flask was added 6-bromo-1-methyl-1,3-dihydro-2,1,3-benzothiadiazole 2,2-dioxide (1-3) (5.32 g, 20.2 mmol), anhydrous NMP (10 mL), anhydrous 1,4 Dioxane (100 mL), cesium carbonate (13.2 g, 40.4 mmol), followed by (bromomethyl)cyclopropane (3.00 g, 22.2 mmol). The reaction mixture was then heated to 100° C. while stirring in a hot oil bath for 18 hours. The crude reaction mixture was then cooled to room temperature, then suspended in ethyl acetate and washed with a saturated solution of sodium bicarbonate, followed by water, then brine, dried over sodium sulfate, filtered, and concentrated. The resulting residue was purified by silica gel chromatography (0-40% EtOAc/Hex) to give 5-bromo-1-(cyclopropylmethyl)-3-methyl-1,3-dihydro-2,1,3-benzothiadiazole 2,2-dioxide (1-4) as a tan solid. HRMS (M+H)$^+$: observed=316.9953, calculated=316.9954.

2-[1-(cyclopropylmethyl)-3-methyl-2,2-dioxido-1,3-dihydro-2,1,3-benzothiadiazol-5-yl]benzonitrile (1-5)

To a microwave vial was added 5-bromo-1-(cyclopropylmethyl)-3-methyl-1,3-dihydro-2,1,3-benzothiadiazole 2,2-dioxide (1-4) (0.074 g, 0.23 mmol), 2-(4,4,5,5-tetramethyl-1,3,2-dioxaborolan-2-yl)benzonitrile (0.070 g, 0.30 mmol), cesium carbonate (0.15 g, 0.47 mmol), palladium bis(tri-tert-butylphosphine) (0.024 g, 0.047 mmol), dioxane (1 mL), and water (0.2 mL). The reaction mixture was then heated under microwave irradiation at 100° C. for 10 minutes. The crude reaction mixture was then allowed to cool to room temperature, diluted with methanol, then filtered and concentrated. Purification of crude reaction mixture by reverse phase chromatography (Waters Sunfire MSC18, 10% acetonitrile/0.1% trifluoroacetic acid/water→100% acetonitrile/0.1% trifluoroacetic acid/water) to give 2-[1-(cyclopropylmethyl)-3-methyl-2,2-dioxido-1,3-dihydro-2,1,3-benzothiadiazol-5-yl]benzonitrile (1-5). $^1$H NMR (400 MHz, CD$_3$OD): δ 7.82 (d, J=7.8 Hz, 1 H); 7.72 (t, J=7.7 Hz, 1 H); 7.61 (d, J=7.9 Hz, 1 H); 7.51 (t, J=7.7 Hz, 1 H); 7.22 (d, J=8.2 Hz, 1 H); 7.15-7.07 (m, 2H); 3.70 (d, J=6.8 Hz, 2 H); 3.31 (s, 3 H); 1.39-1.30 (m, 1 H); 0.66 (d, J=7.7 Hz, 2 H); 0.49 (d, J=5.1 Hz, 2 H). HRMS (M+H)$^+$: observed=340.1114, calculated=340.1114.

SCHEME 2

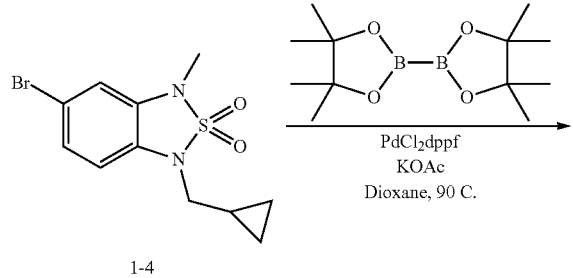

1-4

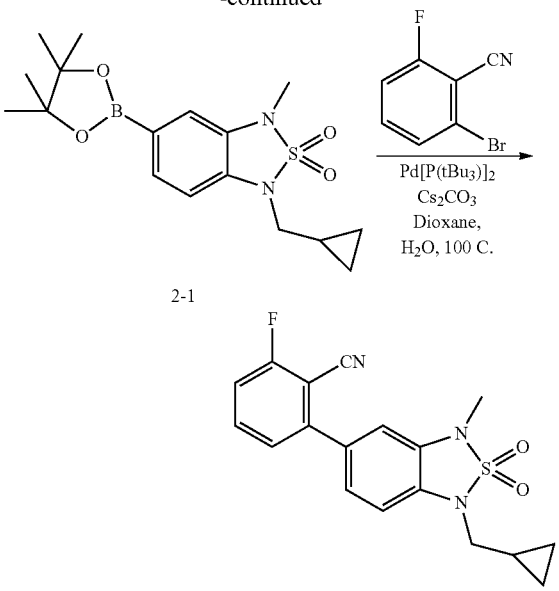

2-1

2-2

2-[1-(cyclopropylmethyl)-3-methyl-2,2-dioxido-1,3-dihydro-2,1,3-benzothiadiazol-5-yl]-6-fluorobenzonitrile (2-2)

1-(cyclopropylmethyl)-3-methyl-5-(4,4,5,5-tetramethyl-1,3,2-dioxaborolan-2-yl)-1,3-dihydro-2,1,3-benzothiadiazole 2,2-dioxide (2-1)

To a round bottom flask was added 5-bromo-1-(cyclopropylmethyl)-3-methyl-1,3-dihydro-2,1,3-benzothiadiazole 2,2-dioxide (1-4) (1.92 g, 6.05 mmol), potassium acetate (2.40 g, 4.04 mmol), 4,4,4',4',5,5'-hexamethyl-2,2'-bi-1,3,2-dioxaborolane (1.76 g, 6.93 mmol), Bis(diphenylphosphino)ferrocene dicholoropalladium (1.03 g, 0.21 mmol), and anhydrous 1,4 Dioxane (20 mL). The reaction mixture was then heated to 90° C. while stirring in a hot oil bath for 18 hours. The crude reaction mixture was then cooled to room temperature, then suspended in ethyl acetate and washed with a saturated solution of sodium bicarbonate, followed by water, then brine, dried over sodium sulfate, filtered, and concentrated. The resulting residue was purified by silica gel chromatography (0-25% EtOAc/Hex) to give 1-(cyclopropylmethyl)-3-methyl-5-(4,4,5,5-tetramethyl-1,3,2-dioxaborolan-2-yl)-1,3-dihydro-2,1,3-benzothiadiazole 2,2-dioxide (2-1) as a tan solid. MS (M+H)$^+$: observed=365.1, calculated=365.3.

2-[1-(cyclopropylmethyl)-3-methyl-2,2-dioxido-1,3-dihydro-2,1,3-benzothiadiazol-5-yl]-6-fluorobenzonitrile (2-2)

To a microwave vial was added 1-(cyclopropylmethyl)-3-methyl-5-(4,4,5,5-tetramethyl-1,3,2-dioxaborolan-2-yl)-1,3-dihydro-2,1,3-benzothiadiazole 2,2-dioxide (2-1) (0.043 g, 0.12 mmol), 2-bromo-6-fluorobenzonitrile (0.035 g, 0.18 mmol), cesium carbonate (0.077 g, 0.24 mmol), palladium bis(tri-tert-butylphosphine) (0.012 g, 0.024 mmol), dioxane (1 mL), and water (0.2 mL). The reaction mixture was then heated under microwave irradiation at 100° C. for 10 minutes. The crude reaction mixture was then allowed to cool to room temperature, diluted with methanol, then filtered and concentrated. Purification of crude reaction mixture by reverse phase chromatography (Waters Sunfire MSC18, 10% acetonitrile/ 0.1% trifluoroacetic acid/water→100% acetonitrile/0.1% trifluoroacetic acid/water) to give 2-[1-(cyclopropylmethyl)-3-methyl-2,2-dioxido-1,3-dihydro-2,1,3-benzothiadiazol-5-yl]-6-fluorobenzonitrile (2-2) as a white solid. HRMS (M+H)⁺: observed=358.1015, calculated=358.1020

TABLE 1

The following compounds were prepared from 1-4 by a reaction sequence analogous to that illustrated in Schemes 1 and 2.

| Cmpd | Structure | IUPAC Name | Exact mass [M + H]+ |
|---|---|---|---|
| 2-3 | 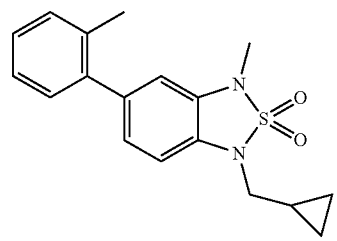 [SMILES: Cc1ccccc1-c1ccc2c(c1)N(C)S(=O)(=O)N2CC1CC1] | 1-(cyclopropylmethyl)-3-methyl-5-(2-methylphenyl)-1,3-dihydro-2,1,3-benzothiadiazole 2,2-dioxide | Calc'd 329.1314, found 329.1318 |
| 2-4 | 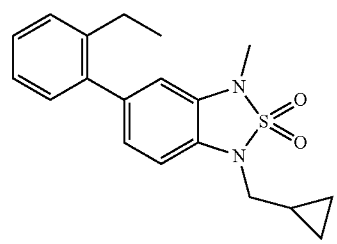 [SMILES: CCc1ccccc1-c1ccc2c(c1)N(C)S(=O)(=O)N2CC1CC1] | 1-(cyclopropylmethyl)-5-(2-ethylphenyl)-3-methyl-1,3-dihydro-2,1,3-benzothiadiazole 2,2-dioxide | Calc'd 343.1475, found 343.1469 |
| 2-5 | 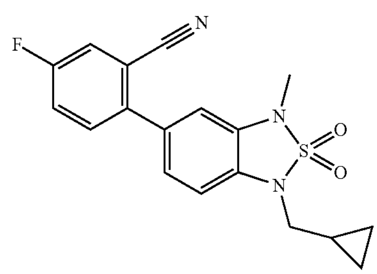 [SMILES: CN1c2cc(-c3ccc(F)cc3C#N)ccc2N(CC2CC2)S1(=O)=O] | 2-[1-(cyclopropylmethyl)-3-methyl-2,2-dioxido-1,3-dihydro-2,1,3-benzothiadiazol-5-yl]-5-fluorobenzonitrile | Calc'd 358.1020, found 358.1014 |
| 2-6 | 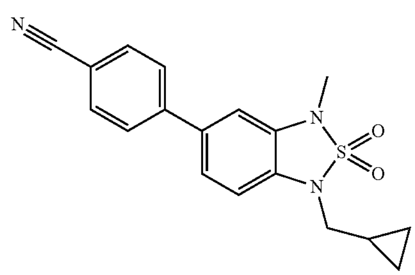 [SMILES: CN1c2cc(-c3ccc(C#N)cc3)ccc2N(CC2CC2)S1(=O)=O] | 4-[1-(cyclopropylmethyl)-3-methyl-2,2-dioxido-1,3-dihydro-2,1,3-benzothiadiazol-5-yl]benzonitrile | Calc'd 340.1114, found 340.1109 |
| 2-7 | 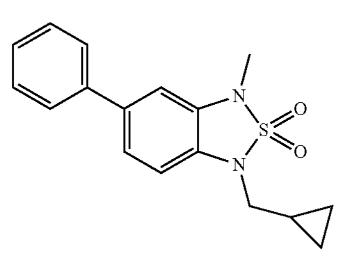 [SMILES: CN1c2cc(-c3ccccc3)ccc2N(CC2CC2)S1(=O)=O] | 1-(cyclopropylmethyl)-3-methyl-5-phenyl-1,3-dihydro-2,1,3-benzothiadiazole 2,2-dioxide | Calc'd 315.1162, found 315.1159 |

TABLE 1-continued

The following compounds were prepared from 1-4 by a reaction sequence analogous to that illustrated in Schemes 1 and 2.

| Cmpd | Structure | IUPAC Name | Exact mass [M + H]+ |
|---|---|---|---|
| 2-8 | 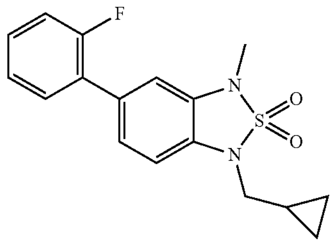 [SMILES: CN1c2cc(-c3ccccc3F)ccc2N(CC2CC2)S1(=O)=O] | 1-(cyclopropylmethyl)-5-(2-fluorophenyl)-3-methyl-1,3-dihydro-2,1,3-benzothiadiazole 2,2-dioxide | Calc'd 333.1068, found 333.1065 |
| 2-9 | 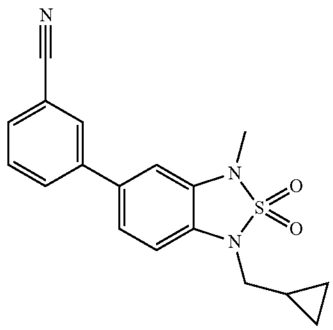 [SMILES: CN1c2cc(-c3cccc(C#N)c3)ccc2N(CC2CC2)S1(=O)=O] | 3-[1-(cyclopropylmethyl)-3-methyl-2,2-dioxido-1,3-dihydro-2,1,3-benzothiadiazol-5-yl]benzonitrile | Calc'd 340.1114, found 340.1109 |
| 2-10 | 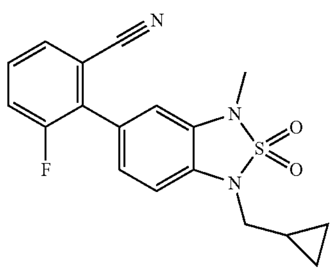 [SMILES: CN1c2cc(-c3c(F)cccc3C#N)ccc2N(CC2CC2)S1(=O)=O] | 2-[1-(cyclopropylmethyl)-3-methyl-2,2-dioxido-1,3-dihydro-2,1,3-benzothiadiazol-5-yl]-3-fluorobenzonitrile | Calc'd 358.1020, found 358.1016 |
| 2-11 | 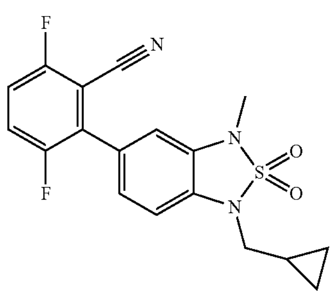 [SMILES: CN1c2cc(-c3c(F)ccc(F)c3C#N)ccc2N(CC2CC2)S1(=O)=O] | 2-[1-(cyclopropylmethyl)-3-methyl-2,2-dioxido-1,3-dihydro-2,1,3-benzothiadiazol-5-yl]-3,6-difluorobenzonitrile | Calc'd 376.0926, found 376.0923 |
| 2-12 | 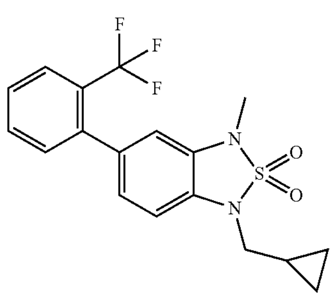 [SMILES: CN1c2cc(-c3ccccc3C(F)(F)F)ccc2N(CC2CC2)S1(=O)=O] | 1-(cyclopropylmethyl)-3-methyl-5-[2-(trifluoromethyl)phenyl]-1,3-dihydro-2,1,3-benzothiadiazole 2,2-dioxide | Calc'd 383.1036, found 383.1031 |

TABLE 1-continued

The following compounds were prepared from 1-4 by a reaction sequence analogous to that illustrated in Schemes 1 and 2.

| Cmpd | Structure | IUPAC Name | Exact mass [M + H]+ |
|---|---|---|---|
| 2-13 | 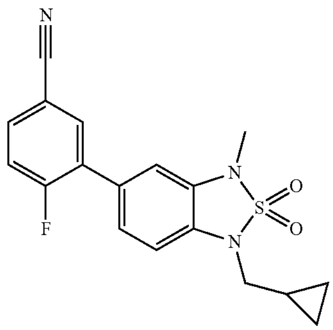 [SMILES: CN1c2cc(-c3cc(C#N)ccc3F)ccc2N(CC2CC2)S1(=O)=O] | 3-[1-(cyclopropylmethyl)-3-methyl-2,2-dioxido-1,3-dihydro-2,1,3-benzothiadiazol-5-yl]-4-fluorobenzonitrile | Calc'd 358.1020, found 358.1012 |
| 2-14 | 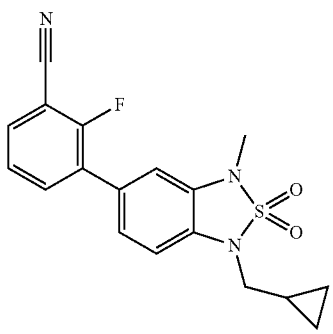 [SMILES: CN1c2cc(-c3cccc(C#N)c3F)ccc2N(CC2CC2)S1(=O)=O] | 3-[1-(cyclopropylmethyl)-3-methyl-2,2-dioxido-1,3-dihydro-2,1,3-benzothiadiazol-5-yl]-2-fluorobenzonitrile | Calc'd 358.1020, found 358.1013 |
| 2-15 | 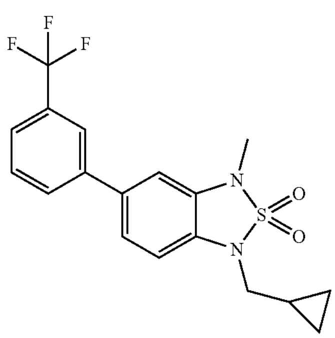 [SMILES: CN1c2cc(-c3cccc(C(F)(F)F)c3)ccc2N(CC2CC2)S1(=O)=O] | 1-(cyclopropylmethyl)-3-methyl-5-[3-(trifluoromethyl)phenyl]-1,3-dihydro-2,1,3-benzothiadiazole 2,2-dioxide | Calc'd 383.1036, found 383.1036 |
| 2-16 | 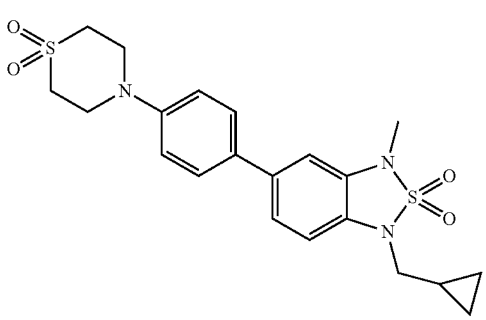 [SMILES: CN1c2cc(-c3ccc(N4CCS(=O)(=O)CC4)cc3)ccc2N(CC2CC2)S1(=O)=O] | 1-(cyclopropylmethyl)-5-[4-(1,1-dioxidothiomorpholin-4-yl)phenyl]-3-methyl-1,3-dihydro-2,1,3-benzothiadiazole 2,2-dioxide | Calc'd 448.1359, found 448.1355 |

TABLE 1-continued

The following compounds were prepared from 1-4 by a reaction sequence analogous to that illustrated in Schemes 1 and 2.

| Cmpd | Structure | IUPAC Name | Exact mass [M + H]+ |
|---|---|---|---|
| 2-17 | 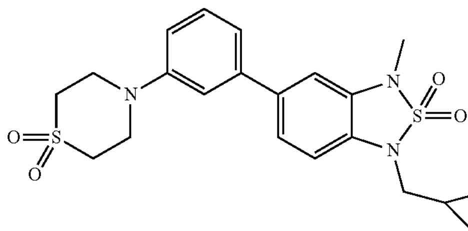 | 1-(cyclopropylmethyl)-5-[3-(1,1-dioxidothiomorpholin-4-yl)phenyl]-3-methyl-1,3-dihydro-2,1,3-benzothiadiazole 2,2-dioxide | Calc'd 448.1359, found 448.1357 |
| 2-18 | 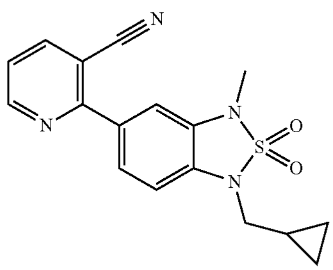 [SMILES: CN1c2cc(-c3ncccc3C#N)ccc2N(CC2CC2)S1(=O)=O] | 2-[1-(cyclopropylmethyl)-3-methyl-2,2-dioxido-1,3-dihydro-2,1,3-benzothiadiazol-5-yl]pyridine-3-carbonitrile | Calc'd 341.1067, found 341.1067 |
| 2-19 | 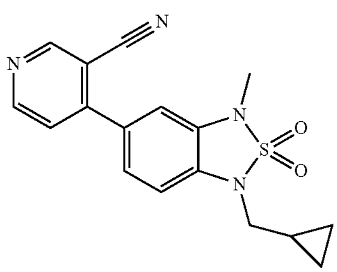 [SMILES: CN1c2cc(-c3ccncc3C#N)ccc2N(CC2CC2)S1(=O)=O] | 4-[1-(cyclopropylmethyl)-3-methyl-2,2-dioxido-1,3-dihydro-2,1,3-benzothiadiazol-5-yl]pyridine-3-carbonitrile | Calc'd 341.1067, found 341.1065 |
| 2-20 | 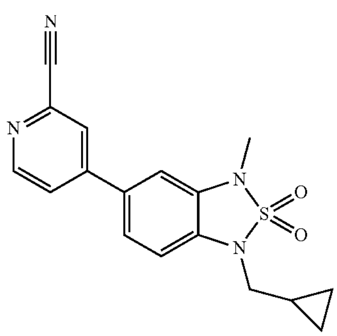 [SMILES: CN1c2cc(-c3ccnc(C#N)c3)ccc2N(CC2CC2)S1(=O)=O] | 4-[1-(cyclopropylmethyl)-3-methyl-2,2-dioxido-1,3-dihydro-2,1,3-benzothiadiazol-5-yl]pyridine-2-carbonitrile | Calc'd 341.1067, found 341.1063 |
| 2-21 | 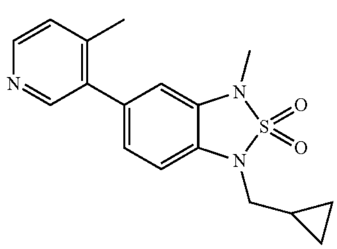 [SMILES: Cc1ccncc1-c1ccc2c(c1)N(C)S(=O)(=O)N2CC1CC1] | 1-(cyclopropylmethyl)-3-methyl-5-(4-methylpyridin-3-yl)-1,3-dihydro-2,1,3-benzothiadiazole 2,2-dioxide | Calc'd 330.1271, found 330.1265 |

TABLE 1-continued

The following compounds were prepared from 1-4 by a reaction sequence analogous to that illustrated in Schemes 1 and 2.

| Cmpd | Structure | IUPAC Name | Exact mass [M + H]+ |
|---|---|---|---|
| 2-22 | 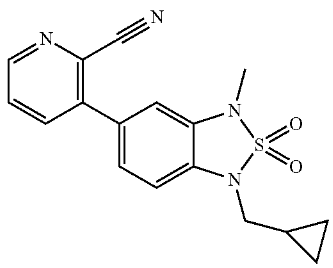 [SMILES: CN1c2cc(-c3cccnc3C#N)ccc2N(CC2CC2)S1(=O)=O] | 3-[1-(cyclopropylmethyl)-3-methyl-2,2-dioxido-1,3-dihydro-2,1,3-benzothiadiazol-5-yl]pyridine-2-carbonitrile | Calc'd 341.1067, found 341.1066 |
| 2-23 | 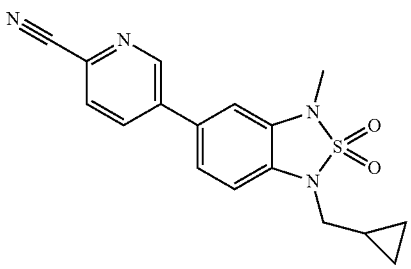 [SMILES: CN1c2cc(-c3ccc(C#N)nc3)ccc2N(CC2CC2)S1(=O)=O] | 5-[1-(cyclopropylmethyl)-3-methyl-2,2-dioxido-1,3-dihydro-2,1,3-benzothiadiazol-5-yl]pyridine-2-carbonitrile | Calc'd 341.1067, found 341.1063 |
| 2-24 | 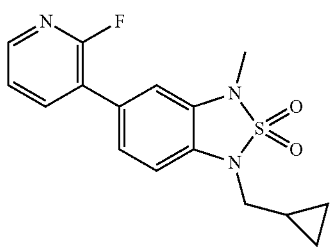 [SMILES: CN1c2cc(-c3cccnc3F)ccc2N(CC2CC2)S1(=O)=O] | 1-(cyclopropylmethyl)-5-(2-fluoropyridin-3-yl)-3-methyl-1,3-dihydro-2,1,3-benzothiadiazole 2,2-dioxide | Calc'd 334.1020, found 334.1021 |
| 2-25 | 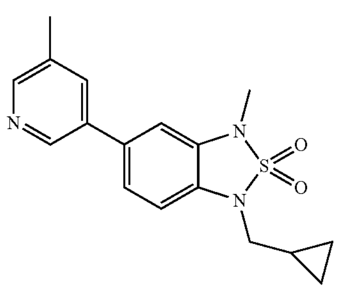 [SMILES: Cc1cncc(-c2ccc3c(c2)N(C)S(=O)(=O)N3CC2CC2)c1] | 1-(cyclopropylmethyl)-3-methyl-5-(5-methylpyridin-3-yl)-1,3-dihydro-2,1,3-benzothiadiazole 2,2-dioxide | Calc'd 330.1271, found 330.1273 |
| 2-26 | 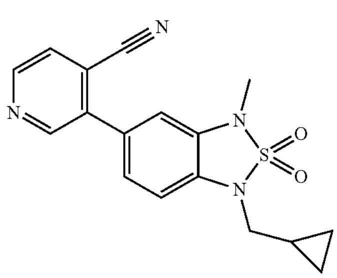 [SMILES: CN1c2cc(-c3cnccc3C#N)ccc2N(CC2CC2)S1(=O)=O] | 3-[1-(cyclopropylmethyl)-3-methyl-2,2-dioxido-1,3-dihydro-2,1,3-benzothiadiazol-5-yl]pyridine-4-carbonitrile | Calc'd 341.1067, found 341.1060 |

TABLE 1-continued

The following compounds were prepared from 1-4 by a reaction sequence analogous to that illustrated in Schemes 1 and 2.

| Cmpd | Structure | IUPAC Name | Exact mass [M + H]+ |
|---|---|---|---|
| 2-27 | 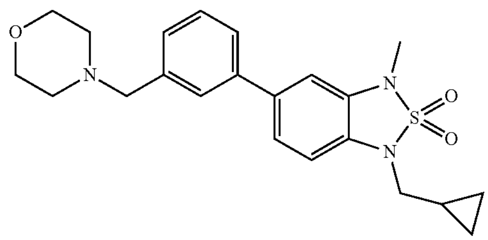 [SMILES: CN1c2cc(-c3cccc(CN4CCOCC4)c3)ccc2N(CC2CC2)S1(=O)=O] | 1-(cyclopropylmethyl)-3-methyl-5-[3-(morpholin-4-ylmethyl)phenyl]-1,3-dihydro-2,1,3-benzothiadiazole 2,2-dioxide | Calc'd 414.1846, found 414.1842 |
| 2-28 | 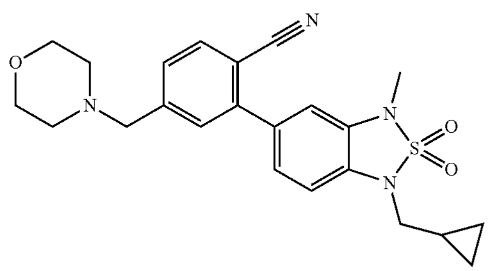 [SMILES: CN1c2cc(-c3cc(CN4CCOCC4)ccc3C#N)ccc2N(CC2CC2)S1(=O)=O] | 2-[1-(cyclopropylmethyl)-3-methyl-2,2-dioxido-1,3-dihydro-2,1,3-benzothiadiazol-5-yl]-4-(morpholin-4-ylmethyl)benzonitrile | Calc'd 439.1798, found 439.1812 |
| 2-29 | 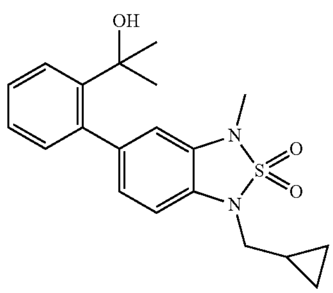 [SMILES: CN1c2cc(-c3ccccc3C(C)(C)O)ccc2N(CC2CC2)S1(=O)=O] | 2-{2-[1-(cyclopropylmethyl)-3-methyl-2,2-dioxido-1,3-dihydro-2,1,3-benzothiadiazol-5-yl]phenyl}propan-2-ol | Calc'd (+Na) 395.1400, found 395.1404 |
| 2-30 | 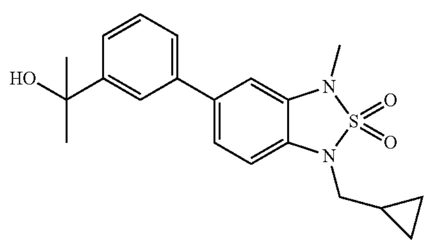 [SMILES: CN1c2cc(-c3cccc(C(C)(C)O)c3)ccc2N(CC2CC2)S1(=O)=O] | 2-{3-[1-(cyclopropylmethyl)-3-methyl-2,2-dioxido-1,3-dihydro-2,1,3-benzothiadiazol-5-yl]phenyl}propan-2-ol | Calc'd 373..1580, found 373.1579 |
| 2-31 | 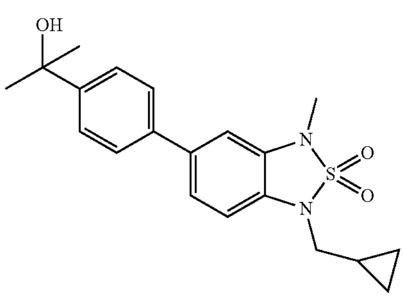 [SMILES: CN1c2cc(-c3ccc(C(C)(C)O)cc3)ccc2N(CC2CC2)S1(=O)=O] | 2-{4-[1-(cyclopropylmethyl)-3-methyl-2,2-dioxido-1,3-dihydro-2,1,3-benzothiadiazol-5-yl]phenyl}propan-2-ol | Calc'd 373.1580, found 373.1580 |

SCHEME 3

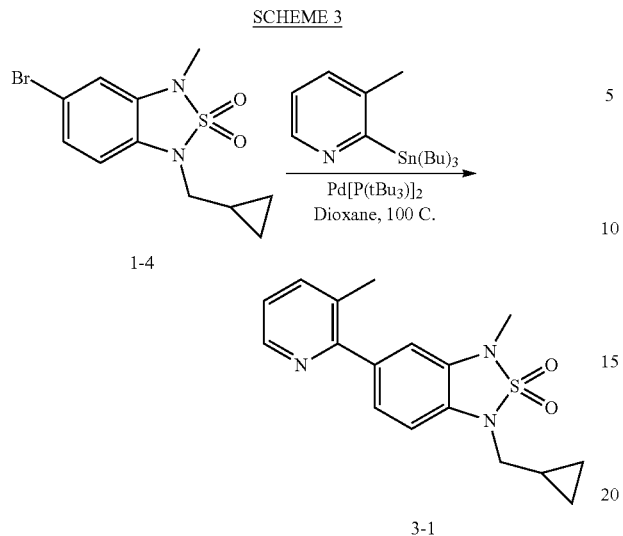

3-1

1-(cyclopropylmethyl)-3-methyl-5-(3-methylpyridin-2-yl)-1,3-dihydro-2,1,3-benzothiadiazole 2,2-dioxide (3-1)

To a microwave vial was added 5-bromo-1-(cyclopropylmethyl)-3-methyl-1,3-dihydro-2,1,3-benzothiadiazole 2,2-dioxide (1-4) (0.043 g, 0.14 mmol), palladium bis(tri-tert-butylphosphine) (0.014 g, 0.027 mmol), 3-methyl-2-(tributylstannyl)pyridine (0.078 g, 0.20 mmol) and finally dioxane (1 mL). The reaction mixture was then heated under microwave irradiation at 100° C. for 10 minutes. The crude reaction mixture was then allowed to cool to room temperature, diluted with methanol, then filtered and concentrated. Purification of crude reaction mixture by reverse phase chromatography (Waters Sunfire MSC18, 10% acetonitrile/0.1% trifluoroacetic acid/water→100% acetonitrile/0.1% trifluoroacetic acid/water) to give 1-(cyclopropylmethyl)-3-methyl-5-(3-methylpyridin-2-yl)-1,3-dihydro-2,1,3-benzothiadiazole 2,2-dioxide (3-1) as a tan solid. HRMS (M+H)$^+$: observed=330.1270, calculated=330.1271.

SCHEME 4

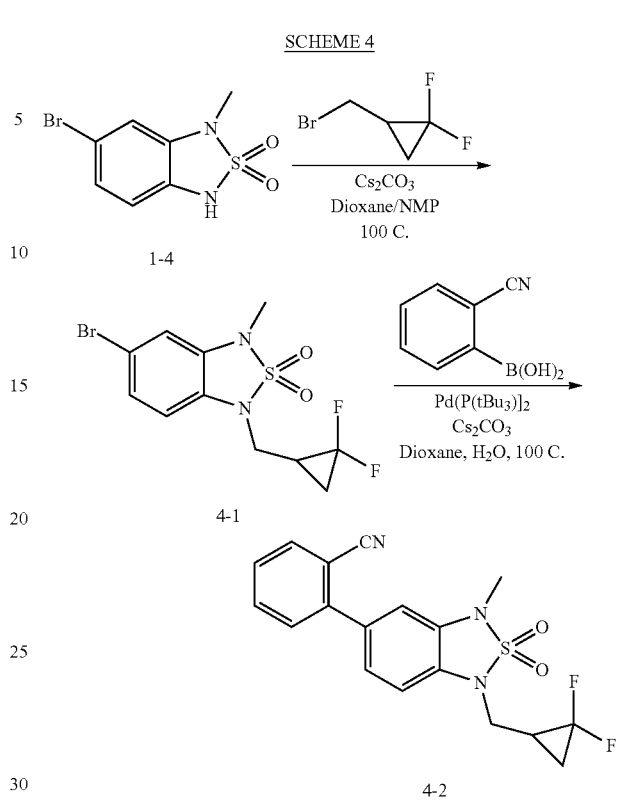

2-{1-[2,2-difluorocyclopropyl)methyl]-3-methyl-2,2-dioxido-1,3-dihydro-2,1,3-benzothiadiazol-5-yl}benzonitrile (4-2)

Prepared from 1-4 according to the procedures reported in Scheme 1. $^1$H NMR (400 MHz, CD$_3$OD): δ 1.40-1.49 (m, 1 H); 1.60-1.69 (m, 1 H); 2.19-2.25 (m, 1 H); 3.31 (s, 3 H); 3.88-4.02 (m, 2 H); 7.10-7.17 (m, 2 H); 7.24 (d, J=8.2 Hz, 1 H); 7.52 (t, J=7.7 Hz, 1 H); 7.62 (d, J=7.9 Hz, 1 H); 7.73 (t, J=7.7 Hz, 1 H); 7.83 (d, J=7.8 Hz, 1H). HRMS m/z (M+H) 376.0933 found, 376.0926 required.

TABLE 2

The following compounds were prepared from by a reaction sequence analogous to that illustrated in Scheme 4.

| Cmpd | Structure | IUPAC Name | Exact Mass [M + H]+ |
|---|---|---|---|
| 4-3 | 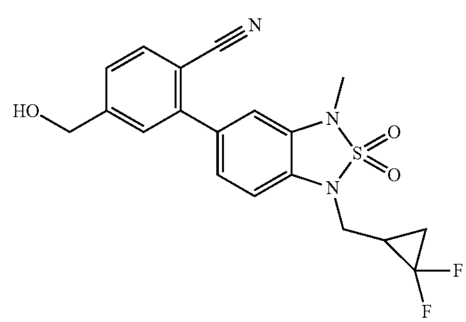 [SMILES: CN1c2cc(-c3cc(CO)ccc3C#N)ccc2N(CC2CC2(F)F)S1(=O)=O] | 2-{1-[(2,2-difluorocyclopropyl)methyl]-3-methyl-2,2-dioxido-1,3-dihydro-2,1,3-benzothiadiazol-5-yl}-4-(hydroxymethyl)benzonitrile | Calc'd 406.1031, found 406.1036 |

TABLE 2-continued

The following compounds were prepared from by a reaction sequence analogous to that illustrated in Scheme 4.

| Cmpd | Structure | IUPAC Name | Exact Mass [M + H]+ |
|---|---|---|---|
| 4-4 | 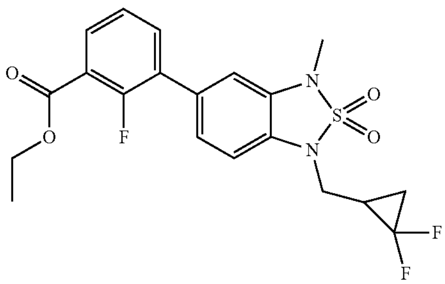 [SMILES: CCOC(=O)c1cccc(-c2ccc3c(c2)N(C)S(=O)(=O)N3CC2CC2(F)F)c1F] | ethyl 3-{1-[(2,2-difluorocyclopropyl)methyl]-3-methyl-2,2-dioxido-1,3-dihydro-2,1,3-benzothiadiazol-5-yl}-2-fluorobenzoate | Calc'd 441.1, found 440.8 |
| 4-5 | 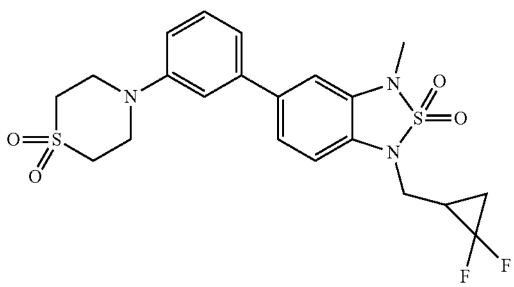 [SMILES: CN1c2cc(-c3cccc(N4CCS(=O)(=O)CC4)c3)ccc2N(CC2CC2(F)F)S1(=O)=O] | 1-[(2,2-difluorocyclopropyl)methyl]-5-[3-(1,1-dioxidothiomorpholin-4-yl)phenyl]-3-methyl-1,3-dihydro-2,1,3-benzothiadiazole 2,2-dioxide | Calc'd 484.1171, found 484.1170 |
| 4-6 | 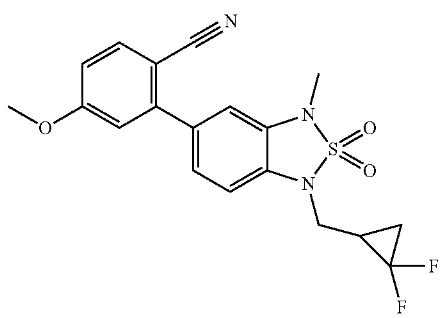 [SMILES: COc1ccc(C#N)c(-c2ccc3c(c2)N(C)S(=O)(=O)N3CC2CC2(F)F)c1] | 2-{1-[(2,2-difluorocyclopropyl)methyl]-3-methyl-2,2-dioxido-1,3-dihydro-2,1,3-benzothiadiazol-5-yl}-4-methoxybenzonitrile | Calc'd 406.1031, found 406.1037 |

SCHEME 5

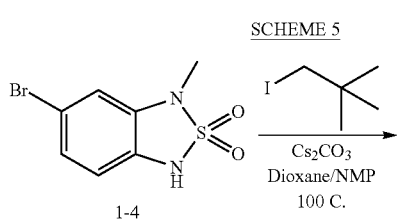

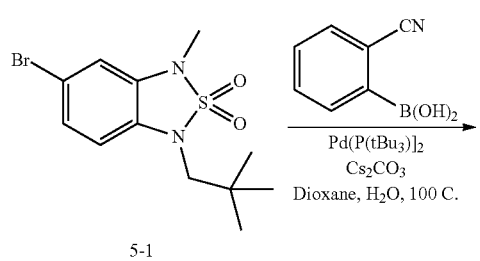

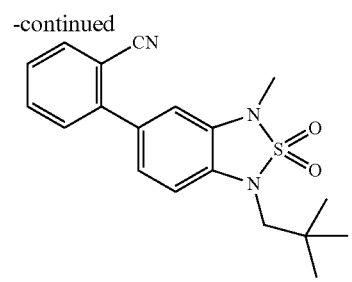

2-[1-(2,2-dimethylpropyl)-3-methyl-2,2-dioxido-1,3-dihydro-2,1,3-benzothiadiazol-5-yl]benzonitrile
(5-2)

Prepared from 1-4 according to the procedures reported in Scheme 1. HRMS m/z (M+H) 356.1423 found, 356.1427 required.

SCHEME 6

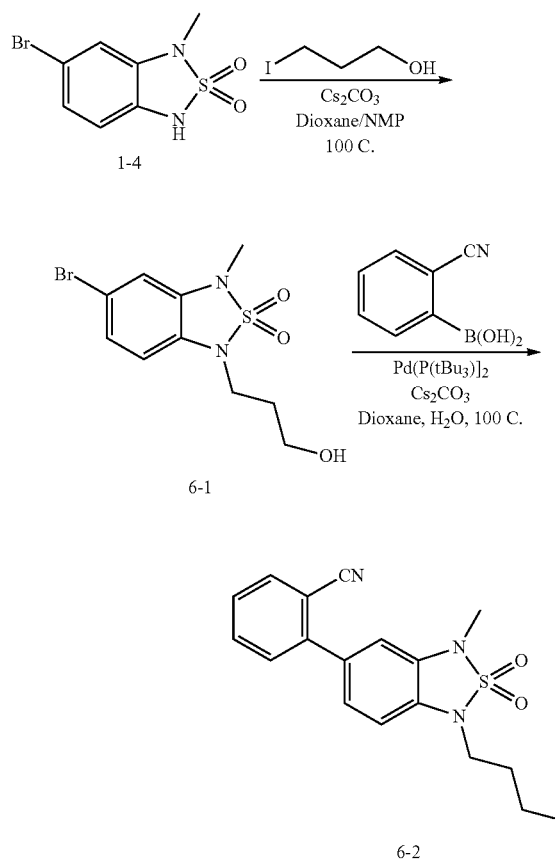

2-[1-(3-hydroxypropyl)-3-methyl-2,2-dioxido-1,3-dihydro-2,1,3-benzothiadiazol-5-yl]benzonitrile (6-2)

Prepared from 1-4 according to the procedures reported in Scheme 1. HRMS m/z (M+H) 344.1065 found, 344.1063 required.

SCHEME 7

2-[1-(cyclobutylmethyl)-3-methyl-2,2-dioxido-1,3-dihydro-2,1,3-benzothiadiazol-5-yl]benzonitrile (7-2)

Prepared from 1-4 according to the procedures reported in Scheme 1. HRMS m/z (M+H) 354.1269 found, 354.1271 required.

SCHEME 8

1-(cyclobutylmethyl)-5-[3-(1,1-dioxidothiomorpholin-4-yl)phenyl]-3-methyl-1,3-dihydro-2,1,3-benzothiadiazole 2,2-dioxide (8-1)

Prepared from 7-1 according to the procedures reported in Scheme 1. $^1$H NMR (400 MHz, CD$_3$OD): δ 1.85-2.01 (m, 4 H); 2.09-2.17 (m, 2 H); 2.88-2.94 (m, 1 H); 3.14-3.19 (m, 4 H); 3.31 (s, 3 H); 3.75 (d, J=7.2 Hz, 2 H); 3.91 (m, 4 H); 6.96 (d, J=8.2 Hz, 1 H); 7.01 (d, J=8.4 Hz, 1 H); 7.10-7.15 (m, 2 H); 7.20-7.27 (m, 2 H); 7.34 (t, J=8.0 Hz, 1 H). HRMS m/z (M+H) 462.1515 found, 462.1516 required.

SCHEME 9

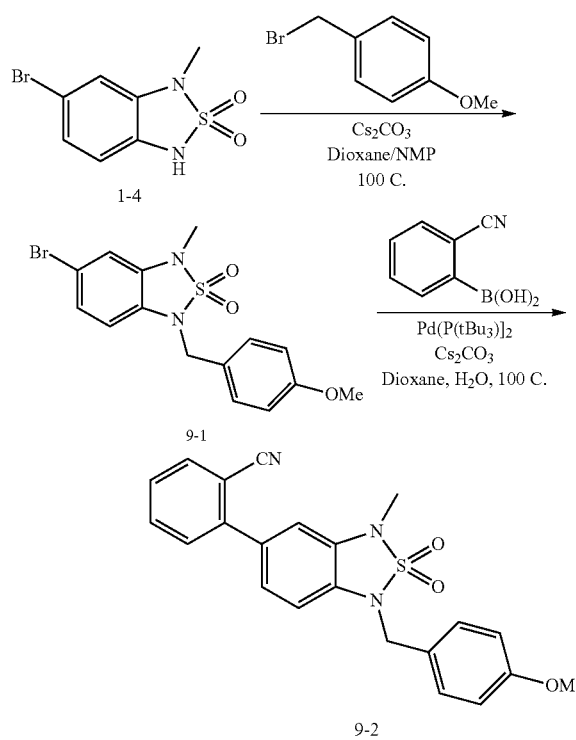

2-[1-(4-methoxybenzyl)-3-methyl-2,2-dioxido-1,3-dihydro-2,1,3-benzothiadiazol-5-yl]benzonitrile (9-2)

Prepared from 1-4 according to the procedures reported in Scheme 1. HRMS m/z (M+Na) 428.1037 found, 428.1039 required.

SCHEME 10

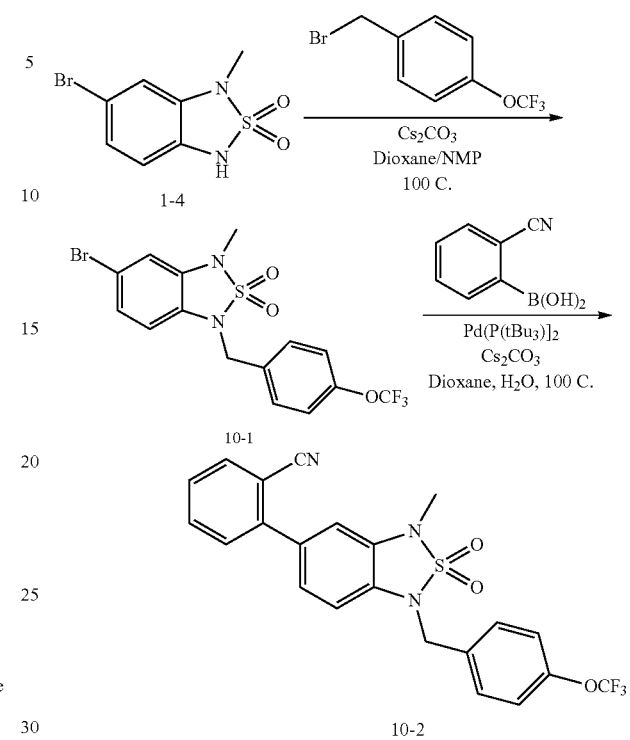

2-{3-methyl-2,2-dioxido-1-[4-(trifluoromethoxy)benzyl]-1,3-dihydro-2,1,3-benzothiadiazol-5-yl}benzonitrile (10-2)

Prepared from 1-4 according to the procedures reported in Scheme 1. HRMS m/z (M+H) 460.0941 found, 460.0937 required.

SCHEME 11

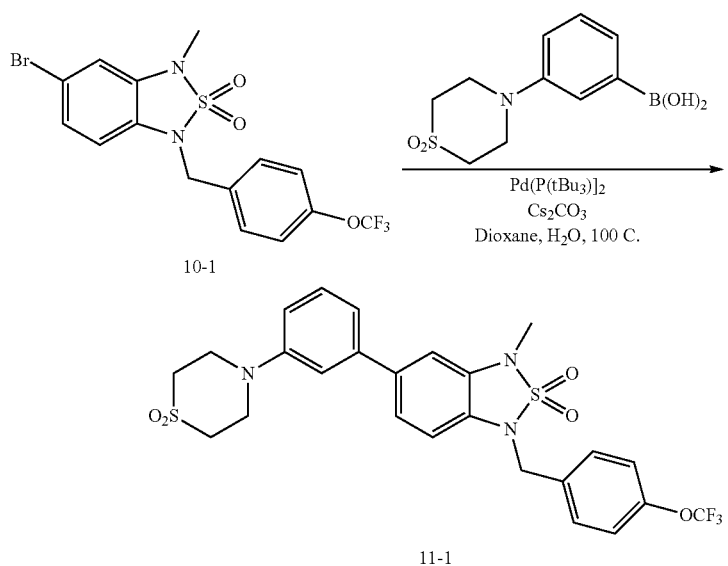

5-[3-(1,1-dioxidothiomorpholin-4-yl)phenyl]-3-methyl-1-[4-(trifluoromethoxy)benzyl]-1,3-dihydro-2,1,3-benzothiadiazole 2,2-dioxide (11-1)

Prepared from 10-1 according to the procedures reported in Scheme 1. HRMS m/z (M+H) 568.1173 found, 568.1182 required.

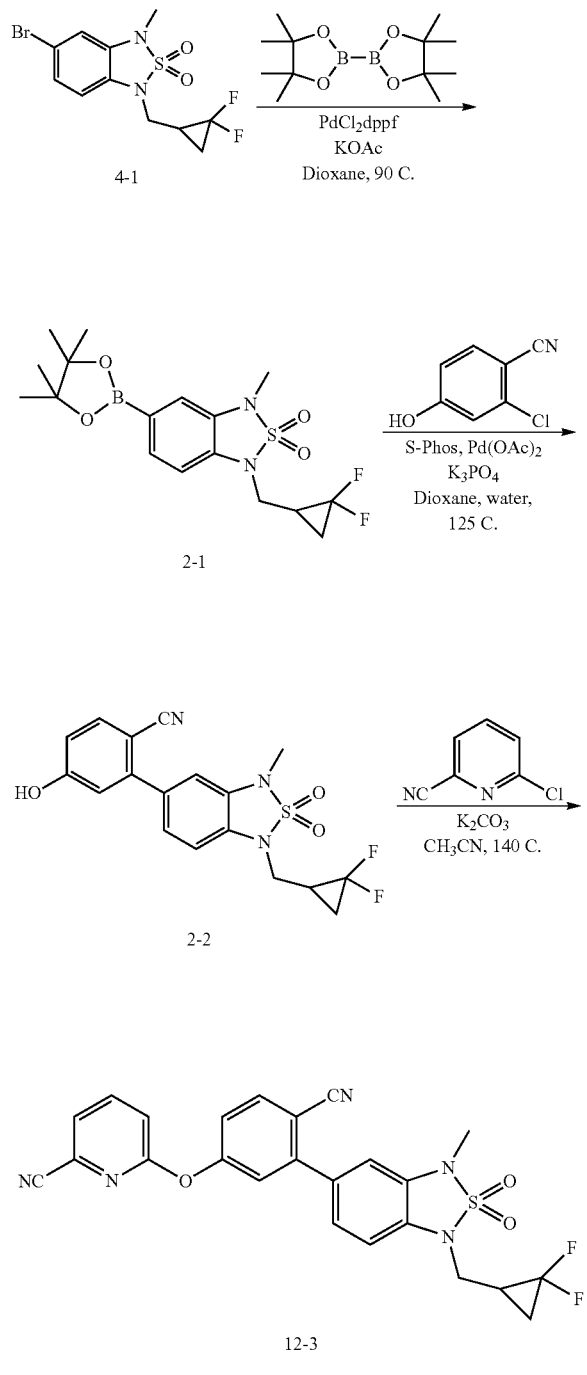

SCHEME 12

4-1

2-1

2-2

12-3

6-(4-cyano-3-{1-[(2,2-difluorocyclopropyl)methyl]-3-methyl-2,2-dioxido-1,3-dihydro-2,1,3-benzothiadiazol-5-yl}phenoxy)pyridine-2-carbonitrile (12-3)

1-[(2,2-difluorocyclopropyl)methyl]-3-methyl-5-(4,4,5,5-tetramethyl-1,3,2-dioxaborolan-2-yl)-1,3-dihydro-2,1,3-benzothiadiazole 2,2-dioxide (12-1)

Prepared from 4-1 according to the procedures reported in Scheme 2. LRMS m/z (M+H)$^+$: observed=401.1, calculated=401.2.

2-{1-[(2,2-difluorocyclopropyl)methyl]-3-methyl-2,2-dioxido-1,3-dihydro-2,1,3-benzothiadiazol-5-yl}-4-hydroxybenzonitrile (12-2)

1-[(2,2-difluorocyclopropyl)methyl]-3-methyl-5-(4,4,5,5-tetramethyl-1,3,2-dioxaborolan-2-yl)-1,3-dihydro-2,1,3-benzothiadiazole 2,2-dioxide (12-1) (2.0 g, 5.0 mmol, 1 eq), 2-chloro-4-hydroxybenzonitrile (0.84 g, 5.5 mmol, 1.1 eq), tripotassium phosphate (2.1 g, 10.0 mmol, 2.0 eq), S-Phos (0.20 g, 0.5 mmol, 0.1 eq), and palladium(II) acetate (56 mg, 0.25 mmol, 0.05 eq) were combined in dioxane (20 mL) and water (3 mL). The resulting mixture was heated at 100° C. for 16 hours. The reaction mixture was allowed to cool to room temperature. The mixture was then diluted with EtOAc (100 mL), washed with water (20 mL) and brine (20 mL), dried over MgSO$_4$, filtered and concentrated. The crude residue was purified by flash chromatography (80 g SiO$_2$, 0-80% EtOAc in hexanes) to afford 2-{1-[(2,2-difluorocyclopropyl)methyl]-3-methyl-2,2-dioxido-1,3-dihydro-2,1,3-benzothiadiazol-5-yl}-4-hydroxybenzonitrile (12-2) as a white solid. LRMS m/z (M+H) 392.3 found, 392.1 required.

6-(4-cyano-3-{1-[(2,2-difluorocyclopropyl)methyl]-3-methyl-2,2-dioxido-1,3-dihydro-2,1,3-benzothiadiazol-5-yl}phenoxy)pyridine-2-carbonitrile (12-3)

2-{1-[(2,2-difluorocyclopropyl)methyl]-3-methyl-2,2-dioxido-1,3-dihydro-2,1,3-benzothiadiazol-5-yl}-4-hydroxybenzonitrile (12-2) (300 mg, 0.77 mmol, 1 eq) was dissolved in acetonitrile (2.5 mL) and 6-chloropyridine-2-carbonitrile (212 mg, 1.5 mmol, 2 eq) and potassium carbonate (424 mg, 3.1 mmol, 4 eq) were added. The resulting mixture was heated in the microwave at 140° C. for 1.5 hours. The mixture was filtered washing with acetonitrile. The crude mixture was purified by reverse phase chromatography (Waters Sunfire MSC18, 10-100% acetonitrile in water with 0.1% TFA modifier) to afford 6-(4-cyano-3-{1-[(2,2-difluorocyclopropyl)methyl]-3-methyl-2,2-dioxido-1,3-dihydro-2,1,3-benzothiadiazol-5-yl}phenoxy)pyridine-2-carbonitrile (12-3) as an off-white solid. $^1$H NMR (400 MHz, CDCl$_3$): δ 7.90 (t, J=8.0 Hz, 1H); 7.82 (d, J=8.4 Hz, 1 H); 7.50 (d, J=7.2 Hz, 1H); 7.34 (s, 1H); 7.29 (t, J=10.4 Hz, 1 H); 6.99 (s, 2 H); 6.92 (d, J=8.0 Hz, 2H); 3.92 (d, J=6.8 Hz, 2H); 3.36 (s, 3 H); 2.14 (m, 1 H); 1.65 (m, 1 H); 1.41 (m, 1 H). HRMS m/z (M+H) 494.1097 found, 494.1093 required.

TABLE 3

The following compounds were prepared by a reaction sequence analogous to that illustrated in Scheme 14:

| Cmpd | Structure | IUPAC Name | Exact Mass [M + H]+ |
|---|---|---|---|
| 12-4 | 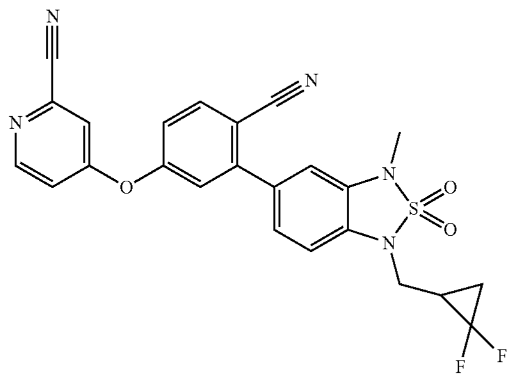 [SMILES: CN1c2cc(-c3cc(Oc4ccnc(C#N)c4)ccc3C#N)ccc2N(CC2CC2(F)F)S1(=O)=O] | 4-(4-cyano-3-{1-[(2,2-difluorocyclopropyl)methyl]-3-methyl-2,2-dioxido-1,3-dihydro-2,1,3-benzothiadiazol-5-yl}phenoxy)pyridine-2-carbonitrile | Calc'd 494.1093, found 494.1087 |
| 12-5 | 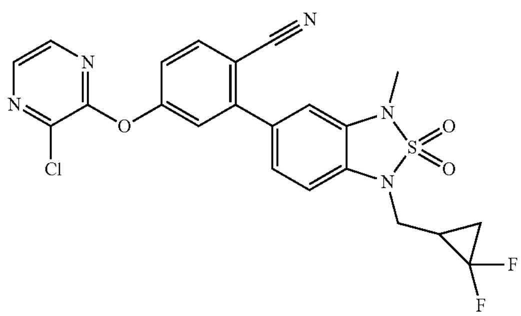 [SMILES: CN1c2cc(-c3cc(Oc4nccnc4Cl)ccc3C#N)ccc2N(CC2CC2(F)F)S1(=O)=O] | 4-[(3-chloropyrazin-2-yl)oxy]-2-{1-[(2,2-difluorocyclopropyl)methyl]-3-methyl-2,2-dioxido-1,3-dihydro-2,1,3-benzothiadiazol-5-yl}benzonitrile | Calc'd 504.0703, found 504.0705 |
| 12-6 | 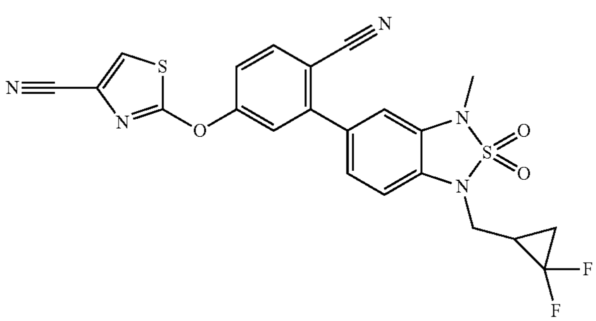 [SMILES: CN1c2cc(-c3cc(Oc4nc(C#N)cs4)ccc3C#N)ccc2N(CC2CC2(F)F)S1(=O)=O] | 2-(4-cyano-3-{1-[(2,2-difluorocyclopropyl)methyl]-3-methyl-2,2-dioxido-1,3-dihydro-2,1,3-benzothiadiazol-5-yl}phenoxy)-1,3-thiazole-4-carbonitrile | Calc'd 500.0657, found 500.0653 |
| 12-7 | 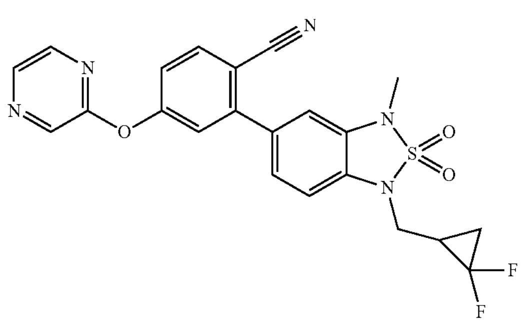 [SMILES: CN1c2cc(-c3cc(Oc4cnccn4)ccc3C#N)ccc2N(CC2CC2(F)F)S1(=O)=O] | 2-{1-[(2,2-difluorocyclopropyl)methyl]-3-methyl-2,2-dioxido-1,3-dihydro-2,1,3-benzothiadiazol-5-yl}-4-(pyrazin-2-yloxy)benzonitrile | Calc'd 470.1093, found 470.1093 |

TABLE 3-continued

The following compounds were prepared by a reaction sequence analogous to that illustrated in Scheme 14:

| Cmpd | Structure | IUPAC Name | Exact Mass [M + H]+ |
|---|---|---|---|
| 12-8 | 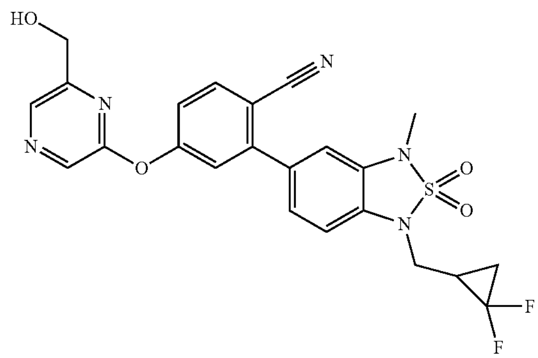 [SMILES: CN1c2cc(-c3cc(Oc4cncc(CO)n4)ccc3C#N)ccc2N(CC2CC2(F)F)S1(=O)=O] | 2-{1-[(2,2-difluorocyclopropyl)methyl]-3-methyl-2,2-dioxido-1,3-dihydro-2,1,3-benzothiadiazol-5-yl}-4-{[6-(hydroxymethyl)pyrazin-2-yl]oxy}benzonitrile | Calc'd 500.1199, found 500.1197 |
| 12-9 | 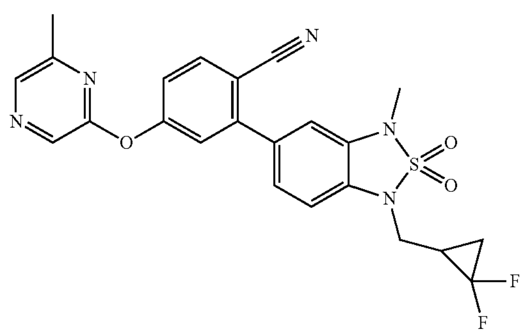 [SMILES: Cc1cncc(Oc2ccc(C#N)c(-c3ccc4c(c3)N(C)S(=O)(=O)N4CC3CC3(F)F)c2)n1] | 2-{1-[(2,2-difluorocyclopropyl)methyl]-3-methyl-2,2-dioxido-1,3-dihydro-2,1,3-benzothiadiazol-5-yl}-4-[(6-methylpyrazin-2-yl)oxy]benzonitrile | Calc'd 484.1249, found 484.1256 |
| 12-10 | 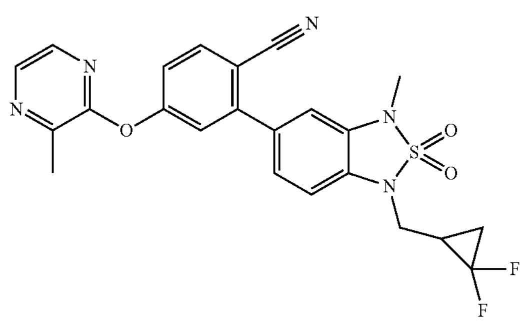 [SMILES: Cc1nccnc1Oc1ccc(C#N)c(-c2ccc3c(c2)N(C)S(=O)(=O)N3CC2CC2(F)F)c1] | 2-{1-[(2,2-difluorocyclopropyl)methyl]-3-methyl-2,2-dioxido-1,3-dihydro-2,1,3-benzothiadiazol-5-yl}-4-[(3-methylpyrazin-2-yl)oxy]benzonitrile | Calc'd 484.1249, found 484.1246 |
| 12-11 | 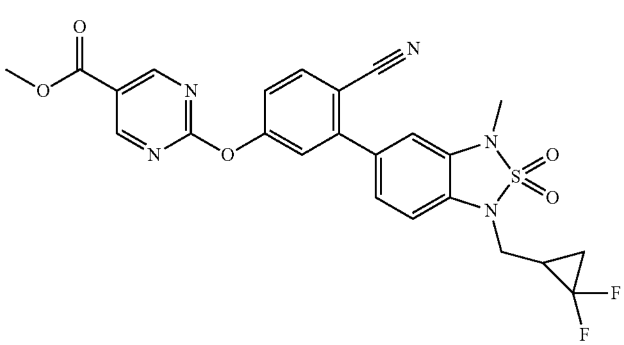 [SMILES: COC(=O)c1cnc(Oc2ccc(C#N)c(-c3ccc4c(c3)N(C)S(=O)(=O)N4CC3CC3(F)F)c2)nc1] | methyl 2-(4-cyano-3-{1-[(2,2-difluorocyclopropyl)methyl]-3-methyl-2,2-dioxido-1,3-dihydro-2,1,3-benzothiadiazol-5-yl}phenoxy)pyrimidine-5-carboxylate | Calc'd 528.1, found 528.3 |

TABLE 3-continued

The following compounds were prepared by a reaction sequence analogous to that illustrated in Scheme 14:

| Cmpd | Structure | IUPAC Name | Exact Mass [M + H]+ |
|---|---|---|---|
| 12-12 | 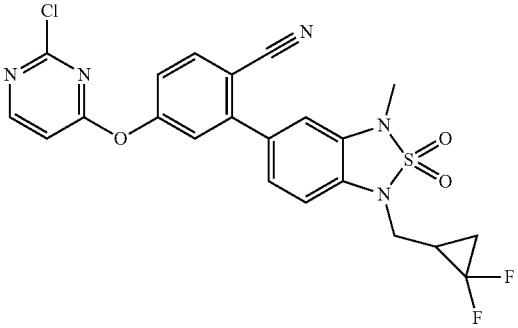 [SMILES: CN1c2cc(-c3cc(Oc4ccnc(Cl)n4)ccc3C#N)ccc2N(CC2CC2(F)F)S1(=O)=O] | 4-[(2-chloropyrimidin-4-yl)oxy]-2-{1-[(2,2-difluorocyclopropyl)methyl]-3-methyl-2,2-dioxido-1,3-dihydro-2,1,3-benzothiadiazol-5-yl}benzonitrile | Calc'd 504.0703, found 504.0704 |
| 12-13 | 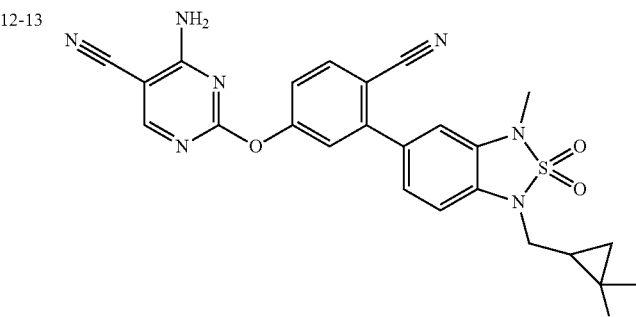 | 4-amino-2-(4-cyano-3-{1-[(2,2-difluorocyclopropyl)methyl]-3-methyl-2,2-dioxido-1,3-dihydro-2,1,3-benzothiadiazol-5-yl}phenoxy)pyrimidine-5-carbonitrile | Calc'd 510.1154, found 510.1156 |
| 12-14 | 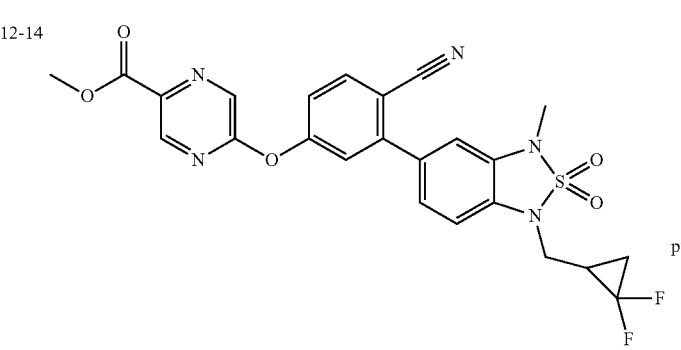 | methyl 5-(4-cyano-3-{1-[(2,2-difluorocyclopropyl)methyl]-3-methyl-2,2-dioxido-1,3-dihydro-2,1,3-benzothiadiazol-5-yl}phenoxy)pyrazine-2-carboxylate | Calc'd 528.1148, found 528.1147 |
| 12-15 | 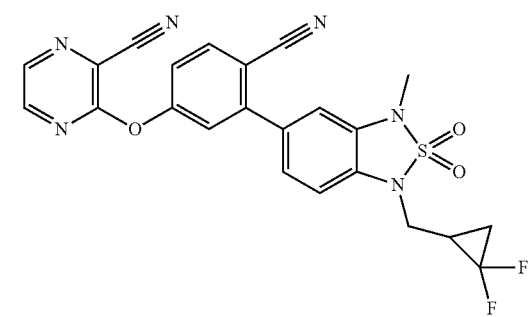 [SMILES: CN1c2cc(-c3cc(Oc4nccnc4C#N)ccc3C#N)ccc2N(CC2CC2(F)F)S1(=O)=O] | 3-(4-cyano-3-{1-[(2,2-difluorocyclopropyl)methyl]-3-methyl-2,2-dioxido-1,3-dihydro-2,1,3-benzothiadiazol-5-yl}phenoxy)pyrazine-2-carbonitrile | Calc'd 495.1045, found 495.1047 |

TABLE 3-continued

The following compounds were prepared by a reaction sequence analogous to that illustrated in Scheme 14:

| Cmpd | Structure | IUPAC Name | Exact Mass [M + H]+ |
|---|---|---|---|
| 12-16 | 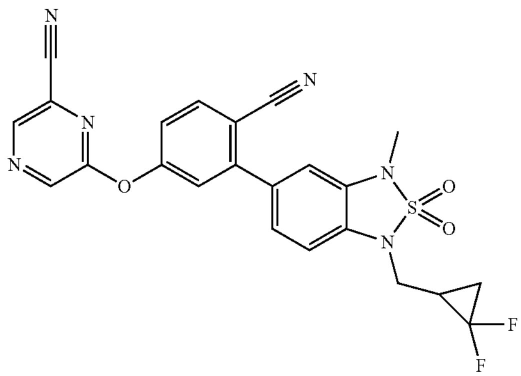 [SMILES: CN1c2cc(-c3cc(Oc4cncc(C#N)n4)ccc3C#N)ccc2N(CC2CC2(F)F)S1(=O)=O] | 6-(4-cyano-3-{1-[(2,2-difluorocyclopropyl)methyl]-3-methyl-2,2-dioxido-1,3-dihydro-2,1,3-benzothiadiazol-5-yl}phenoxy)pyrazine-2-carbonitrile | Calc'd 495.1045, found 495.1046 |
| 12-17 | 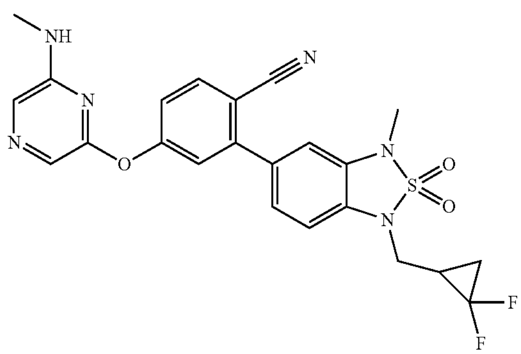 [SMILES: CNc1cncc(Oc2ccc(C#N)c(-c3ccc4c(c3)N(C)S(=O)(=O)N4CC3CC3(F)F)c2)n1] | 2-{1-[(2,2-difluorocyclopropyl)methyl]-3-methyl-2,2-dioxido-1,3-dihydro-2,1,3-benzothiadiazol-5-yl}-4-{[4-(methylamino)pyrimidin-2-yl]oxy}benzonitrile | Calc'd 499.1358, found 499.1356 |
| 12-18 | 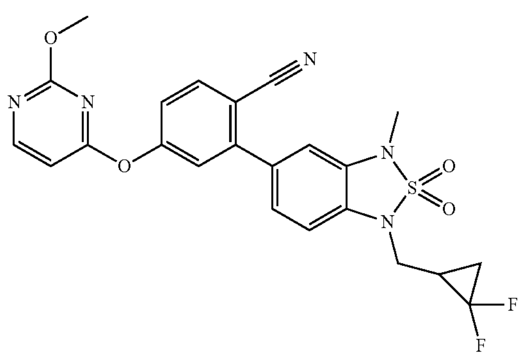 [SMILES: COc1nccc(Oc2ccc(C#N)c(-c3ccc4c(c3)N(C)S(=O)(=O)N4CC3CC3(F)F)c2)n1] | 2-{1-[(2,2-difluorocyclopropyl)methyl]-3-methyl-2,2-dioxido-1,3-dihydro-2,1,3-benzothiadiazol-5-yl}-4-[(2-methoxypyrimidin-4-yl)oxy]benzonitrile | Calc'd 500.1199, found 500.1192 |
| 12-19 | 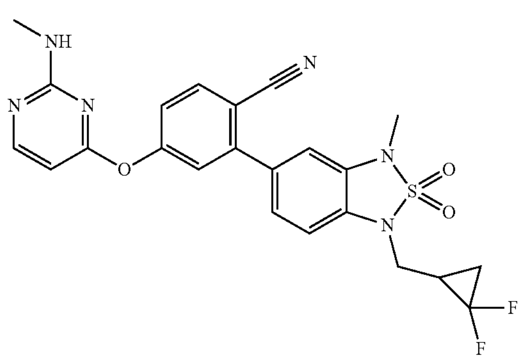 [SMILES: CNc1nccc(Oc2ccc(C#N)c(-c3ccc4c(c3)N(C)S(=O)(=O)N4CC3CC3(F)F)c2)n1] | 2-{1-[(2,2-difluorocyclopropyl)methyl]-3-methyl-2,2-dioxido-1,3-dihydro-2,1,3-benzothiadiazol-5-yl}-4-{[2-(methylamino)pyrimidin-4-yl]oxy}benzonitrile | Calc'd 499.1358, found 499.1360 |

TABLE 3-continued

The following compounds were prepared by a reaction sequence analogous to that illustrated in Scheme 14:

| Cmpd | Structure | IUPAC Name | Exact Mass [M + H]+ |
|---|---|---|---|
| 12-20 | 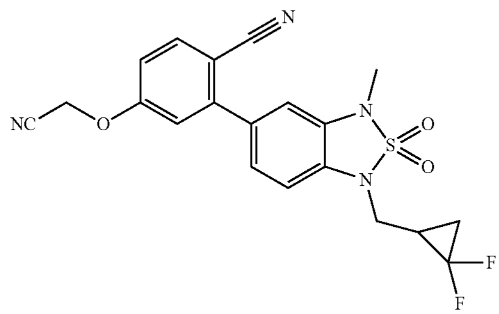 [SMILES: CN1c2cc(-c3cc(OCC#N)ccc3C#N)ccc2N(CC2CC2(F)F)S1(=O)=O] | 4-(cyanomethoxy)-2-{1-[(2,2-difluorocyclopropyl)methyl]-3-methyl-2,2-dioxido-1,3-dihydro-2,1,3-benzothiadiazol-5-yl}benzonitrile | Calc'd 431.0984 found. 431.0984 |

SCHEME 13

4-{4-cyano-3-[1-(2,2-dimethylpropyl)-3-methyl-2,2-dioxido-1,3-dihydro-2,1,3-benzothiadiazol-5-yl]phenoxy}pyridine-2-carbonitrile (13-3)

Prepared from 5-1 according to the procedures reported in Scheme 12. HRMS m/z (M+H) 474.1589 found, 474.1594 required.

SCHEME 14

4-{4-cyano-3-[1-(cyclopropylmethyl)-3-methyl-2,2-dioxido-1,3-dihydro-2,1,3-benzothiadiazol-5-yl]phenoxy}pyridine-2-carbonitrile (14-2)

Prepared from 2-1 according to the procedures reported in Scheme 12. HRMS m/z (M+H) 458.1282 found, 458.1281 required.

SCHEME 15

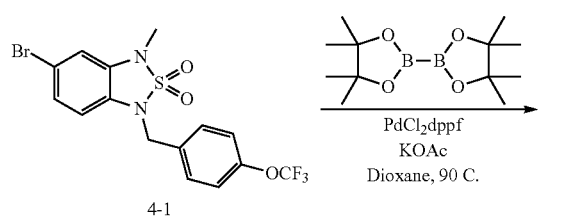

SCHEME 16

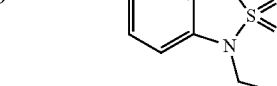

2-{1-[(2,2-difluorocyclopropyl)methyl]-3-methyl-2,2-dioxido-1,3-dihydro-2,1,3-benzothiadiazol-5-yl}-4-(methoxymethoxy)benzonitrile (16-1)

2-{1-[(2,2-difluorocyclopropyl)methyl]-3-methyl-2,2-dioxido-1,3-dihydro-2,1,3-benzothiadiazol-5-yl}-4-hydroxybenzonitrile (12-2) (25 mg, 0.06 mmol, 1 eq) was dissolved in anhydrous DMF (0.5 mL) and sodium hydride (3.1 mg, 0.08 mmol, 1.2 eq, 60% in oil) was added. The resulting mixture was stirred at ambient temperature for 30 minutes and MOM-Cl (0.01 mL, 0.1 mmol, 2 eq) was added. The resulting mixture stirred at ambient temperature for 10 minutes. The crude mixture was purified by reverse phase chromatography (Waters Sunfire MSC18, 10-100% acetonitrile in water with 0.1% TFA modifier) to afford 2-{1-[(2,2-difluorocyclopropyl)methyl]-3-methyl-2,2-dioxido-1,3-dihydro-2,1,3-benzothiadiazol-5-yl}-4-(methoxymethoxy)benzonitrile (16-1) as a white solid. $^1$H NMR (400 MHz, CDCl$_3$): δ 7.68 (d, J=8.4 Hz, 1 H); 7.19 (dd, J=1.6, 8.0 Hz, 1 H); 7.11 (s, 1 H); 7.09 (dd, J=2.4, 8.8 Hz, 1 H); 6.95 (s, 1 H); 6.91 (d, J=8.0 Hz, 1 H); 5.26 (s, 2 H); 3.91 (d, J=6.8 Hz, 2 H); 3.50 (s, 3 H); 3.34 (s, 3 H); 2.11-2.19 (m, 1 H); 1.61-1.69 (m, 1 H); 1.36-1.44 (m, 1 H). LRMS m/z (M+H) 436.3 found, 436.1 required.

4-(4-cyano-3-{3-methyl-2,2-dioxido-1-[4-(trifluoromethoxy)benzyl]-1,3-dihydro-2,1,3-benzothiadiazol-5-yl}phenoxy)pyridine-2-carbonitrile (15-3)

Prepared from 10-1 according to the procedures reported in Scheme 12. HRMS m/z (M+H) 578.1092 found, 578.1104 required.

SCHEME 17

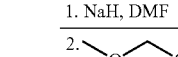

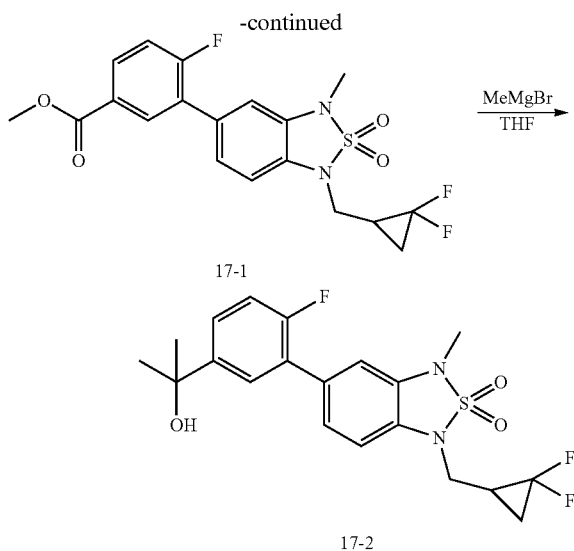

17-1

17-2

2-(3-{1-[(2,2-difluorocyclopropyl)methyl]-3-methyl-2,2-dioxido-1,3-dihydro-2,1,3-benzothiadiazol-5-yl}-4-methylphenyl)propan-2-ol (17-2)

Methyl 3-{1-[(2,2-difluorocyclopropyl)methyl]-3-methyl-2,2-dioxido-1,3-dihydro-2,1,3-benzothiadiazol-5-yl}-4-fluorobenzoate (17-1)

5-bromo-1-[(2,2-difluorocyclopropyl)methyl]-3-methyl-1,3-dihydro-2,1,3-benzothiadiazole 2,2-dioxide (4-1) (100 mg, 0.28 mmol, 1 eq), [2-fluoro-5-(methoxycarbonyl)phenyl]boronic acid (84 mg, 0.43 mmol, 1.5 eq), cesium carbonate (185 mg, 0.57 mmol, 2.0 eq) and bis(tri-t-butylphosphine)palladium(0) (29 mg, 0.06 mmol, 0.2 eq) were combined in dioxane (1.5 mL) and water (0.3 mL). The resulting mixture was heated in the microwave at 100° C. for 10 minutes. The reaction mixture was diluted with EtOAc (10 mL), washed with water (2 mL) and brine (2 mL), dried over MgSO$_4$, filtered and concentrated. The crude residue was purified by flash chromatography (12 g SiO$_2$, 0-70% EtOAc in hexanes) to afford methyl 3-{1-[(2,2-difluorocyclopropyl)methyl]-3-methyl-2,2-dioxido-1,3-dihydro-2,1,3-benzothiadiazol-5-yl}-4-fluorobenzoate (17-1) as a yellow solid. $^1$H NMR (400 MHz, CDCl$_3$): δ 8.14 (dd, J=1.6, 6.0 Hz, 1 H); 8.01 (m, 1 H); 7.21 (m, 2 H); 6.95 (t, J=1.2 Hz, 1 H); 6.90 (d, J=6.4 Hz, 1 H); 3.94 (s, 3 H); 3.91 (d, J=5.6 Hz, 2 H); 3.33 (s, 3 H); 2.14 (m, 1 H); 1.64 (m, 1 H); 1.39 (m, 1 H).

2-(3-{1-[(2,2-difluorocyclopropyl)methyl]-3-methyl-2,2-dioxido-1,3-dihydro-2,1,3-benzothiadiazol-5-yl}-4-methylphenyl)propan-2-ol (17-2)

Methyl 3-{1-[(2,2-difluorocyclopropyl)methyl]-3-methyl-2,2-dioxido-1,3-dihydro-2,1,3-benzothiadiazol-5-yl}-4-fluorobenzoate (17-1) (81 mg, 0.19 mmol, 1 eq) was dissolved in THF (1 mL) and methylmagnesium bromide (0.32 mL, 1.0 mmol, 3.0 M, 5.0 eq) was added. The resulting mixture stirred at ambient temperature for 10 minutes. The reaction was quenched by the addition of NH$_4$Cl (1 mL), extracted with EtOAc (10 mL), washed with water (1 mL) and brine (1 mL), dried over MgSO$_4$, filtered and concentrated. The crude residue was purified by flash chromatography (12 g SiO$_2$, 0-70% EtOAc in hexanes) to afford 2-(3-{1-[(2,2-difluorocyclopropyl)methyl]-3-methyl-2,2-dioxido-1,3-dihydro-2,1,3-benzothiadiazol-5-yl}-4-methylphenyl)propan-2-ol (17-2) as a yellow solid. $^1$H NMR (400 MHz, CDCl$_3$): δ 7.54 (dd, J=2.0, 6.0 Hz, 1 H); 7.41 (m, 1 H); 7.18 (dt, J=1.2, 6.8 Hz, 2 H); 7.11 (dd, J=6.8, 8.0 Hz, 1 H); 6.94 (t, J=1.2 Hz, 1 H); 6.89 (d, J=6.8 Hz, 1 H); 3.90 (d, J=6.0 Hz, 2 H); 3.32 (s, 3 H); 2.14 (m, 1 H); 1.64 (m, 1 H); 1.63 (s, 6 H); 1.39 (m, 1 H). HRMS m/z (M+H) 427.1303 found, 427.1298 required.

TABLE 4

The following compounds were prepared by a reaction sequence analogous to that illustrated in Scheme 17:

| Cmpd | Structure | IUPAC Name | Exact Mass [M + H]+ |
|---|---|---|---|
| 17-3 | 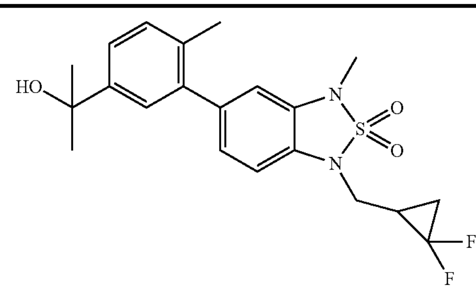 | 2-(3-{1-[(2,2-difluorocyclopropyl)yl]-3-mthyl-2,2-methdioxido-1,3-dihydro-2,1,3-benzothiadiazol-5-yl}-4-methylphenyl)propan-2-ol | Calc'd (—OH) 405.5, found 405.1 |
| 17-4 | 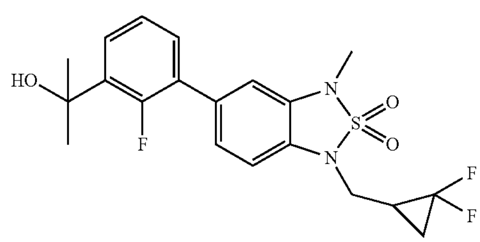 [SMILES: CN1c2cc(-c3cccc(C(C)(C)O)c3F)ccc2N(CC2CC2(F)F)S1(=O)=O] | 2-(3-{1-[(2,2-difluorocyclopropyl)methyl]-3-methyl-2,2-dioxido-1,3-dihydro-2,1,3-benzothiadiazol-5-yl}-2-fluorophenyl)propan-2-ol | Calc'd (—OH) 409.4, found 408.9 |

SCHEME 18

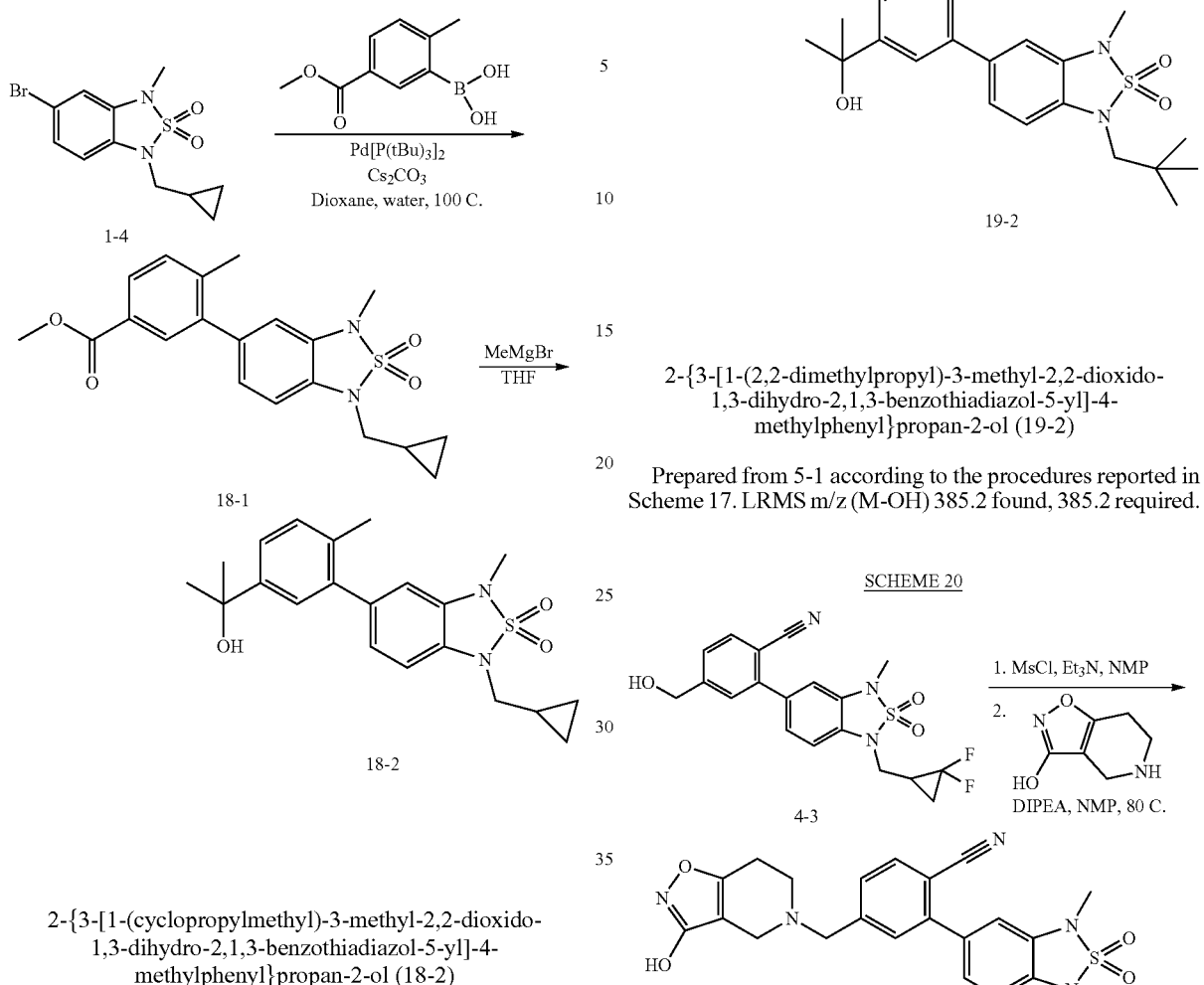

2-{3-[1-(cyclopropylmethyl)-3-methyl-2,2-dioxido-1,3-dihydro-2,1,3-benzothiadiazol-5-yl]-4-methylphenyl}propan-2-ol (18-2)

Prepared from 1-4 according to the procedures reported in Scheme 17. HRMS m/z (M+Na) 409.1580 found, 409.1556 required.

SCHEME 19

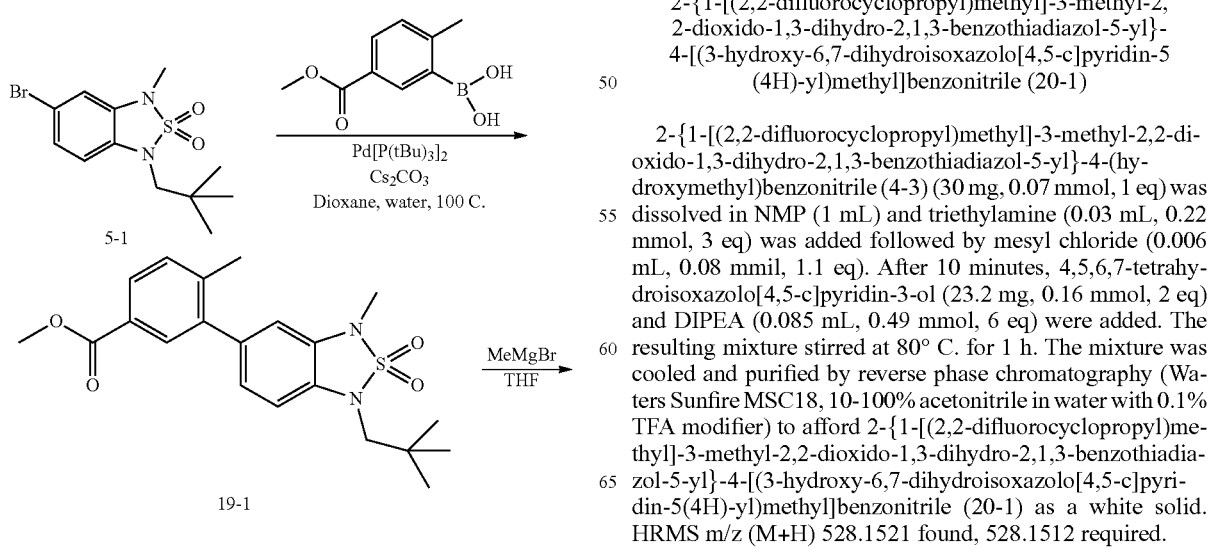

2-{3-[1-(2,2-dimethylpropyl)-3-methyl-2,2-dioxido-1,3-dihydro-2,1,3-benzothiadiazol-5-yl]-4-methylphenyl}propan-2-ol (19-2)

Prepared from 5-1 according to the procedures reported in Scheme 17. LRMS m/z (M-OH) 385.2 found, 385.2 required.

SCHEME 20

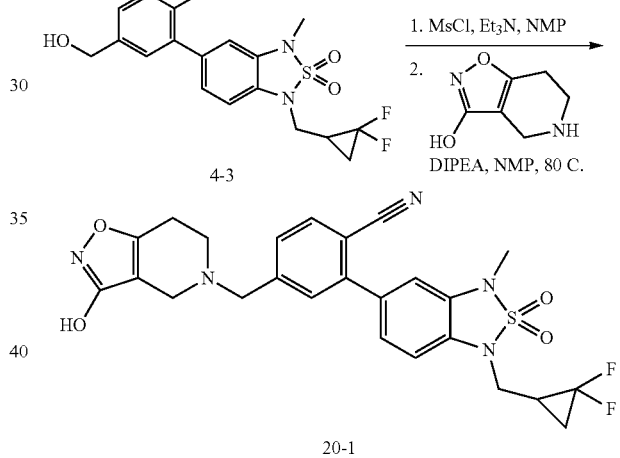

2-{1-[(2,2-difluorocyclopropyl)methyl]-3-methyl-2,2-dioxido-1,3-dihydro-2,1,3-benzothiadiazol-5-yl}-4-[(3-hydroxy-6,7-dihydroisoxazolo[4,5-c]pyridin-5(4H)-yl)methyl]benzonitrile (20-1)

2-{1-[(2,2-difluorocyclopropyl)methyl]-3-methyl-2,2-dioxido-1,3-dihydro-2,1,3-benzothiadiazol-5-yl}-4-(hydroxymethyl)benzonitrile (4-3) (30 mg, 0.07 mmol, 1 eq) was dissolved in NMP (1 mL) and triethylamine (0.03 mL, 0.22 mmol, 3 eq) was added followed by mesyl chloride (0.006 mL, 0.08 mmil, 1.1 eq). After 10 minutes, 4,5,6,7-tetrahydroisoxazolo[4,5-c]pyridin-3-ol (23.2 mg, 0.16 mmol, 2 eq) and DIPEA (0.085 mL, 0.49 mmol, 6 eq) were added. The resulting mixture stirred at 80° C. for 1 h. The mixture was cooled and purified by reverse phase chromatography (Waters Sunfire MSC18, 10-100% acetonitrile in water with 0.1% TFA modifier) to afford 2-{1-[(2,2-difluorocyclopropyl)methyl]-3-methyl-2,2-dioxido-1,3-dihydro-2,1,3-benzothiadiazol-5-yl}-4-[(3-hydroxy-6,7-dihydroisoxazolo[4,5-c]pyridin-5(4H)-yl)methyl]benzonitrile (20-1) as a white solid. HRMS m/z (M+H) 528.1521 found, 528.1512 required.

TABLE 5

The following compounds were prepared by a reaction sequence analogous to that illustrated in Scheme 20:

| Cmpd | Structure | IUPAC Name | Exact Mass [M + H]+ |
|---|---|---|---|
| 20-2 | 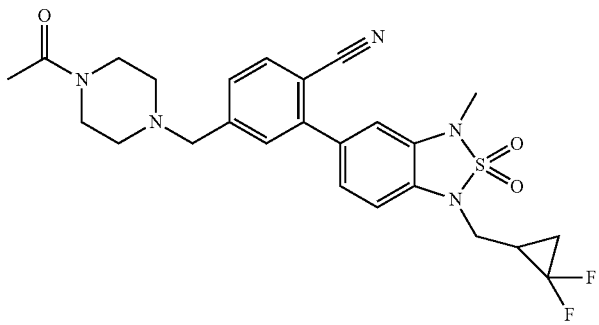 [SMILES: CC(=O)N1CCN(Cc2ccc(C#N)c(-c3ccc4c(c3)N(C)S(=O)(=O)N4CC3CC3(F)F)c2)CC1] | 4-[(4-acetylpiperazin-1-yl)methyl]-2-{1-[(2,2-difluorocyclopropyl)methyl]-3-methyl-2,2-dioxido-1,3-dihydro-2,1,3-benzothiadiazol-5-yl}benzonitrile | Calc'd 516.1875, found 516.1887 |
| 20-3 | 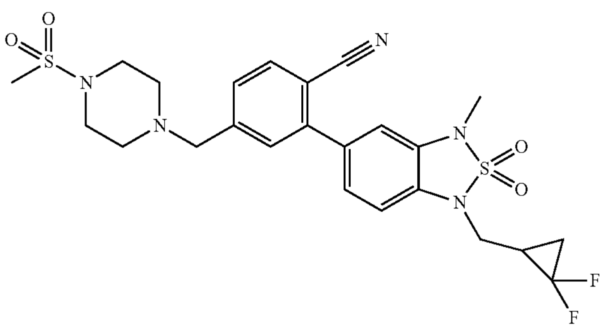 [SMILES: CN1c2cc(-c3cc(CN4CCN(S(C)(=O)=O)CC4)ccc3C#N)ccc2N(CC2CC2(F)F)S1(=O)=O] | 2-{1-[(2,2-difluorocyclopropyl)methyl]-3-methyl-2,2-dioxido-1,3-dihydro-2,1,3-benzothiadiazol-5-yl}-4-{[4-(methylsulfonyl)piperazin-1-yl]methyl}benzonitrile | Calc'd 552.1545, found 552.1556 |
| 20-4 | 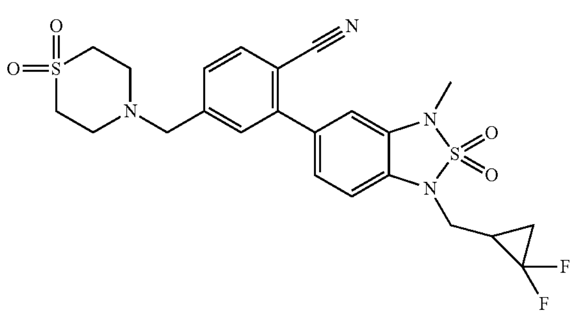 [SMILES: CN1c2cc(-c3cc(CN4CCS(=O)(=O)CC4)ccc3C#N)ccc2N(CC2CC2(F)F)S1(=O)=O] | 2-{1-[(2,2-difluorocyclopropyl)methyl]-3-methyl-2,2-dioxido-1,3-dihydro-2,1,3-benzothiadiazol-5-yl}-4-[(1,1-dioxidothiomorpholin-4-yl)methyl]benzonitrile | Calc'd 523.1280, found 523.1286 |

SCHEME 21

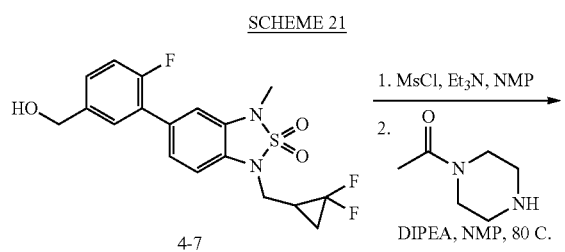

5-{5-[(4-acetylpiperazin-1-yl)methyl]-2-fluorophenyl}-1-[(2,2-difluorocyclopropyl)methyl]-3-methyl-1,3-dihydro-2,1,3-benzothiadiazole 2,2-dioxide (21-1)

Prepared from 4-7 according to the procedures reported in Scheme 20. HRMS m/z (M+H) 509.1837 found, 509.1829 required.

SCHEME 22

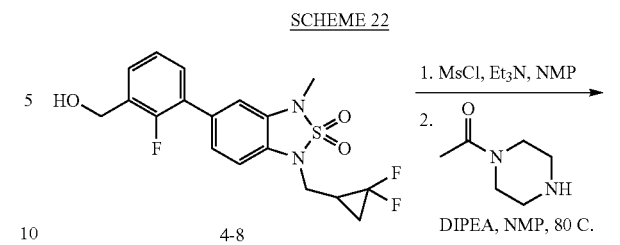

5-{3-[(4-acetylpiperazin-1-yl)methyl]-2-fluorophenyl}-1-[(2,2-difluorocyclopropyl)methyl]-3-methyl-1,3-dihydro-2,1,3-benzothiadiazole 2,2-dioxide (22-1)

Prepared from 4-8 according to the procedures reported in Scheme 20. HRMS m/z (M+H) 509.1836 found, 509.1829 required.

TABLE 6

The following compounds were prepared by a reaction sequence analogous to that illustrated in Scheme 21:

| Cmpd | Structure | IUPAC Name | Exact Mass [M + H]+ |
|---|---|---|---|
| 21-2 | 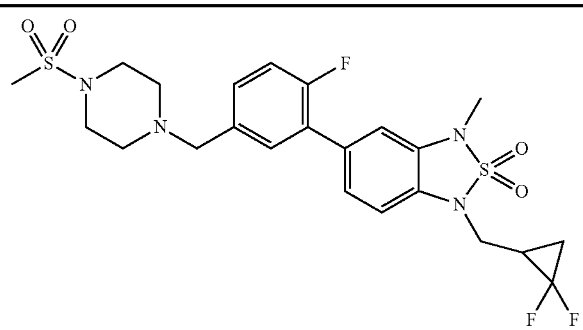 | 1-[(2,2-difluorocyclopropyl)methyl]-5-(2-fluoro-5-{[4-(methylsulfonyl)piperazin-1-yl]methyl}phenyl)-3-methyl-1,3-dihydro-2,1,3-benzothiadiazole 2,2-dioxide | Calc'd 545.1499, found 545.1511 |
| 21-3 | 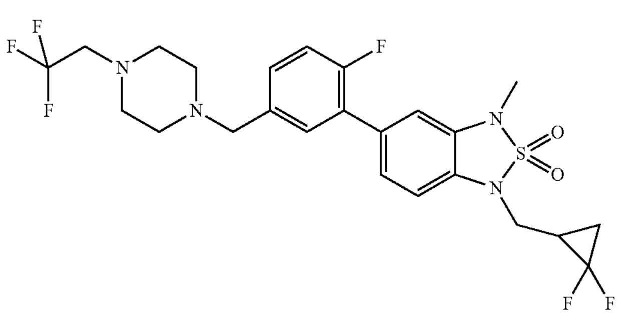 [SMILES: CN1c2cc(-c3cc(CN4CCN(CC(F)(F)F)CC4)ccc3F)ccc2N(CC2CC2(F)F)S1(=O)=O] | 1-[(2,2-difluorocyclopropyl)methyl]-5-(2-fluoro-5-{[4-(2,2,2-trifluoroethyl)piperazin-1-yl]methyl}phenyl)-3-methyl-1,3-dihydro-2,1,3-benzothiadiazole 2,2-dioxide | Calc'd 549.1753, found 549.1757 |

TABLE 7

The following compounds were prepared by a reaction sequence analogous to that illustrated in Scheme 22.

| Cmpd | Structure | IUPAC Name | Exact Mass [M + H]+ |
|---|---|---|---|
| 22-2 | 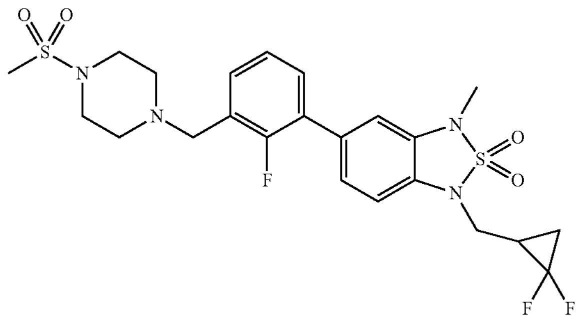 [SMILES: CN1c2cc(-c3cccc(CN4CCN(S(C)(=O)=O)CC4)c3F)ccc2N(CC2CC2(F)F)S1(=O)=O] | 1-[(2,2-difluorocyclopropyl)methyl]-5-(2-fluoro-3-{[4-(methylsulfonyl)piperazin-1-yl]methyl}phenyl)-3-methyl-1,3-dihydro-2,1,3-benzothiadiazole 2,2-dioxide | Calc'd 545.1499, found 545.1513 |
| 22-3 | 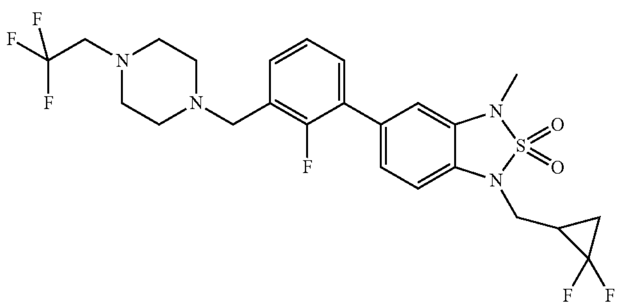 [SMILES: CN1c2cc(-c3cccc(CN4CCN(CC(F)(F)F)CC4)c3F)ccc2N(CC2CC2(F)F)S1(=O)=O] | 1-[(2,2-difluorocyclopropyl)methyl]-5-(2-flouro-3-{[4-(2,2,2-trifluoroethyl)piperazin-1-yl]methyl}phenyl)-3-methyl-1,3-dihydro-2,1,3-benzothiadiazole 2,2-dioxide | Calc'd 549.1753, found 549.1753 |

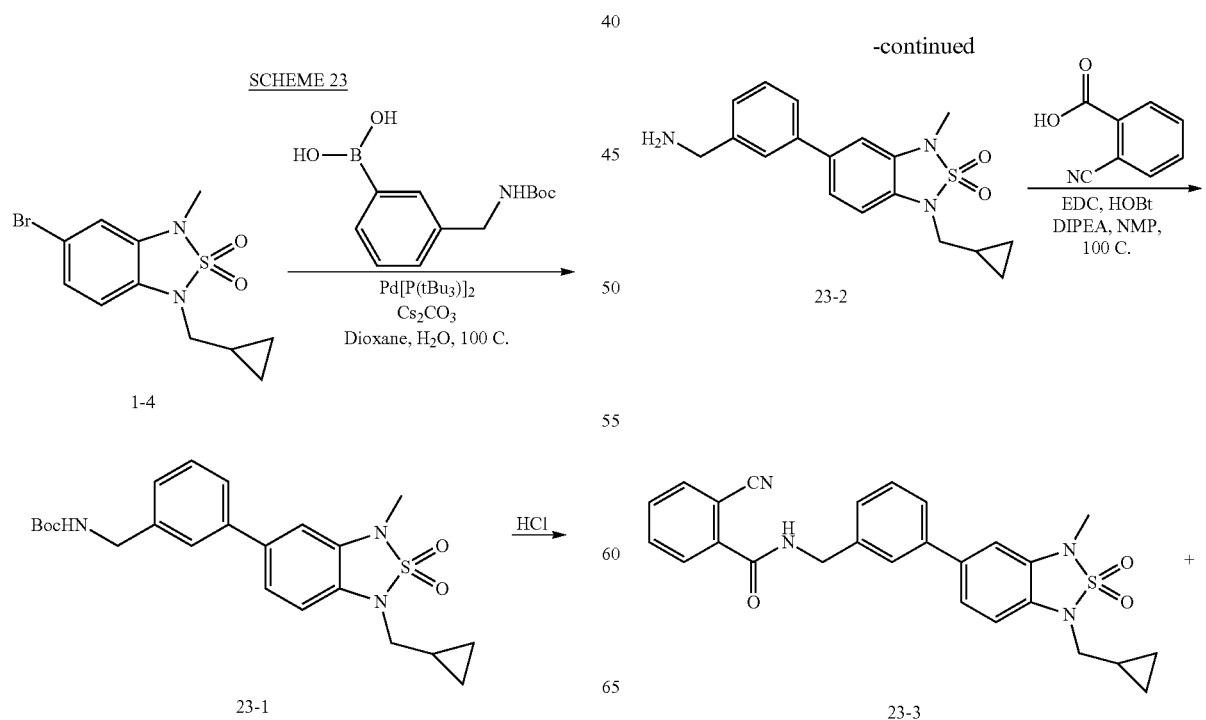

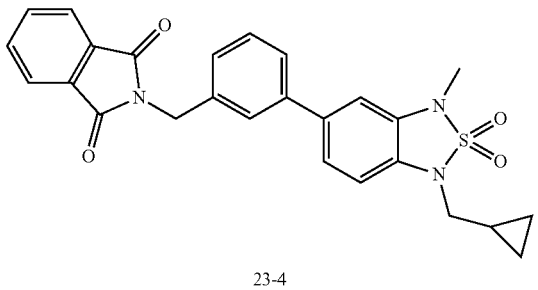

23-4

2-cyano-N-{3-[1-(cyclopropylmethyl)-3-methyl-2,2-dioxido-1,3-dihydro-2,1,3-benzothiadiazol-5-yl]benzyl}benzamide (23-3) and 2-{3-[1-(cyclopropylmethyl)-3-methyl-2,2-dioxido-1,3-dihydro-2,1,3-benzothiadiazol-5-yl]benzyl}-1H-isoindole-1,3(2H)-dione (23-4)

tert-butyl {3-[1-(cyclopropylmethyl)-3-methyl-2,2-dioxido-1,3-dihydro-2,1,3-benzothiadiazol-5-yl]benzyl}carbamate (23-1)

tert-butyl {3-[1-(cyclopropylmethyl)-3-methyl-2,2-dioxido-1,3-dihydro-2,1,3-benzothiadiazol-5-yl]benzyl}carbamate (23-1) was prepared from 1-4 according to the procedures reported in Scheme 1. MS (M-55)$^+$: Calc'd 388.2, found 388.1.

1-{3-[1-(cyclopropylmethyl)-3-methyl-2,2-dioxido-1,3-dihydro-2,1,3-benzothiadiazol-5-yl]phenyl}methanamine hydrochloride (23-2)

To a round bottom flask was added tert-butyl {3-[1-(cyclopropylmethyl)-3-methyl-2,2-dioxido-1,3-dihydro-2,1,3-benzothiadiazol-5-yl]benzyl}carbamate (23-1) (0.250 g, 0.564 mmol), DCM (2 mL), MeOH (2 mL), and finally a saturated solution of HCl in EtOAc (4N) (0.705 mL, 2.82 mmol). The reaction mixture was then capped and permitted to stir at room temperature for an hour at which point it was concentrated to give 1-{3-[1-(cyclopropylmethyl)-3-methyl-2,2-dioxido-1,3-dihydro-2,1,3-benzothiadiazol-5-yl]phenyl}methanamine hydrochloride (23-2) as a waxy pink solid. HRMS (M+H)$^+$: observed=344.1429, calculated=344.1427.

2-cyano-N-{3-[1-(cyclopropylmethyl)-3-methyl-2,2-dioxido-1,3-dihydro-2,1,3-benzothiadiazol-5-yl]benzyl}benzamide (23-3) and 2-{3-[1-(cyclopropylmethyl)-3-methyl-2,2-dioxido-1,3-dihydro-2,1,3-benzothiadiazol-5-yl]benzyl}-1H-isoindole-1,3(2H)-dione (23-4)

To a microwave vial was added 1-{3-[1-(cyclopropylmethyl)-3-methyl-2,2-dioxido-1,3-dihydro-2,1,3-benzothiadiazol-5-yl]phenyl}methanamine hydrochloride (23-2) (0.025 g, 0.066 mmol), EDC (0.016 g, 0.086 mmol), HOBt (0.012 g, 0.086 mmol), NMP (1 mL), and finally DIPEA (0.024 mL, 0.14 mmol). The reaction mixture was then heated under microwave irradiation at 100° C. for 10 minutes. The crude reaction mixture was then allowed to cool to room temperature, diluted with methanol, then filtered and concentrated. Purification of crude reaction mixture by reverse phase chromatography (Waters Sunfire MSC18, 10% acetonitrile/0.1% trifluoroacetic acid/water→100% acetonitrile/0.1% trifluoroacetic acid/water) to give 2-cyano-N-{3-[1-(cyclopropylmethyl)-3-methyl-2,2-dioxido-1,3-dihydro-2,1,3-benzothiadiazol-5-yl]benzyl}benzamide (23-3) as a tan solid and 2-{3-[1-(cyclopropylmethyl)-3-methyl-2,2-dioxido-1,3-dihydro-2,1,3-benzothiadiazol-5-yl]benzyl}-1H-isoindole-1,3(2H)-dione (23-4) as a tan solid.

23-3: HRMS (M+H)$^+$: observed=473.1641, calculated=473.1642.

23-4: HRMS (M+H)$^+$: observed=474.1477, calculated=474.1482.

TABLE 8

The following compounds were prepared by a reaction sequence analogous to that illustrated in Scheme 23.

| Cmpd | Structure | IUPAC Name | Exact Mass [M + H]+ |
|---|---|---|---|
| 23-5 | 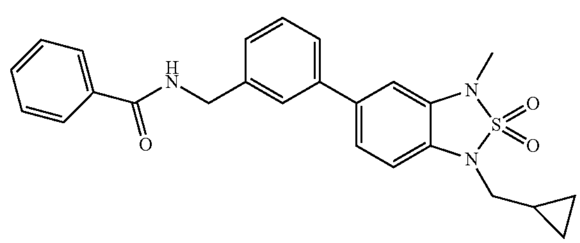 [SMILES: CN1c2cc(-c3cccc(CNC(=O)c4ccccc4)c3)ccc2N(CC2CC2)S1(=O)=O] | N-{3-[1-(cyclopropylmethyl)-3-methyl-2,2-dioxido-1,3-dihydro-2,1,3-benzothiadiazol-5-yl]benzyl}benzamide | Calc'd 448.1689, found 448.1688 |

TABLE 8-continued

The following compounds were prepared by a reaction sequence analogous to that illustrated in Scheme 23.

| Cmpd | Structure | IUPAC Name | Exact Mass [M + H]+ |
|---|---|---|---|
| 23-6 | 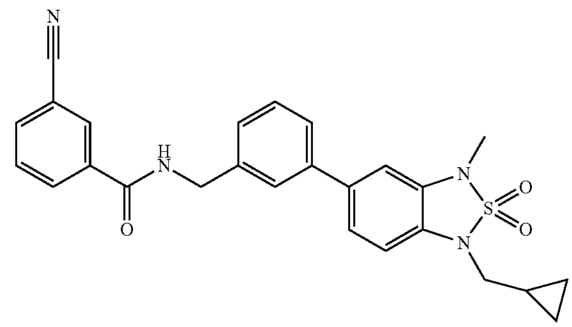 [SMILES: CN1c2cc(-c3cccc(CNC(=O)c4cccc(C#N)c4)c3)ccc2N(CC2CC2)S1(=O)=O] | 3-cyano-N-{3-[1-(cyclopropylmethyl)-3-methyl-2,2-dioxido-1,3-dihydro-2,1,3-benzothiadiazol-5-yl]benzyl}benzamide | Calc'd 473.1642, found 473.1636 |
| 23-7 | 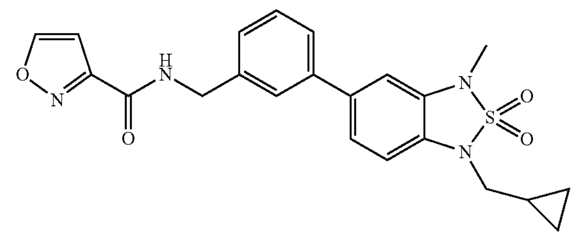 [SMILES: CN1c2cc(-c3cccc(CNC(=O)c4ccon4)c3)ccc2N(CC2CC2)S1(=O)=O] | N-{3-[1-(cyclopropylmethyl)-3-methyl-2,2-dioxido-1,3-dihydro-2,1,3-benzothiadiazol-5-yl]benzyl}isoxazole-3-carboxamide | Calc'd 439.1435, found 439.1434 |
| 23-8 | 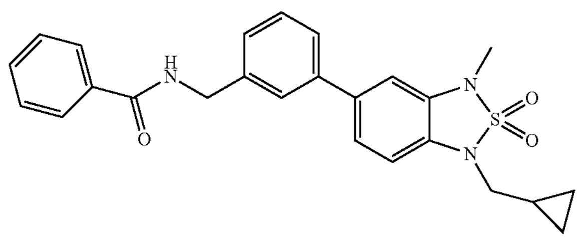 [SMILES: CN1c2cc(-c3cccc(CNC(=O)c4ccccc4)c3)ccc2N(CC2CC2)S1(=O)=O] | N-{3-[1-(cyclopropylmethyl)-3-methyl-2,2-dioxido-1,3-dihydro-2,1,3-benzothiadiazol-5-yl]benzyl}benzamide | Calc'd 448.1689, found 448.1688 |

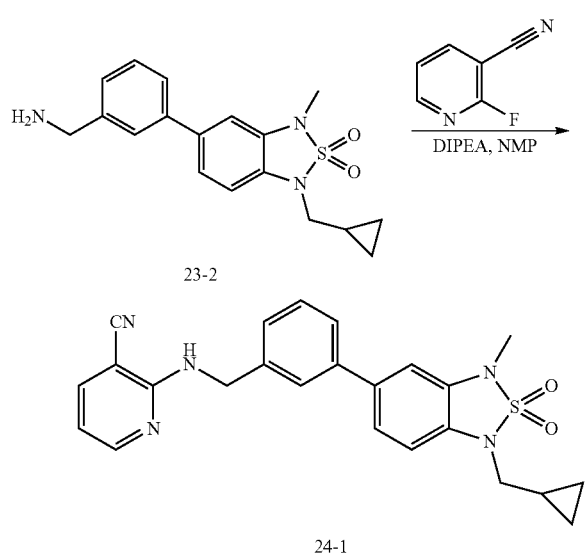

SCHEME 24

2-({3-[1-(cyclopropylmethyl)-3-methyl-2,2-dioxido-1,3-dihydro-2,1,3-benzothiadiazol-5-yl]benzyl}amino)nicotinonitrile (24-1)

To a microwave vial was added 1-{3-[1-(cyclopropylmethyl)-3-methyl-2,2-dioxido-1,3-dihydro-2,1,3-benzothiadiazol-5-yl]phenyl}methanamine hydrochloride (23-2) (0.037 g, 0.097 mmol), 2-fluoronicotinonitrile (0.18 g, 0.15 mmol), NMP (0.7 mL), and finally DIPEA (0.039 mL, 0.22 mmol). The reaction mixture was then heated under microwave irradiation at 100° C. for 10 minutes. The crude reaction mixture was then allowed to cool to room temperature, diluted with methanol, then filtered and concentrated. Purification of crude reaction mixture by reverse phase chromatography (Waters Sunfire MSC18, 10% acetonitrile/0.1% trifluoroacetic acid/water→100% acetonitrile/0.1% trifluoroacetic acid/water) to give 2-({3-[1-(cyclopropylmethyl)-3-methyl-2,2-dioxido-1,3-dihydro-2,1,3-benzothiadiazol-5-yl]benzyl}amino)nicotinonitrile (24-1) as a tan solid. HRMS (M+H)$^+$: observed=446.1642, calculated=446.1645.

TABLE 9

The following compounds were prepared by a reaction sequence analogous to that illustrated in Scheme 24:

| Cmpd | Structure | IUPAC Name | Exact Mass [M + H]+ |
|---|---|---|---|
| 24-2 | 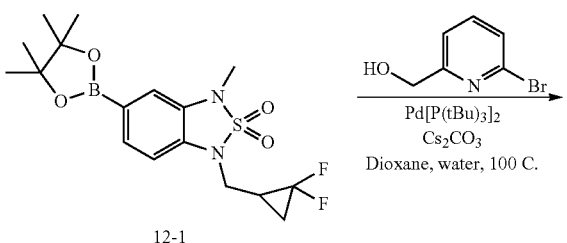 | 4-({3-[1-(cyclopropylmethyl)-3-methyl-2,2-dioxido-1,3-dihydro-2,1,3-benzothiadiazol-5-yl]benzyl}amino)pyridine-2-carbonitrile | Calc'd 446.1645, found 446.1640 |

SCHEME 25

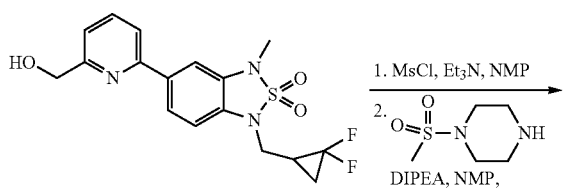

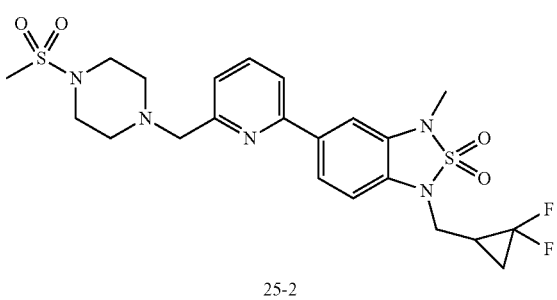

1-[(2,2-difluorocyclopropyl)methyl]-3-methyl-5-(6-{[4-methylsulfonyl)piperazin-1-yl]methyl}pyridin-2-yl)-1,3-dihydro-2,1,3-benzothiadiazole 2,2-dioxide (25-2)

(6-{1-[(2,2-difluorocyclopropyl)methyl]-3-methyl-2,2-dioxido-1,3-dihydro-2,1,3-benzothiadiazol-5-yl}pyridin-2-yl)methanol (25-1)

1-[(2,2-difluorocyclopropyl)methyl]-3-methyl-5-(4,4,5,5-tetramethyl-1,3,2-dioxaborolan-2-yl)-1,3-dihydro-2,1,3-benzothiadiazole 2,2-dioxide (12-1) (131 mg, 0.33 mmol, 1.0 eq), (6-bromopyridin-2-yl)methanol (61 mg, 0.33 mmol, 1.0 eq), cesium carbonate (317 mg, 0.97 mmol, 3.0 eq) and bis(tri-t-butylphosphine) palladium(0) (16.6 mg, 0.03 mmol, 0.1 eq) were combined in dioxane (1.0 mL) and water (0.2 mL). The resulting mixture was heated in the microwave at 120° C. for 20 minutes. The reaction mixture was diluted with EtOAc (10 mL), washed with water (2 mL) and brine (2 mL), dried over MgSO$_4$, filtered and concentrated. The crude residue was purified by flash chromatography (12 g SiO$_2$, 0-80% EtOAc in hexanes) to afford (6-{1-[(2,2-difluorocyclopropyl)methyl]-3-methyl-2,2-dioxido-1,3-dihydro-2,1,3-benzothiadiazol-5-yl}pyridin-2-yl)methanol (25-1). LRMS m/z (M+H) 382.2 found, 382.1 required.

1-[(2,2-difluorocyclopropyl)methyl]-3-methyl-5-(6-{[4-(methylsulfonyl)piperazin-1-yl]methyl}pyridin-2-yl)-1,3-dihydro-2,1,3-benzothiadiazole 2,2-dioxide (25-2)

To (6-{1-[(2,2-difluorocyclopropyl)methyl]-3-methyl-2,2-dioxido-1,3-dihydro-2,1,3-benzothiadiazol-5-yl}pyridin-2-yl)methanol (25-1) (30 mg, 0.079 mmol, 1.0 eq) was dissolved in NMP (1 mL) and triethylamine (0.04 mL, 0.24 mmol, 3.0 eq) was added followed by mesyl chloride (0.008 mL, 0.1 mmol, 1.2 eq). After 10 minutes, 1-(methylsulfonyl)piperazine (28.6 mg, 0.17 mmol, 2.1 eq) and DIPEA (0.061 mL, 0.35 mmol, 4.4 eq) were added. The resulting mixture stirred at 80° C. for 10 minutes. The mixture was cooled and purified by reverse phase chromatography (Waters Sunfire MSC18, 10-100% acetonitrile in water with 0.1% TFA modifier) to afford 1-[(2,2-difluorocyclopropyl)methyl]-3-methyl-5-(6-{[4-(methylsulfonyl)piperazin-1-yl]methyl}pyridin-2-yl)-1,3-dihydro-2,1,3-benzothiadiazole 2,2-dioxide (25-2) as a white solid. $^1$H NMR (400 MHz, CD$_3$OD): δ 7.99 (s, 1 H); 7.98 (d, J=8.0 Hz, 1 H); 7.84 (dd, J=1.6, 8.4 Hz, 1 H); 7.77 (d, J=1.6 Hz, 1 H); 7.44 (dd, J=1.6, 6.0 Hz, 1 H); 7.13 (d, J=8.4 Hz, 1 H); 4.66 (s, 2 H); 3.97 (d, J=7.2 Hz, 2 H); 3.62 (brs, 8 H); 3.39 (s, 3 H); 2.99 (s, 3 H); 2.21 (m, 1 H); 1.65 (m, 1 H); 1.44 (m, 1 H). HRMS m/z (M+H) 528.1538 found, 528.1545 required.

TABLE 10

The following compounds were prepared by a reaction sequence analogous to that illustrated in Scheme 25.

| Cmpd | Structure | IUPAC Name | Exact Mass [M + H]+ |
|---|---|---|---|
| 25-3 | 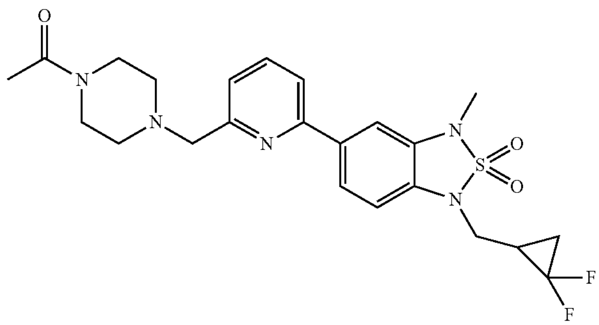 [SMILES: CC(=O)N1CCN(Cc2cccc(-c3ccc4c(c3)N(C)S(=O)(=O)N4CC3CC3(F)F)n2)CC1] | 5-{6-[(4-acetyl piperazin-1-yl) methyl]pyridin-2-yl}-1-[(2,2-difluorocyclopropyl) methyl]-3-methyl-1,3-dihydro-2,1,3-benzothiadiazole 2,2-dioxide | Calc'd 492.1875, found 492.1876 |
| 25-4 | 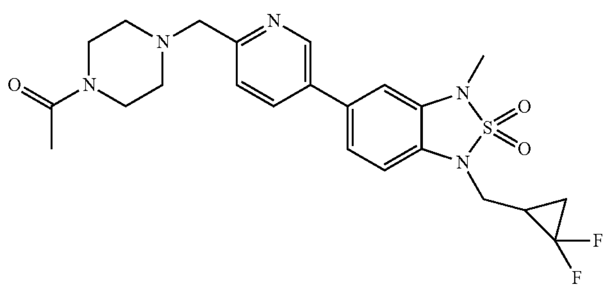 [SMILES: CC(=O)N1CCN(Cc2ccc(-c3ccc4c(c3)N(C)S(=O)(=O)N4CC3CC3(F)F)cn2)CC1] | 5-{6-[(4-acetylpiperazin-1-yl)methyl]pyridin-3-yl}-1-[(2,2-difluorocyclopropyl) methyl]-3-methyl-1,3-dihydro-2,1,3-benzothiadiazole 2,2-dioxide | Calc'd 492.1875, found 492.1875 |
| 25-5 | 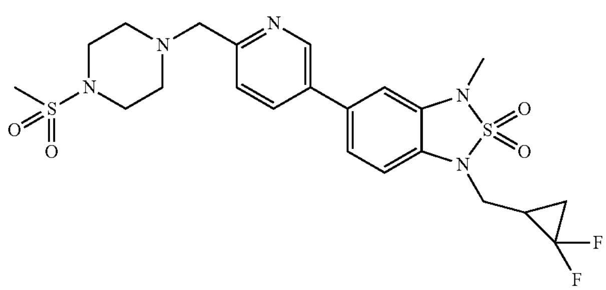 [SMILES: CN1c2cc(-c3ccc(CN4CCN(S(C)(=O)=O)CC4)nc3)ccc2N(CC2CC2(F)F)S1(=O)=O] | 1-[(2,2-difluorocyclopropyl) methyl]-3-methyl-5-(6-{[4-(methylsulfonyl) piperazin-1-yl]methyl}pyridin-3-yl)-1,3-dihydro-2,1,3-benzothiadiazole 2,2-dioxide | Calc'd 528.1545, found 528.1538 |
| 25-6 | 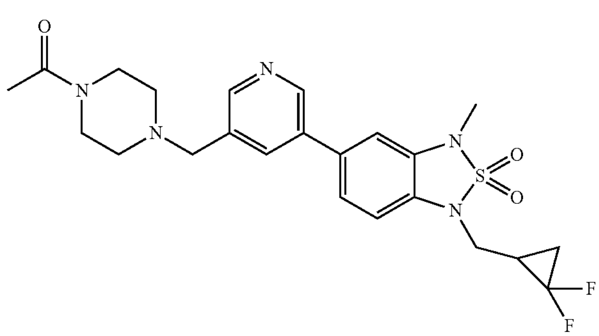 [SMILES: CC(=O)N1CCN(Cc2cncc(-c3ccc4c(c3)N(C)S(=O)(=O)N4CC3CC3(F)F)c2)CC1] | 5-{5-[(4-acetylpiperazin-1-yl)methyl]pyridin-3-yl}-1-[(2,2-difluorocyclopropyl) methyl]-3-methyl-1,3-dihydro-2,1,3-benzothiadiazole 2,2-dioxide | Calc'd 492.1875, found 492.1878 |

TABLE 10-continued

The following compounds were prepared by a reaction sequence analogous to that illustrated in Scheme 25.

| Cmpd | Structure | IUPAC Name | Exact Mass [M + H]+ |
|---|---|---|---|
| 25-7 | 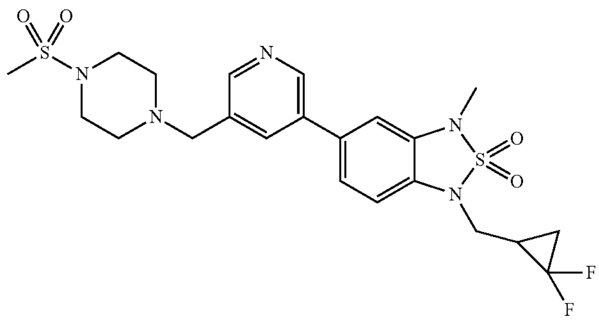 [SMILES: CN1c2cc(-c3cncc(CN4CCN(S(C)(=O)=O)CC4)c3)ccc2N(CC2CC2(F)F)S1(=O)=O] | 1-[(2,2-difluorocyclopropyl)methyl]-3-methyl-5-(5-{[4-(methylsulfonyl)piperazin-1-yl]methyl}pyridin-3-yl)-1,3-dihydro-2,1,3-benzothiadiazole 2,2-dioxide | Calc'd 528.1545, found 528.1543 |
| 25-8 | 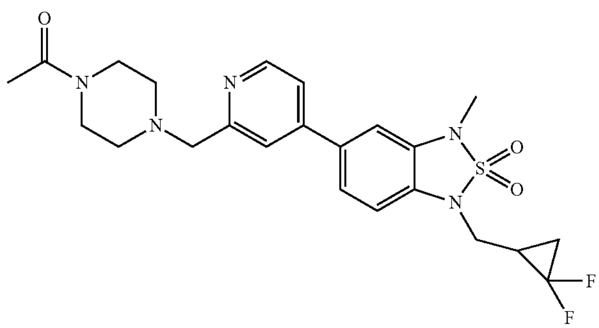 [SMILES: CC(=O)N1CCN(Cc2cc(-c3ccc4c(c3)N(C)S(=O)(=O)N4CC3CC3(F)F)ccn2)CC1] | 5-{2-[(4-acetylpiperazin-1-yl)methyl]pyridin-4-yl}-1-[(2,2-difluorocyclopropyl)methyl]-3-methyl-1,3-dihydro-2,1,3-benzothiadiazole 2,2-dioxide | Calc'd 492.1875, found 492.1873 |
| 25-9 | 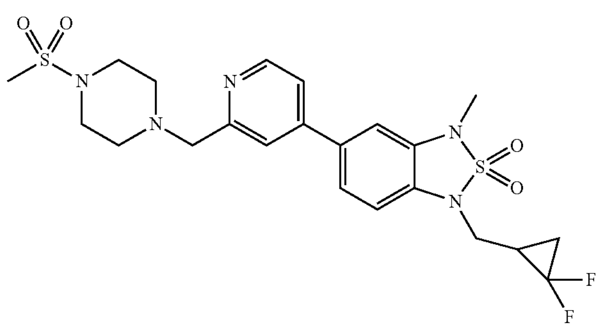 [SMILES: CN1c2cc(-c3ccnc(CN4CCN(S(C)(=O)=O)CC4)c3)ccc2N(CC2CC2(F)F)S1(=O)=O] | 1-[(2,2-difluorocyclopropyl)methyl]-3-methyl-5-(2-{[4-(methylsulfonyl)piperazin-1-yl]methyl}pyridin-4-yl)-1,3-dihydro-2,1,3-benzothiadiazole 2,2-dioxide | Calc'd 528.1545, found 528.1537 |
| 25-10 | 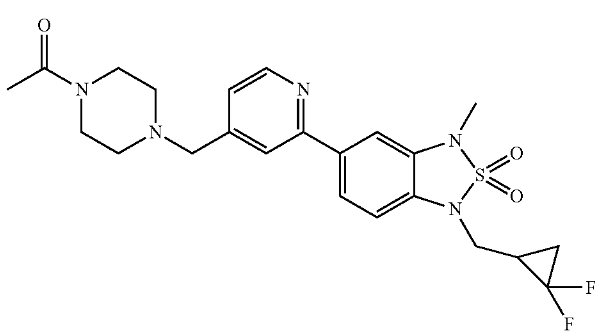 [SMILES: CC(=O)N1CCN(Cc2ccnc(-c3ccc4c(c3)N(C)S(=O)(=O)N4CC3CC3(F)F)c2)CC1] | 5-{4-[(4-acetylpiperazin-1-yl)methyl]pyridin-2-yl}-1-[(2,2-difluorocyclopropyl)methyl]-3-methyl-1,3-dihydro-2,1,3-benzothiadiazole 2,2-dioxide | Calc'd 492.1875, found 492.1875 |

SCHEME 26

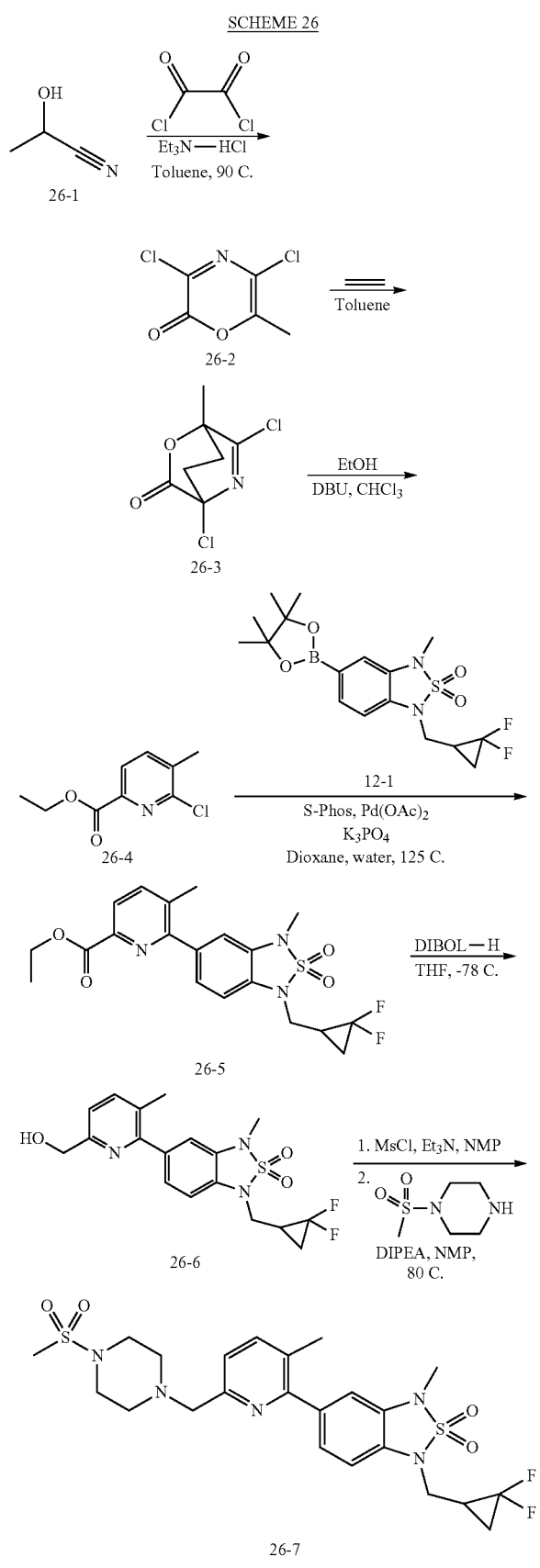

1-[(2,2-difluorocyclopropyl)methyl]-3-methyl-5-(3-methyl-6-{[4-(methylsulfonyl)piperazin-1-yl]methyl}pyridin-2-yl)-1,3-dihydro-2,1,3-benzothiadiazole 2,2-dioxide (26-7)

3,5-Dichloro-6-methyl-2H-1,4-oxazin-2-one (26-2)

2-Hydroxypropanenitrile (26-1) (5.0 g, 70 mmol, 1 eq) in toluene (60 mL) was added dropwise to a stirring solution of oxalyl chloride (24.6 mL, 281 mmol, 4 eq) in toluene (165 mL) at 0° C. After 30 minutes, the reaction mixture was heated to 90° C. and triethylamine hydrochloride (4.8 g, 35.2 mmol, 0.5 eq) was added. The mixture stirred for 4 hours at the same temperature and then was concentrated in vacuo at 60° C. The resulting mixture was suspended in $Et_2O$ (300 mL), filtered washing with $Et_2O$ (3×100 mL), and the filtrates were combined and concentrated. Purification by flash chromatography (330 g $SiO_2$, 0-50% EtOAc in hexanes) afforded 3,5-dichloro-6-methyl-2H-1,4-oxazin-2-one (26-2) as a white solid. $^1$H NMR (400 MHz, $CDCl_3$): δ 2.38 (s, 3H).

4,6-Dichloro-1-methyl-2-oxa-5-azabicyclo[2.2.2]oct-5-en-3-one (26-3)

3,5-Dichloro-6-methyl-2H-1,4-oxazin-2-one (26-2) (3.0 g, 17 mmol, 1 eq) was dissolved in toluene (42 mL) and the mixture stirred at 40° C. under 1 atmosphere of ethylene gas for 4 days. The mixture was concentrated in vacuo to afford 4,6-dichloro-1-methyl-2-oxa-5-azabicyclo[2.2.2]oct-5-en-3-one (26-3) as a white solid. $^1$H NMR (400 MHz, $CDCl_3$): δ 2.20-2.44 (m, 3H); 1.93 (m, 1H); 1.77 (s, 3H). LRMS m/z (M+H) 207.0 found, 207.0 required.

Ethyl 6-chloro-5-methylpyridine-2-carboxylate (26-4)

4,6-Dichloro-1-methyl-2-oxa-5-azabicyclo[2.2.2]oct-5-en-3-one (26-3) (3.0 g, 14.4 mmol, 1 eq) was dissolved in chloroform (30 mL) and DBU (6.5 mL, 43 mmol, 3 eq) was added. After 5 minutes of stirring at ambient temperature, ethanol (0.84 mL, 16 mmol, 1.1 eq) was added and there was a slight exotherm. After 15 minutes of stirring at ambient temperature, the reaction mixture was concentrated and the crude residue was purified by flash chromatography (80 g $SiO_2$, 0-100% EtOAc in hexanes) to afford ethyl 6-chloro-5-methylpyridine-2-carboxylate (26-4) as a colorless oil. $^1$H NMR (400 MHz, $CDCl_3$): δ 7.97 (d, J=7.6 Hz, 1 H); 7.69 (d, J=7.6 Hz, 1 H); 4.47 (q, J=7.2 Hz, 2 H); 2.46 (s, 3 H); 1.43 (t, J=7.2 Hz, 3H). LRMS m/z (M+H) 200.0 found, 200.0 required.

Ethyl 6-{1-[(2,2-difluorocyclopropyl)methyl]-3-methyl-2,2-dioxido-1,3-dihydro-2,1,3-benzothiadiazol-5-yl}-5-methylpyridine-2-carboxylate (26-5)

1-[(2,2-difluorocyclopropyl)methyl]-3-methyl-5-(4,4,5,5-tetramethyl-1,3,2-dioxaborolan-2-yl)-1,3-dihydro-2,1,3-benzothiadiazole 2,2-dioxide (12-1) (100 mg, 0.25 mmol, 1 eq), ethyl 6-chloro-5-methylpyridine-2-carboxylate (26-4) (75 mg, 0.38 mmol, 1.5 eq), tripotassium phosphate (106 mg, 0.50 mmol, 2.0 eq), S-Phos (10 mg, 0.025 mmol, 0.1 eq), and palladium(II) acetate (2.8 mg, 0.012 mmol, 0.05 eq) were combined in THF (1 mL) and water (0.2 mL). The resulting mixture was heated at 75° C. for 14 hours. The reaction mixture was allowed to cool to room temperature. The mixture was then diluted with EtOAc (10 mL), washed with water (1 mL) and brine (1 mL), dried over $MgSO_4$, filtered and concentrated. The crude residue was purified by flash chromatography (12 g $SiO_2$, 0-80% EtOAc in hexanes) to afford ethyl 6-{1-[(2,2-difluorocyclopropyl)methyl]-3-methyl-2,2- dioxido-1,3-dihydro-2,1,3-benzothiadiazol-5-yl}-5-methylpyridine-2-carboxylate (26-5). HRMS m/z (M+H) 438.1291 found, 438.1294 required.

(6-{1-[(2,2-difluorocyclopropyl)methyl]-3-methyl-2,2-dioxido-1,3-dihydro-2,1,3-benzothiadiazol-5-yl}-5-methylpyridin-2-yl)methanol (26-6)

Ethyl 6-{1-[(2,2-difluorocyclopropyl)methyl]-3-methyl-2,2-dioxido-1,3-dihydro-2,1,3-benzothiadiazol-5-yl}-5-methylpyridine-2-carboxylate (26-5) (85 mg, 0.19 mmol, 1 eq) was dissolved in THF (1 mL) and cooled to −78° C. DIBAL-H (0.97 mL, 0.97 mmol, 5.0 eq, 1.0 M in heptane) was added and the mixture was stirred at the same temperature. After 20 minutes the reaction was quenched by an addition of Rochelle's Salt (1 mL) and stirred for 2 hours warming to ambient temperature. The mixture was extracted with EtOAc (10 mL), washed with water (1 mL) and brine (1 mL), dried over MgSO$_4$, filtered and concentrated to afford (6-{1-[(2,2-difluorocyclopropyl)methyl]-3-methyl-2,2-dioxido-1,3-dihydro-2,1,3-benzothiadiazol-5-yl}-5-methylpyridin-2-yl)methanol (26-6). HRMS m/z (M+H) 396.1186 found, 396.1188 required.

1-[(2,2-difluorocyclopropyl)methyl]-3-methyl-5-(3-methyl-6-{[4-(methylsulfonyl)piperazin-1-yl]methyl}pyridin-2-yl)-1,3-dihydro-2,1,3-benzothiadiazole 2,2-dioxide (26-7)

(6-{1-[(2,2-difluorocyclopropyl)methyl]-3-methyl-2,2-dioxido-1,3-dihydro-2,1,3-benzothiadiazol-5-yl}-5-methylpyridin-2-yl)methanol (26-6) (25 mg, 0.06 mmol, 1 eq) was dissolved in NMP (0.5 mL) and triethylamine (0.03 mL, 0.18 mmol, 3.0 eq) was added followed by mesyl chloride (0.01 mL, 0.12 mmol, 2.0 eq). After 10 minutes, 1-(methylsulfonyl)piperazine (20.8 mg, 0.13 mmol, 2.0 eq) and DIPEA (0.033 mL, 0.19 mmol, 3.0 eq) were added. The resulting mixture stirred at 80° C. for 10 minutes. The mixture was cooled and purified by reverse phase chromatography (Waters Sunfire MSC18, 15-65% acetonitrile in water with 0.1% TFA modifier) to afford 1-[(2,2-difluorocyclopropyl)methyl]-3-methyl-5-(3-methyl-6-{[4-(methylsulfonyl)piperazin-1-yl]methyl}pyridin-2-yl)-1,3-dihydro-2,1,3-benzothiadiazole 2,2-dioxide (26-7) as a white solid. $^1$H NMR (400 MHz, CD$_3$OD): δ 7.91 (d, J=7.6 Hz, 1 H); 7.48 (d, J=7.6 Hz, 1 H); 7.25 (dd, J=1.6, 8.4 Hz, 1 H); 7.19 (s, 1 H); 7.13 (d, J=8.0 Hz, 1 H); 4.53 (s, 2 H); 3.97 (d, J=7.2 Hz, 2 H); 3.56 (m, 4 H); 3.49 (m, 4 H); 3.33 (s, 3 H); 2.95 (s, 3 H); 2.43 (s, 3 H); 2.21 (m, 1 H); 1.64 (m, 1 H); 1.42 (m, 1H). HRMS m/z (M+H) 542.1693 found, 542.1702 required.

TABLE 11

The following compounds were prepared by a reaction sequence analogous to that illustrated in Scheme 26.

| Cmpd | Structure | IUPAC Name | Exact Mass [M + H]+ |
|---|---|---|---|
| 26-8 | 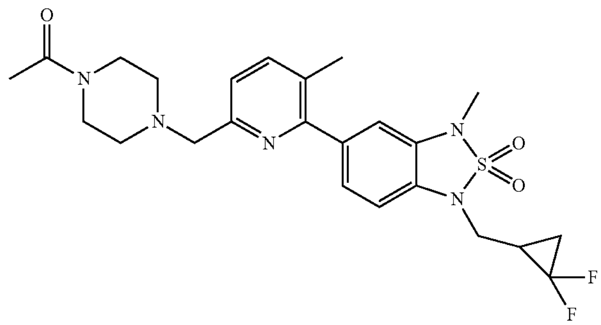 [SMILES: CC(=O)N1CCN(Cc2ccc(C)c(-c3ccc4c(c3)N(C)S(=O)(=O)N4CC3CC3(F)F)n2)CC1] | 1-{4-[(6-{1-[(2,2-difluorocyclopropyl)methyl]-3-methyl-2,2-dioxido-1,3-dihydro-2,1,3-benzothiadiazol-5-yl}-5-methylpyridin-2-yl)methyl]piperazin-1-yl}ethanone | Calc'd 506.2032, found 506.2024 |

SCHEME 27

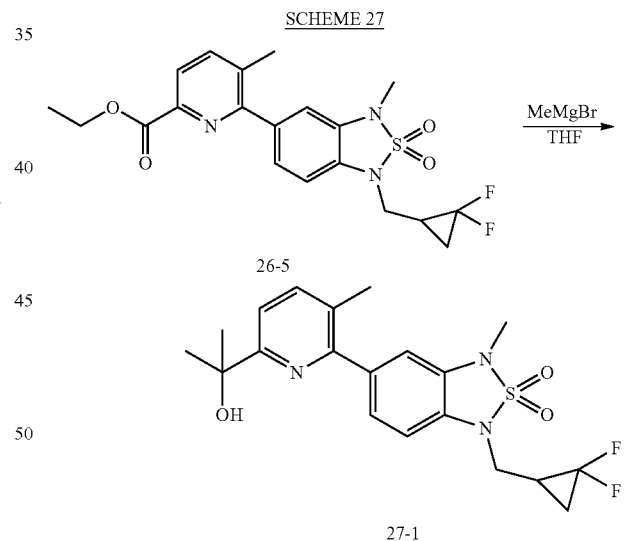

2-(6-{1-[(2,2-difluorocyclopropyl)methyl]-3-methyl-2,2-dioxido-1,3-dihydro-2,1,3-benzothiadiazol-5-yl}-5-methylpyridin-2-yl)propan-2-ol (27-1)

Ethyl 6-{1-[(2,2-difluorocyclopropyl)methyl]-3-methyl-2,2-dioxido-1,3-dihydro-2,1,3-benzothiadiazol-5-yl}-5-methylpyridine-2-carboxylate (26-5) (30 mg, 0.07 mmol, 1 eq) was dissolved in THF (0.5 mL) and methylmagnesium bromide (0.11 mL, 0.34 mmol, 3.0 M, 5.0 eq) was added. The resulting mixture stirred at ambient temperature for 10 minutes. The reaction was quenched by the addition of NH$_4$Cl (1 mL), extracted with EtOAc (10 mL), washed with water (1 mL) and brine (1 mL), dried over MgSO$_4$, filtered and concentrated. The crude residue was purified by flash chromatography (4 g SiO$_2$, 0-70% EtOAc in hexanes) to afford 2-(6-{1-[(2,2-difluorocyclopropyl)methyl]-3-methyl-2,2-dioxido-1,3-dihydro-2,1,3-benzothiadiazol-5-yl}-5-methylpyridin-2-yl)propan-2-ol (27-1) as a white solid. $^1$H NMR (400 MHz, CD$_3$OD): δ 7.68 (d, J=7.6 Hz, 1 H); 7.49 (d, J=8.0 Hz, 1 H); 7.20 (dd, J=1.6, 8.0 Hz, 1 H); 7.10 (s, 1 H); 7.09 (d, J=8.4 Hz, 1 H); 3.95 (m, 2 H); 3.31 (s, 3 H); 2.30 (s, 3 H); 2.21 (m, 1 H); 1.64 (m, 1 H); 1.55 (s, 6 H); 1.42 (m, 1 H). HRMS m/z (M+H) 424.1501 found, 424.1501 required.

SCHEME 28

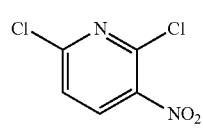

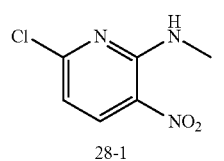

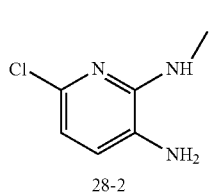

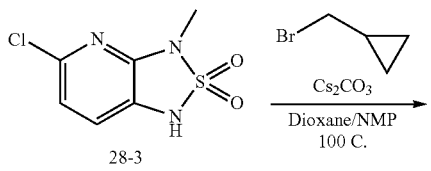

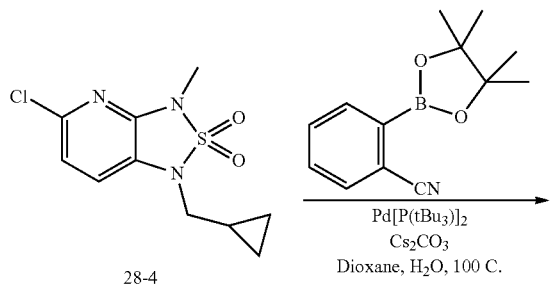

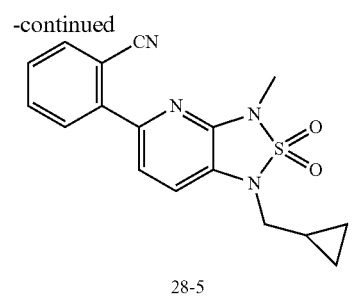

2-[1-(cyclopropylmethyl)-3-methyl-2,2-dioxido-1,3-dihydro[1,2,5]thiadiazolo[3,4-b]pyridin-5-yl]benzonitrile (28-5)

6-Chloro-N-methyl-3-nitropyridin-2-amine (28-1)

2,6-Dichloro-3-nitropyridine (2.0 g, 10 mmol) and sodium carbonate (2.8 g, 25.9 mmol) were added to a round bottom flask under nitrogen, and suspended in ethanol (100 mL). Methylamine in methanol (7.8 mL, 16 mmol, 2M) was then added and stirred at room temperature for 3 hours. The yellow solution was concentrated, and then re-dissolved in ethyl acetate followed by washing with sodium bicarbonate and brine. The organic phase was dried over sodium sulfate, filtered, and concentrated. The yellow solid was then re-dissolved in ethanol and recrystallized to give 6-chloro-N-methyl-3-nitropyridin-2-amine (28-1) as a yellow solid. HRMS (M+H)$^+$: observed=188.0216, calculated=188.0221.

6-Chloro-N$^2$-methylpyridine-2,3-diamine (28-2)

6-Chloro-N-methyl-3-nitropyridin-2-amine (28-1, 10.5 g, 56 mmol) and tin(II) chloride dihydrate (50.5 g, 224 mmol) were suspended in concentrated HCl (80 mL) and refluxed overnight. The solution was cooled to room temperature and then added very slowly to a NaOH/ethyl acetate solution at −78° C., until the solution had a slightly basic pH. The suspension was washed with sodium bicarbonate, brine, dried over sodium sulfate, filtered, and concentrated to produce 6-chloro-N$^2$-methylpyridine-2,3-diamine (28-2) as a black solid. HRMS (M+H)$^+$: observed=158.0471, calculated=158.0480.

5-chloro-3-methyl-1,3-dihydro[1,2,5]thiadiazolo[3,4-b]pyridine 2,2-dioxide (28-3)

5-chloro-3-methyl-1,3-dihydro[1,2,5]thiadiazolo[3,4-b]pyridine 2,2-dioxide (3-3) was prepared from (28-2) according to the procedures reported in Scheme 1. HRMS (M+H)$^+$: observed=219.9946, calculated=219.9942.

5-chloro-1-(cyclopropylmethyl)-3-methyl-1,3-dihydro[1,2,5]thiadiazolo[3,4-b]pyridine-2,2-dioxide (28-4)

5-chloro-1-(cyclopropylmethyl)-3-methyl-1,3-dihydro[1,2,5]thiadiazolo[3,4-b]pyridine-2,2-dioxide (28-4) was prepared from (28-3) according to the procedures reported in Scheme 1. HRMS (M+H)+: observed=274.0415, calculated=274.0412.

2-[1-(cyclopropylmethyl)-3-methyl-2,2-dioxido-1,3-dihydro[1,2,5]thiadiazolo[3,4-b]pyridin-5-yl]benzonitrile (28-5)

2-[1-(cyclopropylmethyl)-3-methyl-2,2-dioxido-1,3-dihydro[1,2,5]thiadiazolo[3,4-b]pyridin-5-yl]benzonitrile (28-5) was prepared from (28-4) according to the procedures reported in Scheme 1. HRMS (M+H)+: observed=341.1064, calculated=341.1067.

TABLE 12

The following compounds were prepared by a reaction sequence analogous to that illustrated in Scheme 28.

| Cmpd | Structure | IUPAC Name | Exact Mass [M + H]+ |
|---|---|---|---|
| 28-6 | 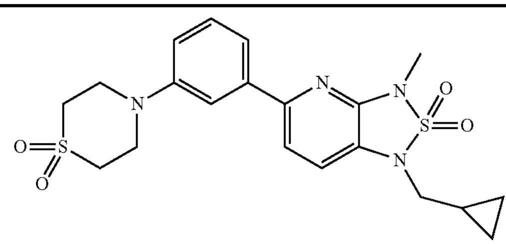 | 1-(cyclopropylmethyl)-5-[3-(1,1-dioxidothiomorpholin-4-yl)phenyl]-3-methyl-1,3-dihydro[1,2,5]thiadiazolo[3,4-b]pyridine 2,2-dioxide | Calc'd 449.1312, found 449.1308 |

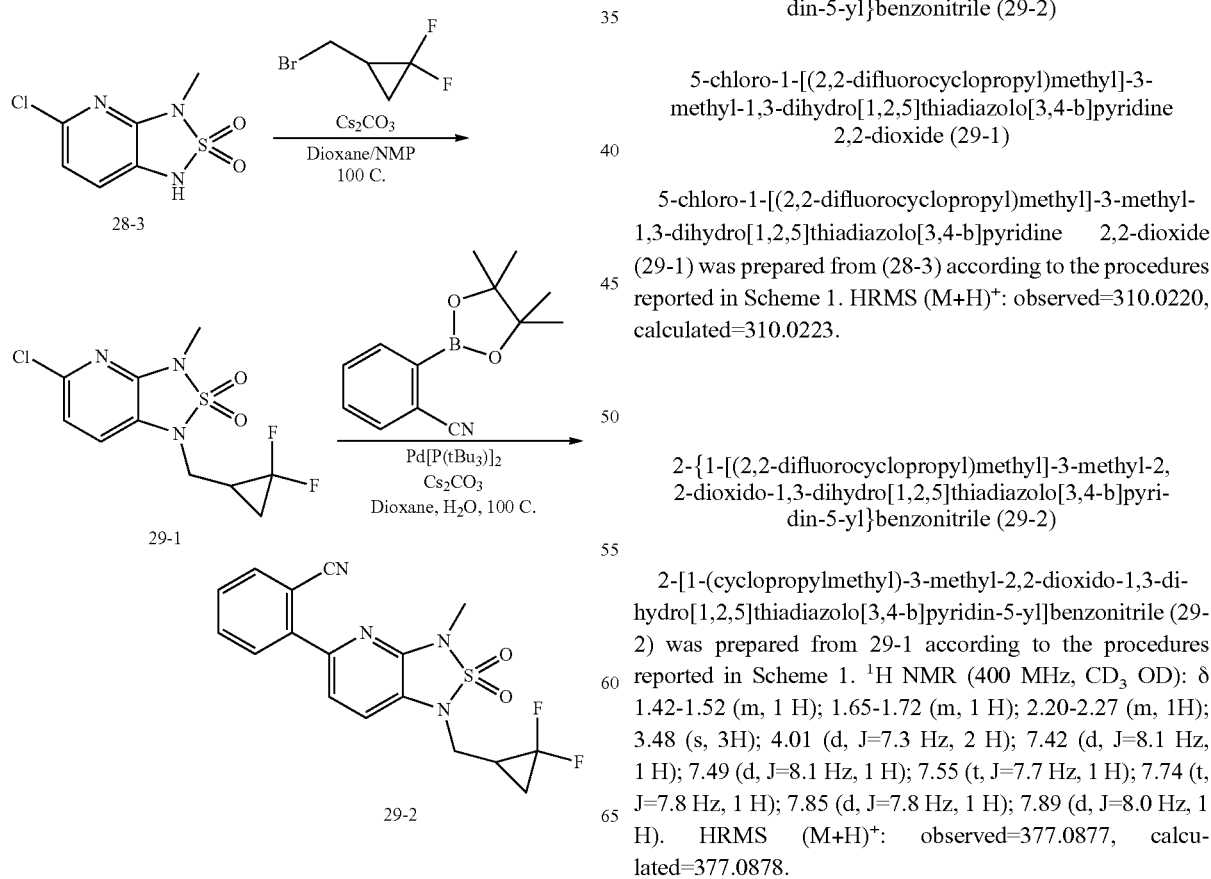

5-chloro-1-[(2,2-difluorocyclopropyl)methyl]-3-methyl-1,3-dihydro[1,2,5]thiadiazolo[3,4-b]pyridine 2,2-dioxide (29-1)

5-chloro-1-[(2,2-difluorocyclopropyl)methyl]-3-methyl-1,3-dihydro[1,2,5]thiadiazolo[3,4-b]pyridine 2,2-dioxide (29-1) was prepared from (28-3) according to the procedures reported in Scheme 1. HRMS (M+H)+: observed=310.0220, calculated=310.0223.

2-{1-[(2,2-difluorocyclopropyl)methyl]-3-methyl-2,2-dioxido-1,3-dihydro[1,2,5]thiadiazolo[3,4-b]pyridin-5-yl}benzonitrile (29-2)

2-[1-(cyclopropylmethyl)-3-methyl-2,2-dioxido-1,3-dihydro[1,2,5]thiadiazolo[3,4-b]pyridin-5-yl]benzonitrile (29-2) was prepared from 29-1 according to the procedures reported in Scheme 1. $^1$H NMR (400 MHz, CD$_3$OD): δ 1.42-1.52 (m, 1 H); 1.65-1.72 (m, 1 H); 2.20-2.27 (m, 1H); 3.48 (s, 3H); 4.01 (d, J=7.3 Hz, 2 H); 7.42 (d, J=8.1 Hz, 1 H); 7.49 (d, J=8.1 Hz, 1 H); 7.55 (t, J=7.7 Hz, 1 H); 7.74 (t, J=7.8 Hz, 1 H); 7.85 (d, J=7.8 Hz, 1 H); 7.89 (d, J=8.0 Hz, 1 H). HRMS (M+H)+: observed=377.0877, calculated=377.0878.

TABLE 13

The following compounds were prepared by a reaction sequence analogous to that illustrated in Scheme 29.

| Cmpd | Structure | IUPAC Name | Exact Mass [M + H]+ |
| --- | --- | --- | --- |
| 29-3 | 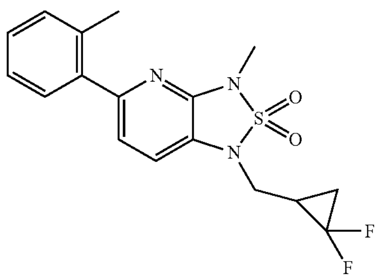 [SMILES: Cc1ccccc1-c1ccc2c(n1)N(C)S(=O)(=O)N2CC1CC1(F)F] | 1-[(2,2-difluorocyclopropyl)methyl]-3-methyl-5-(2-methylphenyl)-1,3-dihydro[1,2,5]thiadiazolo[3,4-b]pyridine 2,2-dioxide | Calc'd 366.1082, found 366.1082 |
| 29-4 | 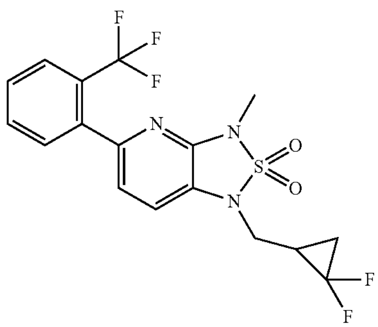 [SMILES: CN1c2nc(-c3ccccc3C(F)(F)F)ccc2N(CC2CC2(F)F)S1(=O)=O] | 1-[(2,2-difluorocyclopropyl)methyl]-3-methyl-5-[2-(trifluoromethyl)phenyl]-1,3-dihydro[1,2,5]thiadiazolo[3,4-b]pyridine 2,2-dioxide | Calc'd 420.0800, found 420.0799 |
| 29-5 | 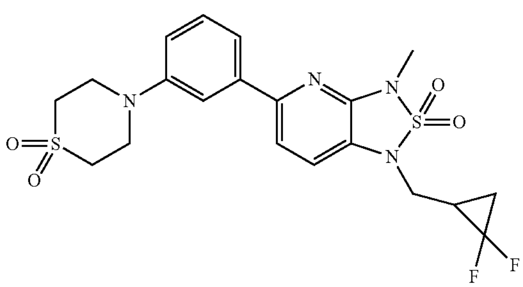 [SMILES: CN1c2nc(-c3cccc(N4CCS(=O)(=O)CC4)c3)ccc2N(CC2CC2(F)F)S1(=O)=O] | 1-[(2,2-difluorocyclopropyl)methyl]-5-[3-(1,1-dioxidothiomorpholin-4-yl)phenyl]-3-methyl-1,3-dihydro[1,2,5]thiadiazolo[3,4-b]pyridine 2,2-dioxide | Calc'd 485.1123, found 485.1125 |
| 29-6 | 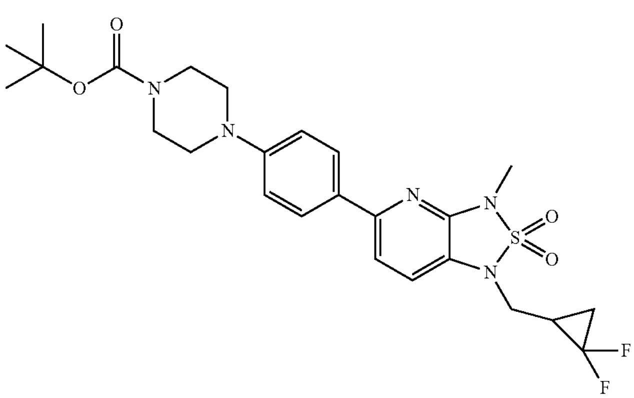 [SMILES: CN1c2nc(-c3ccc(N4CCN(C(=O)OC(C)(C)C)CC4)cc3)ccc2N(CC2CC2(F)F)S1(=O)=O] | tert-butyl 4-(4-{1-[(2,2-difluorocyclopropyl)methyl]-3-methyl-2,2-dioxido-1,3-dihydro[1,2,5]thiadiazolo[3,4-b]pyridin-5-yl}phenyl)piperazine-1-carboxylate | Calc'd 536.2138, found 536.2136 |

TABLE 13-continued

The following compounds were prepared by a reaction sequence analogous to that illustrated in Scheme 29.

| Cmpd | Structure | IUPAC Name | Exact Mass [M + H]+ |
|---|---|---|---|
| 29-7 | 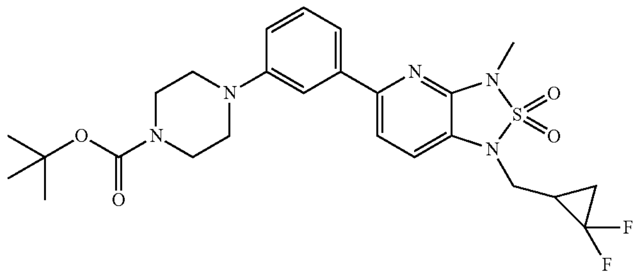 [SMILES: CN1c2nc(-c3cccc(N4CCN(C(=O)OC(C)(C)C)CC4)c3)ccc2N(CC2CC2(F)F)S1(=O)=O] | tert-butyl 4-(3-{1-[(2,2-difluorocyclopropyl)methyl]-3-methyl-2,2-dioxido-1,3-dihydro[1,2,5]thiadiazolo[3,4-b]pyridin-5-yl}phenyl)piperazine-1-carboxylate | Calc'd 536.2138, found 536.2134 |
| 29-8 | 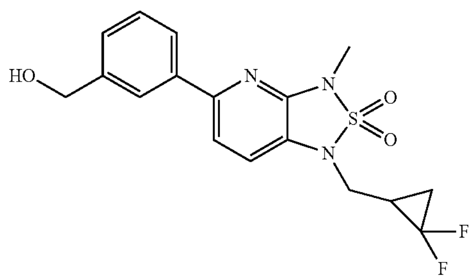 [SMILES: CN1c2nc(-c3cccc(CO)c3)ccc2N(CC2CC2(F)F)S1(=O)=O] | (3-{1-[(2,2-difluorocyclopropyl)methyl]-3-methyl-2,2-dioxido-1,3-dihydro[1,2,5]thiadiazolo[3,4-b]pyridin-5-yl}phenyl)methanol | Calc'd 382.1031, found 382.1028 |
| 29-9 | 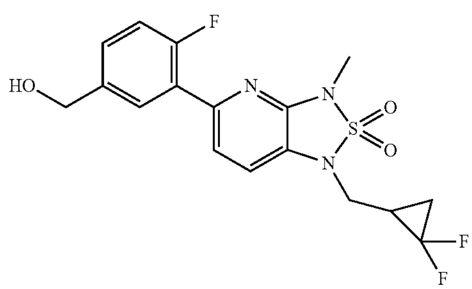 [SMILES: CN1c2nc(-c3cc(CO)ccc3F)ccc2N(CC2CC2(F)F)S1(=O)=O] | (3-{1-[(2,2-difluorocyclopropyl)methyl]-3-methyl-2,2-dioxido-1,3-dihydro[1,2,5]thiadiazolo[3,4-b]pyridin-5-yl}-4-fluorophenyl)methanol | Calc'd 400.0937, found 400.0933 |
| 29-10 | 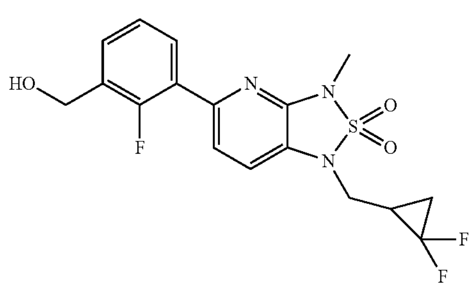 [SMILES: CN1c2nc(-c3cccc(CO)c3F)ccc2N(CC2CC2(F)F)S1(=O)=O] | (3-{1-[(2,2-difluorocyclopropyl)methyl]-3-methyl-2,2-dioxido-1,3-dihydro[1,2,5]thiadiazolo[3,4-b]pyridin-5-yl}-2-fluorophenyl)methanol | Calc'd 400.0937, found 400.0933 |

SCHEME 30

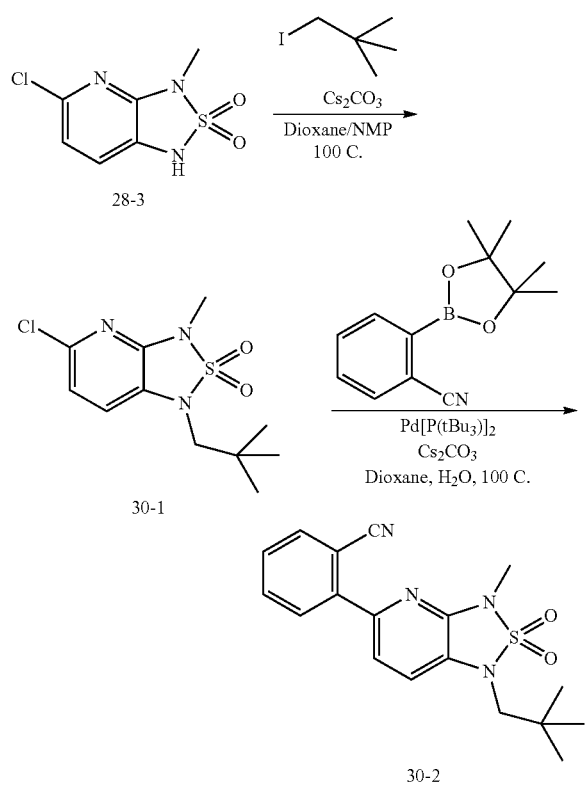

2-[1-(2,2-dimethylpropyl)-3-methyl-2,2-dioxido-1,3-dihydro[1,2,5]thiadiazolo[3,4-b]pyridin-5-yl]benzonitrile (30-2)

2-[1-(2,2-dimethylpropyl)-3-methyl-2,2-dioxido-1,3-dihydro[1,2,5]thiadiazolo[3,4-b]pyridin-5-yl]benzonitrile (30-2) was prepared from 28-3 according to the procedures reported in Schemes 1 and 28. $^1$H NMR (400 MHz, CD$_3$OD): δ 1.14 (s, 9 H); 3.47 (s, 3 H); 3.61 (s, 2 H); 7.38 (d, J=8.1 Hz, 1 H); 7.46 (d, J=8.1 Hz, 1 H); 7.54 (t, J=7.7 Hz, 1 H); 7.73 (t, J=7.8 Hz, 1H); 7.84 (d, J=7.8 Hz, 1 H); 7.89 (d, J=8.0 Hz, 1 H). HRMS (M+H)$^+$: observed=357.1378, calculated=357.1380.

SCHEME 31

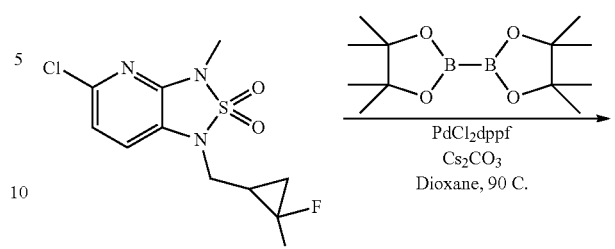

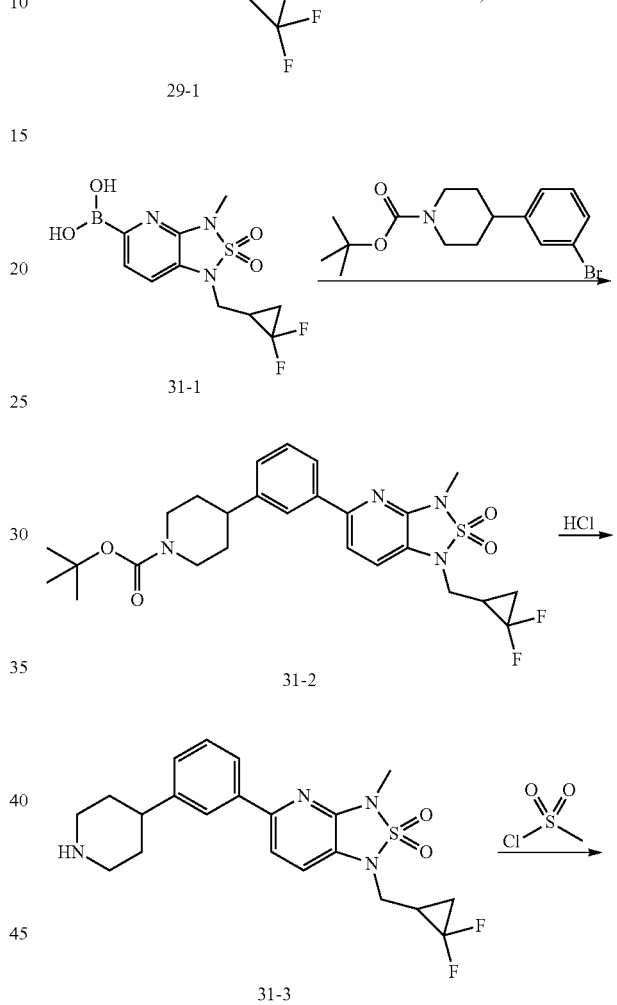

TABLE 14

The following compounds were prepared by a reaction sequence analogous to that illustrated in Scheme 30.

| Cmpd | Structure | IUPAC Name | Exact Mass [M + H]+ |
|---|---|---|---|
| 30-3 | (structure shown) | 1-(2,2-dimethylpropyl)-5-[3-(1,1-dioxidothiomorpholin-4-yl)phenyl]-3-methyl-1,3-dihydro[1,2,5]thiadiazolo[3,4-b]pyridine 2,2-dioxide | Calc'd 465.1625, found 465.1617 |

-continued

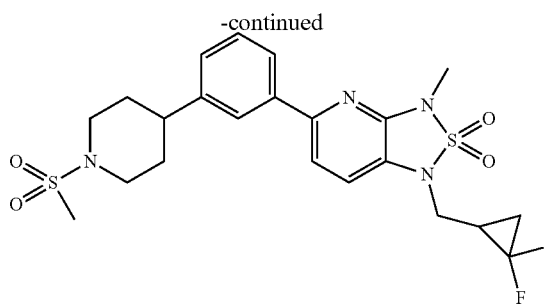

31-4

1-[(2,2-difluorocyclopropyl)methyl]-3-methyl-5-{3-[1-(methylsulfonyl)piperidin-4-yl]phenyl}-1,3-dihydro[1,2,5]thiadiazolo[3,4-b]pyridine 2,2-dioxide (31-4)

{1-[(2,2-difluorocyclopropyl)methyl]-3-methyl-2,2-dioxido-1,3-dihydro[1,2,5]thiadiazolo[3,4-b]pyridin-5-yl}boronic acid (31-1)

{1-[(2,2-difluorocyclopropyl)methyl]-3-methyl-2,2-dioxido-1,3-dihydro[1,2,5]thiadiazolo[3,4-b]pyridin-5-yl}boronic acid (31-1) was prepared from (29-1) according to the procedures reported in Scheme 1, and the crude material was utilized in next step.

tert-butyl 4-(3-{1-[(2,2-difluorocyclopropyl)methyl]-3-methyl-2,2-dioxido-1,3 dihydro[1,2,5]thiadiazolo[3,4-b]pyridin-5-yl}phenyl)piperidine-1-carboxylate (31-2)

tert-butyl 4-(3-{1-[(2,2-difluorocyclopropyl)methyl]-3-methyl-2,2-dioxido-1,3-dihydro[1,2,5]thiadiazolo[3,4-b]pyridin-5-yl}phenyl)piperidine-1-carboxylate (31-2) was prepared from crude (31-1) by the same procedure as (2-2). HRMS (M+H)$^+$: observed=535.2179, calculated=535.2185.

1-[(2,2-difluorocyclopropyl)methyl]-3-methyl-5-(3-piperidin-4-ylphenyl)-1,3-dihydro[1,2,5]thiadiazolo[3,4-b]pyridine 2,2-dioxide (31-3)

1-[(2,2-difluorocyclopropyl)methyl]-3-methyl-5-(3-piperidin-4-ylphenyl)-1,3-dihydro[1,2,5]thiadiazolo[3,4-b]pyridine 2,2-dioxide (31-3) was prepared from (31-2) according to the procedures reported in Scheme 4.

1-[(2,2-difluorocyclopropyl)methyl]-3-methyl-5-{3-[1-(methylsulfonyl)piperidin-4-yl]phenyl}-1,3-dihydro[1,2,5]thiadiazolo[3,4-b]pyridine 2,2-dioxide (31-4)

To a vial was added 1-[(2,2-difluorocyclopropyl)methyl]-3-methyl-5-(3-piperidin-4-ylphenyl)-1,3-dihydro[1,2,5]thiadiazolo[3,4-b]pyridine 2,2-dioxide (31-3) (0.030 g, 0.064 mmol), NMP (1 mL), DIPEA (0.060 mL, 0.344 mmol), and finally methanesulfonyl chloride (0.0374 mL, 0.480 mmol).

The reaction mixture was then permitted to stir at room temperature for 1 hour. The crude reaction mixture was then diluted with methanol, then filtered. Purification of crude reaction mixture by reverse phase chromatography (Waters Sunfire MSC18, 10% acetonitrile/0.1% trifluoroacetic acid/water→100% acetonitrile/0.1% trifluoroacetic acid/water) to give 1-[(2,2-difluorocyclopropyl)methyl]-3-methyl-5-{3-[1-(methylsulfonyl)piperidin-4-yl]phenyl}-1,3-dihydro[1,2,5]thiadiazolo[3,4-b]pyridine 2,2-dioxide (31-4) as a tan solid. HRMS (M+H)$^+$: observed=513.1430, calculated=513.1436.

SCHEME 32

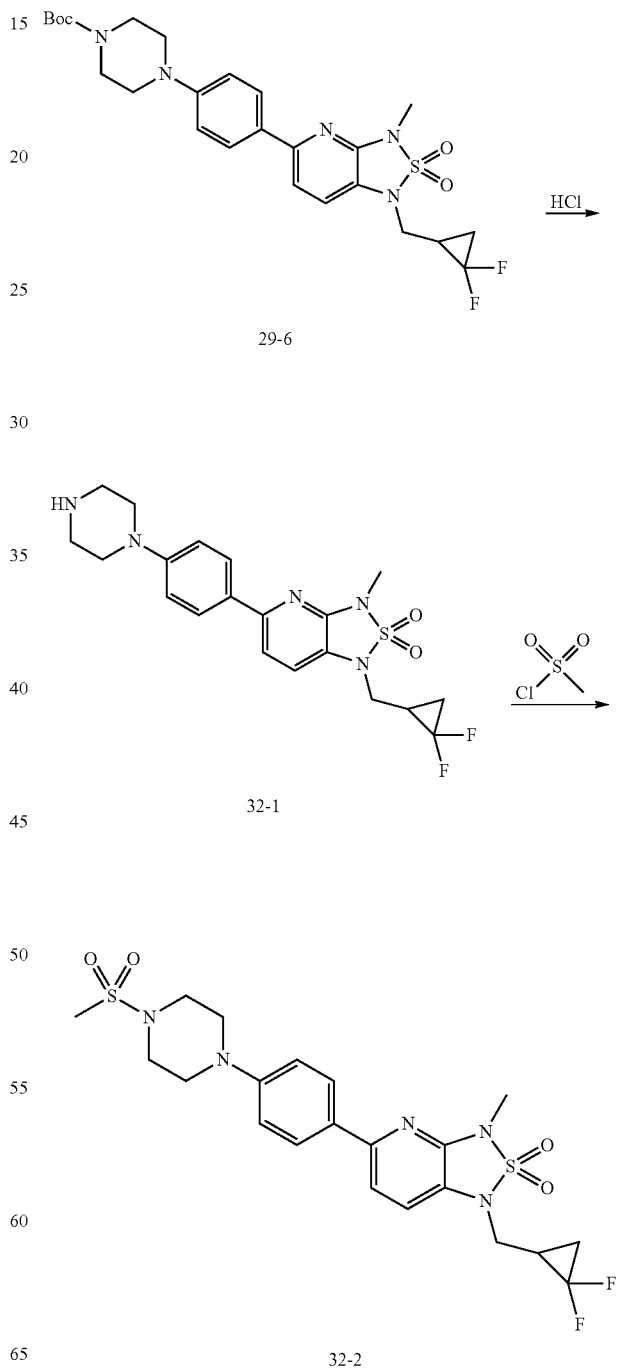

1-[(2,2-difluorocyclopropyl)methyl]-3-methyl-5-{4-[4-(methylsulfonyl)piperazin-1-yl]phenyl}-1,3-dihydro[1,2,5]thiadiazolo[3,4-b]pyridine 2,2-dioxide (32-2)

1-[(2,2-difluorocyclopropyl)methyl]-3-methyl-5-(4-piperazin-1-ylphenyl)-1,3-dihydro[1,2,5]thiadiazolo[3,4-b]pyridine 2,2-dioxide hydrochloride (32-1)

1-[(2,2-difluorocyclopropyl)methyl]-3-methyl-5-(4-piperazin-1-ylphenyl)-1,3-dihydro[1,2,5]thiadiazolo[3,4-b]pyridine 2,2-dioxide hydrochloride (32-1) was prepared from (29-6) according to the procedures reported in Scheme 23.

1-[(2,2-difluorocyclopropyl)methyl]-3-methyl-5-{4-[4-(methylsulfonyl)piperazin-1-yl]phenyl}-1,3-dihydro[1,2,5]thiadiazolo[3,4-b]pyridine 2,2-dioxide (32-2)

1-[(2,2-difluorocyclopropyl)methyl]-3-methyl-5-{4-[4-(methylsulfonyl)piperazin-1-yl]phenyl}-1,3-dihydro[1,2,5]thiadiazolo[3,4-b]pyridine 2,2-dioxide (32-2) was prepared from 32-1 using the similar procedures to that reported in Scheme 31. HRMS (M+H)$^+$: observed=514.1389, calculated=514.1383.

1-[(2,2-difluorocyclopropyl)methyl]-3-methyl-5-{3-[4-(methylsulfonyl)piperazin-1-yl]phenyl}-1,3-dihydro[1,2,5]thiadiazolo[3,4-b]pyridine 2,2-dioxide (33-1)

1-[(2,2-difluorocyclopropyl)methyl]-3-methyl-5-{3-[4-(methylsulfonyl)piperazin-1-yl]phenyl}-1,3-dihydro[1,2,5]thiadiazolo[3,4-b]pyridine 2,2-dioxide (33-1) was prepared from (29-7) using the similar procedures to that reported in Scheme 31. HRMS (M+H)$^+$: observed=514.1389, calculated=514.1385.

SCHEME 34

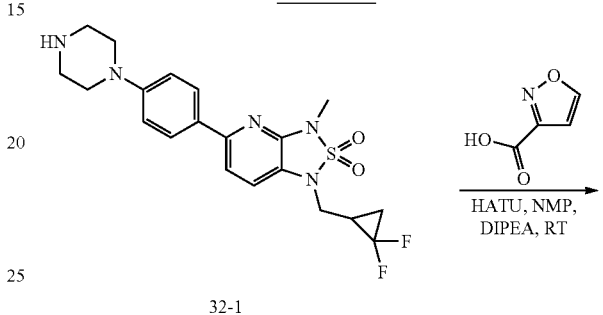

32-1

SCHEME 33

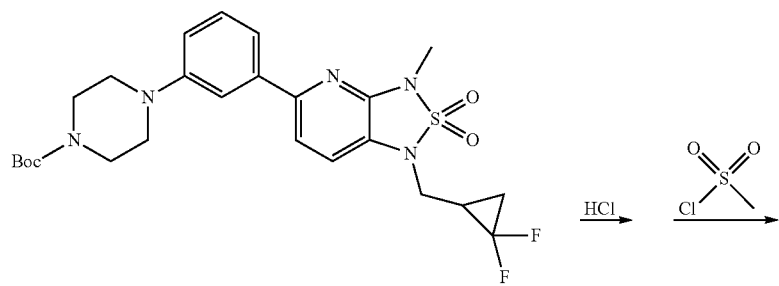

29-7

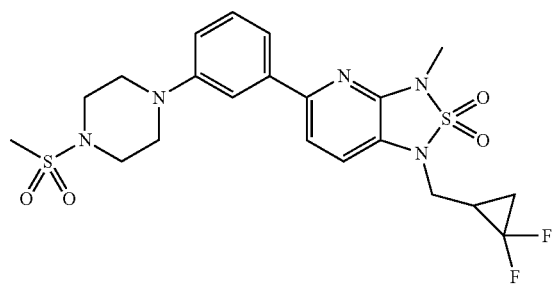

33-1

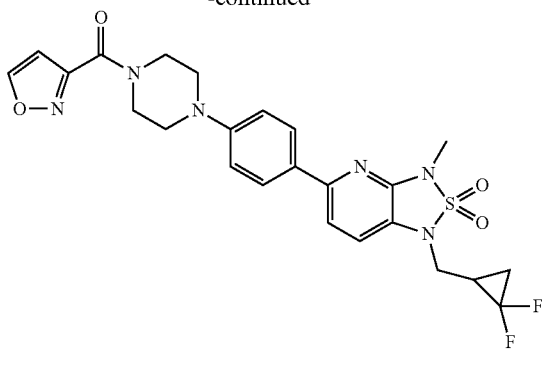

34-1

1-[(2,2-difluorocyclopropyl)methyl]-5-{4-[4-(isoxazol-3-ylcarbonyl)piperazin-1-yl]phenyl}-3-methyl-1,3-dihydro[1,2,5]thiadiazolo[3,4-b]pyridine 2,2-dioxide (34-1)

To a microwave vial was added 1-[(2,2-difluorocyclopropyl)methyl]-3-methyl-5-(4-piperazin-1-ylphenyl)-1,3-dihydro[1,2,5]thiadiazolo[3,4-b]pyridine 2,2-dioxide hydrochloride (8-3) (0.028 g, 0.059 mmol), HATU (0.029 g, 0.077 mmol), isoxazole-3-carboxylic acid (0.0087 g, 0.077 mmol), NMP (1 mL), and finally DIPEA (0.060 mL, 0.344 mmol). The reaction mixture was then stirred at room temperature for 1 hour. The crude reaction mixture was then diluted with methanol, then filtered. Purification of crude reaction mixture by reverse phase chromatography (Waters Sunfire MSC18, 10% acetonitrile/0.1% trifluoroacetic acid/water→100% acetonitrile/0.1% trifluoroacetic acid/water) to give 1-[(2,2-difluorocyclopropyl)methyl]-5-{4-[4-(isoxazol-3-ylcarbonyl)piperazin-1-yl]phenyl}-3-methyl-1,3-dihydro[1,2,5]thiadiazolo[3,4-b]pyridine 2,2-dioxide (34-1) as a tan solid. HRMS (M+H)$^+$: observed=531.1613, calculated=531.1621.

1-[4-(3-{1-[(2,2-difluorocyclopropyl)methyl]-3-methyl-2,2-dioxido-1,3-dihydro[1,2,5]thiadiazolo[3,4-b]pyridin-5-yl}phenyl)piperazin-1-yl]ethanone (35-1)

1-[4-(3-{1-[(2,2-difluorocyclopropyl)methyl]-3-methyl-2,2-dioxido-1,3-dihydro[1,2,5]thiadiazolo[3,4-b]pyridin-5-yl}phenyl)piperazin-1-yl]ethanone (35-1) was prepared from (29-7) using similar procedures to that reported for 23-2 and in Scheme 34. HRMS (M+H)$^+$: observed=478.1723, calculated=478.1719.

SCHEME 36

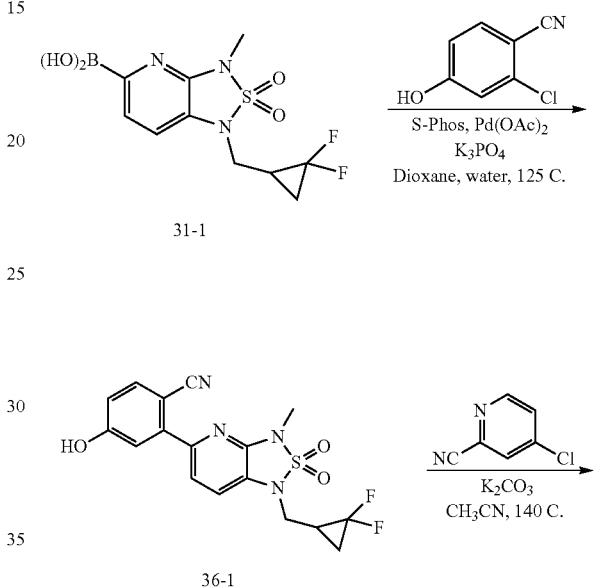

31-1

36-1

SCHEME 35

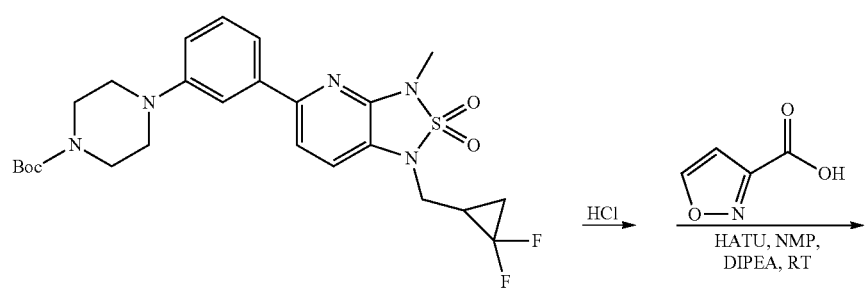

29-7

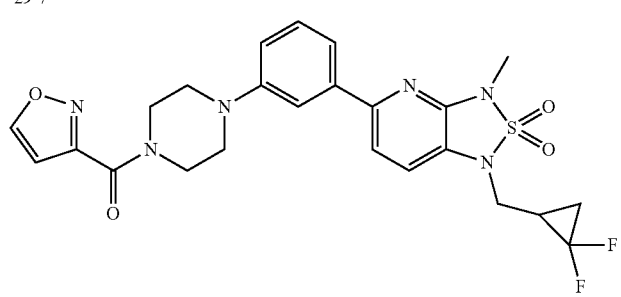

35-1

SCHEME 37

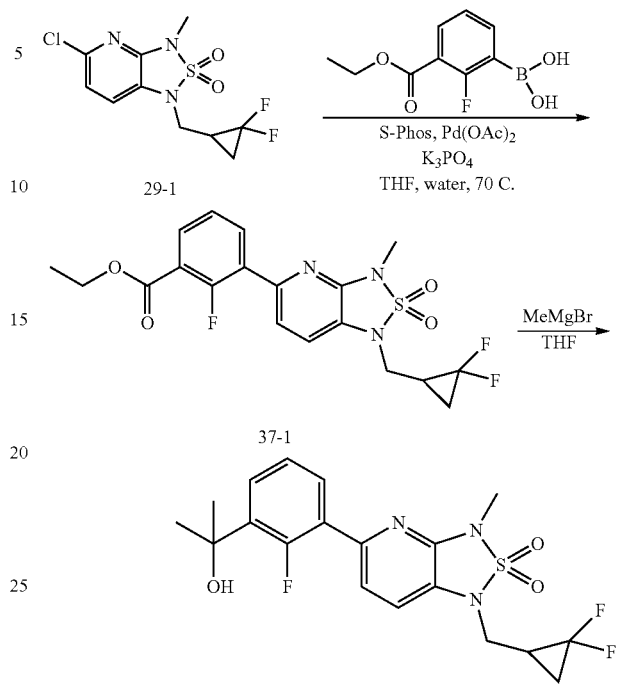

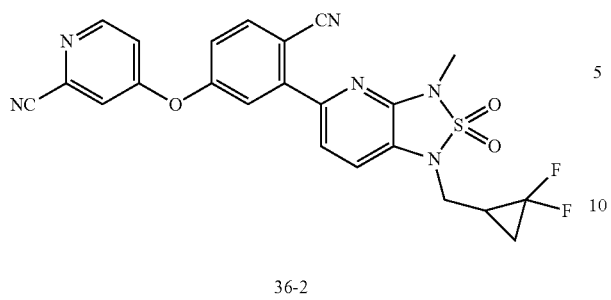

4-(4-cyano-3-{1-[(2,2-difluorocyclopropyl)methyl]-3-methyl-2,2-dioxido-1,3-dihydro[1,2,5]thiadiazolo[3,4-b]pyridin-5-yl}phenoxy)pyridine-2-carbonitrile (36-2)

4-(4-cyano-3-{1-[(2,2-difluorocyclopropyl)methyl]-3-methyl-2,2-dioxido-1,3-dihydro[1,2,5]thiadiazolo[3,4-b]pyridin-5-yl}phenoxy)pyridine-2-carbonitrile (36-2) was prepared from 31-1 using similar procedures to that reported in Scheme 12. $^1$H NMR (400 MHz, CD$_3$OD): δ 1.40-1.49 (m, 1 H); 1.63-1.72 (m, 1 H); 2.18-2.28 (m, 1 H); 3.48 (s, 3 H); 4.02 (d, J=7.1 Hz, 2 H); 7.29-7.38 (m, 2 H); 7.42 (d, J=8.0 Hz, 1 H); 7.54 (d, J=8.1 Hz, 1 H); 7.64 (d, J=2.6 Hz, 1 H); 7.75 (d, J=2.5 Hz, 1 H); 7.98 (d, J=8.4 Hz, 1 H); 8.62 (d, J=5.7 Hz, 1 H). HRMS m/z (M+H) 495.1044 found, 495.1045 required.

TABLE 15

The following compounds were prepared by a reaction sequence analogous to that illustrated in Scheme 36.

| Cmpd | Structure | IUPAC Name | Exact Mass [M + H]+ |
|---|---|---|---|
| 36-3 | 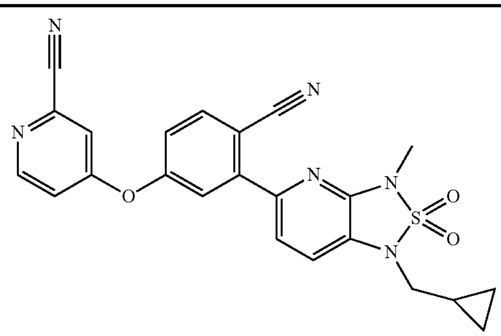 | 4-{4-cyano-3-[1-(cyclopropylmethyl)-3-methyl-2,2-dioxido-1,3-dihydro[1,2,5]thiathazolo[3,4-b]pyridin-5-yl]phenoxy}pyridine-2-carbonitrile | Calc'd 459.1234, found 459.1230 |
| 36-4 | 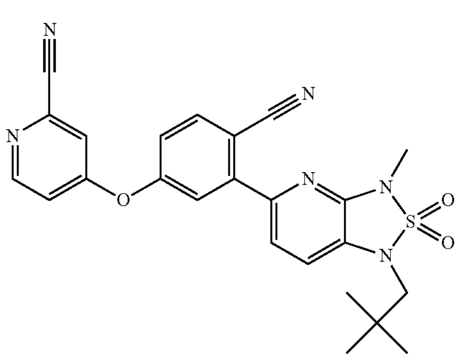 [SMILES: CN1c2nc(-c3cc(Oc4ccnc(C#N)c4)ccc3C#N)ccc2N(CC(C)(C)C)S1(=O)=O] | 4-{4-cyano-3-[1-(2,2-dimethylpropyl)-3-methyl-2,2-dioxido-1,3-dihydro[1,2,5]thiadiazolo[3,4-b]pyridin-5-yl]phenoxy}pyridine-2-carbonitrile | Calc'd 475.1547, found 475.1532 |

2-(3-{1-[(2,2-difluorocyclopropyl)methyl]-3-methyl-2,2-dioxido-1,3-dihydro[1,2,5]thiadiazolo[3,4-b]pyridin-5-yl}-2-fluorophenyl)propan-2-ol (37-2)

Ethyl 3-{1-[(2,2-difluorocyclopropyl)methyl]-3-methyl-2,2-dioxido-1,3-dihydro[1,2,5]thiadiazolo[3,4-b]pyridin-5-yl}-2-fluorobenzoate (37-1)

5-chloro-1-[(2,2-difluorocyclopropyl)methyl]-3-methyl-1,3-dihydro[1,2,5]thiadiazolo[3,4-b]pyridine 2,2-dioxide (29-1) (2.2 g, 7.1 mmol, 1.0 eq), [3-(ethoxycarbonyl)-2-fluorophenyl]boronic acid (3.0 g, 14 mmol, 2.0 eq), tripotassium phosphate (3.0 g, 14.2 mmol, 2.0 eq), S-Phos (0.29 g, 0.71 mmol, 0.1 eq), and palladium(II) acetate (0.080 mg, 0.36 mmol, 0.05 eq) were combined in THF (15 mL) and water (2 mL). The resulting mixture was heated at 75° C. for 14 hours. The reaction mixture was allowed to cool to room temperature. The mixture was then diluted with EtOAc (100 mL), washed with water (10 mL) and brine (10 mL), dried over MgSO₄, filtered and concentrated. The crude residue was purified by flash chromatography (120 g SiO₂, 0-60% EtOAc in hexanes) to afford ethyl 3-{1-[(2,2-difluorocyclopropyl)methyl]-3-methyl-2,2-dioxido-1,3-dihydro[1,2,5]thiadiazolo[3,4-b]pyridin-5-yl}-2-fluorobenzoate (37-1) as a yellow solid. LRMS m/z (M+H) 442.2 found, 442.1 required.

2-(3-{1-[(2,2-difluorocyclopropyl)methyl]-3-methyl-2,2-dioxido-1,3-dihydro[1,2,5]thiadiazolo[3,4-b]pyridin-5-yl}-2-fluorophenyl)propan-2-ol (37-2)

Ethyl 3-{1-[(2,2-difluorocyclopropyl)methyl]-3-methyl-2,2-dioxido-1,3-dihydro[1,2,5]thiadiazolo[3,4-b]pyridin-5-yl}-2-fluorobenzoate (37-1) (240 mg, 0.54 mmol, 1.0 eq) was dissolved in THF (4 mL). The reaction mixture was cooled to −78° C. and methylmagnesium bromide (0.91 mL, 2.7 mmol, 3.0 M, 5.0 eq) was added. The resulting mixture stirred at ambient temperature for 30 minutes. The reaction was quenched by the addition of NH₄Cl (2 mL), extracted with EtOAc (50 mL), washed with water (10 mL) and brine (10 mL), dried over MgSO₄, filtered and concentrated. The crude residue was purified by flash chromatography (40 g SiO₂, 10-70% EtOAc in hexanes) to afford 2-(3-{1-[(2,2-difluorocyclopropyl)methyl]-3-methyl-2,2-dioxido-1,3-dihydro[1,2,5]thiadiazolo[3,4-b]pyridin-5-yl}-2-fluorophenyl)propan-2-ol (37-2) as a yellow solid. ¹H NMR (400 MHz, CDCl₃): δ 7.81 (td, J=1.6, 7.6 Hz, 1 H); 7.59 (td, J=1.6, 7.6 Hz, 1 H); 7.42 (dd, J=2.0, 8.0 Hz, 1 H); 7.23 (t, J=7.6 Hz, 1 H); 7.06 (d, J=8.0 Hz, 1 H); 3.81-4.03 (m, 2 H); 3.49 (s, 3 H); 2.15 (m, 1 H); 1.69 (s, 6 H); 1.66 (m, 1 H); 1.39 (m, 1 H). HRMS m/z (M+H) 428.1242 found, 428.1250 required.

SCHEME 38

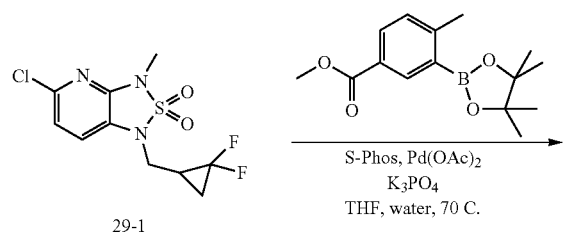

29-1

S-Phos, Pd(OAc)₂
K₃PO₄
THF, water, 70 C.

-continued

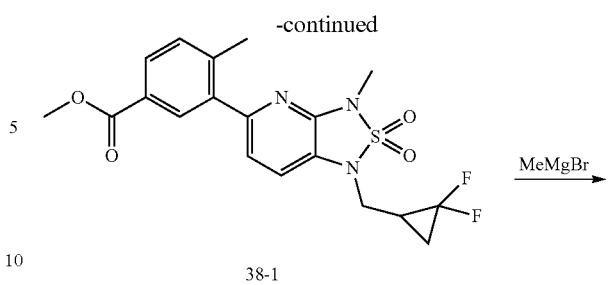

38-1

MeMgBr

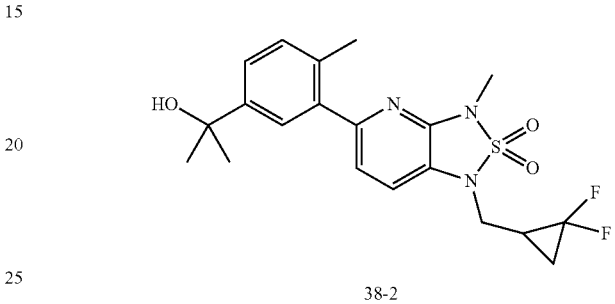

38-2

2-(3-{1-[(2,2-difluorocyclopropyl)methyl]-3-methyl-2,2-dioxido-1,3dihydro[1,2,5]thiadiazolo[3,4-b]pyridin-5-yl}-4-methylphenyl)propan-2-ol (38-2)

Methyl 3-{1-[(2,2-difluorocyclopropyl)methyl]-3-methyl-2,2-dioxido-1,3-dihydro[1,2,5]thiadiazolo[3,4-b]pyridin-5-yl}-4-methylbenzoate (38-1)

5-chloro-1-[(2,2-difluorocyclopropyl)methyl]-3-methyl-1,3-dihydro[1,2,5]thiadiazolo[3,4-b]pyridine 2,2-dioxide (29-1) (6.6 g, 21.3 mmol, 1.0 eq), methyl 4-methyl-3-(4,4,5,5-tetramethyl-1,3,2-dioxaborolan-2-yl)benzoate (8.8 g, 32.0 mmol, 1.5 eq), tripotassium phosphate (9.0 g, 42.6 mmol, 2.0 eq), S-Phos (875 mg, 2.1 mmol, 0.1 eq), and palladium(II) acetate (239 mg, 1.1 mmol, 0.05 eq) were combined in THF (90 mL) and water (15 mL). The resulting mixture was heated at 75° C. for 14 hours. The reaction mixture was allowed to cool to room temperature. The mixture was then diluted with EtOAc (300 mL), washed with water (100 mL) and brine (100 mL), dried over MgSO₄, filtered and concentrated. The crude residue was purified by flash chromatography (330 g SiO₂, 0-60% EtOAc in hexanes) to afford methyl 3-{1-[(2,2-difluorocyclopropyl)methyl]-3-methyl-2,2-dioxido-1,3-dihydro[1,2,5]thiadiazolo[3,4-b]pyridin-5-yl}-4-methylbenzoate (38-1) as a yellow solid. HRMS m/z (M+H) 424.1135 found, 424.1137 required.

2-(3-{1-[(2,2-difluorocyclopropyl)methyl]-3-methyl-2,2-dioxido-1,3dihydro[1,2,5]thiadiazolo[3,4-b]pyridin-5-yl}-4-methylphenyl)propan-2-ol (38-2)

Prepared from 38-1 according to the procedures reported in Scheme 37. HRMS m/z (M+H) 424.1494 found, 424.1501 required.

TABLE 16

The following compounds were prepared by a reaction sequence analogous to that illustrated in Scheme 38.

| Cmpd | Structure | IUPAC Name | Exact Mass [M + H]+ |
|---|---|---|---|
| 38-3 | 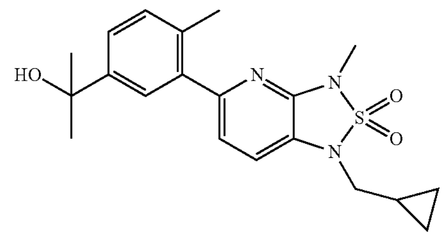 [SMILES: Cc1ccc(C(C)(C)O)cc1-c1ccc2c(n1)N(C)S(=O)(=O)N2CC1CC1] | 2-{3-[1-(cyclopropyl methyl)-3-methyl-2,2-dioxido-1,3-dihydro [1,2,5]thiadiazolo[3,4-b]pyridin-5-yl]-4-methyl phenyl}propan-2-ol | Calc'd 388.1689, found 388.1689 |
| 38-4 | 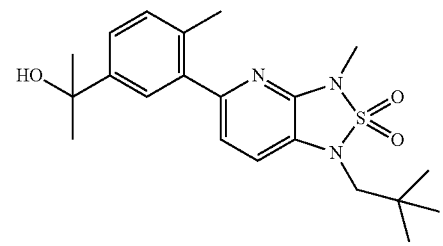 [SMILES: Cc1ccc(C(C)(C)O)cc1-c1ccc2c(n1)N(C)S(=O)(=O)N2CC(C)(C)C] | 2-{3-[1-(2,2-dimethyl propyl)-3-methyl-2,2-dioxido-1,3-dihydro [1,2,5]thiadiazolo[3,4-b]pyridin-5-yl]-4-methyl phenyl}propan-2-ol | Calc'd 404.2002, found 404.1992 |

SCHEME 39

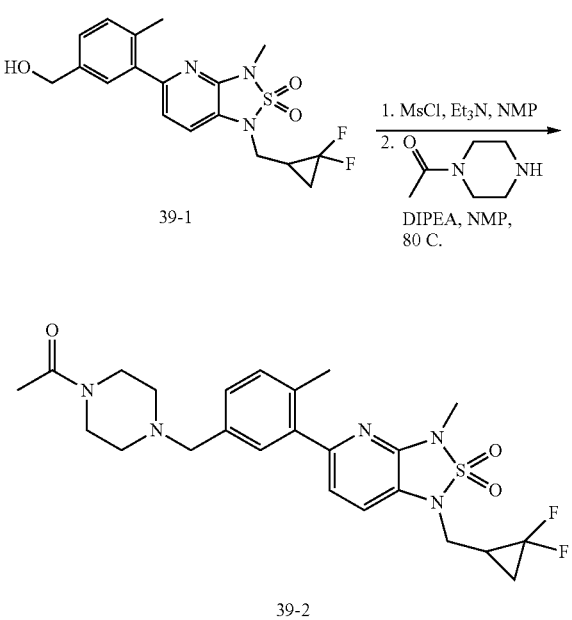

(3-{1-[(2,2-difluorocyclopropyl)methyl]-3-methyl-2,2-dioxido-1,3 dihydro[1,2,5]thiadiazolo[3,4-b]pyridin-5-yl}-4-methylphenyl)methanol (39-1)

Methyl 3-{1-[(2,2-difluorocyclopropyl)methyl]-3-methyl-2,2-dioxido-1,3-dihydro[1,2,5]thiadiazolo[3,4-b]pyridin-5-yl}-4-methylbenzoate (38-1) (8.0 g, 18.9 mmol, 1.0 eq) dissolved in THF (100 mL) and cooled to −78° C. DIBAL-H (60.0 mL, 60.0 mmol, 3.2 eq, 1.0 M in heptane) was added and the mixture was stirred at the same temperature. After 10 minutes the reaction was carefully quenched by an addition of Rochelle's Salt (15 mL) and stirred for 3 hours warming to ambient temperature. The mixture was extracted with EtOAc (300 mL), washed with water (2×50 mL) and brine (50 mL), dried over MgSO₄, filtered and concentrated to afford (3-{1-[(2,2-difluorocyclopropyl)methyl]-3-methyl-2,2-dioxido-1,3-dihydro[1,2,5]thiadiazolo[3,4-b]pyridin-5-yl}-4-methylphenyl)methanol (39-1) as a tan solid. No further purification was necessary. HRMS m/z (M+H) 396.1188 found, 396.1188 required.

1-[4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazin-1-yl]ethanone (39-2)

(3-{1-[(2,2-difluorocyclopropyl)methyl]-3-methyl-2,2-dioxido-1,3-dihydro[1,2,5]thiadiazolo[3,4-b]pyridin-5-yl}-4-methylphenyl)methanol (39-1) (7.3 g, 18.4 mmol, 1.0 eq) was dissolved in NMP (90 mL) and triethylamine (7.7 mL, 55.2 mmol, 3.0 eq) was added followed by mesyl chloride (1.6 mL, 20.3 mmol, 1.1 eq). After 20 minutes, 1-acetylpiperazine (3.3 g, 25.7 mmol, 2.0 eq) and DIPEA (9.0 mL, 51.3 mmol, 3.0 eq) were added. The resulting mixture stirred at 80° C. for 2 hours minutes. The mixture was cooled, diluted with EtOAc (300 mL), washed with sodium bicarbonate (50 mL), water (6×50 mL) and brine (50 mL), dried over MgSO$_4$, filtered and concentrated. The crude residue was purified by flash chromatography (330 g SiO$_2$, 0-20% IPA in DCM) to afford 1-[4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazin-1-yl]ethanone (39-2) as an off-white solid. $^1$H NMR (400 MHz, CD$_3$OD): δ 7.36 (d, J=8.0 Hz, 1 H); 7.35 (s, 1 H); 7.25 (s, 2 H); 7.08 (d, J=8.0 Hz, 1 H); 3.97 (d, J=6.8 Hz, 2 H); 3.56 (s, 2 H); 3.54 (dt, J=5.2, 20.4 Hz, 4 H); 3.38 (s, 3 H); 2.46 (dt, J=5.2, 18.8 Hz, 4 H); 2.35 (s, 3 H); 2.21 (m, 1 H); 2.07 (s, 3 H); 1.67 (m, 1 H); 1.43 (m, 1 H). HRMS m/z (M+H) 506.2029 found, 506.2032 required.

TABLE 17

The following compounds were prepared by a reaction sequence analogous to that illustrated in Scheme 39.

| Cmpd | Structure | IUPAC Name | Exact Mass [M + H]+ |
| --- | --- | --- | --- |
| 39-3 | 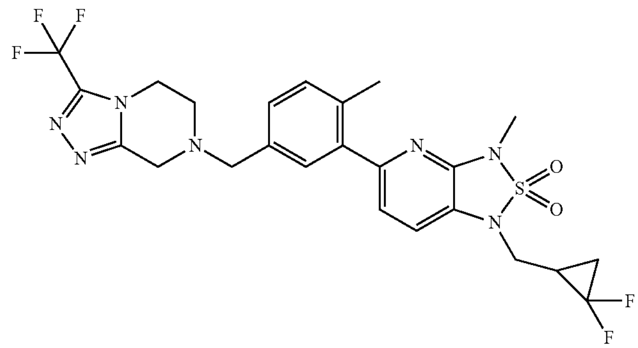 [SMILES: Cc1ccc(CN2CCn3c(nnc3C(F)(F)F)C2)cc1-c1ccc2c(n1)N(C)S(=O)(=O)N2CC1CC1(F)F] | 1-[(2,2-difluorocyclopropyl)methyl]-3-methyl-5-(2-methyl-5-{[3-trifluoromethyl)-5,6-dihydro[1,2,4]triazolo[4,3-a]pyrazin-7(8H)-yl]methyl}phenyl)-1,3-dihydro[1,2,5]thiadiazolo[3,4-b]pyridine 2,2-dioxide | Calc'd 570.1705, found 570.1694 |
| 39-4 | 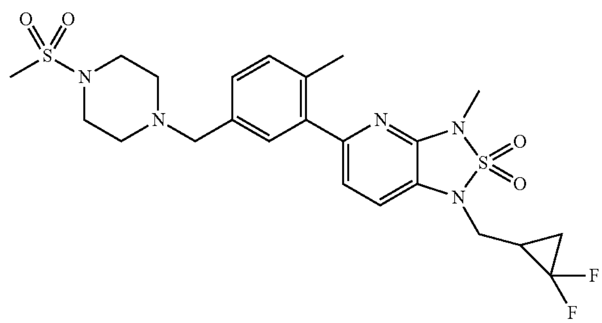 [SMILES: Cc1ccc(CN2CCN(S(C)(=O)=O)CC2)cc1-c1ccc2c(n1)N(C)S(=O)(=O)N2CC1CC1(F)F] | 1-[(2,2-difluorocyclopropyl)methyl]-3-methyl-5-(2-methyl-5-{[4-(methylsulfonyl)piperazin-1-yl]methyl}phenyl)-1,3-dihydro[1,2,5]thiadiazolo[3,4-b]pyridine 2,2-dioxide | Calc'd 542.1702, found 542.1695 |
| 39-5 | 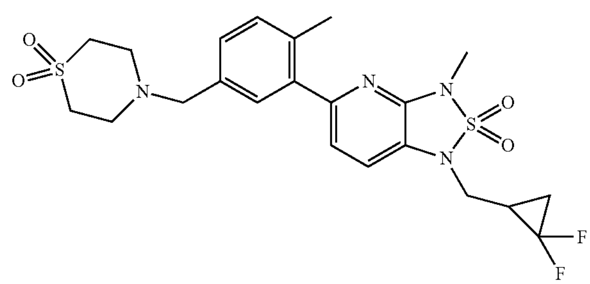 [SMILES: Cc1ccc(CN2CCS(=O)(=O)CC2)cc1-c1ccc2c(n1)N(C)S(=O)(=O)N2CC1CC1(F)F] | 1-[(2,2-difluorocyclopropyl)methyl]-5-{5-[(1,1-dioxidothiomorpholin-4-yl)methyl]-2-methylphenyl}-3-methyl-1,3-dihydro[1,2,5]thiadiazolo[3,4-b]pyridine 2,2-dioxide | Calc'd 513.1436, found 513.1427 |
| 39-6 | 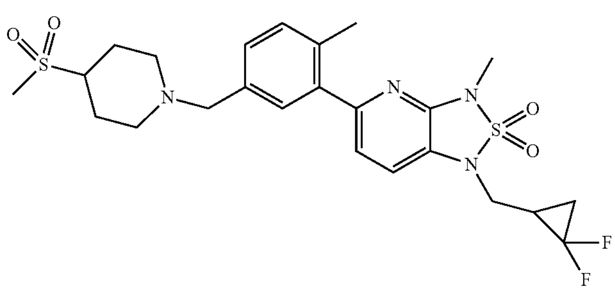 [SMILES: Cc1ccc(CN2CCC(S(C)(=O)=O)CC2)cc1-c1ccc2c(n1)N(C)S(=O)(=O)N2CC1CC1(F)F] | 1-[(2,2-difluorocyclopropyl)methyl]-3-methyl-5-(2-methyl-5-{[4-(methylsulfonyl)piperidin-1-yl]methyl}phenyl)-1,3-dihydro[1,2,5]thiadiazolo[3,4-b]pyridine 2,2-dioxide | Calc'd 541.1749, found 541.1737 |

TABLE 17-continued

The following compounds were prepared by a reaction sequence analogous to that illustrated in Scheme 39.

| Cmpd | Structure | IUPAC Name | Exact Mass [M + H]+ |
|---|---|---|---|
| 39-7 | 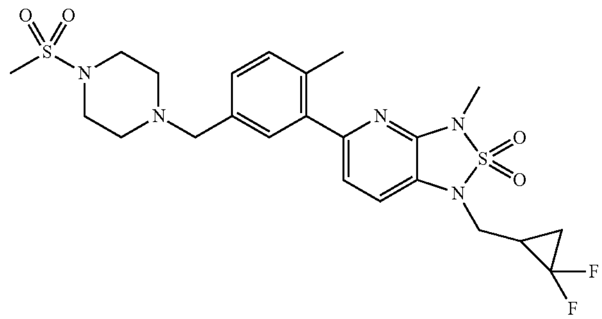 [SMILES: Cc1ccc(CN2CCN(S(C)(=O)=O)CC2)cc1-c1ccc2c(n1)N(C)S(=O)(=O)N2CC1CC1(F)F] | 1-[(2,2-difluorocyclopropyl)methyl]-3-methyl-5-(2-methyl-5-{[4-(methylsulfonyl)piperazin-1-yl]methyl}phenyl)-1,3-dihydro[1,2,5]thiadiazolo[3,4-b]pyridine 2,2-dioxide | Calc'd 542.1702, found 542.1693 |
| 39-8 | 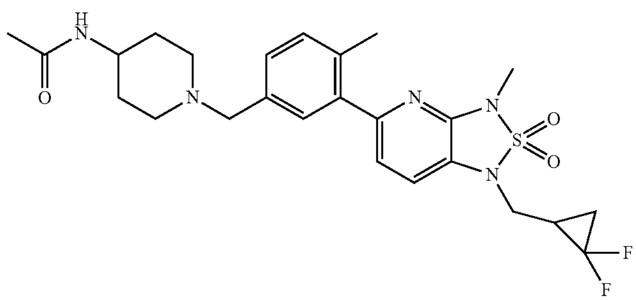 [SMILES: CC(=O)NC1CCN(Cc2ccc(C)c(-c3ccc4c(n3)N(C)S(=O)(=O)N4CC3CC3(F)F)c2)CC1] | N-[1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidin-4-yl]acetamide | Calc'd 520.2188, found 520.2191 |
| 39-9 | 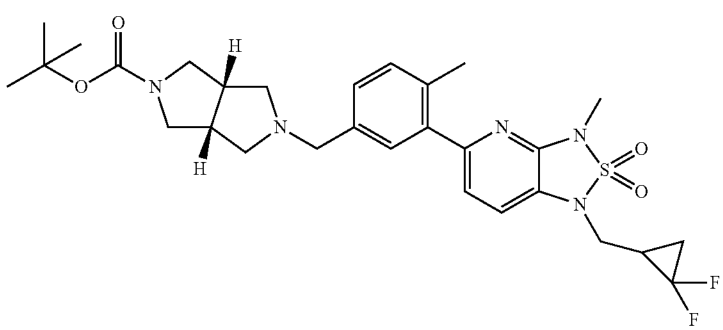 [SMILES: Cc1ccc(CN2C[C@@H]3CN(C(=O)OC(C)(C)C)C[C@@H]3C2)cc1-c1ccc2c(n1)N(C)S(=O)(=O)N2CC1CC1(F)F] | tert-butyl(3aR,6aS)-5-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)hexahydropyrrolo[3,4-c]pyrrole-2(1H)-carboxylate | Calc'd 590.2607, found 590.2605 |
| 39-10 | 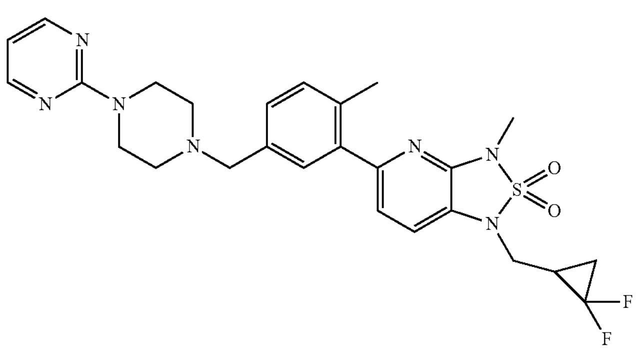 | 1-[(2,2-difluorocyclopropyl)methyl]-3-methyl-5-(2-methyl-5-{[4-(pyrimidin-2-yl)piperazin-1-yl]methyl}phenyl)-1,3-dihydro[1,2,5]thiadiazolo[3,4-b]pyridine 2,2-dioxide | Calc'd 542.2144, found 542.2136 |

TABLE 17-continued

The following compounds were prepared by a reaction sequence analogous to that illustrated in Scheme 39.

| Cmpd | Structure | IUPAC Name | Exact Mass [M + H]+ |
|---|---|---|---|
| 39-11 | 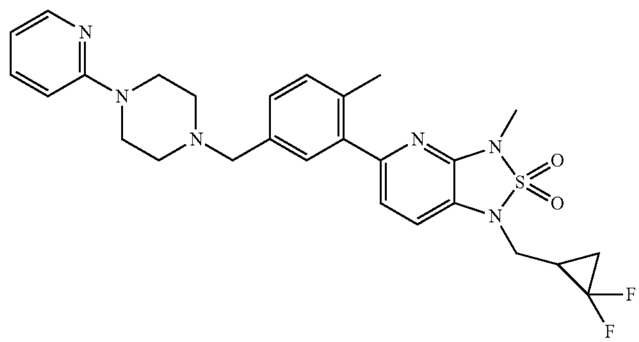 [SMILES: Cc1ccc(CN2CCN(c3ccccn3)CC2)cc1-c1ccc2c(n1)N(C)S(=O)(=O)N2CC1CC1(F)F] | 1-[(2,2-difluorocyclopropyl)methyl]-3-methyl-5-(2-methyl-5-{[4-(pyridin-2-yl)piperazin-1-yl]methyl}phenyl)-1,3-dihydro[1,2,5]thiadiazolo[3,4-b]pyridine 2,2-dioxide | Calc'd 541.2192, found 541.2185 |
| 39-12 | 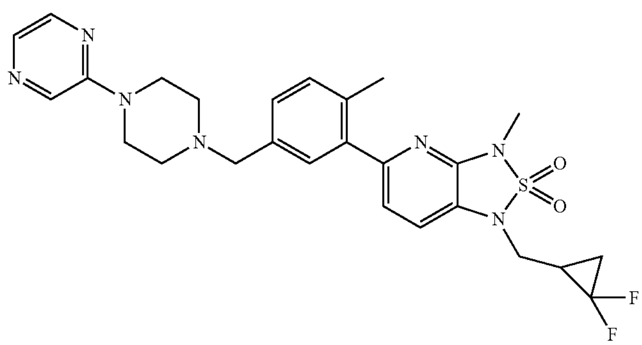 [SMILES: Cc1ccc(CN2CCN(c3cnccn3)CC2)cc1-c1ccc2c(n1)N(C)S(=O)(=O)N2CC1CC1(F)F] | 1-[(2,2-difluorocyclopropyl)methyl]-3-methyl-5-(2-methyl-5-{[4-(pyrazin-2-yl)piperazin-1-yl]methyl}phenyl)-1,3-dihydro[1,2,5]thiadiazolo[3,4-b]pyridine 2,2-dioxide | Calc'd 542.2144, found 542.2135 |
| 39-13 | 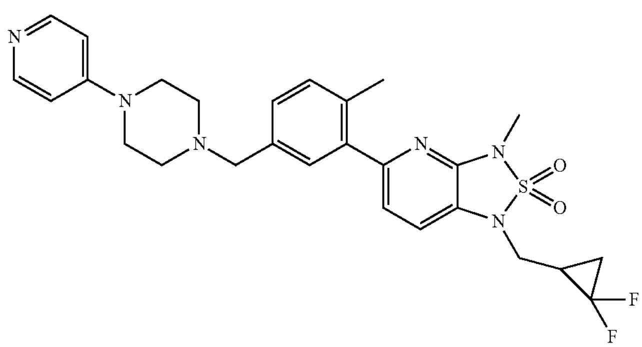 [SMILES: Cc1ccc(CN2CCN(c3ccncc3)CC2)cc1-c1ccc2c(n1)N(C)S(=O)(=O)N2CC1CC1(F)F] | 1-[(2,2-difluorocyclopropyl)methyl]-3-methyl-5-(2-methyl-5-{[4-(pyridin-4-yl)piperazin-1-yl]methyl}phenyl)-1,3-dihydro[1,2,5]thiadiazolo[3,4-b]pyridine 2,2-dioxide | Calc'd 540.6, found 540.2 |
| 39-14 | 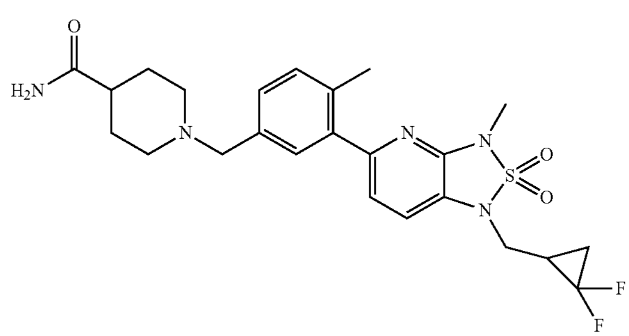 [SMILES: Cc1ccc(CN2CCC(C(N)=O)CC2)cc1-c1ccc2c(n1)N(C)S(=O)(=O)N2CC1CC1(F)F] | 1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidine-4-carboxamide | Calc'd 506.2032, found 506.2027 |

TABLE 17-continued

The following compounds were prepared by a reaction sequence analogous to that illustrated in Scheme 39.

| Cmpd | Structure | IUPAC Name | Exact Mass [M + H]+ |
|---|---|---|---|
| 39-15 | 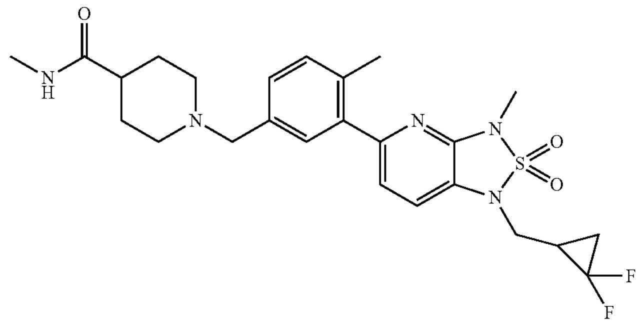 [SMILES: CNC(=O)C1CCN(Cc2ccc(C)c(-c3ccc4c(n3)N(C)S(=O)(=O)N4CC3CC3(F)F)c2)CC1] | 1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-N-methylpiperidine-4-carboxamide | Calc'd 520.2188, found 520.2183 |
| 39-16 | 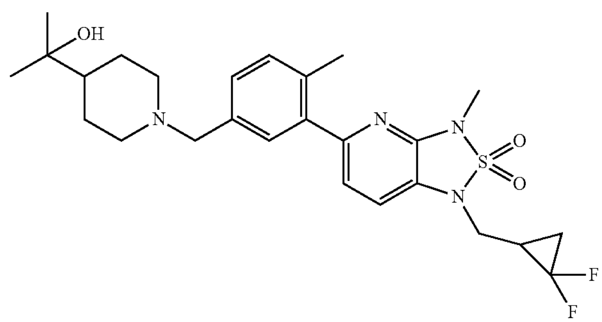 [SMILES: Cc1ccc(CN2CCC(C(C)(C)O)CC2)cc1-c1ccc2c(n1)N(C)S(=O)(=O)N2CC1CC1(F)F] | 2-[1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidin-4-yl]propan-2-ol | Calc'd 521.2392, found 521.2398 |
| 39-17 | 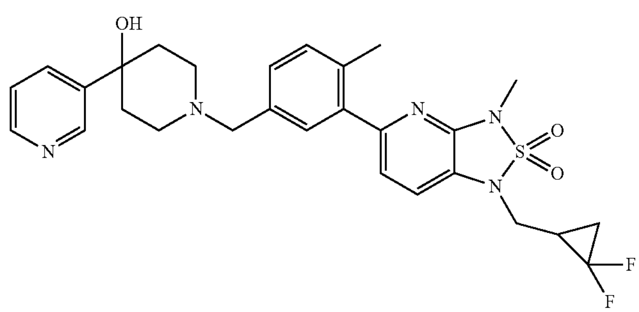 [SMILES: Cc1ccc(CN2CCC(O)(c3cccnc3)CC2)cc1-c1ccc2c(n1)N(C)S(=O)(=O)N2CC1CC1(F)F] | 1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-4-(pyridin-3-yl)piperidin-4-ol | Calc'd 556.2188, found 556.2185 |
| 39-18 | 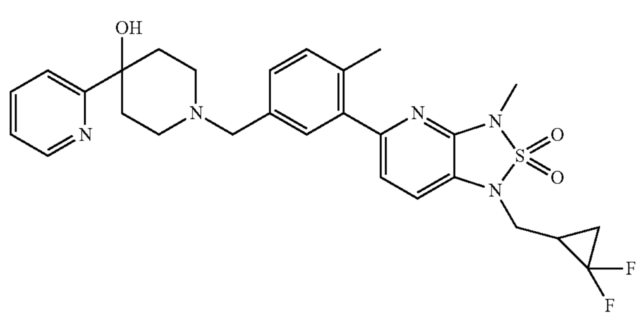 [SMILES: Cc1ccc(CN2CCC(O)(c3ccccn3)CC2)cc1-c1ccc2c(n1)N(C)S(=O)(=O)N2CC1CC1(F)F] | 1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-4-(pyridin-2-yl)piperidin-4-ol | Calc'd 556.2188, found 556.2184 |

TABLE 17-continued

The following compounds were prepared by a reaction sequence analogous to that illustrated in Scheme 39.

| Cmpd | Structure | IUPAC Name | Exact Mass [M + H]+ |
|---|---|---|---|
| 39-19 | 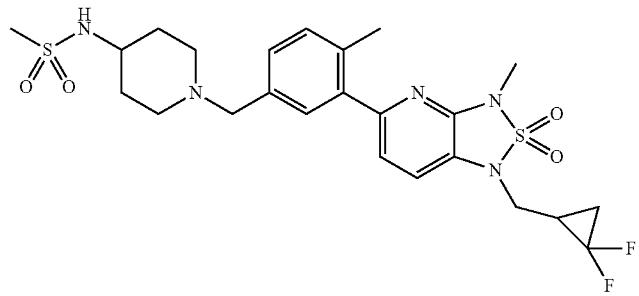 [SMILES: Cc1ccc(CN2CCC(NS(C)(=O)=O)CC2)cc1-c1ccc2c(n1)N(C)S(=O)(=O)N2CC1CC1(F)F] | N-[1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidin-4-yl]methanesulfonamide | Calc'd 556.1858, found 556.1854 |
| 39-20 | 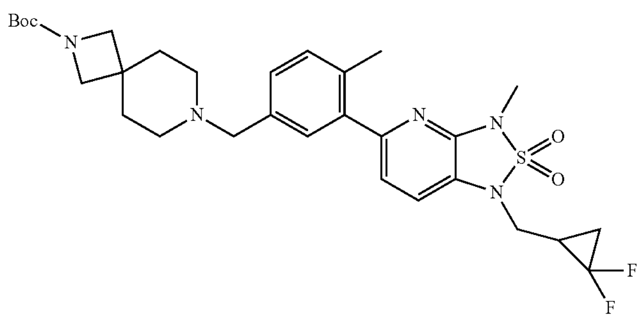 [SMILES: Cc1ccc(CN2CCC3(CC2)CN(C(=O)OC(C)(C)C)C3)cc1-c1ccc2c(n1)N(C)S(=O)(=O)N2CC1CC1(F)F] | tert-butyl 7-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-2,7-diazaspiro[3.5]nonane-2-carboxylate | Calc'd 604.2764, found 604.2756 |
| 39-21 | 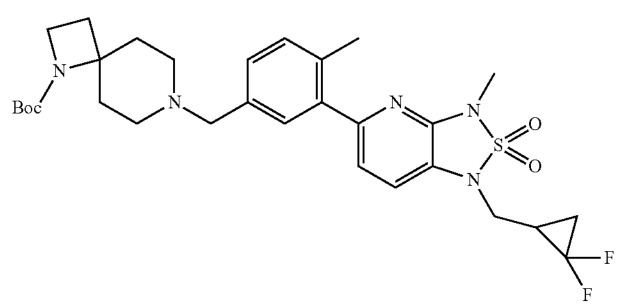 [SMILES: Cc1ccc(CN2CCC3(CC2)CCN3C(=O)OC(C)(C)C)cc1-c1ccc2c(n1)N(C)S(=O)(=O)N2CC1CC1(F)F] | tert-butyl 7-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-1,7-diazaspiro[3.5]nonane-1-carboxylate | Calc'd 604.2764, found 604.2765 |
| 39-22 | 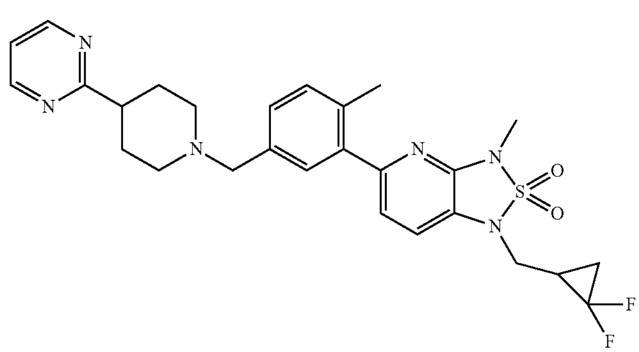 [SMILES: Cc1ccc(CN2CCC(c3ncccn3)CC2)cc1-c1ccc2c(n1)N(C)S(=O)(=O)N2CC1CC1(F)F] | 1-[(2,2-difluorocyclopropyl)methyl]-3-methyl-5-(2-methyl-5-{[4-(pyrimidin-2-yl)piperidin-1-yl]methyl}phenyl)-1,3-dihydro[1,2,5]thiadiazolo[3,4-b]pyridine 2,2-dioxide | Calc'd 541.2192, found 541.2184 |

TABLE 17-continued

The following compounds were prepared by a reaction sequence analogous to that illustrated in Scheme 39.

| Cmpd | Structure | IUPAC Name | Exact Mass [M + H]+ |
|---|---|---|---|
| 39-23 | 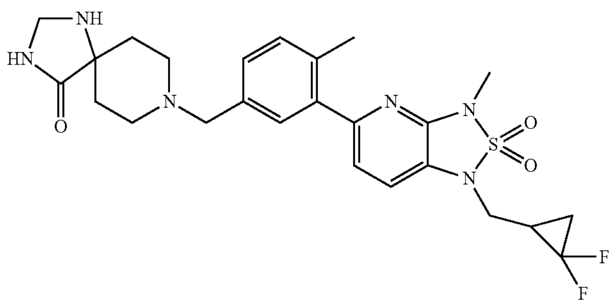 [SMILES: Cc1ccc(CN2CCC3(CC2)NCNC3=O)cc1-c1ccc2c(n1)N(C)S(=O)(=O)N2CC1CC1(F)F] | 8-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-1,3,8-triazaspiro[4.5]decan-4-one | Calc'd 533.2141, found 533.2135 |
| 39-24 | 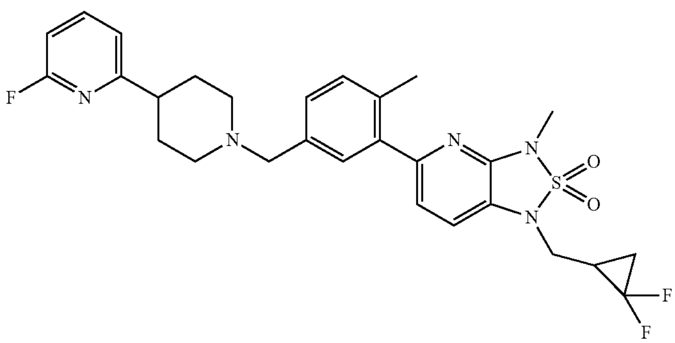 [SMILES: Cc1ccc(CN2CCC(c3cccc(F)n3)CC2)cc1-c1ccc2c(n1)N(C)S(=O)(=O)N2CC1CC1(F)F] | 1-[(2,2-difluorocyclopropyl)methyl]-5-(5-{[4-(6-fluoropyridin-2-yl)piperidin-1-yl]methyl}-2-methylphenyl)-3-methyl-1,3-dihydro[1,2,5]thiadiazolo[3,4-b]pyridine 2,2-dioxide | Calc'd 558.2145, found 558.2142 |
| 39-25 | 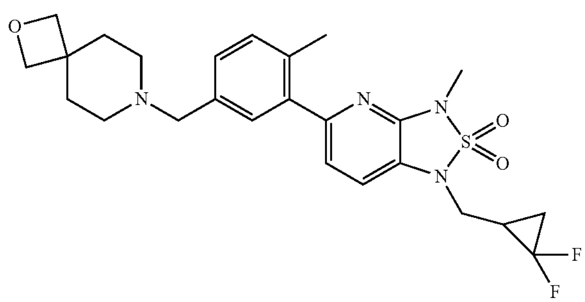 [SMILES: Cc1ccc(CN2CCC3(CC2)COC3)cc1-c1ccc2c(n1)N(C)S(=O)(=O)N2CC1CC1(F)F] | 1-[(2,2-difluorocyclopropyl)methyl]-3-methyl-5-[2-methyl-5-(2-oxa-7-azaspiro[3.5]non-7-ylmethyl)phenyl]-1,3-dihydro[1,2,5]thiadiazolo[3,4-b]pyridine 2,2-dioxide | Calc'd 505.2079, found 505.2070 |
| 39-26 | 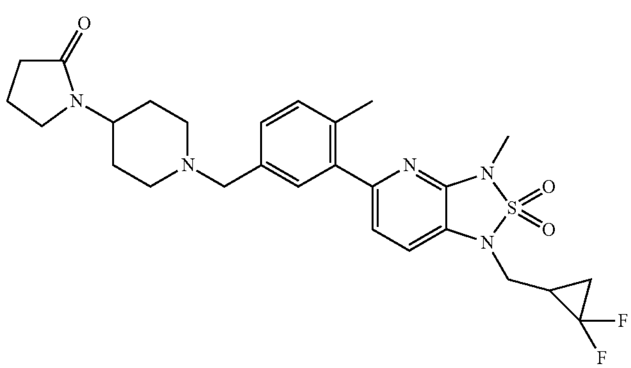 [SMILES: Cc1ccc(CN2CCC(N3CCCC3=O)CC2)cc1-c1ccc2c(n1)N(C)S(=O)(=O)N2CC1CC1(F)F] | 1-[1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidin-4-yl]pyrrolidin-2-one | Calc'd 546.2345, found 546.2339 |

TABLE 17-continued

The following compounds were prepared by a reaction sequence analogous to that illustrated in Scheme 39.

| Cmpd | Structure | IUPAC Name | Exact Mass [M + H]+ |
|---|---|---|---|
| 39-27 | 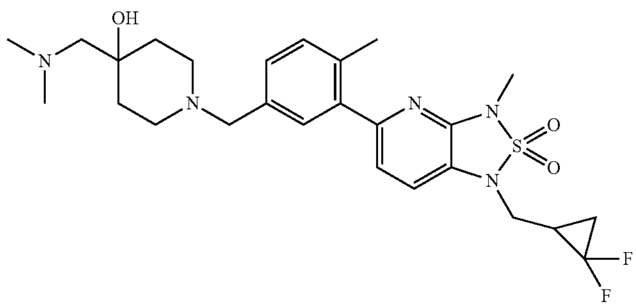 [SMILES: Cc1ccc(CN2CCC(O)(CN(C)C)CC2)cc1-c1ccc2c(n1)N(C)S(=O)(=O)N2CC1CC1(F)F] | 1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-4-[(dimethylamino)methyl]piperidin-4-ol | Calc'd 536.2501, found 536.2498 |
| 39-28 | 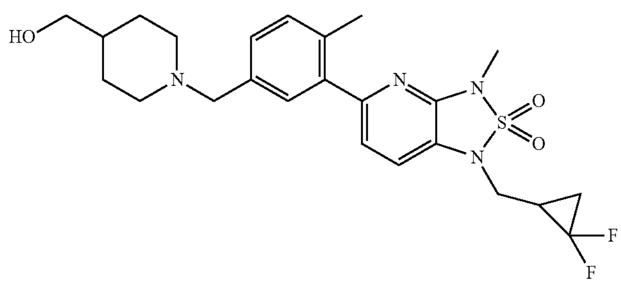 [SMILES: Cc1ccc(CN2CCC(CO)CC2)cc1-c1ccc2c(n1)N(C)S(=O)(=O)N2CC1CC1(F)F] | [1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidin-4-yl]methanol | Calc'd 493.2079, found 493.2073 |
| 39-29 | 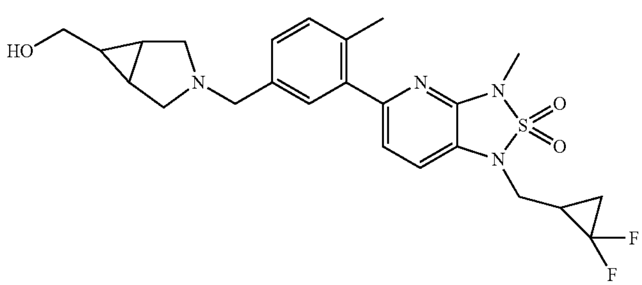 [SMILES: Cc1ccc(CN2CC3C(CO)C3C2)cc1-c1ccc2c(n1)N(C)S(=O)(=O)N2CC1CC1(F)F] | [3-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-3-azabicyclo[3.1.0]hex6-yl]methanol | Calc'd 491.1923, found 491.1929 |
| 39-30 | 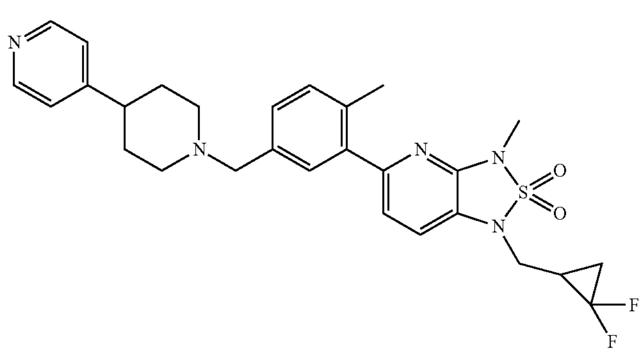 [SMILES: Cc1ccc(CN2CCC(c3ccncc3)CC2)cc1-c1ccc2c(n1)N(C)S(=O)(=O)N2CC1CC1(F)F] | 1-[(2,2-difluorocyclopropyl)methyl]-3-methyl-5-(2-methyl-5-{[4-(pyridin-4-yl)piperidin-1-yl]methyl}phenyl)-1,3-dihydro[1,2,5]thiadiazolo[3,4-b]pyridine 2,2-dioxide | Calc'd 540.2239, found 540.2235 |

TABLE 17-continued

The following compounds were prepared by a reaction sequence analogous to that illustrated in Scheme 39.

| Cmpd | Structure | IUPAC Name | Exact Mass [M + H]+ |
|---|---|---|---|
| 39-31 | 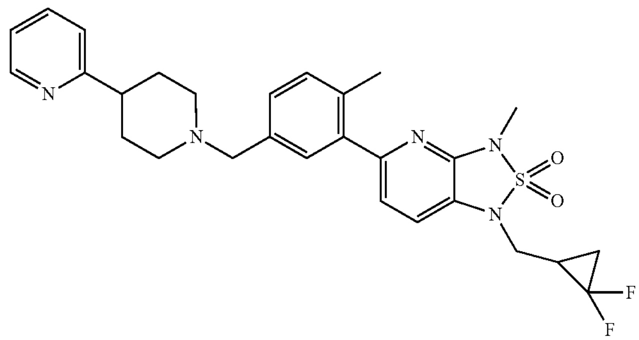 [SMILES: Cc1ccc(CN2CCC(c3ccccn3)CC2)cc1-c1ccc2c(n1)N(C)S(=O)(=O)N2CC1CC1(F)F] | 1-[(2,2-difluorocyclopropyl)methyl]-3-methyl-5-(2-methyl-5-{[4-(pyridin-2-yl)piperidin-1-yl]methyl}phenyl)-1,3-dihydro[1,2,5]thiadiazolo[3,4-b]pyridine 2,2-dioxide | Calc'd 540.2239, found 540.2234 |
| 39-32 | 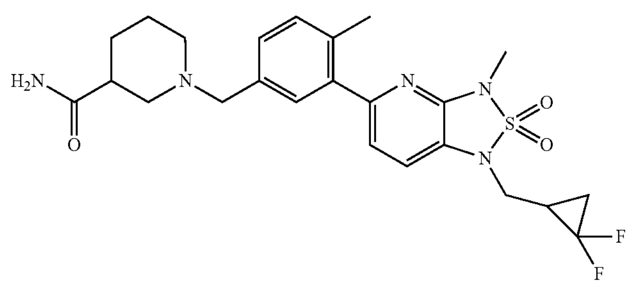 [SMILES: Cc1ccc(CN2CCCC(C(N)=O)C2)cc1-c1ccc2c(n1)N(C)S(=O)(=O)N2CC1CC1(F)F] | 1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidine-3-carboxamide | Calc'd 506.2032, found 506.2032 |
| 39-33 | 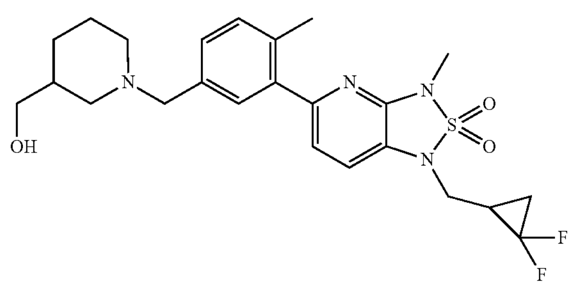 [SMILES: Cc1ccc(CN2CCCC(CO)C2)cc1-c1ccc2c(n1)N(C)S(=O)(=O)N2CC1CC1(F)F] | [1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidin-3-yl]methanol | Calc'd 493.2079, found 493.2075 |
| 39-34 | 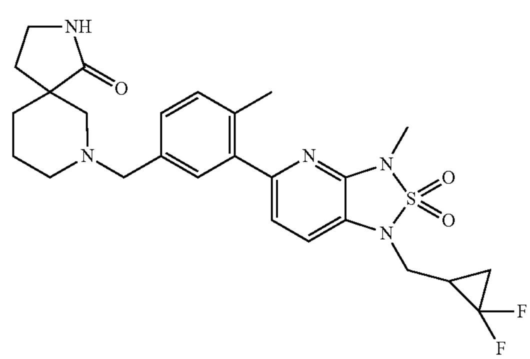 [SMILES: Cc1ccc(CN2CCCC3(CCNC3=O)C2)cc1-c1ccc2c(n1)N(C)S(=O)(=O)N2CC1CC1(F)F] | 7-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-2,7-diazaspiro[4.5]decan-1-one | Calc'd 532.2188, found 532.2182 |

TABLE 17-continued

The following compounds were prepared by a reaction sequence analogous to that illustrated in Scheme 39.

| Cmpd | Structure | IUPAC Name | Exact Mass [M + H]+ |
|---|---|---|---|
| 39-35 | 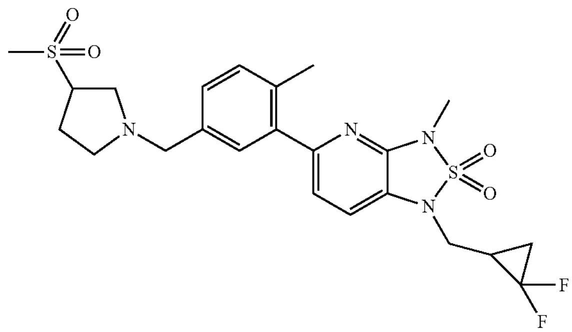 [SMILES: Cc1ccc(CN2CCC(S(C)(=O)=O)C2)cc1-c1ccc2c(n1)N(C)S(=O)(=O)N2CC1CC1(F)F] | 1-[(2,2-difluorocyclopropyl)methyl]-3-methyl-5-(2-methyl-5-{[3-(methylsulfonyl)pyrrolidin-1-yl]methyl}phenyl)-1,3-dihydro[1,2,5]thiadiazolo[3,4-b]pyridine 2,2-dioxide | Calc'd 527.1593, found 527.1588 |
| 39-36 | 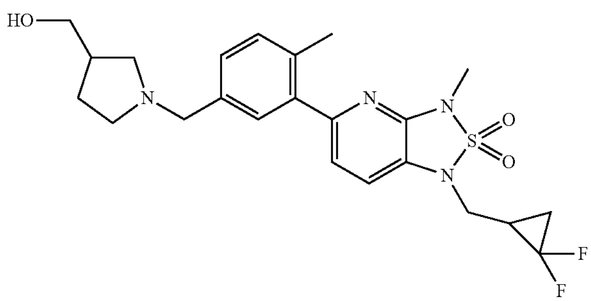 [SMILES: Cc1ccc(CN2CCC(CO)C2)cc1-c1ccc2c(n1)N(C)S(=O)(=O)N2CC1CC1(F)F] | [1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)pyrrolidin-3-yl]methanol | Calc'd 479.1923, found 479.1925 |
| 39-37 | 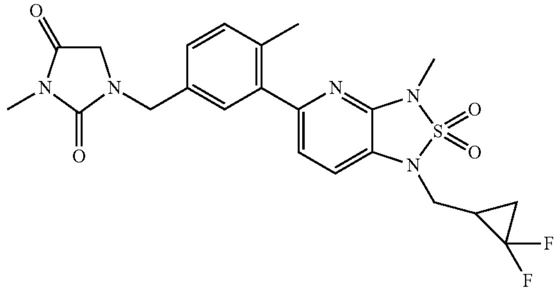 [SMILES: Cc1ccc(CN2CC(=O)N(C)C2=O)cc1-c1ccc2c(n1)N(C)S(=O)(=O)N2CC1CC1(F)F] | 1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-3-methylimidazolidine-2,4-dione | Calc'd 492.1512, found 492.1504 |

SCHEME 40

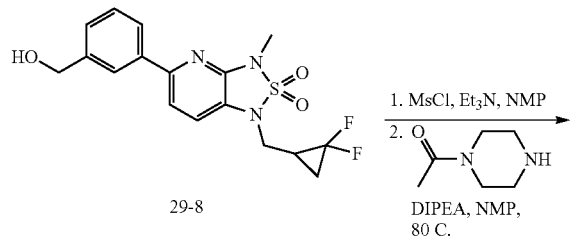

SCHEME 41

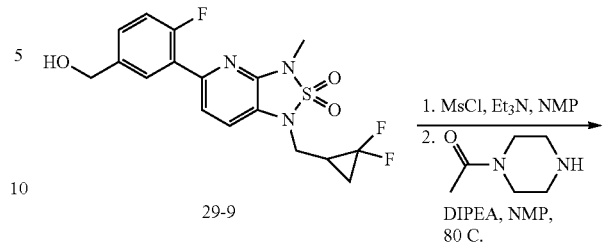

1-[4-(3-{1-[(2,2-difluorocyclopropyl)methyl]-3-methyl-2,2-dioxido-1,3-dihydro[1,2,5]thiadiazolo[3,4-b]pyridin-5-yl}benzyl)piperazin-1-yl]ethanone (40-1)

Prepared from 29-8 according to the procedures reported in Scheme 39. HRMS m/z (M+H) 492.1878 found, 492.1875 required.

1-[4-(3-{1-[(2,2-difluorocyclopropyl)methyl]-3-methyl-2,2-dioxido-1,3-dihydro[1,2,5]thiadiazolo[3,4-b]pyridin-5-yl}-4-fluorobenzyl)piperazin-1-yl]ethanone (41-1)

Prepared from 29-9 according to the procedures reported in Scheme 39. HRMS m/z (M+H) 510.1778 found, 510.1781 required.

TABLE 18

The following compounds were prepared by a reaction sequence analogous to that illustrated in Scheme 39.

| Cmpd | Structure | IUPAC Name | Exact Mass [M + H]+ |
|---|---|---|---|
| 40-2 | 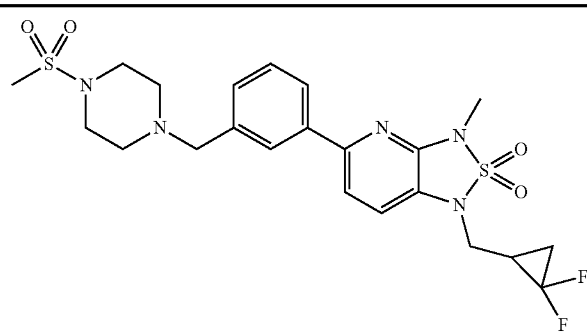 | 1-[(2,2-difluorocyclopropyl)methyl]-3-methyl-5-(3-{[4-(methylsulfonyl)piperazin-1-yl]methyl}phenyl)-1,3-dihydro[1,2,5]thiadiazolo[3,4-b]pyridine 2,2-dioxide | Calc'd 528.1545, found 528.1547 |

TABLE 19

The following compounds were prepared by a reaction sequence analogous to that illustrated in Scheme 39.

| Cmpd | Structure | IUPAC Name | Exact Mass [M + H]+ |
|---|---|---|---|
| 41-2 | 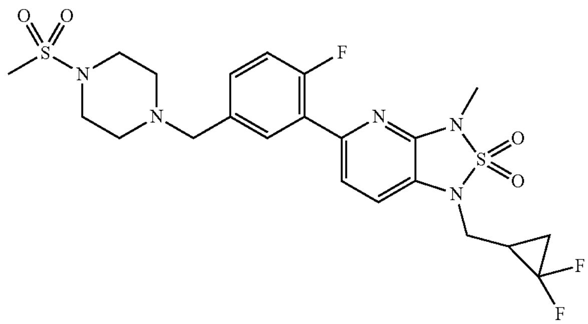 [SMILES: CN1c2nc(-c3cc(CN4CCN(S(C)(=O)=O)CC4)ccc3F)ccc2N(CC2CC2(F)F)S1(=O)=O] | 1-[(2,2-difluorocyclopropyl)methyl]-5-(2-fluoro-5-{[4-(methylsulfonyl)piperazin-1-yl]methyl}phenyl)-3-methyl-1,3-dihydro[1,2,5]thiadiazolo[3,4-b]pyridine 2,2-dioxide | Calc'd 546.1451, found 546.1455 |

SCHEME 42

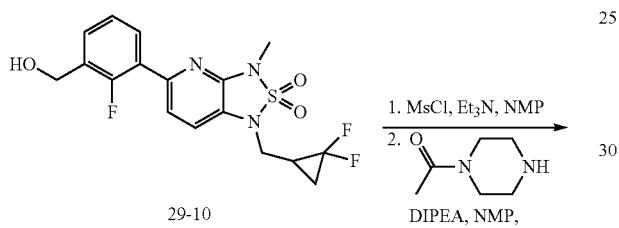

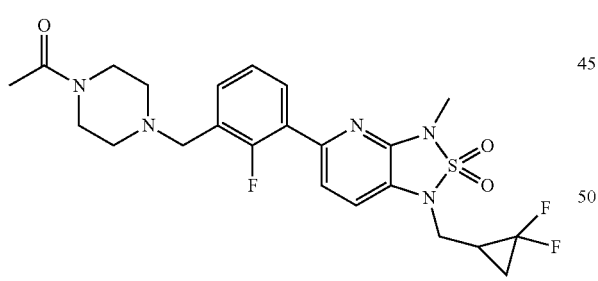

1-[4-(3-{1-[(2,2-difluorocyclopropyl)methyl]-3-methyl-2,2-dioxido-1,3-dihydro[1,2,5]thiadiazolo[3,4-b]pyridin-5-yl}-2-fluorobenzyl)piperazin-1-yl]ethanone (42-1)

Prepared from 29-10 according to the procedures reported in Scheme 39. HRMS m/z (M+H) 510.1776 found, 510.1781 required.

TABLE 20

The following compounds were prepared by a reaction sequence analogous to that illustrated in Scheme 39.

| Cmpd | Structure | IUPAC Name | Exact Mass [M + H]+ |
|---|---|---|---|
| 42-2 | 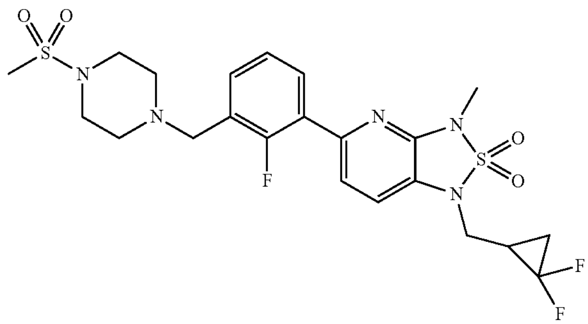 [SMILES: CN1c2nc(-c3cccc(CN4CCN(S(C)(=O)=O)CC4)c3F)ccc2N(CC2CC2(F)F)S1(=O)=O] | 1-[(2,2-difluorocyclopropyl)methyl]-5-(2-fluoro-3-{[4-(methylsulfonyl)piperazin-1-yl]methyl}phenyl)-3-methyl-1,3-dihydro[1,2,5]thiadiazolo[3,4-b]pyridine 2,2-dioxide | Calc'd 546.1451, found 546.1446 |
| 42-3 | 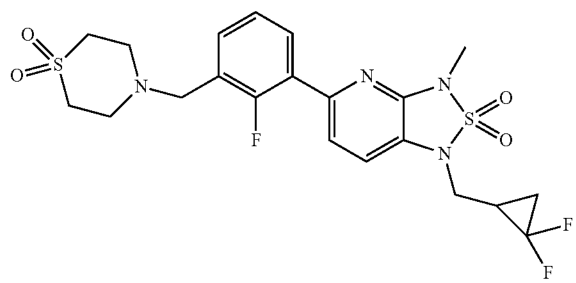 [SMILES: CN1c2nc(-c3cccc(CN4CCS(=O)(=O)CC4)c3F)ccc2N(CC2CC2(F)F)S1(=O)=O] | 1-[(2,2-difluorocyclopropyl)methyl]-5-{3-[(1,1-dioxidothiomorpholin-4-yl)methyl]-2-fluorophenyl}-3-methyl-1,3-dihydro[1,2,5]thiadiazolo[3,4-b]pyridine 2,2-dioxide | Calc'd 517.1186, found 517.1176 |
| 42-4 | 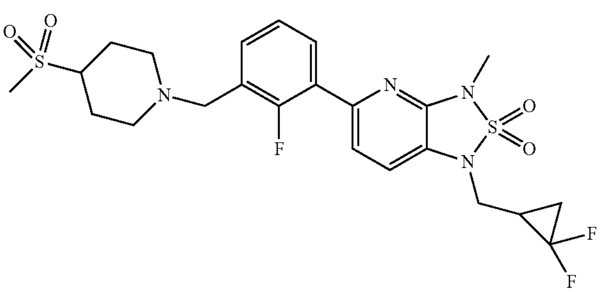 [SMILES: CN1c2nc(-c3cccc(CN4CCC(S(C)(=O)=O)CC4)c3F)ccc2N(CC2CC2(F)F)S1(=O)=O] | 1-[(2,2-difluoro-cyclopropyl)methyl]-5-(2-fluoro-3-{[4-(methylsulfonyl)piper-idin-1-yl]methyl}phenyl)-3-methyl-1,3-dihydro[1,2,5]thia-diazolo[3,4-b]pyridine 2,2-dioxide | Calc'd 545.1499, found 545.1487 |

SCHEME 43

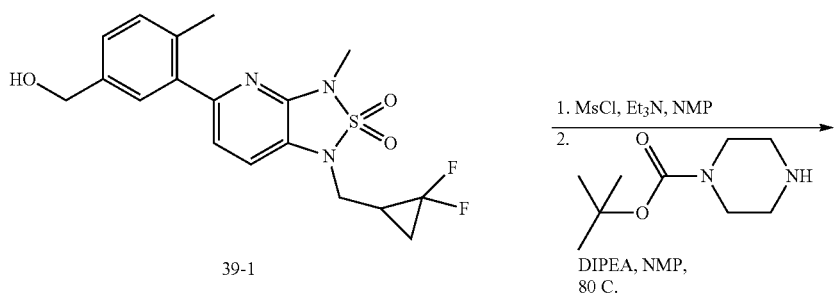

39-1

1. MsCl, Et₃N, NMP
2.

DIPEA, NMP, 80 C.

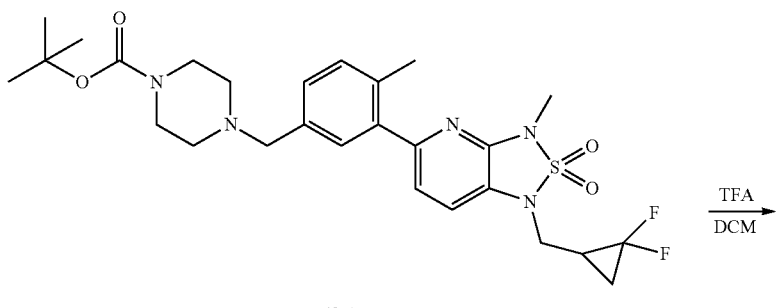

43-1

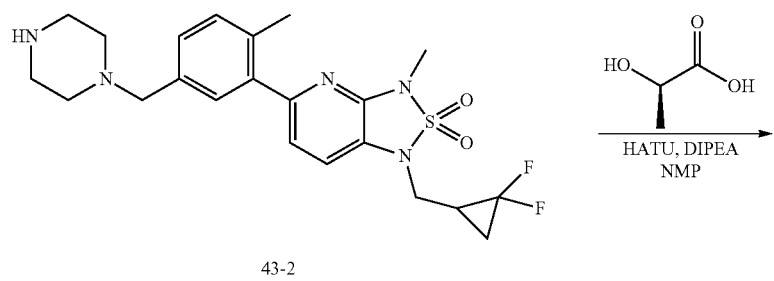

43-2

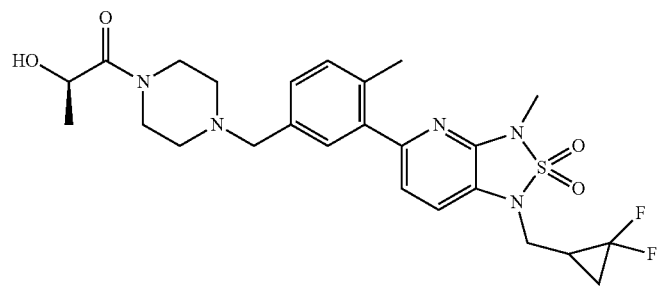

43-3

(2R)-1-[4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazin-1-yl]-2-hydroxypropan-1-one (43-3)

tert-butyl 4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazine-1-carboxylate (43-1)

(3-{1-[(2,2-difluorocyclopropyl)methyl]-3-methyl-2,2-dioxido-1,3-dihydro[1,2,5]thiadiazolo[3,4-b]pyridin-5-yl}-4-methylphenyl)methanol (39-1) (1.5 g, 3.8 mmol, 1.0 eq) was dissolved in NMP (19 mL) and triethylamine (1.6 mL, 11.4 mmol, 3.0 eq) was added followed by mesyl chloride (0.59 mL, 7.6 mmol, 2.0 eq). After 20 minutes, tert-butyl piperazine-1-carboxylate (1.8 g, 9.7 mmol, 3.0 eq) and DIPEA (2.8 mL, 16.2 mmol, 5.0 eq) were added. The resulting mixture stirred at 80° C. for 2 hours minutes. The mixture was cooled, diluted with EtOAc (200 mL), washed with sodium bicarbonate (50 mL), water (6×50 mL) and brine (50 mL), dried over MgSO$_4$, filtered and concentrated. The crude residue was purified by flash chromatography (330 g SiO$_2$, 0-80% EtOAc in hexanes) to afford tert-butyl 4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazine-1-carboxylate (43-1) as a tan solid. HRMS m/z (M+H) 564.2446 found, 564.2451 required.

1-[(2,2-difluorocyclopropyl)methyl]-3-methyl-5-[2-methyl-5-(piperazin-1-yl methyl)phenyl]-1,3-dihydro[1,2,5]thiadiazolo[3,4-b]pyridine 2,2-dioxide (43-2)

Tert-butyl 4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazine-1-carboxylate (43-1) (3.3 g, 5.7 mmol, 1.0 eq) was dissolved in DCM (40 mL) and TFA (4.4 mL, 56.7 mmol, 10 eq) was added and the reaction mixture stirred at ambient temperature for 45 minutes. Toluene (10 mL) was added and the reaction mixture was concentrated. The residue was dissolved in EtOAc (100 mL) and then washed with sodium bicarbonate (3×20 mL), water (20 mL) and brine (20 mL), dried over MgSO$_4$, filtered and concentrated to afford 1-[(2,2-difluorocyclopropyl)methyl]-3-methyl-5-[2-methyl-5-(piperazin-1-ylmethyl)phenyl]-1,3-dihydro[1,2,5]thiadiazolo[3,4-b]pyridine 2,2-dioxide (43-2) as a tan solid. No further purification was necessary. HRMS m/z (M+H) 463.1925 found, 463.1926 required.

washed with sodium bicarbonate (4×30 mL) and brine (30 mL), dried over MgSO$_4$, filtered and concentrated. The crude residue was purified by flash chromatography (120 g SiO$_2$, 0-40% IPA in DCM) to afford (2R)-1-[4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazin-1-yl]-2-hydroxypropan-1-one (43-3) as a white solid. $^1$H NMR (400 MHz, CD$_3$OD): δ 7.37 (d, J=8.4 Hz, 1 H); 7.35 (s, 1 H); 7.26 (s, 2 H); 7.08 (d, J=8.4 Hz, 1 H); 4.54 (q, J=6.8 Hz, 1 H); 3.98 (d, J=6.8 Hz, 2 H); 3.64 (m, 4 H); 3.57 (s, 2 H); 3.38 (s, 3 H); 2.49 (m, 4 H); 2.36 (s, 3 H); 2.21 (m, 1 H); 1.67 (m, 1 H); 1.43 (m, 1 H); 1.18 (d, J=6.8 Hz, 3 H). HRMS m/z (M+H) 536.2136 found, 536.2138 required.

TABLE 21

The following compounds were prepared by a reaction sequence analogous to that illustrated in Scheme 43.

| Cmpd | Structure | IUPAC Name | Exact Mass [M + H]+ |
|---|---|---|---|
| 43-4 | 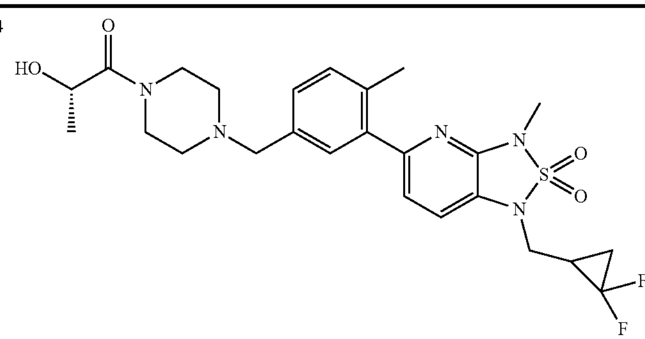 | (2S)-1-[4-(3-{1-[(2,2-difluorocyclopropyl)methyl]-3-methyl-2,2-dioxido-1,3-dihydro[1,2,5]thiadiazol[3,4-b]pyridin-5-yl}-4-methylbenzyl)piperazin-1-yl]-2-hydroxypropan-1-one | Calc'd 536.2138, found 536.2139 |
| 43-5 | 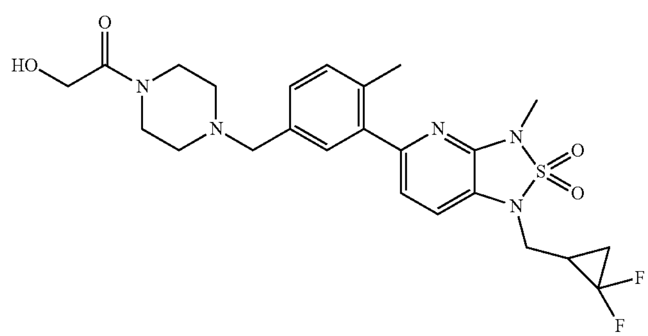 [SMILES: Cc1ccc(CN2CCN(C(=O)CO)CC2)cc1-c1ccc2c(n1)N(C)S(=O)(=O)N2CC1CC1(F)F] | 1-[4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazin-1-yl]-2-hydroxyethanone | Calc'd 522.1981, found 522.1974 |

(2R)-1-[4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazin-1-yl]-2-hydroxypropan-1-one (43-3)

1-[(2,2-difluorocyclopropyl)methyl]-3-methyl-5-[2-methyl-5-(piperazin-1-ylmethyl)phenyl]-1,3-dihydro[1,2,5]thiadiazolo[3,4-b]pyridine 2,2-dioxide (43-2) (2.3 g, 5.0 mmol, 1.0 eq) was dissolved in NMP (25 mL) and DIPEA (2.6 mL, 14.9 mmol, 3.0 eq), D-lactic acid (536 mg, 6.0 mmol, 1.2 eq) and HATU (2.8 g, 7.4 mmol, 1.5 eq) were added. The reaction mixture stirred at ambient temperature for 5 minutes and was then diluted with EtOAc (200 mL),

SCHEME 44

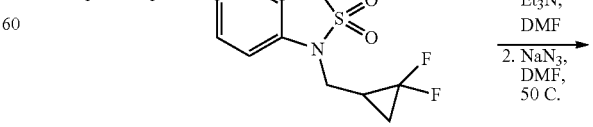

39-1

-continued

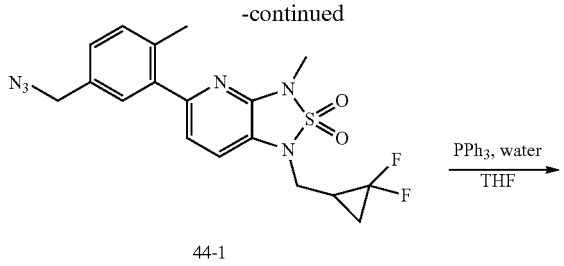

44-1

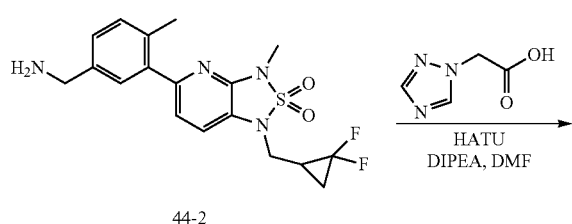

44-2

[Structure 44-3]

44-3

5-[5-(azidomethyl)-2-methylphenyl]-1-[(2,2-difluorocyclopropyl)methyl]-3-methyl-1,3-dihydro[1,2,5]thiadiazolo[3,4-b]pyridine 2,2-dioxide (44-1)

Prepared from 39-1 according to the procedures reported in Scheme 39. LRMS m/z (M+H) 421.0 found, 421.1 required.

1-(3-{1-[(2,2-difluorocyclopropyl)methyl]-3-methyl-2,2-dioxido-1,3-dihydro[1,2,5]thiadiazolo[3,4-b]pyridin-5-yl}-4-methylphenyl)methanamine (44-2)

To 5-[5-(azidomethyl)-2-methylphenyl]-1-[(2,2-difluorocyclopropyl)methyl]-3-methyl-1,3-dihydro[1,2,5]thiadiazolo[3,4-b]pyridine 2,2-dioxide (44-1) (480 mg, 1.1 mmol, 1.0 eq) in THF (6.7 mL) was added triphenylphosphine (600 mg, 2.3 mmol, 2.0 eq) followed by water (0.31 mL, 17.1 mmol, 15 eq). The reaction mixture stirred at ambient temperature overnight and was then diluted with EtOAc (100 mL), washed with sodium bicarbonate (4×10 mL) and brine (20 mL), dried over MgSO$_4$, filtered and concentrated. The crude residue was purified by flash chromatography (24 g SiO$_2$, 20-100% EtOAc in hexanes) to afford 1-(3-{1-[(2,2-difluorocyclopropyl)methyl]-3-methyl-2,2-dioxido-1,3-dihydro[1,2,5]thiadiazolo[3,4-b]pyridin-5-yl}-4-methylphenyl)methanamine (44-2). HRMS m/z (M+H) 395.1348 found, 395.1348 required.

N-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-2-(1H-1,2,4-triazol-1-yl)acetamide (44-3)

Prepared from 44-2 according to the procedures reported in Scheme 43. HRMS m/z (M+H) 504.1637 found, 504.1624 required.

TABLE 22

The following compound was prepared by a reaction sequence analogous to that illustrated in Scheme 44.

| Cmpd | Structure | IUPAC Name | Exact Mass [M + H]+ |
|---|---|---|---|
| 44-4 | [Structure] | (2R)-1-[4-(4-chloro-3-{1-(2R)-N-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-2-hydroxypropanamide | Calc'd 467.1553, found 467.1559 |

SCHEME 45

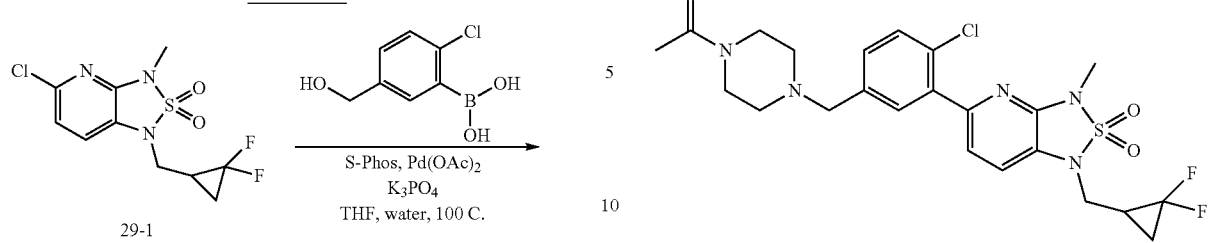

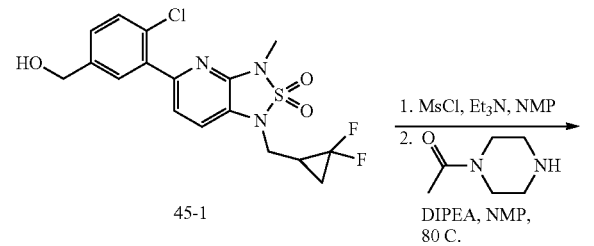

(4-chloro-3-{1-[2,2-difluorocyclopropyl)methyl]-3-methyl-2,2-dioxido-1,3-dihydro[1,2,5]thiadiazolo[3,4-b]pyridin-5-yl}phenyl)methanol (45-1)

Prepared from 29-1 according to the procedures reported in Scheme 38. HRMS m/z (M+H) 416.0647 found, 416.0642 required.

1-[4-(4-chloro-3-{1-[(2,2-difluorocyclopropyl)methyl]-3-methyl-2,2-dioxido-1,3-dihydro[1,2,5]thiadiazolo[3,4-b]pyridin-5-yl}benzyl)piperazin-1-yl]ethanone (45-2)

Prepared from 45-1 according to the procedures reported in Scheme 39. HRMS m/z (M+H) 526.1497 found, 526.1486 required.

TABLE 23

The following compound was prepared by a reaction sequence analogous to that illustrated in Scheme 45.

| Cmpd | Structure | IUPAC Name | Exact Mass [M + H]+ |
|---|---|---|---|
| 45-3 | 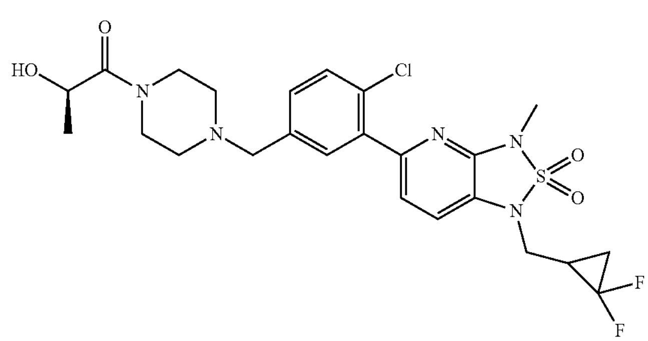 [SMILES: C[C@@H](O)C(=O)N1CCN(Cc2ccc(Cl)c(-c3ccc4c(n3)N(C)S(=O)(=O)N4CC3CC3(F)F)c2)CC1] | (2R)-1-[4-(4-chloro-3-{1-[(2,2-difluorocyclopropyl)methyl]-3-methyl-2,2-dioxido-1,3-dihydro[1,2,5]thiadiazolo[3,4-b]pyridin-5-yl}benzyl)piperazin-1-yl]-2-hydroxypropan-1-one | Calc'd 556.1591, found 556.1607 |

SCHEME 46
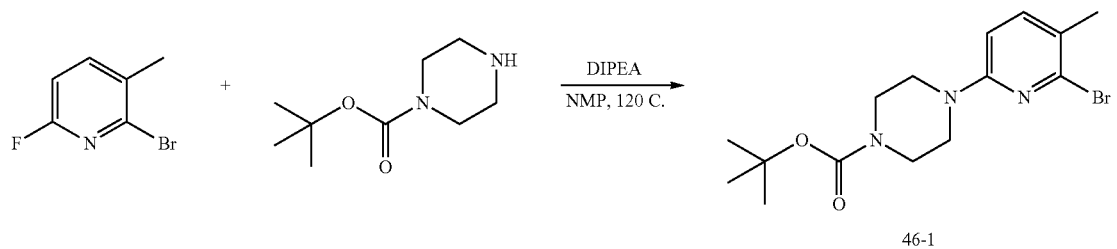
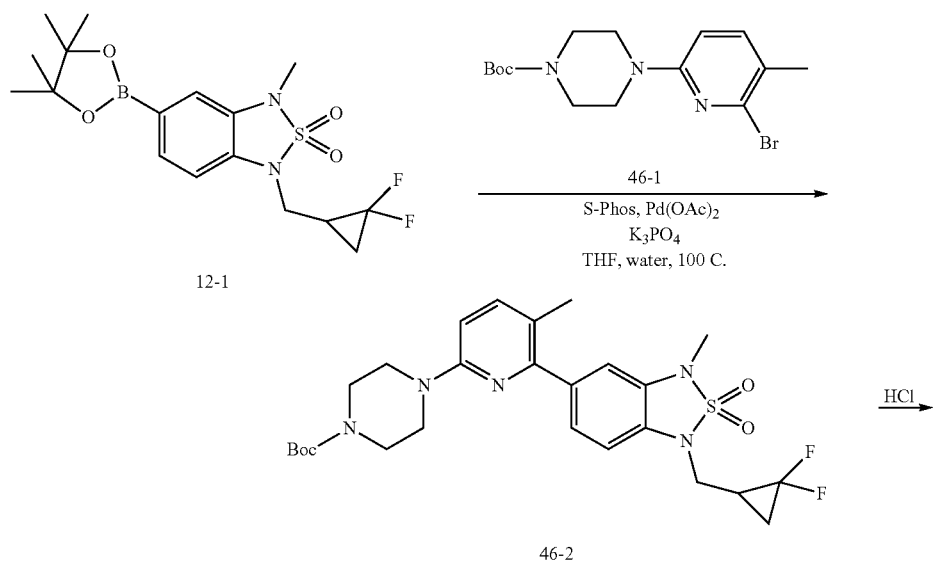
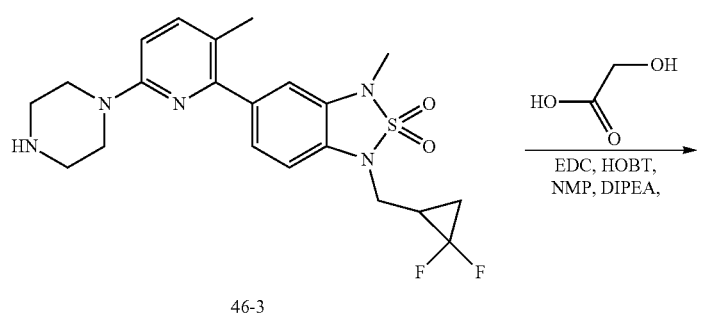
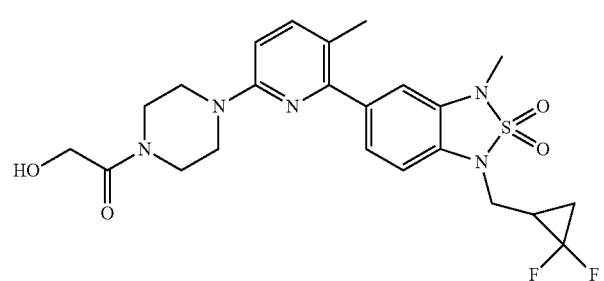

2-[4-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperazin-1-yl]-2-oxoethanol (46-4)

tert-butyl 4-(6-bromo-5-methylpyridin-2-yl)piperazine-1-carboxylate (46-1)

To microwave vial was added 2-bromo-6-fluoro-3-methylpyridine (1355 mg, 7.13 mmol), tert-butyl piperazine-1-carboxylate (1338 mg, 7.18 mmol), anhydrous NMP (3.5 mL), and DIPEA (1.65 ml, 9.45 mmol). The resulting mixture was heated at 120° C. for 16 hours. The reaction mixture was allowed to cool to room temperature. The mixture was then diluted with EtOAc (100 mL), washed with water (20 mL) and brine (20 mL), dried over sodium sulfate, filtered and concentrated. The crude residue was purified by flash chromatography (80 g $SiO_2$, 0-25% EtOAc in hexanes) to afford tert-butyl 4-(6-bromo-5-methylpyridin-2-yl)piperazine-1-carboxylate (46-1) as a waxy tan solid. HRMS m/z (M+H) 356.0971 measured, 356.0968 calculated.

tert-butyl 4-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperazine-1-carboxylate (46-2)

Prepared from 12-1 & 46-1 according to the procedures reported in Scheme 12. HRMS m/z (M+H) 550.2308 measured, 550.2294 calculated.

1-[(2,2-difluorocyclopropyl)methyl]-3-methyl-5-(3-methyl-6-piperazin-1-ylpyridin-2-yl)-1,3-dihydro-2,1,3-benzothiadiazole 2,2-dioxide (46-3)

Prepared from 46-2 according to the procedures reported in Scheme 23. HRMS m/z (M+H) 450.1774 measured, 450.1770 calculated.

2-[4-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperazin-1-yl]-2-oxoethanol (46-4)

Prepared from 46-3 according to the procedures reported in Scheme 23. HRMS m/z (M+H) 508.1834 measured, 508.1825 calculated.

TABLE 24

The following compounds were prepared by a reaction sequence analogous to that illustrated in Scheme 46, Scheme 21, Scheme 31, & Scheme 41.

| Cmpd | Structure | IUPAC Name | Exact Mass [M + H]+ |
|---|---|---|---|
| 46-5 | 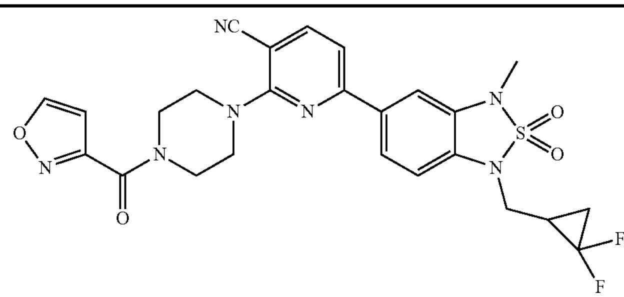 | 3-cyano-6-{1-[(2,2-difluorocyclopropyl)methyl]-3-methyl-2,2-dioxido-1,3-dihydro-2,1,3-benzothiadiazol-5-yl}-2-[4-(isoxazol-3-ylcarbonyl)piperazin-1-yl]pyridinium chloride | Calc'd 556.1573, found 556.1607 |
| 46-6 | 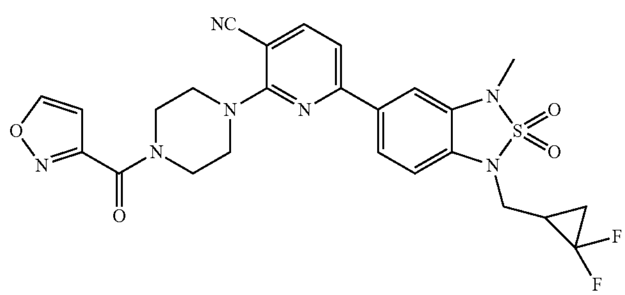 [SMILES: CN1c2cc(-c3ccc(C#N)c(N4CCN(C(=O)c5ccon5)CC4)n3)ccc2N(CC2CC2(F)F)S1(=O)=O] | 3-cyano-2-{1-[(2,2-difluorocyclopropyl)methyl]-3-methyl-2,2-dioxido-1,3-dihydro-2,1,3-benzothiadiazol-5-yl}-6-[4-(isoxazol-3-ylcarbonyl)piperazin-1-yl]pyridinium chloride | Calc'd 556.1573, found 556.1564 |
| 46-7 | 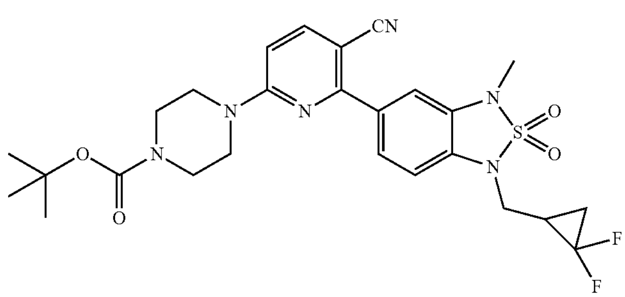 [SMILES: CN1c2cc(-c3nc(N4CCN(C(=O)OC(C)(C)C)CC4)ccc3C#N)ccc2N(CC2CC2(F)F)S1(=O)=O] | tert-butyl 4-(5-cyano-6-{1-[(2,2-difluorocyclopropyl)methyl]-3-methyl-2,2-dioxido-1,3-dihydro-2,1,3-benzothiadiazol-5-yl}pyridin-2-yl)piperazine-1-carboxylate | Calc'd 561.2090, found 561.2106 |

TABLE 24-continued

The following compounds were prepared by a reaction sequence analogous to that illustrated in Scheme 46, Scheme 21, Scheme 31, & Scheme 41.

| Cmpd | Structure | IUPAC Name | Exact Mass [M + H]+ |
|---|---|---|---|
| 46-8 | 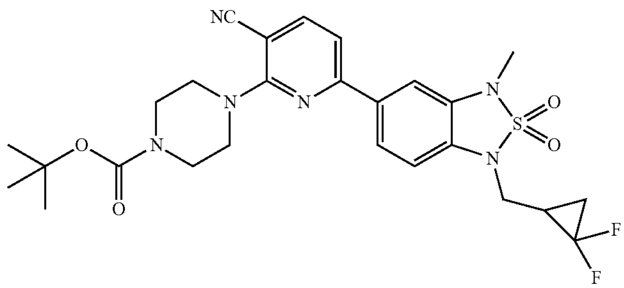 [SMILES: CN1c2cc(-c3ccc(C#N)c(N4CCN(C(=O)OC(C)(C)C)CC4)n3)ccc2N(CC2CC2(F)F)S1(=O)=O] | tert-butyl 4-(3-cyano-6-{1-[(2,2-difluorocyclopropyl)methyl]-3-methyl-2,2-dioxido-1,3-dihydro-2,1,3-benzothiadiazol-5-yl}pyridin-2-yl)piperazine-1-carboxylate | Calc'd 561.2090, found 561.2091 |
| 46-9 | 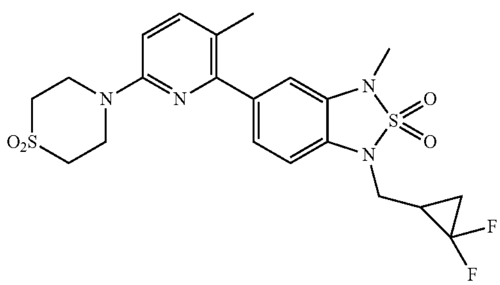 [SMILES: Cc1ccc(N2CCS(=O)(=O)CC2)nc1-c1ccc2c(c1)N(C)S(=O)(=O)N2CC1CC1(F)F] | 2-{1-[(2,2-difluorocyclopropyl)methyl]-3-methyl-2,2-dioxido-1,3-dihydro-2,1,3-benzothiadiazol-5-yl}-6-(1,1-dioxidothiomorpholin-4-yl)-3-methylpyridinium chloride | Calc'd 499.1280, found 499.1282 |
| 46-10 | 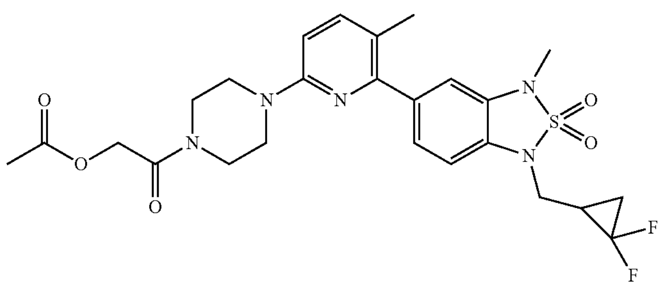 [SMILES: CC(=O)OCC(=O)N1CCN(c2ccc(C)c(-c3ccc4c(c3)N(C)S(=O)(=O)N4CC3CC3(F)F)n2)CC1] | 6-{4-[(acetyloxy)acetyl]piperazin-1-yl}-2-{1-[(2,2-difluorocyclopropyl)methyl]-3-methyl-2,2-dioxido-1,3-dihydro-2,1,3-benzothiadiazol-5-yl}-3-methylpyridinium trifluoroacetate | Calc'd 550.1930, found 550.1928 |
| 46-11 | 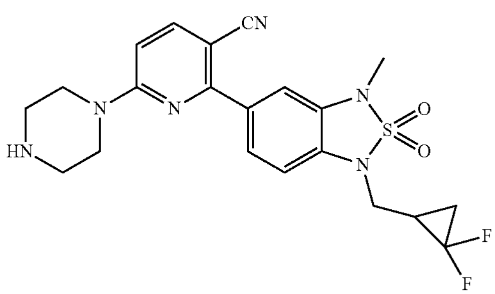 [SMILES: CN1c2cc(-c3nc(N4CCNCC4)ccc3C#N)ccc2N(CC2CC2(F)F)S1(=O)=O] | 4-(5-cyano-6-{1-[(2,2-difluorocyclopropyl)methyl]-3-methyl-2,2-dioxido-1,3-dihydro-2,1,3-benzothiadiazol-5-yl}pyridin-2-yl)piperazin-1-ium chloride | Calc'd 461.1566, found 461.1570 |
| 46-13 | 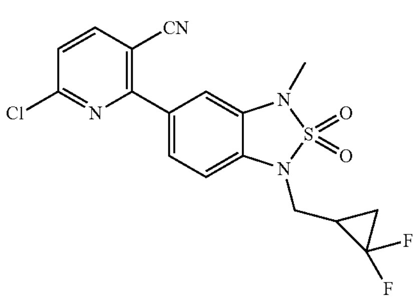 [SMILES: CN1c2cc(-c3nc(Cl)ccc3C#N)ccc2N(CC2CC2(F)F)S1(=O)=O] | 6-chloro-2-{1-[(2,2-difluorocyclopropyl)methyl]-3-methyl-2,2-dioxido-1,3-dihydro-2,1,3-benzothiadiazol-5-yl}nicotinonitrile | Calc'd 411.0489, found 411.0488 |

TABLE 24-continued

The following compounds were prepared by a reaction sequence analogous to that illustrated in Scheme 46, Scheme 21, Scheme 31, & Scheme 41.

| Cmpd | Structure | IUPAC Name | Exact Mass [M + H]+ |
|---|---|---|---|
| 46-14 | 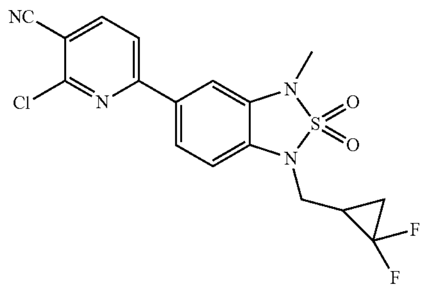 [SMILES: CN1c2cc(-c3ccc(C#N)c(Cl)n3)ccc2N(CC2CC2(F)F)S1(=O)=O] | 2-chloro-6-{1-[(2,2-difluorocyclopropyl)methyl]-3-methyl-2,2-dioxido-1,3-dihydro-2,1,3-benzothiadiazol-5-yl}nicotinonitrile | Calc'd 411.0489, found 411.0489 |
| 46-15 | 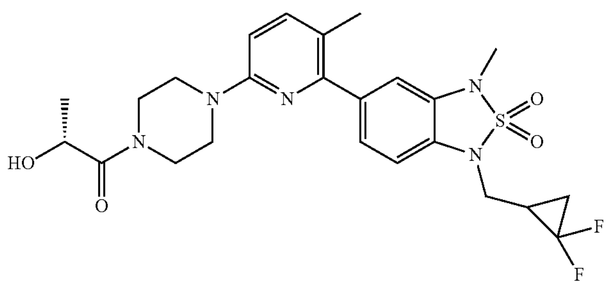 [SMILES: Cc1ccc(N2CCN(C(=O)[C@@H](C)O)CC2)nc1-c1ccc2c(c1)N(C)S(=O)(=O)N2CC1CC1(F)F] | (2R)-1-[4-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperazin-1-yl]-1-oxopropan-2-ol | Calc'd 522.1981, found 522.1979 |
| 46-16 | 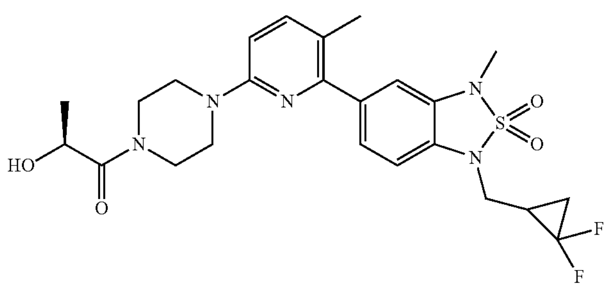 [SMILES: Cc1ccc(N2CCN(C(=O)[C@H](C)O)CC2)nc1-c1ccc2c(c1)N(C)S(=O)(=O)N2CC1CC1(F)F] | (2S)-1-[4-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperazin-1-yl]-1-oxopropan-2-ol | Calc'd 522.1981, found 522.1980 |
| 46-17 | 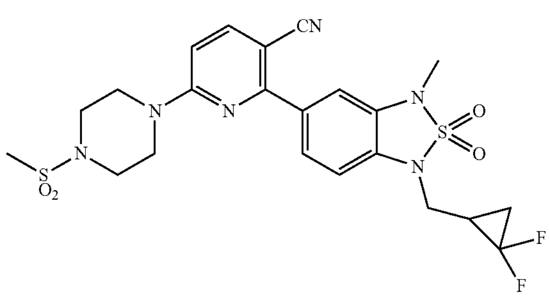 [SMILES: CN1c2cc(-c3nc(N4CCN(S(C)(=O)=O)CC4)ccc3C#N)ccc2N(CC2CC2(F)F)S1(=O)=O] | 2-{1-[(2,2-difluorocyclopropyl)methyl]-3-methyl-2,2-dioxido-1,3-dihydro-2,1,3-benzothiadiazol-5-yl}-6-[4-(methylsulfonyl)piperazin-1-yl]nicotinonitrile | Calc'd 539.1341, found 539.1342 |
| 46-18 | 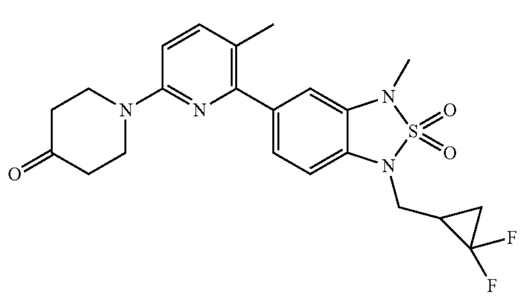 [SMILES: Cc1ccc(N2CCC(=O)CC2)nc1-c1ccc2c(c1)N(C)S(=O)(=O)N2CC1CC1(F)F] | 1-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperidin-4-one | Calc'd 463.1610, found 463.1617 |

TABLE 24-continued

The following compounds were prepared by a reaction sequence analogous to that illustrated in Scheme 46, Scheme 21, Scheme 31, & Scheme 41.

| Cmpd | Structure | IUPAC Name | Exact Mass [M + H]+ |
| --- | --- | --- | --- |
| 46-19 | 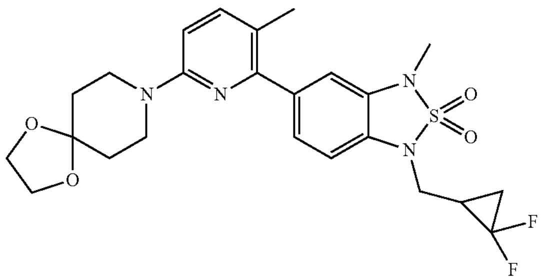 [SMILES: Cc1ccc(N2CCC3(CC2)OCCO3)nc1-c1ccc2c(c1)N(C)S(=O)(=O)N2CC1CC1(F)F] | 8-(6-{1-[(2,2-difluorocyclopropyl)methyl]-3-methyl-2,2-dioxido-1,3-dihydro-2,1,3-benzothiadiazol-5-yl}-5-methylpyridin-2-yl)-1,4-dioxa-8-azaspiro[4.5]decane | Calc'd 507.1872, found 507.1875 |
| 46-20 | 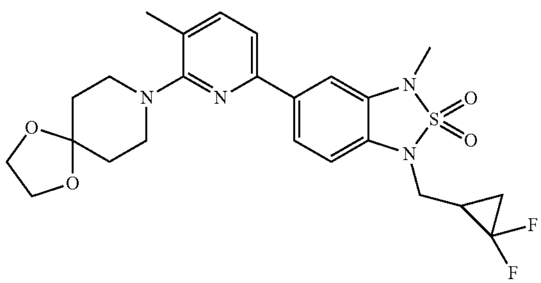 [SMILES: Cc1ccc(-c2ccc3c(c2)N(C)S(=O)(=O)N3CC2CC2(F)F)nc1N1CCC2(CC1)OCCO2] | 8-(6-{1-[(2,2-difluorocyclopropyl)methyl]-3-methyl-2,2-dioxido-1,3-dihydro-2,1,3-benzothiadiazol-5-yl}-3-methylpyridin-2-yl)-1,4-dioxa-8-azaspiro[4.5]decane | Calc'd 507.1872, found 507.1876 |
| 46-21 | 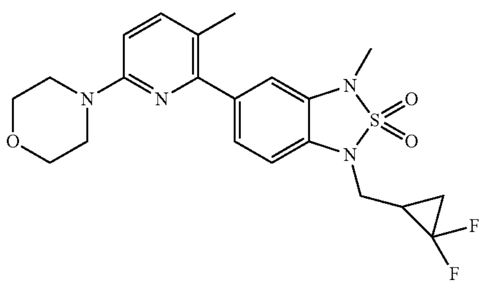 [SMILES: Cc1ccc(N2CCOCC2)nc1-c1ccc2c(c1)N(C)S(=O)(=O)N2CC1CC1(F)F] | 2-{1-{(2,2-difluorocyclopropyl)methyl]-3-methyl-2,2-dioxido-1,3-dihydro-2,1,3-benzothiadiazol-5-yl}-3-methyl-6-morpholin-4-ylpyrimidinium chloride | Calc'd 451.1610, found 451.1614 |
| 46-22 | 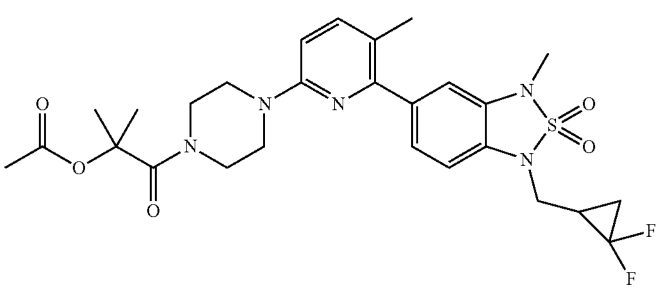 [SMILES: CC(=O)OC(C)(C)C(=O)N1CCN(c2ccc(C)c(-c3ccc4c(c3)N(C)S(=O)(=O)N4CC3CC3(F)F)n2)CC1] | 6-{4-[2-(acetyloxy)-2-methylpropanoyl]piperazin-1-yl}-2-{1-[(2,2-difluorocyclopropyl)methyl]-3-methyl-2,2-dioxido-1,3-dihydro-2,1,3-benzothiadiazol-5-yl}-3-methylpyridinium trifluoroacetate | Calc'd 578.2243, found 578.2265 |
| 46-23 | 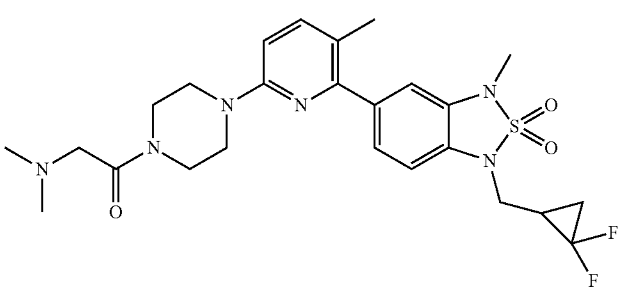 [SMILES: Cc1ccc(N2CCN(C(=O)CN(C)C)CC2)nc1-c1ccc2c(c1)N(C)S(=O)(=O)N2CC1CC1(F)F] | 2-{1-[(2,2-difluorocyclopropyl)methyl]-3-methyl-2,2-dioxido-1,3-dihydro-2,1,3-benzothiadiazol-5-yl}-6-{4-[(dimethylammonio)acetyl]piperazin-1-yl}-3-methylpyridinium dichloride | Calc'd 535.2297, found 535.2306 |

TABLE 24-continued

The following compounds were prepared by a reaction sequence analogous to that illustrated in Scheme 46, Scheme 21, Scheme 31, & Scheme 41.

| Cmpd | Structure | IUPAC Name | Exact Mass [M + H]+ |
|---|---|---|---|
| 46-24 | 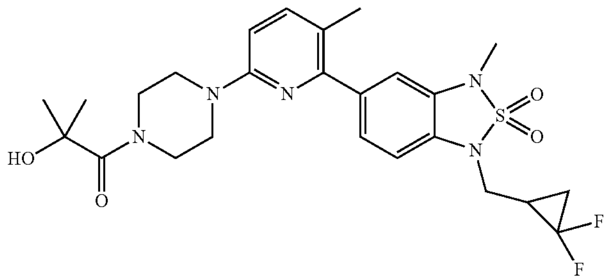 [SMILES: Cc1ccc(N2CCN(C(=O)C(C)(C)O)CC2)nc1-c1ccc2c(c1)N(C)S(=O)(=O)N2CC1CC1(F)F] | 1-[4-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperazin-1-yl]-2-methyl-1-oxopropan-2-ol | Calc'd 536.2138, found 536.2148 |
| 46-25 | 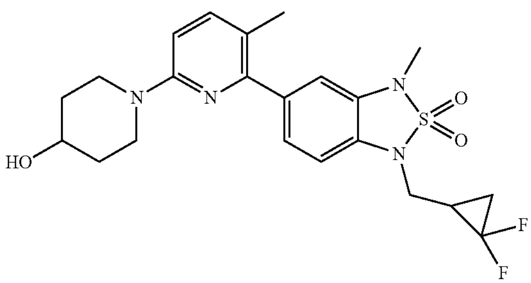 [SMILES: Cc1ccc(N2CCC(O)CC2)nc1-c1ccc2c(c1)N(C)S(=O)(=O)N2CC1CC1(F)F] | 1-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperidin-4-ol | Calc'd 465.1766, found 465.1764 |
| 46-26 | 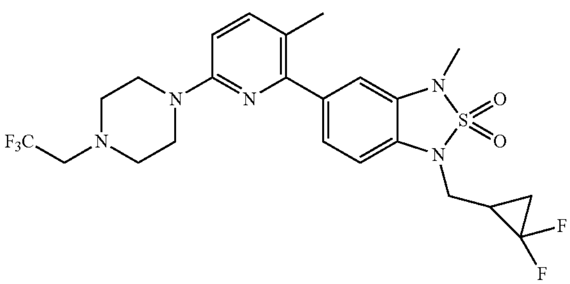 [SMILES: Cc1ccc(N2CCN(CC(F)(F)F)CC2)nc1-c1ccc2c(c1)N(C)S(=O)(=O)N2CC1CC1(F)F] | 4-(6-{1-[(2,2-difluorocyclopropyl)methyl]-3-methyl-2,2-dioxido-1,3-dihydro-2,1,3-benzothiadiazol-5-yl}-5-mthylpyridin-2-yl)-1-(2,2,2-trifluoroethyl)piperazin-1-ium chloride | Calc'd 532.1800, found 532.1802 |
| 46-27 | 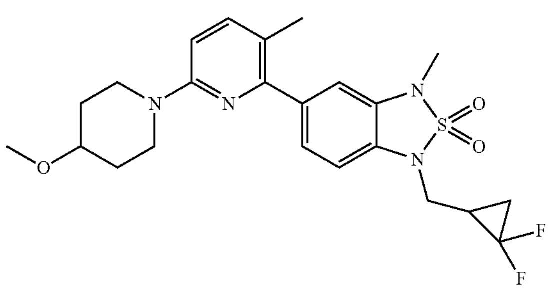 [SMILES: COC1CCN(c2ccc(C)c(-c3ccc4c(c3)N(C)S(=O)(=O)N4CC3CC3(F)F)n2)CC1] | 2-{1-[(2,2-difluorocyclopropyl)methyl]-3-methyl-2,2-dioxido-1,3-dihydro-2,1,3-benzothiadiazol-5-yl}-6-(4-methoxypiperidin-1-yl)-3-methylpyridinium chloride | Calc'd 479.1923, found 479.1905 |
| 46-28 | 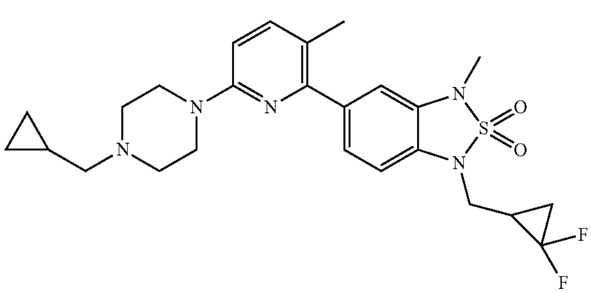 [SMILES: Cc1ccc(N2CCN(CC3CC3)CC2)nc1-c1ccc2c(c1)N(C)S(=O)(=O)N2CC1CC1(F)F] | 1-(cyclopropylmethyl)-4-(6-[{1-[(2,2-difluorocyclopropyl)methyl]-3-methyl-2,2-dioxido-1,3-dihydro-2,1,3-benzothiadiazol-5-yl}-5-methylpyridinium-2-yl)piperazin-1-ium dichloride | Calc'd 504.2239, found 504.2247 |

TABLE 24-continued

The following compounds were prepared by a reaction sequence analogous to that illustrated in Scheme 46, Scheme 21, Scheme 31, & Scheme 41.

| Cmpd | Structure | IUPAC Name | Exact Mass [M + H]+ |
|---|---|---|---|
| 46-29 | 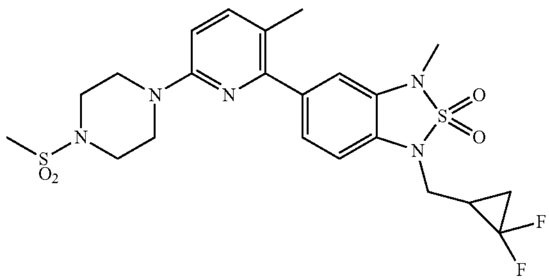 [SMILES: Cc1ccc(N2CCN(S(C)(=O)=O)CC2)nc1-c1ccc2c(c1)N(C)S(=O)(=O)N2CC1CC1(F)F] | 2-{1-[(2,2-difluorocyclopropyl)methyl]-3-methyl-2,2-dioxido-1,3-dihydro-2,1,3-benzothiadiazol-5-yl}-3-methyl-6-[4-(methylsulfonyl)piperazin-1-yl]pyridinium chloride | Calc'd 528.1545, found 528.1539 |
| 46-30 | 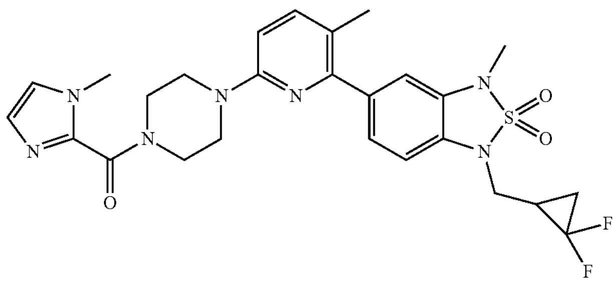 [SMILES: Cc1ccc(N2CCN(C(=O)c3nccn3C)CC2)nc1-c1ccc2c(c1)N(C)S(=O)(=O)N2CC1CC1(F)F] | 2-{1-[(2,2-difluorocyclopropyl)methyl]-3-methyl-2,2-dioxido-1,3-dihydro-2,1,3-benzothiadiazol-5-yl}-3-methyl-6-{4-[(1-methyl-1H-imidazol-3-ium-2-yl)carbonyl]piperazin-1-yl}pyridinium chloride | Calc'd 558.2093, found 558.2102 |
| 46-31 | 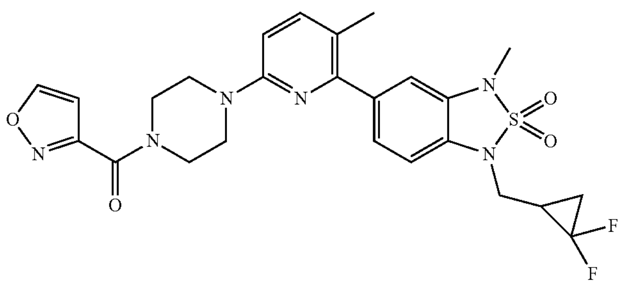 [SMILES: Cc1ccc(N2CCN(C(=O)c3ccon3)CC2)nc1-c1ccc2c(c1)N(C)S(=O)(=O)N2CC1CC1(F)F] | 2-{1-[(2,2-difluorocyclopropyl)methyl]-3-methyl-2,2-dioxido-1,3-dihydro-2,1,3-benzothiadiazol-5-yl}-6-[4-(isoxazol-3-ylcarbonyl)piperazin-1-yl]-3-methylpyridinium chloride | Calc'd 545.1777, found 545.1774 |
| 46-32 | 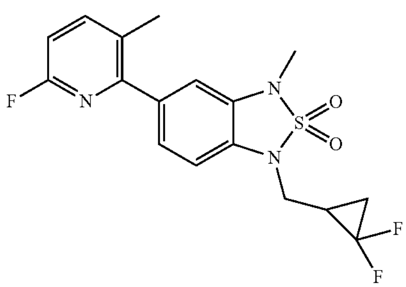 [SMILES: Cc1ccc(F)nc1-c1ccc2c(c1)N(C)S(=O)(=O)N2CC1CC1(F)F] | 1-[(2,2-difluorocyclopropyl)methyl]-5-(6-fluoro-3-methylpyridin-2-yl)-3-methyl-1,3-dihydro-2,1,3-benzothiadiazole 2,2-dioxide | Calc'd 384.0988, found 384.0995 |

What is claimed is:

1. A compound according to Formula I

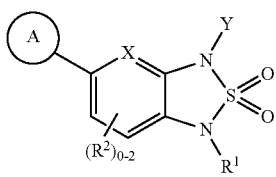

wherein:
X is selected from the group consisting of C and N;
Y is $C_{1-6}$alkyl;
$R^1$ is selected from the group consisting of:
(1) $C_{2-8}$alkyl,
(2) $C_{2-8}$alkenyl,
(3) $C_{2-8}$alkynyl,
(4) $C_{3-6}$cycloalkyl-$(CH_2)_p$—, wherein p is 1, 2, 3 or 4, and
(5) benzyl,
wherein groups (1) to (5) above are optionally substituted with 1 to 3 $R^2$ groups;

each R² is independently selected from the group consisting of: halo, OH, $C_{1-4}$alkyl, $C_{1-4}$alkoxy, $CF_3$, —$OCF_3$ and —CN;

ring A is selected from the group consisting of phenyl and pyridyl, wherein said phenyl and pyridyl are optionally substituted with one or more R³ groups up to the maximum number of substitutable positions;

each R³ is independently selected from the group consisting of:
(1) halo,
(2) $C_{1-8}$alkyl,
(3) $C_{2-6}$alkenyl,
(4) $C_{2-6}$alkynyl,
(5) $C_{3-6}$cycloalkyl,
(6) $C_{1-6}$alkoxy,
(7) $C_{3-6}$cycloalkoxy,
(8) —CN,
(9) —OH,
(10) —C(O)—O—$C_{1-4}$alkyl,
(11) —C(O)—$C_{1-4}$alkyl,
(12) —N(R)₂,
(13) —C(O)—N(R)₂,
(14) —S(O)$_k$—$C_{1-4}$alkyl, wherein k is 0, 1 or 2,
(15) -aryl,
(16) -heteroaryl,
(17) -heterocycle,
(18) —C(O)-aryl,
(19) —N(R)-aryl,
(20) benzyl,
(21) benzyloxy,
(22) aryl-O—,
(23) heteroaryl-O—,
(24) heterocycle-O—
(23) —CO₂H,
(24) —SH,
(25) —SO₂N(R)R,
(26) —N(R)C(O)N(R)R,
(27) —N(R)C(O)$C_{1-4}$alkyl,
(28) —N(R)SO₂N(R)R,
(29) —B(OH)₂,
(30) heteroaryl-CH₂—,
(31) heterocycle-CH₂—,
(32) aryl-C(O)—N(R)—CH₂—,
(33) heteroaryl-C(O)—N(R)—CH₂—,
(34) heteroaryl-CH₂—C(O)—N(R)—CH₂—,
(35) heterocycle-CH₂—C(O)—N(R)—CH₂—, and
(36) $C_{1-6}$alkyl-C(O)—N(R)—CH₂—, wherein groups (2) to (7), (10), (11), (14) to (24), (27) and (30) to (36) above are optionally substituted from one up to the maximum number of substitutable positions with one or more substituents independently selected from the group consisting of: OH, CN, halo, —N(R)₂, —C(O)—N(R)₂, —CH₂—N(R)₂, —C(O)—CH₂—N(R)₂, carboxy, —C(O)—O—$C_{1-4}$alkyl, —C(O)—C(R)₂—C(O)—O—$C_{1-4}$alkyl, —CH₂—$C_{3-6}$cycloalkyl, $C_{1-4}$alkoxy, $C_{1-4}$alkylamino, acetyl, acetylamino, methylsulfonyl, methylsulfonylamino, phenyl, heterocycle, heteroaryl, heteroaryl-C(O)—, $C_{1-4}$alkyl and $C_{1-4}$alkyl-C(O)—, said $C_{1-4}$alkyl, $C_{1-4}$alkyl-C(O)—, heteroaryl and heteroaryl-C(O)-optionally substituted with 1 to 3 halogen atoms and hydroxyl, and heteroaryl and heteroaryl-C(O)— additionally optionally substituted with methyl, and each R is independently selected from the group consisting of: H and $C_{1-4}$alkyl;

aryl at each occurrence is independently selected from the group consisting of: phenyl, naphthyl, anthryl and phenanthryl;

heteroaryl at each occurrence independently means a 5- or 6-membered monocyclic aromatic or 9- or 10-membered bicyclic aromatic, wherein at least one atom in the aromatic is selected from the group consisting of N(R), O and S, the sulfur optionally oxidized to sulfone or sulfoxide, and the remaining atoms are selected from the group consisting of C, N(R), O and S, the sulfur optionally oxidized to sulfone or sulfoxide;

heterocycle at each occurrence independently means a 5- or 6-membered monocyclic non-aromatic ring or 9- or 10-membered bi- or spiro-cyclic fully or partially unsaturated ring, wherein each said ring is optionally substituted with 1 to 2 oxo groups, wherein at least one atom of said 5- or 6-membered monocyclic non-aromatic ring or said 9- or 10-membered bi-or spiro-cyclic fully or partially unsaturated ring is selected from the group consisting of N(R), O and S, the sulfur optionally oxidized to sulfone or sulfoxide, and the remaining atoms are selected from the group consisting of C, N(R), O and S, the sulfur optionally oxidized to sulfone or sulfoxide;

or a pharmaceutically acceptable salt thereof.

2. A compound according to claim 1 wherein each R³ is independently selected from the group consisting of:
(1) halo,
(2) $C_{1-8}$ alkyl,
(3) $C_{2-6}$alkenyl,
(4) $C_{2-6}$alkynyl,
(5) $C_{3-6}$cycloalkyl,
(6) $C_{1-6}$alkoxy,
(7) $C_{3-6}$cycloalkoxy,
(8) —CN,
(9) —OH,
(10) —C(O)—O—$C_{1-4}$alkyl,
(11) —C(O)-$C_{1-4}$alkyl,
(12) —N(R)₂,
(13) —C(O)—N(R)₂,
(14) —S(O)k-$C_{1-4}$alkyl, wherein k is 0, 1 or 2,
(15) -aryl,
(16) -hetero aryl,
(17) -heterocycle,
(18) —C(O)-aryl,
(19) —N(R)-aryl,
(20) benzyl,
(21) benzyloxy,
(22) aryl-O—,
(23) heteroaryl-O—,
(24) heterocycle-O—
(23) —CO₂H,
(24) —SH,
(25) —SO₂N(R)R,
(26) —N(R)C(O)N(R)R,
(27) —N(R)C(O)$C_{1-4}$alkyl,
(28) —N(R)SO₂N(R)R,
(29) —B(OH)₂,
(30) heteroaryl-CH₂—,
(31) heterocycle-CH₂—,
(32) aryl-C(O)—N(R)—CH₂—, and
(33) heteroaryl-C(O)—N(R)—CH₂—, wherein groups (2) to (7), (10), (11), (14) to (24), (27) and (30) to (33) above are optionally substituted from one up to the maximum number of substitutable positions with one or more substituents independently selected from the group consisting of: OH, CN, halo, —N(R)₂, —C(O)—N(R)₂, —CH₂—N(R)₂, carboxy, —C(O)—O—$C_{1-4}$alkyl, C$_{1-4}$alkoxy, C$_{1-4}$alkylamino, acetyl, acetylamino, methylsulfonyl, methylsulfonylamino, phenyl, heterocycle, heteroaryl, heteroaryl-C(O)—, C$_{1-4}$alkyl and C$_{1-4}$alkyl-C(O)—, said C$_{1-4}$alkyl, C$_{1-4}$alkyl-C(O)— and heteroaryl optionally substituted with 1 to 3 halogen atoms and hydroxy, and each R is independently selected from the group consisting of: H and C$_{1-4}$alkyl.

3. The compound according to claim 2 wherein X is C.

4. The compound according to claim 2 wherein X is N.

5. The compound according to claim 2 wherein Y is methyl.

6. The compound according to claim 2 wherein R$^1$ is selected from the group consisting of: cyclopropylmethyl, 2,2-difluorocyclopropylmethyl, cyclobutylmethyl, 2,2-dimethylpropyl and benzyl, optionally substituted with methoxy or —OCF$_3$.

7. The compound according to claim 2 of Formula Ia

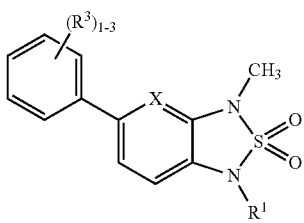

or a pharmaceutically acceptable salt thereof.

8. The compound according to claim 7 wherein R$^3$ is selected from the group consisting of: (1) —CN, (2) halo, (3) —CF$_3$, (4) 1,1-dioxidothiomorpholin-4-yl, (5) morpholin-4-ylmethyl, (6) —C(O)—O—C$_{1-4}$alkyl, (7) C$_{1-6}$alkoxy, (8) C$_{1-6}$alkyl, optionally substituted with hydroxy, (9) piperazinyl, optionally substituted with —C(O)—O—C$_{1-4}$alkyl or isoxazolylcarbonyl, and (10) piperidinyl, optionally substituted with —C(O)—O—C$_{1-4}$alkyl or isoxazolylcarbonyl.

9. The compound according to claim 2 of Formula Ib

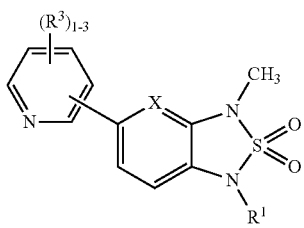

or a pharmaceutically acceptable salt thereof.

10. The compound according to claim 9 wherein R$^3$ is selected from the group consisting of: (1) —CN, (2) halo, (3) —CF$_3$, (4) 1,1-dioxidothiomorpholin-4-yl, (5) morpholin-4-ylmethyl, (6) —C(O)—O—C$_{1-4}$alkyl, (7) C$_{1-6}$alkoxy, (8) C$_{1-6}$alkyl, optionally substituted with hydroxy, (9) piperazinyl, optionally substituted with —C(O)—O—C$_{1-4}$alkyl or isoxazolylcarbonyl, and (10) piperidinyl, optionally substituted with —C(O)—O—C$_{1-4}$alkyl or isoxazolylcarbonyl.

11. The compound according to claim 2 of Formula Ic

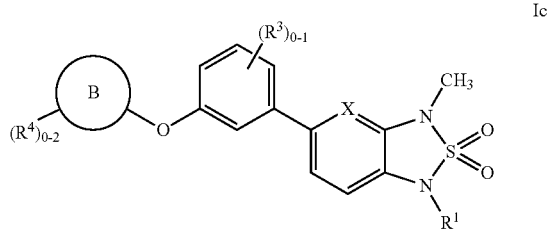

or a pharmaceutically acceptable salt thereof, wherein
ring B is heteroaryl,
R$^3$ is CN, halo or C$_{1-4}$alkyl, optionally substituted with 1-5 halo atoms, and
each R$^4$ is independently selected from the group consisting of: —CN, halo, —N(R)$_2$, C$_{1-4}$alkoxy, —C(O)—O—C$_{1-4}$alkyl, and C$_{1-4}$alkyl, optionally substituted with hydroxy.

12. The compound according to claim 2 of Formula Id

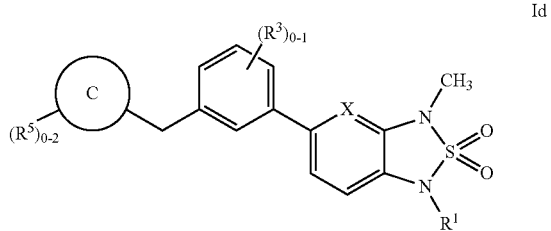

or a pharmaceutically acceptable salt thereof, wherein
ring C is heterocycle,
R$^3$ is CN, halo or C$_{1-4}$alkyl, optionally substituted with 1-5 halo atoms, and
each R$^5$ is independently selected from the group consisting of: OH, acetyl, methylsulfonyl, acetylamino, —C(O)—O—C$_{1-4}$alkyl and C$_{1-4}$alkyl, optionally substituted with 1-3 halo atoms or hydroxy.

13. The compound according to claim 2 of Formula Ie

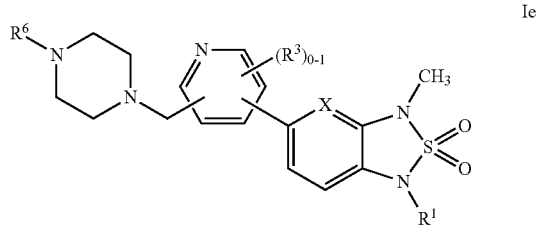

or a pharmaceutically acceptable salt thereof, wherein
R$^3$ is CN, halo or C$_{1-4}$alkyl, optionally substituted with 1-5 halo atoms, and
R$^6$ is independently selected from the group consisting of: pyrimidinyl, pyridyl, methylsulfonyl, acetyl, 2-hydroxypropanoyl and 2-hydroxyethanoyl.

14. The compound according to claim 2 of Formula If

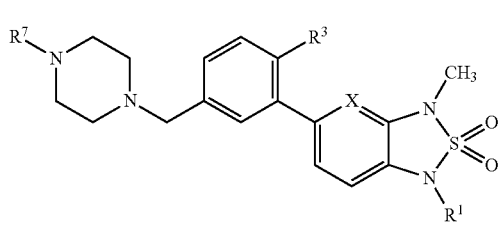

or a pharmaceutically acceptable salt thereof, wherein
$R^3$ is CN, halo or $C_{1-4}$alkyl, optionally substituted with 1-5 halo atoms, and
$R^7$ is selected from the group consisting of: pyrimidinyl, pyridyl, methylsulfonyl, acetyl, 2-hydroxypropanoyl and 2-hydroxyethanoyl.

15. The compound according to claim 2 of Formula Ig

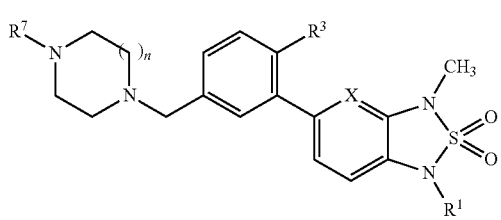

or a pharmaceutically acceptable salt thereof, wherein
n is 0 or 1,
$R^3$ is CN, halo or $C_{1-4}$alkyl, optionally substituted with 1-5 halo atoms, and
$R^8$ is selected from the group consisting of: acetylamino, methylsulfonyl, methylsulfonylamino, pyrimidinyl, pyridyl, 2-oxo-1-pyrrolidinyl, —C(O)—N(R)$_2$ and $C_{1-4}$alkyl, said $C_{1-4}$alkyl optionally substituted with 1-3 halo atoms or hydroxy, and said pyridyl optionally substituted with fluoro.

16. The compound according to claim 2 of Formula Ih

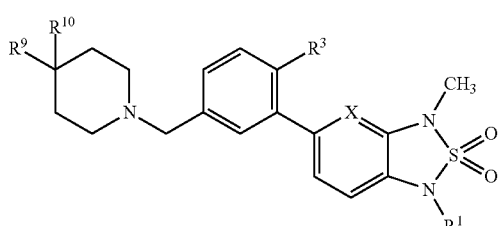

or a pharmaceutically acceptable salt thereof, wherein
$R^3$ is CN, halo or $C_{1-4}$alkyl, optionally substituted with 1-5 halo atoms, and
$R^9$ is pyridyl and $R^{10}$ is hydroxy or $R^9$ and $R^{10}$ and joined together with the atom to which they are attached to form 5-oxo-imidazolidine, oxetane or azetidine, said azetidine optionally substituted with —C(O)—O—$C_{1-4}$alkyl.

17. The compound according to claim 2 of Formula Ij

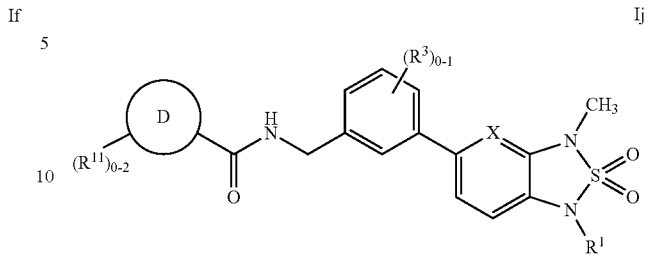

or a pharmaceutically acceptable salt thereof, wherein
ring D is heteroaryl,
$R^3$ is CN, halo or $C_{1-4}$alkyl, optionally substituted with 1-5 halo atoms, and
each $R^{11}$ is independently selected from the group consisting of: —CN, halo, —N(R)$_2$, $C_{1-4}$alkoxy, —C(O)—O—$C_{1-4}$alkyl, and $C_{1-4}$alkyl, optionally substituted with hydroxy.

18. A compound of Formula Ik

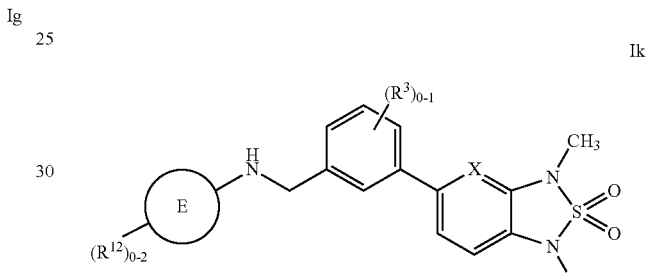

or a pharmaceutically acceptable salt thereof, wherein
X is selected from the group consisting of C and N;
$R^1$ is selected from the group consisting of:
(1) $C_{2-8}$alkyl,
(2) $C_{2-8}$alkenyl,
(3) $C_{2-8}$alkynyl,
(4) $C_{3-6}$cycloalkyl-(CH$^2$)$_p$—, wherein p is 1, 2, 3 or 4, and
(5) benzyl,
wherein groups (1) to (5) above are optionally substituted with 1 to 3 $R^2$ groups;
each $R^2$ is independently selected from the group consisting of: halo, OH, $C_{1-4}$alkyl, $C_{1-4}$alkoxy, CF$_3$, —OCF$_3$ and —CN;
ring E is heteroaryl,
$R^3$ is CN, halo or $C_{1-4}$alkyl, optionally substituted with 1-5 halo atoms, and
each $R^{12}$ is independently selected from the group consisting of: —CN, halo, —N(R)$_2$, $C_{1-4}$alkoxy, —C(O)—O—$C_{1-4}$alkyl, and $C_{1-4}$alkyl, optionally substituted with hydroxy.

19. A compound according to claim 2 wherein said compound is:
2-[1-(cyclopropylmethyl)-3-methyl-2,2-dioxido-1,3-dihydro-2,1,3-benzothiadiazol-5-yl]benzonitrile;
2-[1-(cyclopropylmethyl)-3-methyl-2,2-dioxido-1,3-dihydro-2,1,3-benzothiadiazol-5-yl]-6-fluorobenzonitrile;
1-(cyclopropylmethyl)-3-methyl-5-(2-methylphenyl)-1,3-dihydro-2,1,3-benzothiadiazole2,2-dioxide;
1-(cyclopropylmethyl)-5-(2-ethylphenyl)-3-methyl-1,3-dihydro-2,1,3-benzothiadiazole2,2-dioxide;

2-[1-(cyclopropylmethyl)-3-methyl-2,2-dioxido-1,3-di-
hydro-2,1,3-benzothiadiazol-5-yl]-5-fluorobenzoni-
trile;
4-[1-(cyclopropylmethyl)-3-methyl-2,2-dioxido-1,3-di-
hydro-2,1,3-benzothiadiazol-5-yl]benzonitrile;
1-(cyclopropylmethyl)-3-methyl-5-phenyl-1,3-dihydro-2,
1,3-benzothiadiazole2,2-dioxide;
1-(cyclopropylmethyl)-5-(2-fluorophenyl)-3-methyl-1,3-
dihydro-2,1,3-benzothiadiazole2,2-dioxide;
3-[1-(cyclopropylmethyl)-3-methyl-2,2-dioxido-1,3-di-
hydro-2,1,3-benzothiadiazol-5-yl]benzonitrile;
2-[1-(cyclopropylmethyl)-3-methyl-2,2-dioxido-1,3-di-
hydro-2,1,3-benzothiadiazol-5-yl]-3-fluorobenzoni-
trile;
2-[1-(cyclopropylmethyl)-3-methyl-2,2-dioxido-1,3-di-
hydro-2,1,3-benzothiadiazol-5-yl]-3,6-difluoroben-
zonitrile;
1-(cyclopropylmethyl)-3-methyl-5-[2-(trifluoromethyl)
phenyl]-1,3-dihydro-2,1,3-benzothiadiazole 2,2-diox-
ide;
3-[1-(cyclopropylmethyl)-3-methyl-2,2-dioxido-1,3-di-
hydro-2,1,3-benzothiadiazol-5-yl]-4-fluorobenzoni-
trile;
3-[1-(cyclopropylmethyl)-3-methyl-2,2-dioxido-1,3-di-
hydro-2,1,3-benzothiadiazol-5-yl]-2-fluorobenzoni-
trile;
1-(cyclopropylmethyl)-[3-methyl-5-3-(trifluoromethyl)
phenyl]-1,3-dihydro-2,1,3-benzothiadiazole 2,2-diox-
ide;
1-(cyclopropylmethyl)-5-[4-(1,1-dioxidothiomorpholin-
4-yl)phenyl]-3-methyl-1,3-dihydro-2,1,3-benzothia-
diazole 2,2-dioxide;
1-(cyclopropylmethyl)-5-[3-(1,1-dioxidothiomorpholin-
4-yl)phenyl]-3-methyl-1,3-dihydro-2,1,3-benzothia-
diazole 2,2-dioxide;
2-[1-(cyclopropylmethyl)-3-methyl-2,2-dioxido-1,3-di-
hydro-2,1,3-benzothiadiazol-5-yl]pyridine-3-carboni-
trile;
4-[1-(cyclopropylmethyl)-3-methyl-2,2-dioxido-1,3-di-
hydro-2,1,3-benzothiadiazol-5-yl]pyridine-3-carboni-
trile;
4-[1-(cyclopropylmethyl)-3-methyl-2,2-dioxido-1,3-di-
hydro-2,1,3-benzothiadiazol-5-yl]pyridine-2-carboni-
trile;
1-(cyclopropylmethyl)-3-methyl-5-(4-methylpyridin-3-
yl)-1,3-dihydro-2,1,3-benzothiadiazole2,2-dioxide;
3-[1-(cyclopropylmethyl)-3-methyl-2,2-dioxido-1,3-di-
hydro-2,1,3-benzothiadiazol-5-yl]pyridine-2-carboni-
trile;
5-[1-(cyclopropylmethyl)-3-methyl-2,2-dioxido-1,3-di-
hydro-2,1,3-benzothiadiazol-5--yl]pyridine-2-carboni-
trile;
1-(cyclopropylmethyl)-5-(2-fluoropyridin-3-yl)-3-me-
thyl-1,3-dihydro-2,1,3-benzothiadiazole2,2-dioxide;
1-(cyclopropylmethyl)-3-methyl-5-(5-methylpyridin-3-
yl)-1,3-dihydro-2,1,3-benzothiadiazole2,2-dioxide;
3-[1-(cyclopropylmethyl)-3-methyl-2,2-dioxido-1,3-di-
hydro-2,1,3-benzothiadiazol-5-yl]pyridine-4-carboni-
trile;
1-(cyclopropylmethyl)-3-methyl-5-[3-(morpholin-4-ylm-
ethyl)phenyl]-1,3-dihydro-2,1,3-benzothiadiazole 2,2-
dioxide;
2-[1-(cyclopropylmethyl)-3-methyl-2,2-dioxido-1,3-di-
hydro-2,1,3-benzothiadiazol-5-yl]-4-(morpholin-4-yl-
methyl)benzonitrile;

2-{2-[1-(cyclopropylmethyl)-3-methyl-2,2-dioxido-1,3-
dihydro-2,1,3-benzothiadiazol-5-yl]phenyl}propan-2-
ol;
2-{3-[1-(cyclopropylmethyl)-3-methyl-2,2-dioxido-1,3-
dihydro-2,1,3-benzothiadiazol-5-yl]phenyl}propan-2-
ol;
2-{4-[1-(cyclopropylmethyl)-3-methyl-2,2-dioxido-1,3-
dihydro-2,1,3-benzothiadiazol-5-yl]phenyl}propan-2-
ol;
1-(cyclopropylmethyl)-3-methyl-5-(3-methylpyridin-2-
yl)-1,3-dihydro-2,1,3-benzothiadiazole2,2-dioxide;
2-{1-[(2,2-difluorocyclopropyl)methyl]-3-methyl-2,2-di-
oxido-1,3-dihydro-2,1,3-benzothiadiazol-5-
yl}benzonitrile;
2-{1-[(2,2-difluorocyclopropyl)methyl]-3-methyl-2,2-di-
oxido-1,3-dihydro-2,1,3-benzothiadiazol-5-yl}-4-(hy-
droxymethyl)benzonitrile;
ethyl 3-{1-[(2,2-difluorocyclopropyl)methyl]-3-methyl-2,
2-dioxido-1,3-dihydro-2,1,3-benzothiadiazol-5-yl}-2-
fluorobenzoate;
1-[(2,2-difluorocyclopropyl)methyl]-5-[3-(1,1-dioxidot-
hiomorpholin-4-yl)phenyl]-3-methyl-1,3-dihydro-2,1,
3-benzothiadiazole2,2-dioxide;
2-{1-[(2,2-difluorocyclopropyl)methyl]-3-methyl-2,2-di-
oxido-1,3-dihydro-2,1,3-benzothiadiazol-5-yl}-4-
methoxybenzonitrile;
2-[1-(2,2-dimethylpropyl)-3-methyl-2,2-dioxido-1,3-di-
hydro-2,1,3-benzothiadiazol-5-yl]benzonitrile;
2-[1-(3-hydroxypropyl)-3-methyl-2,2-dioxido-1,3-dihy-
dro-2,1,3-benzothiadiazol-5-yl]benzonitrile;
2-[1-(cyclobutylmethyl)-3-methyl-2,2-dioxido-1,3-dihy-
dro-2,1,3-benzothiadiazol-5-yl]benzonitrile;
1-(cyclobutylmethyl) -5-[3-(1,1-dioxidothiomorpholin-4-
yl)phenyl]-3-methyl-1,3-dihydro-2,1,3-benzothiadiaz-
ole 2,2-dioxide;
2-[1-(4-methoxybenzyl)-3-methyl-2,2-dioxido-1,3-dihy-
dro-2,1,3-benzothiadiazol-5-yl]benzonitrile;
2-{3-methyl-2,2-dioxido-1-[4-(trifluoromethoxy)ben-
zyl]-1,3-dihydro-2,1,3-benzothiadiazol-5-
yl}benzonitrile;
5-[3-(1,1-dioxidothiomorpholin-4-yl)phenyl]-3-methyl-
1-[4-(trifluoromethoxy)benzyl]-1,3-dihydro-2,1,3-ben-
zothiadiazole2,2-dioxide;
6-(4-cyano-3-{1-[(2,2-difluorocyclopropyl)methyl]-3-
methyl-2,2-dioxido-1,3-dihydro-2,1,3-benzothiadia-
zol-5-yl}phenoxy)pyridine-2-carbonitrile;
4-(4-cyano-3-{1-[(2,2-difluorocyclopropyl)methyl]-3-
methyl-2,2-dioxido-1,3-dihydro-2,1,3-benzothiadia-
zol-5-yl}phenoxy)pyridine-2-carbonitrile;
4-[(3-chloropyrazin-2-yl)oxy]-2-{1-[(2,2-difluorocyclo-
propyl)methyl]-3-methyl-2,2-dioxido-1,3-dihydro-2,1,
3-benzothiadiazol-5-yl}benzonitrile;
2-(4-cyano-3-{1-[(2,2-difluorocyclopropyl)methyl]-3-
methyl-2,2-dioxido-1,3-dihydro-2,1,3-benzothiadia-
zol-5-yl}phenoxy)-1,3-thiazole-4-carbonitrile;
2-{1-[(2,2-difluorocyclopropyl)methyl]-3-methyl-2,2-di-
oxido-1,3-dihydro-2,1,3-benzothiadiazol-5-yl}-4-
(pyrazin-2-yloxy)benzonitrile;
2-{1-[(2,2-difluorocyclopropyl)methyl]-3-methyl-2,2-di-
oxido-1,3-dihydro-2,1,3-benzothiadiazol-5-yl}-4-{[6-
(hydroxymethyl)pyrazin-2-yl]oxy}benzonitrile;
2-{1-[(2,2-difluorocyclopropyl)methyl]-3-methyl-2,2-di-
oxido-1,3-dihydro-2,1,3-benzothiadiazol-5-yl}-4-[(6-
methylpyrazin-2-yl)oxy]benzonitrile;
2-{1-[(2,2-difluorocyclopropyl)methyl]-3-methyl-2,2-di-
oxido-1,3-dihydro-2,1,3-benzothiadiazol-5-yl}-4-[(3-
methylpyrazin-2-yl)oxy]benzonitrile;

methyl 2-(4-cyano-3-{1-[(2,2-difluorocyclopropyl)methyl]-3-methyl-2,2-dioxido-1,3-dihydro-2,1,3-benzothiadiazol-5-yl}phenoxy)pyrimidine-5-carboxylate;
4-[(2-chloropyrimidin-4-yl)oxy]-2-{1-[(2,2-difluorocyclopropyl)methyl]-3-methyl-2,2-dioxido-1,3-dihydro-2,1,3-benzothiadiazol-5-yl}benzonitrile;
4-amino-2-(4-cyano-3-{1-[(2,2-difluorocyclopropyl)methyl]-3-methyl-2,2-dioxido-1,3-dihydro-2,1,3-benzothiadiazol-5-yl}phenoxy)pyrimidine-5-carbonitrile;
methyl 5-(4-cyano-3-{1-[(2,2-difluorocyclopropyl)methyl]-3-methyl-2,2-dioxido-1,3-dihydro-2,1,3-benzothiadiazol-5-yl}phenoxy)pyrazine-2-carboxylate;
3-(4-cyano-3-{1-[(2,2-difluorocyclopropyl)methyl]-3-methyl-2,2-dioxido-1,3-dihydro-2,1,3-benzothiadiazol-5-yl}phenoxy)pyrazine-2-carbonitrile;
6-(4-cyano-3-{1-[(2,2-difluorocyclopropyl)methyl]-3-methyl-2,2-dioxido-1,3-dihydro-2,1,3-benzothiadiazol-5-yl}phenoxy)pyrazine-2-carbonitrile;
2-{1-[(2,2-difluorocyclopropyl)methyl]-3-methyl-2,2-dioxido-1,3-dihydro-2,1,3-benzothiadiazol-5-yl}-4-{[4-(methylamino)pyrimidin-2-yl]oxy}benzonitrile;
2-{1-[(2,2-difluorocyclopropyl)methyl]-3-methyl-2,2-dioxido-1,3-dihydro-2,1,3-benzothiadiazol-5-yl}-4-[(2-methoxypyrimidin-4-yl)oxy]benzonitrile;
2-{1-[(2,2-difluorocyclopropyl)methyl]-3-methyl-2,2-dioxido-1,3-dihydro-2,1,3-benzothiadiazol-5-yl}-4-{[2-(methylamino)pyrimidin-4-yl]oxy}benzonitrile;
4-{4-cyano-3-[1-(2,2-dimethylpropyl)-3-methyl-2,2-dioxido-1,3-dihydro-2,1,3-benzothiadiazol-5-yl]phenoxy}pyridine-2-carbonitrile;
4-{4-cyano-3-[1-(cyclopropylmethyl)-3-methyl-2,2-dioxido-1,3-dihydro-2,1,3-benzothiadiazol-5-yl]phenoxy}pyridine-2-carbonitrile;
4-(4-cyano-3-{3-methyl-2,2-dioxido-1-[4-(trifluoromethoxy)benzyl]-1,3-dihydro-2,1,3-benzothiadiazol-5-yl}phenoxy)pyridine-2-carbonitrile;
4-(cyanomethoxy)-2-{1-[(2,2-difluorocyclopropyl)methyl]-3-methyl-2,2-dioxido-1,3-dihydro-2,1,3-benzothiadiazol-5-yl}benzonitrile;
2-(3-{1-[(2,2-difluorocyclopropyl)methyl]-3-methyl-2,2-dioxido-1,3-dihydro-2,1,3-benzothiadiazol-5-yl}-4-methylphenyl)propan-2-ol;
2-(3-{1-[(2,2-difluorocyclopropyl)methyl]-3-methyl-2,2-dioxido-1,3-dihydro-2,1,3-benzothiadiazol-5-yl}-4-methylphenyl)propan-2-ol;
2-(3-{1-[(2,2-difluorocyclopropyl)methyl]-3-methyl-2,2-dioxido-1,3-dihydro-2,1,3-benzothiadiazol-5-yl}-2-fluorophenyl)propan-2-ol;
2-{3-[1-(cyclopropylmethyl)-3-methyl-2,2-dioxido-1,3-dihydro-2,1,3-benzothiadiazol-5-yl]-4-methylphenyl}propan-2-ol;
2-{3-[1-(2,2-dimethylpropyl)-3-methyl-2,2-dioxido-1,3-dihydro-2,1,3-benzothiadiazol-5-yl]-4-methylphenyl}propan-2-ol;
2-{1-[(2,2-difluorocyclopropyl)methyl]-3-methyl-2,2-dioxido-1,3-dihydro-2,1,3-benzothiadiazol-5-yl}-4-[(3-hydroxy-6,7-dihydroisoxazolo[4,5-c]pyridin-5(4H)-yl)methyl]benzonitrile;
4-[(4-acetylpiperazin-1-yl)methyl]-2-{1-[(2,2-difluorocyclopropyl)methyl]-3-methyl-2,2-dioxido-1,3-dihydro-2,1,3-benzothiadiazol-5-yl}benzonitrile;
2-{1-[(2,2-difluorocyclopropyl)methyl]-3-methyl-2,2-dioxido-1,3-dihydro-2,1,3-benzothiadiazol-5-yl}-4-{[4-(methylsulfonyl)piperazin-1-yl]methyl}benzonitrile;
2-{1-[(2,2-difluorocyclopropyl)methyl]-3-methyl-2,2-dioxido-1,3-dihydro-2,1,3-benzothiadiazol-5-yl}-4-[(1,1-dioxidothiomorpholin-4-yl)methyl]benzonitrile;
5-{5-[(4-acetylpiperazin-1-yl)methyl]-2-fluorophenyl}-1-[(2,2-difluorocyclopropyl)methyl]-3-methyl-1,3-dihydro-2,1,3-benzothiadiazole2,2-dioxide;
1-[(2,2-difluorocyclopropyl)methyl]-5-(2-fluoro-5-{[4-(methylsulfonyl)piperazin-1-yl]methyl}phenyl)-3-methyl-1,3-dihydro-2,1,3-benzothiadiazole2,2-dioxide;
1-[(2,2-difluorocyclopropyl)methyl]-5-(2-fluoro-5-{[4-(2,2,2-trifluoroethyl)piperazin-1-yl]methyl}phenyl)-3-methyl-1,3-dihydro-2,1,3-benzothiadiazole2,2-dioxide;
5-{3-[(4-acetylpiperazin-1-yl)methyl]-2-fluorophenyl}-1-[(2,2-difluorocyclopropyl)methyl]-3-methyl-1,3-dihydro-2,1,3-benzothiadiazole2,2-dioxide;
1-[(2,2-difluorocyclopropyl)methyl]-5-(2-fluoro-3-{[4-(methylsulfonyl)piperazin-1-yl]methyl}phenyl)-3-methyl-1,3-dihydro-2,1,3-benzothiadiazole2,2-dioxide;
1-[(2,2-difluorocyclopropyl)methyl]-5-(2-fluoro-3-{[4-(2,2,2-trifluoroethyl)piperazin-1-yl]methyl}phenyl)-3-methyl-1,3-dihydro-2,1,3-benzothiadiazole2,2-dioxide;
2-cyano-N-{3-[1-(cyclopropylmethyl)-3-methyl-2,2-dioxido-1,3-dihydro-2,1,3-benzothiadiazol-5-yl]benzyl}benzamide;
2-{3-[1-(cyclopropylmethyl)-3-methyl-2,2-dioxido-1,3-dihydro-2,1,3-benzothiadiazol-5-yl]benzyl}-1H-isoindole-1,3(2H)-dione;
N-{3-[1-(cyclopropylmethyl)-3-methyl-2,2-dioxido-1,3-dihydro-2,1,3-benzothiadiazol-5-yl]benzyl}benzamide;
3-cyano-N-{3-[1-(cyclopropylmethyl)-3-methyl-2,2-dioxido-1,3-dihydro-2,1,3-benzothiadiazol-5-yl]benzyl}benzamide;
N-{3-[1-(cyclopropylmethyl)-3-methyl-2,2-dioxido-1,3-dihydro-2,1,3-benzothiadiazol-5-yl]benzyl}isoxazole-3-carboxamide;
2-({3-[1-(cyclopropylmethyl)-3-methyl-2,2-dioxido-1,3-dihydro-2,1,3-benzothiadiazol-5-yl]benzyl}amino)nicotinonitrile;
4-({3-[1-(cyclopropylmethyl)-3-methyl-2,2-dioxido-1,3-dihydro-2,1,3-benzothiadiazol-5-yl]benzyl}amino)pyridine-2-carbonitrile;
1-[(2,2-difluorocyclopropyl)methyl]-3-methyl-5-(6-{[4-(methylsulfonyl)piperazin-1-yl]methyl}pyridin-2-yl)-1,3-dihydro-2,1,3-benzothiadiazole2,2-dioxide;
5-{6-[(4-acetylpiperazin-1-yl)methyl]pyridin-2-yl}-1-[(2,2-difluorocyclopropyl)methyl]-3-methyl-1,3-dihydro-2,1,3-benzothiadiazole2,2-dioxide;
5-{6-[(4-acetylpiperazin-1-yl)methyl]pyridin-3-yl}-1-[(2,2-difluorocyclopropyl)methyl]-3-methyl-1,3-dihydro-2,1,3-benzothiadiazole2,2-dioxide;
1-[(2,2-difluorocyclopropyl)methyl]-3-methyl-5-(6-{[4-(methylsulfonyl)piperazin-1-yl]methyl}pyridin-3-yl)-1,3-dihydro-2,1,3-benzothiadiazole2,2-dioxide;
5-{5-[(4-acetylpiperazin-1-yl)methyl]pyridin-3-yl}-1-[(2,2-difluorocyclopropyl)methyl]-3-methyl-1,3-dihydro-2,1,3-benzothiadiazole2,2-dioxide;
1-[(2,2-difluorocyclopropyl)methyl]-3-methyl-5-(5-{[4-(methylsulfonyl)piperazin-1-yl]methyl}pyridin-3-yl)-1,3-dihydro-2,1,3-benzothiadiazole2,2-dioxide;
5-{2-[(4-acetylpiperazin-1-yl)methyl]pyridin-4-yl}-1-[(2,2-difluorocyclopropyl)methyl]-3-methyl-1,3-dihydro-2,1,3-benzothiadiazole2,2-dioxide;
1-[(2,2-difluorocyclopropyl)methyl]-3-methyl-5-(2-{[4-(methylsulfonyl)piperazin-1-yl]methyl}pyridin-4-yl)-1,3-dihydro-2,1,3-benzothiadiazole2,2-dioxide;

5-{4-[(4-acetylpiperazin-1-yl)methyl]pyridin-2-yl}-1-[(2,2-difluorocyclopropyl)methyl]-3-methyl-1,3-dihydro-2,1,3-benzothiadiazole2,2-dioxide;

1-[(2,2-difluorocyclopropyl)methyl]-3-methyl-5-(3-methyl-6-{[4-(methylsulfonyl)piperazin-1-yl]methyl}pyridin-2-yl)-1,3-dihydro-2,1,3-benzothiadiazole2,2-dioxide;

1-{4-[(6-{1-[(2,2-difluorocyclopropyl)methyl]-3-methyl-2,2-dioxido-1,3-dihydro-2,1,3-benzothiadiazol-5-yl}-5-methylpyridin-2-yl)methyl]piperazin-1-yl}ethanone;

2-(6-{1-[(2,2-difluorocyclopropyl)methyl]-3-methyl-2,2-dioxido-1,3-dihydro-2,1,3-benzothiadiazol-5-yl}-5-methylpyridin-2-yl)propan-2-ol;

2-[1-(cyclopropylmethyl)-3-methyl-2,2-dioxido-1,3-dihydro[1,2,5]thiadiazolo[3,4-b]pyridin-5-yl]benzonitrile;

1-(cyclopropylmethyl)-5-[3-(1,1-dioxidothiomorpholin-4-yl)phenyl]-3-methyl-1,3-dihydro[1,2,5]thiadiazolo[3,4-b]pyridine 2,2-dioxide;

2-{1-[(2,2-difluorocyclopropyl)methyl]-3-methyl-2,2-dioxido-1,3-dihydro[1,2,5]thiadiazolo[3,4-b]pyridin-5-yl}benzonitrile;

1-[(2,2-difluorocyclopropyl)methyl]-3-methyl-5-(2-methylphenyl)-1,3-dihydro[1,2,5]thiadiazolo[3,4-b]pyridine 2,2-dioxide;

1-[(2,2-difluorocyclopropyl)methyl]-3-methyl-5-[2-(trifluoromethyl)phenyl]-1,3-dihydro[1,2,5]thiadiazolo[3,4-b]pyridine 2,2-dioxide;

1-[(2,2-difluorocyclopropyl)methyl]-5-[3-(1,1-dioxidothiomorpholin-4-yl)phenyl]-3-methyl-1,3-dihydro[1,2,5]thiadiazolo[3,4-b]pyridine 2,2-dioxide;

tert-butyl 4-(4-{1-[(2,2-difluorocyclopropyl)methyl]-3-methyl-2,2-dioxido-1,3-dihydro[1,2,5]thiadiazolo[3,4-b]pyridin-5-yl}phenyl)piperazine-1-carboxylate;

tert-butyl 4-(3-{1-[(2,2-difluorocyclopropyl)methyl]-3-methyl-2,2-dioxido-1,3-dihydro[1,2,5]thiadiazolo[3,4-b]pyridin-5-yl}phenyl)piperazine-1-carboxylate;

(3-{1-[(2,2-difluorocyclopropyl)methyl]-3-methyl-2,2-dioxido-1,3-dihydro[1,2,5]thiadiazolo[3,4-b]pyridin-5-yl}phenyl)methanol;

(3-{1-[(2,2-difluoro cyclopropyl)methyl]-3-methyl-2,2-dioxido-1,3-dihydro[1,2,5]thiadiazolo[3,4-b]pyridin-5-yl}-4-fluorophenyl)methanol;

(3-{1-[(2,2-difluoro cyclopropyl)methyl]-3-methyl-2,2-dioxido-1,3-dihydro[1,2,5]thiadiazolo[3,4-b]pyridin-5-yl}-2-fluorophenyl)methanol;

2-[1-(2,2-dimethylpropyl)-3-methyl-2,2-dioxido-1,3-dihydro[1,2,5]thiadiazolo[3,4-b]pyridin-5-yl]benzonitrile;

1-(2,2-dimethylpropyl)-5-[3-(1,1-dioxidothiomorpholin-4-yl)phenyl]-3-methyl-1,3-dihydro[1,2,5]thiadiazolo[3,4-b]pyridine 2,2-dioxide;

1-[(2,2-difluorocyclopropyl)methyl]-3-methyl-5-{3-[1-(methylsulfonyl)piperidin-4-yl]phenyl}-1,3-dihydro[1,2,5]thiadiazolo[3,4-b]pyridine 2,2-dioxide;

1-[(2,2-difluorocyclopropyl)methyl]-3-methyl-5-{4-[4-(methylsulfonyl)piperazin-1-yl]phenyl}-1,3-dihydro[1,2,5]thiadiazolo[3,4-b]pyridine 2,2-dioxide;

1-[(2,2-difluorocyclopropyl)methyl]-3-methyl-5-{3-[4-(methylsulfonyl)piperazin-1-yl]phenyl}-1,3-dihydro[1,2,5]thiadiazolo[3,4-b]pyridine 2,2-dioxide;

1-[(2,2-difluorocyclopropyl)methyl]-5-{4-[4-(isoxazol-3-ylcarbonyl)piperazin-1-yl]phenyl}-3-methyl-1,3-dihydro[1,2,5]thiadiazolo[3,4-b]pyridine 2,2-dioxide;

1-[4-(3-{1-[(2,2-difluorocyclopropyl)methyl]-3-methyl-2,2-dioxido-1,3-dihydro[1,2,5]thiadiazolo [3,4-b]pyridin-5-yl}phenyl)piperazin-1-yl]ethanone;

4-(4-cyano-3-{1-[(2,2-difluorocyclopropyl)methyl]-3-methyl-2,2-dioxido-1,3-dihydro[1,2,5]thiadiazolo[3,4-b]pyridin-5-yl}phenoxy)pyridine-2-carbonitrile;

4-{4-cyano-3-[1-(cyclopropylmethyl)-3-methyl-2,2-dioxido-1,3-dihydro[1,2,5]thiadiazolo[3,4-b]pyridin-5-yl]phenoxy}pyridine-2-carbonitrile;

4-{4-cyano-3-[1-(2,2-dimethylpropyl)-3-methyl-2,2-dioxido-1,3-dihydro[1,2,5]thiadiazolo[3,4-b]pyridin-5-yl]phenoxy}pyridine-2-carbonitrile;

2-(3-{1-[(2,2-difluorocyclopropyl)methyl]-3-methyl-2,2-dioxido-1,3-dihydro[1,2,5]thiadiazolo[3,4-b]pyridin-5-yl}-2-fluorophenyl)propan-2-ol;

2-(3-{1-[(2,2-difluorocyclopropyl)methyl]-3-methyl-2,2-dioxido-1,3dihydro[1,2,5]thiadiazolo[3,4-b]pyridin-5-yl}-4-methylphenyl) propan-2-ol;

2-{3-[1-(cyclopropyl methyl)-3-methyl-2,2-dioxido-1,3-dihydro[1,2,5]thiadiazolo[3,4-b]pyridin-5-y1]-4-methyl phenyl}propan-2-ol;

2-{3-[1-(2,2-dimethyl propyl)-3-methyl-2,2-dioxido-1,3-dihydro[1,2,5]thiadiazolo[3,4-b]pyridin-5-y1]-4-methyl phenyl}propan-2-ol;

1-[4-(3-{1-[(2,2-difluorocyclopropyl)methyl]-3-methyl-2,2-dioxido-1,3-dihydro[1,2,5]thiadiazolo [3,4-b]pyridin-5-yl}-4-methylb enzyl)piperazin-1-yl]ethanone;

1-[(2,2-difluorocyclopropyl)methyl]-3-methyl-5-(2-methyl-5-{[3-(trifluoromethyl)-5,6-dihydro[1,2,4]triazolo[4,3-a]pyrazin-7(8H)-yl]methyl}phenyl)-1,3-dihydro[1,2,5]thiadiazolo[3,4-b]pyridine 2,2-dioxide;

1-[(2,2-difluorocyclopropyl)methyl]-3-methyl-5-(2-methyl-5-{[4-(methylsulfonyl)piperazin-1-yl]methyl}phenyl)-1,3-dihydro[1,2,5]thiadiazolo[3,4-b]pyridine 2,2-dioxide;

1-[(2,2-difluorocyclopropyl)methyl]-5-{5-[(1,1-dioxidothiomorpholin-4-yl)methyl]-2-methylphenyl}-3-methyl-1,3-dihydro[1,2,5 ]thiadiazolo[3,4-b]pyridine 2,2-dioxide;

1-[(2,2-difluorocyclopropyl)methyl]-3-methyl-5-(2-methyl-5-{[4-(methylsulfonyl)piperidin-1-yl]methyl}phenyl)-1,3-dihydro[1,2,5]thiadiazolo[3,4-b]pyridine 2,2-dioxide;

1-[(2,2-difluorocyclopropyl)methyl]-3-methyl-5-(2-methyl-5-{[4-(methylsulfonyl)piperazin-1-yl]methyl}phenyl)-1,3-dihydro[1,2,5]thiadiazolo[3,4-b]pyridine 2,2-dioxide;

N-[1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidin-4-yl]acetamide;

tert-butyl (3aR,6aS)-5-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)hexahydropyrrolo[3,4-c]pyrrole-2(1H)-carboxylate;

1-[(2,2-difluorocyclopropyl)methyl]-3-methyl-5-(2-methyl-5-{[4-(pyrimidin-2-yl)piperazin-1-yl]methyl}phenyl)-1,3-dihydro[1,2,5]thiadiazolo[3,4-b]pyridine 2,2-dioxide;

1-[(2,2-difluorocyclopropyl)methyl]-3-methyl-5-(2-methyl-5-{[4-(pyridin-2-yl)piperazin-1-yl]methyl}phenyl)-1,3-dihydro[1,2,5]thiadiazolo[3,4-b]pyridine 2,2-dioxide;

1-[(2,2-difluorocyclopropyl)methyl]-3-methyl-5-(2-methyl-5-{[4-(pyrazin-2-yl)piperazin-1-yl]methyl}phenyl)-1,3-dihydro[1,2,5]thiadiazolo[3,4-b]pyridine 2,2-dioxide;

1-[(2,2-difluorocyclopropyl)methyl]-3-methyl-5-(2-methyl-5-{[4-(pyridin-4-yl)piperazin-1-yl]methyl}phenyl)-1,3-dihydro[1,2,5]thiadiazolo[3,4-b]pyridine 2,2-dioxide;

1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidine-4-carboxamide;
1-(3-{1-[(2,2-difluorocyclopropyl)methyl]-3-methyl-2,2-dioxido-1,3-dihydro[1,2,5]thiadiazolo[3,4-b]pyridin-5-yl}-4-methylb enzyl)-N-methylpiperidine-4-carbox amide;
2-[1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidin-4-yl]propan-2-ol;
1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-4-(pyridin-3-yl)piperidin-4-ol;
1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-4-(pyridin-2-yl)piperidin-4-ol;
N-[1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidin-4-yl]methanesulfonamide;
tert-butyl 7-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-2,7-diazaspiro[3.5]nonane-2carboxylate;
tert-butyl 7-(3-{1-[(2,2-difluorocyclopropyl)methyl]-3-methyl-2,2-dioxido-1,3-dihydro[1,2,5]thiadiazolo[3,4-b]pyridin-5-yl}-4-methylb enzyl)-1 ,7-diazaspiro[3.5]nonane-1-carboxylate;
1-[(2,2-difluorocyclopropyl)methyl]-3-methyl-5-(2-methyl-5-{[4-(pyrimidin-2-yl)pip eridin-1-yl]methyl}phenyl)-1,3-dihydro[1,2,5]thiadiazolo[3,4-b]pyridine 2,2-dioxide;
8-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-1,3,8-triazaspiro[4.5]decan-4-one
1-[(2,2-difluorocyclopropyl)methyl]-5-(5-{[4-(6-fluoropyridin-2-yl)piperidin-1-yl]methyl}-2-methylphenyl)-3-methyl-1,3-dihydro[1,2,5]thiadiazolo[3,4-b]pyridine 2,2-dioxide;
1-[(2,2-difluorocyclopropyl)methyl]-3-methyl-5 42-methyl-5-(2-oxa-7-azaspiro[3.5]non-7-ylmethyl)phenyl]-1,3-dihydro[1,2,5]thiadiazolo[3,4-b]pyridine 2,2-dioxide;
1-[1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidin-4-yl]pyrrolidin-2-one;
1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-4-[(dimethylamino)methyl]piperidin-4-ol;
[1-(3-{1-[(2,2-difluorocyclopropyl)methyl]-3-methyl-2, 2-dioxido-1,3-dihydro[1,2,5]thiadiazolo[3,4-b]pyridin-5-yl}-4-methylbenzyl)piperidin-4-yl]methanol;
[3-(3-{1-[(2,2-difluorocyclopropyl)methyl]-3-methyl-2, 2-dioxido-1,3-dihydro[1,2,5]thiadiazolo[3,4-b]pyridin-5-yl}-4-methylbenzyl)-3-azabicyclo[3.1.0]hex-6-yl]methanol;
1-[(2,2-difluorocyclopropyl)methyl]-3-methyl-5-(2-methyl-5-{[4-(pyridin-4-yl)piperidin-1-yl]methyl}phenyl)-1,3-dihydro[1,2,5]thiadiazolo[3,4-b]pyridine 2,2-dioxide;
1-[(2,2-difluorocyclopropyl)methyl]-3-methyl-5-(2-methyl-5-{[4-(pyridin-2-yl)piperidin-1-yl]methyl}phenyl)-1,3-dihydro[1,2,5]thiadiazolo[3,4-b]pyridine 2,2-dioxide;
1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperidine-3-carboxamide;
[1-(3-{1-[(2,2-difluorocyclopropyl)methyl]-3-methyl-2, 2-dioxido-1,3-dihydro[1,2,5]thiadiazolo[3,4-b]pyridin-5-yl}-4-methylbenzyl)piperidin-3-yl]methanol;
7-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-2,7-diazaspiro[4.5]decan-1-one;
1-[(2,2-difluorocyclopropyl)methyl]-3-methyl-5-(2-methyl-5-{[3-(methylsulfonyl)pyrrolidin-1-yl]methyl}phenyl)-1,3-dihydro[1,2,5]thiadiazolo[3,4-b]pyridine 2,2-dioxide;
[1-(3-{1-[(2,2-difluorocyclopropyl)methyl]-3-methyl-2, 2-dioxido-1,3-dihydro[1,2,5]thiadiazolo[3,4-b]pyridin-5-yl}-4-methylbenzyl)pyrrolidin-3-yl]methanol;
1-[4-(3-{1-[(2,2-difluorocyclopropyl)methyl]-3-methyl-2,2-dioxido-1,3-dihydro[1,2,5]thiadiazolo[3,4-b]pyridin-5-yl}benzyl)piperazin-1-yl]ethanone;
1-[(2,2-difluorocyclopropyl)methyl]-3-methyl-5-(3-{[4-(methylsulfonyl)piperazin-1-yl]methyl}phenyl)-1,3-dihydro[1,2,5]thiadiazolo[3,4-b]pyridine 2,2-dioxide;
1-[4-(3-{1-[(2,2-difluorocyclopropyl)methyl]-3-methyl-2,2-dioxido-1,3-dihydro[1,2,5]thiadiazolo[3,4-b]pyridin-5-yl}-4-fluorobenzyl)piperazin-1-yl]ethanone;
1-[(2,2-difluorocyclopropyl)methyl]-5-(2-fluoro-5-{[4-(methylsulfonyl)piperazin-1-yl]methyl}phenyl)-3-methyl-1,3-dihydro[1,2,5]thiadiazolo[3,4-b]pyridine 2,2-dioxide;
1-[4-(3-{1-[(2,2-difluorocyclopropyl)methyl]-3-methyl-2,2-dioxido-1,3-dihydro[1,2,59 thiadiazolo[3,4-b]pyridin-5-yl}-2-fluorobenzyl)piperazin-1-yl]ethanone;
1-[(2,2-difluorocyclopropyl)methyl]-5-(2-fluoro-3-{[4-(methylsulfonyl)piperazin-1-yl]methyl}phenyl)-3-methyl-1,3-dihydro[1,2,5]thiadiazolo[3,4-b]pyridine 2,2-dioxide;
1-[(2,2-difluorocyclopropyl)methyl]-5-{3-[(1,1-dioxidothiomorpholin-4-yl)methyl]-2-fluorophenyl}-3-methyl-1,3-dihydro[1,2,5]thiadiazolo[3,4-b]pyridine 2,2-dioxide;
1-[(2,2-difluorocyclopropyl)methyl]-5-(2-fluoro-3-{[4-(methylsulfonyl)piperidin-1-yl]methyl}phenyl)-3-methyl-1,3-dihydro[1,2,5]thiadiazolo[3,4-b]pyridine 2,2-dioxide;
(2R)-1-[4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazin-1-yl]-2-hydroxyprop an-1-one;
(2S)-1-[4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazin-1-yl]-2-hydroxypropan-1-one; or 1-[4-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)piperazin-1-yl]-2-hydroxyethanone;
or a pharmaceutically acceptable salt thereof.

20. A compound according to claim 1 wherein said compound is
N-{3-[1-(cyclopropylmethyl)-3-methyl-2,2-dioxido-1,3-dihydro-2,1,3-benzothiadiazol-5-yl]benzyl}benzamide;
1-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-3-methylimidazolidine-2,4-dione;

N-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-2-(1H-1,2,4-triazol-1-yl)acetamide;

(2R)-1-[4-(4-chloro-3-{1-(2R)-N-(3-{1-[(2,2-difluorocyclopropyl)methyl]-3-methyl-2,2-dioxido-1,3-dihydro[1,2,5]thiadiazolo[3,4-b]pyridin-5-yl}-4-methylbenzyl)-2-hydroxypropanamide;

1-[4-(4-chloro-3-{1-[(2,2-difluorocyclopropyl)methyl]-3-methyl-2,2-dioxido-1,3-dihydro[1,2,5]thiadiazolo[3,4-b]pyridin-5-yl}benzyl)piperazin-1-yl]ethanone;

(2R)-1-[4-(4-chloro-3-{1-[(2,2-difluorocyclopropyl)methyl]-3-methyl-2,2-dioxido-1,3-dihydro[1,2,5]thiadiazolo[3,4-b]pyridin-5-yl}benzyl)piperazin-1-yl]-2-hydroxyprop an-1-one;

2-[4-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperazin-1-yl]-2-oxoethanol;

3-cyano-6-{1-[(2,2-difluorocyclopropyl)methyl]-3-methyl-2,2-dioxido-1,3-dihydro-2,1,3-benzothiadiazol-5-yl}-2-[4-(isoxazol-3-ylcarbonyl)piperazin-1-yl]pyridinium chloride;

3-cyano-2-{1-[(2,2-difluorocyclopropyl)methyl]-3-methyl-2,2-dioxido-1,3-dihydro-2,1,3-benzothiadiazol-5-yl}-6-[4-(isoxazol-3-ylcarbonyl)piperazin-1-yl]pyridinium chloride;

tert-butyl 4-(5-cyano-6-{1-[(2,2-difluorocyclopropyl)methyl]-3-methyl-2,2-dioxido-1,3-dihydro-2,1,3-benzothiadiazol-5-yl}pyridin-2-yl)piperazine-1-carboxylate;

tert-butyl 4-(3-cyano-6-{1-[(2,2-difluorocyclopropyl)methyl]-3-methyl-2,2-dioxido-1,3-dihydro-2,1,3-benzothiadiazol-5-yl}pyridin-2-yl)piperazine-1-carboxylate;

2-{1-[(2,2-difluorocyclopropyl)methyl]-3-methyl-2,2-dioxido-1,3-dihydro-2,1,3-benzothiadiazol-5-yl}-6-(1,1-dioxidothiomorpholin-4-yl)-3-methylpyridinium chloride;

6-{4-[(acetyloxy)acetyl]piperazin-1-yl}-2-{1-[(2,2-difluorocyclopropyl)methyl]-3-methyl-2,2-dioxido-1,3-dihydro-2,1,3-benzothiadiazol-5-yl}-3-methylpyridinium trifluoroacetate;

4-(5-cyano-6-{1-[(2,2-difluorocyclopropyl)methyl]-3-methyl-2,2-dioxido-1,3-dihydro-2,1,3-benzothiadiazol-5-yl}pyridin-2-yl)piperazin-1-ium chloride;

6-chloro-2-{1-[(2,2-difluorocyclopropyl)methyl]-3-methyl-2,2-dioxido-1,3-dihydro-2,1,3-benzothiadiazol-5-yl}nicotinonitrile;

2-chloro-6-{1-[(2,2-difluorocyclopropyl)methyl]-3-methyl-2,2-dioxido-1,3-dihydro-2,1,3-benzothiadiazol-5-yl}nicotinonitrile;

(2R)-1-[4-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperazin-1-yl]-1-oxopropan-2-ol;

(2S)-1-[4-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperazin-1-yl]-1-oxopropan-2-ol;

2-{1-[(2,2-difluorocyclopropyl)methyl]-3-methyl-2,2-dioxido-1,3-dihydro-2,1,3-benzothiadiazol-5-yl}-6-[4-(methylsulfonyl)piperazin-1-yl]nicotinonitrile;

1-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperidin-4-one;

8-(6-{1-[(2,2-difluorocyclopropyl)methyl]-3-methyl-2,2-dioxido-1,3-dihydro-2,1,3-benzothiadiazol-5-yl}-5-methylpyridin-2-yl)-1,4-dioxa-8-azaspiro[4.5 ]decane;

8-(6-{1-[(2,2-difluorocyclopropyl)methyl]-3-methyl-2,2-dioxido-1,3-dihydro-2,1,3-benzothiadiazol-5-yl}-3-methylpyridin-2-yl)-1,4-dioxa-8-azaspiro[4.5 ]decane;

2-{1-[(2,2-difluorocyclopropyl)methyl]-3-methyl-2,2-dioxido-1,3-dihydro-2,1,3-benzothiadiazol-5-yl}-3-methyl-6-morpholin-4-ylpyridinium chloride;

6-{4-[2-(acetyloxy)-2-methylpropanoyl]piperazin-1-yl}-2-{1-[(2,2-difluorocyclopropyl)methyl]-3-methyl-2,2-dioxido-1,3-dihydro-2,1,3-benzothiadiazol-5-yl}-3-methylpyridinium trifluoroacetate;

2-{1-[(2,2-difluorocyclopropyl)methyl]-3-methyl-2,2-dioxido-1,3-dihydro-2,1,3-benzothiadiazol-5-yl}-6-{4-[(dimethylammonio)acetyl]piperazin-1-yl}-3-methylpyridinium dichloride;

1-[4-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperazin-1-yl]-2-methyl-1-oxopropan-2-ol;

1-(6-{1-[(2,2-difluorocyclopropyl)methyl]-3-methyl-2,2-dioxido-1,3-dihydro-2,1,3-benzothiadiazol-5-yl}-5-methylpyridin-2-yl)piperidin-4-ol;

4-(6-{1-[(2,2-difluorocyclopropyl)methyl]-3-methyl-2,2-dioxido-1,3-dihydro-2,1,3-benzothiadiazol-5-yl}-5-methylpyridin-2-yl)-1-(2,2,2-trifluoroethyl)piperazin-1-ium chloride;

2-{1-[(2,2-difluorocyclopropyl)methyl]-3-methyl-2,2-dioxido-1,3-dihydro-2,1,3-benzothiadiazol-5-yl}-6-(4-methoxypiperidin-1-yl)-3-methylpyridinium chloride;

1-(cyclopropylmethyl)-4-(6-{1-[(2,2-difluorocyclopropyl)methyl]-3-methyl-2,2-dioxido-1,3-dihydro-2,1,3-benzothiadiazol-5-yl}-5-methylpyridinium-2-yl)piperazin-1-ium dichloride;

2-{1-[(2,2-difluorocyclopropyl)methyl]-3-methyl-2,2-dioxido-1,3-dihydro-2,1,3-benzothiadiazol-5-yl}-3-methyl-644-(methylsulfonyl)piperazin-1-yl]pyridinium chloride;

2-{1-[(2,2-difluorocyclopropyl)methyl]-3-methyl-2,2-dioxido-1,3-dihydro-2,1,3-benzothiadiazol-5-yl}-3-methyl-6-{4-[(1-methyl-1H-imidazol-3-ium-2-yl)carbonyl]piperazin-1-yl}pyridinium dichloride;

2-{1-[(2,2-difluorocyclopropyl)methyl]-3-methyl-2,2-dioxido-1,3-dihydro-2,1,3-benzothiadiazol-5-yl}-6-[4-(isoxazol-3-ylcarbonyl)piperazin-1-yl]-3-methylpyridinium chloride; or 1-[(2,2-difluorocyclopropyl)methyl]-5-(6-fluoro-3-methylpyridin-2-yl)-3-methyl-1,3-dihydro-2,1,3-benzothiadiazole 2,2-dioxide;

or a pharmaceutically acceptable salt thereof.

21. The compound according to claim 1 wherein $R^1$ is 2,2-difluorocyclopropylmethyl.

22. A compound according to claim 1 of Formula II

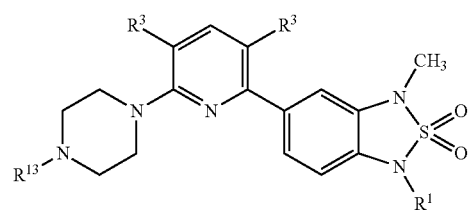

or pharmaceutically acceptable salts thereof, wherein:
one of the $R^3$ groups shown in Formula II is selected from the group consisting of H, CN and methyl; the other $R^3$ group is H;
$R^{13}$ is selected from the group consisting of: —C(O)—CH$_2$—N(R)$_2$, —C(O)—O—C$_{1-4}$alkyl, —C(O)-C(R)$_2$—C(O)—O—C$_{1-4}$alkyl, —CH$_2$—C$_{3-6}$cycloalkyl, C$_{1-4}$alkoxy, methylsulfonyl, heteroaryl -C(O)—, C$_{1-4}$alkyl and C$_{1-4}$alkyl-C(O)—, said C$_{1-4}$alkyl, C$_{1-4}$alkyl-C(O)— and heteroaryl-C(O)— optionally substituted with 1 to 3 halogen atoms and hydroxy and heteroaryl-C(O)-additionally optionally substituted with methyl, and each R is independently selected from the group consisting of: H and C$_{1-4}$alkyl.

23. A pharmaceutical composition comprising a compound according to claim 1 in combination with a pharmaceutically acceptable carrier.

24. A method for treating schizophrenia in a patient in need thereof comprising administering to the patient a therapeutically effective amount of a compound according to claim 1.

25. A method for treating schizophrenia in a patient in need thereof comprising administering to the patient a therapeutically effective amount of a compound according to claim 19.

26. A method for treating schizophrenia in a patient in need thereof comprising administering to the patient a therapeutically effective amount of a compound according to claim 20.

* * * * *